United States Patent
Ji et al.

(10) Patent No.: US 12,286,422 B2
(45) Date of Patent: Apr. 29, 2025

(54) METHODS AND COMPOSITIONS OF 4-SUBSTITUTED BENZOYLPIPERAZINE-1-SUBSTITUTED CARBONYLS AS β-CATENIN/B-CELL LYMPHOMA 9 INHIBITORS

(71) Applicant: University of Utah Research Foundation, Salt Lake City, UT (US)

(72) Inventors: Haitao Ji, Salt Lake City, UT (US); Min Zhang, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 43 days.

(21) Appl. No.: 17/968,408

(22) Filed: Oct. 18, 2022

(65) Prior Publication Data
US 2023/0122912 A1    Apr. 20, 2023

Related U.S. Application Data

(62) Division of application No. 16/087,553, filed as application No. PCT/US2017/024130 on Mar. 24, 2017, now Pat. No. 11,542,254.

(60) Provisional application No. 62/313,604, filed on Mar. 25, 2016.

(51) Int. Cl.
C07D 403/12    (2006.01)
C07D 403/14    (2006.01)

(52) U.S. Cl.
CPC ......... *C07D 403/12* (2013.01); *C07D 403/14* (2013.01)

(58) Field of Classification Search
CPC .......................... C07D 403/12; C07D 403/14
See application file for complete search history.

(56) References Cited

U.S. PATENT DOCUMENTS

| | | | |
|---|---|---|---|
| 2010/0204219 A1 | 8/2010 | Garcia et al. | |
| 2013/0079328 A1 | 3/2013 | Cheng et al. | |
| 2013/0079329 A1 | 3/2013 | Hood et al. | |
| 2013/0171639 A1 | 7/2013 | Sokolova et al. | |
| 2015/0038506 A1 | 2/2015 | Nacro et al. | |

FOREIGN PATENT DOCUMENTS

| | | |
|---|---|---|
| WO | WO-2015/140195 A1 | 9/2015 |
| WO | WO-2016/168524 A1 | 10/2016 |

OTHER PUBLICATIONS

Adachi, S. et al., Role of a BCL9-related 3-catenin-binding protein, B9L, in tumorigenesis induced by aberrant activation of Wnt signaling. Cancer Res. 2004; 64:8496-501.

Anastas, J.N. and Moon, R.T., Wnt signalling pathways as therapeutic targets in cancer. Nat Rev Cancer. 2013; 13:11-26.

Azzarito, V. et al., Inhibition of a-Helix-mediated protein-protein interactions using designed molecules. Nat Chem. 2013; 5:161-173.

Baell, J. nad Walters, M.A., Chemistry: Chemical Con Artists Foil Drug Discovery. Nature. 2014; 513(7519):481-3.

Baell, J.B. and Holloway, G.A., New Substructure Filters for Removal of Pan Assay Interference Compounds (PAINS) from Screening Libraries and for Their Exclusion in Bioassays. J Med Chem. 2010; 53(7):2719-40.

Bergey, C.M. et al., HippDB: a database of readily targeted helical protein-protein interactions. Bioinformatics. 2013; 29(21):2806-7.

Brembeck, F.H. et al., BCL9-2 Promotes Early Stages of Intestinal Tumor Progression. Gastroenterology. 2011; 141(4):1359-70.

Brembeck, F.H. et al., Essential Role of BCL9-2 in the Switch Between 3-Catenin's Adhesive and Transcriptional Functions. Genes Dev. 2004; 18(18):2225-30.

Bullock, B.N. et al., Assessing Helical Protein Interfaces for Inhibitor Design. J Am Chem Soc. 2011; 133(36):14220-3.

(Continued)

*Primary Examiner* — Brian E McDowell
(74) *Attorney, Agent, or Firm* — Ballard Spahr LLP

(57) ABSTRACT

In one aspect, the invention relates to 4-substituted benzoylpiperazine-1-substituted carbonyls having a structure represented by a formula:

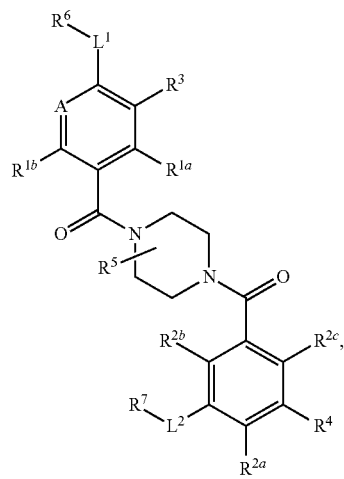

derivatives thereof, and related compounds; synthetic methods for making the compounds; pharmaceutical compositions comprising the compounds; and methods of treating disorders, e.g., various tumors and cancers, associated with β-catenin/BCL9 protein-protein interaction dysfunction using the compounds and compositions. This abstract is intended as a scanning tool for purposes of searching in the particular art and is not intended to be limiting of the present invention.

5 Claims, 21 Drawing Sheets

(56) References Cited

OTHER PUBLICATIONS

Camacho, C.J. et al., Fast Contact: rapid estimate of contact and binding free energies. Bioinformatics. 2005; 21(10):2534-6.
Camacho, C.J. et al., Scoring a diverse set of high-quality docked conformations: a metascore based on electrostatic and desolvation interactions. Proteins. 2006; 63(4):868-77.
Chen, G.et al., Crystal Structure and Mechanism of TraM2, a Second Quorum-Sensing Antiactivator of Agrobacterium tumefaciens Strain A6. J Bacteriol. 2006; 188(23):8244-51.
Clackson, T. et al., A hot spot of binding energy in a hormone-receptor interface. Science. 1995; 267:383-6.
Clevers, H. and Nusse, R., Wnt/[3-catenin signaling and disease. Cell. 2012; 149:1192-205.
Clevers, H. et al., Stem Cell Signaling. An Integral Program for Tissue Renewal and Regeneration: Wnt Signaling and Stem Cell Control. Science. 2014; 346 (6205):1248012 (7 pages).
Czabotar, P.E. et al., Bax crystal structures reveal how BH3 domains activate Bax and nucleate its oligomerization to induce apoptosis. Cell. 2013; 152(3):519-31.
Czabotar, P.E. et al., Structural insights into the degradation of Mcl-1 induced by BH3 domains. Proc Natl Acad Sci USA. 2007; 104(15):6217-22.
De la Roche, M. et al., An Intrinsically Labile a-Helix Abutting the BCL9-Binding Site for 13-Catenin is Required for Its Inhibition by Carnosic Acid. Nature Commun. 2012; 3:680 (10 pages).
De la Roche, M. et al., The Function of BCL9 in Wnt/[3-Catenin Signaling and Colorectal Cancer Cells. BMC Cancer. 2008; 8:199 (13 pages).
Deka, J. et al., BCL9/BCL91 are Critical for Wnt-Mediated Regulation of Stem Cell Traits in Colon Epithelium and Adenocarcinomas. Cancer Res. 2010; 70(16):6619-28.
Everson, D.A. et al., Replacing Conventional Carbon Nucleophiles with Electrophiles: Nickel-Catalyzed Reductive Alkylation of Aryl Bromides and Chlorides. J Am Chem Soc. 2012; 134(14):6146-59.
Friberg, A. et al., Discovery of potent myeloid cell leukemia 1 (Mcl 1) inhibitors using fragment based methods and structure based design. J Med Chem. 2013; 56(1): 15-30 (38 pages).
Friesner, R.A. et al. Extra precision glide: docking and scoring incorporating a model of hydrophobic enclosure for protein-ligand complexes. J Med Chem. 2006; 49(21) 6177-96.
Grigoriu, S. et al., The Molecular Mechanism of Substrate Engagement and Immunosuppressant Inhibition of Calcineurin. PLoS Biol. 2013; 11(2):e1001492 (13 pages).
Guo, W. et al., Hot spot-based design of small-molecule inhibitors for protein-protein interactions. Bioorg Med Chem Lett. 2014; 24:2546-54.
Hahne, G. and Grossmann, T.N., Direct Targeting of 6-Catenin: Inhibition of Protein-Protein Interaction for the Inactivation of Wnt Signaling. Bioorg Med Chem. 2013; 21(14):4020-6.
Halgren, T.A., Identifying and Characterizing Binding Sites and Assessing Druggability. J Chem Inf Model. 2009; 49(2): 377-89.
Heikkila, T. et al., Co-Crystal Structures of Inhibitors with MRCK6, a Key Regulator of Tumor Cell Invasion. PLoS One. 2011; 6(9):e24825 (12 pages).
Hoffmans, R. et al., Identification and in vivo role of the Armadillo-Legless interaction. Development. 2004; 131(17):4393-400.
Hoffmans, R. & Basler, K., BCL9-2 binds Arm/13-catenin in a Tyr142-independent manner and requires Pygopus for its function in Wg/Wnt signaling. Mech Dev. 2007; 124(1):59-67.
Hoggard, L.R. et al., Rational Design of Selective Small-Molecule Inhibitors for Catenin/B-Cell Lymphoma 9 Protein-Protein Interactions. J Am Chem Soc. 2015; 137(38):12249-60.
Jayatunga, M.K.P. et al., a-Helix mimetics: outwards and upwards. Bioorg Med Chem Lett. 2014; 24(3):717-24.
Ji, H. et al., Discovery of Highly Potent and Selective Inhibitors of Neuronal Nitric Oxide Synthase by Fragment Hopping. J Med Chem. 2009; 52:779-97 (44 pages).
Ji, H. et al., Minimal Pharmacophoric Elements and Fragment Hopping, an Approach Directed at Molecular Diversity and Isozyme Selectivity. Design of Selective Neuronal Nitric Oxide Synthase Inhibitors. J Am Chem Soc. 2008; 130:3900-14 (30 pages).
Jiao, L. et al., Structure of severe fever with thrombocytopenia syndrome virus nucleocapsid protein in complex with suramin reveals therapeutic potential. J Virol. 2013; 87(12):6829-39.
Jochim, A.L. et al., Assessment of helical interfaces in protein-protein interactions. Mol Biosyst. 2009; 5(9):924-6 (10 pages).
Jochim, A.L. et al., Systematic analysis of helical protein interfaces reveals targets for synthetic inhibitors. ACS Chem Biol. 2010; 5(10):919-23 (10 pages).
Kawamoto, S.A. et al., Analysis of the Interaction of BCL9 with 13-Catenin and Development of Fluorescence Polarization and Surface Plasmon Resonance Binding Assays for this Interaction. Biochemistry. 2009; 48(40):9534-41.
Kawamoto, S.A. et al., Design of Triazole-Stapled BCL9 a-Helical Peptides to Target the PCatenin/B-Cell CLL/Lymphoma 9 (BCL9) Protein-Protein Interaction. J Med Chem. 2012; 55(3):1137-46.
Koes, D.R. et al., Pocket Query: protein-protein interaction inhibitor starting points from protein-protein interaction structure. Nucleic Acids Res. 2012; 40:W387-92.
Kortemme, T. et al., Computational alanine scanning of protein-protein interfaces. Sci STKE. 2004; 2004(219):pl2 (8 pages).
Kosloff, M. et al., Integrating energy calculations with functional assays to decipher the specificity of G protein-RGS protein interactions. Nat Struct Mol Biol. 2011; 18:846-53 (23 pages).
Ku, B. et al., Evidence that inhibition of BAX activation by BCL-2 involves its tight and preferential interaction with the BH3 domain of BAX. Cell Res. 2011; 21 (4):627-41.
Ku, B. et al., Structural and Biochemical Bases for the Inhibition of Autophagy and Apoptosis by Viral BCL-2 of Murine y-Herpesvirus 68. PLoS Pathog. 2008; 4(2):e25 (12 pages).
Lee, E F et al., Discovery and molecular characterization of a BCL-2-regulated cell death pathway in schistosomes. Proc Natl Acad Sci USA. 2011; 108(17):6999-7003.
Leppanen, V.M. et al., Structural determinants of growth factor binding and specificity by VEGF receptor 2. Proc Natl Acad Sci USA. 2010; 107(6):2425-30.
Levin, K.B. et al. Following evolutionary paths to protein-protein interactions with high affinity and selectivity. Nat Struct Mol Biol. 2009; 16:1049-55.
Li, Z. et al., Structural insights into the YAP and TEAD complex. Genes Dev. 2010; 24(3):235-40.
Liu, X. et al., The structure of a Bcl-XL/Bim fragment complex: implications for Bim function. Immunity. 2003; 19(3):341-52.
Malanchi, I. et al., Cutaneous Cancer Stem Cell Maintenance is Dependent on 13-Catenin Signalling. Nature. 2008; 452(7187):650-3.
Mani, M. et al., BCL9 promotes tumor progression by conferring enhanced proliferative, metastatic, and angiogenic properties to cancer cells. Cancer Res. 2009; 69:7577-86 (22 pages).
Meenan, N.A.G. et al., The structural and energetic basis for high selectivity in a high-affinity protein-protein interaction. Proc Natl Acad Sci USA. 2010; 107:10080-5.
Meireles, L.M.C. et al., ANCHOR: a web server and database for analysis of protein-protein interaction binding pockets for drug discovery. Nucleic Acids Res. 2010; 38:W407-11.
Milburn, M.V. et al., A novel dimer configuration revealed by the crystal structure at 2.4 A resolution of human interleukin-5. Nature. 1993; 363(6425):172-6.
Milroy, L.G. et al., Modulators of protein-protein interactions. Chem Rev. 2014; 114(9):4695-748.
Moor, A.E. et al., BCL9/9L-PCatenin Signaling is Associated with Poor Outcome in Colorectal Cancer. EBioMedicine. 2015; 2(12):1932-43.
Morris, G.M. et al., AutoDock4 and AutoDockTools4: Automated docking with selective receptor flexibility. J Comput Chem. 2009; 30:2785-91.
Mosimann, C. et al., 13-Catenin Hits Chromatin: Regulation of Wnt Target Gene Activation. Nat Rev Mol Cell Biol. 2009; 10(4):276-86.
Muto, S. et al., Relationship between the structure of SET/TAF-Ip/INHAT and its histone chaperone activity. Proc Natl Acad Sci USA. 2007; 104(11):4285-90.

(56) References Cited

OTHER PUBLICATIONS

Nikolovska-Coleska, Z. et al., Development and optimization of a binding assay for the XIAP BIR3 domain using fluorescence polarization. Anal Biochem. 2004; 32:261-73.
O'Brien, C.A. et al., A Human Colon Cancer Cell Capable of Initiating Tumour Growth in Immunodeficient Mice. Nature. 2007; 445(7123):106-10.
Quinaud, M. et al., A Structure of the heterotrimeric complex that regulates type III secretion needle formation. Proc Natl Acad Sci USA. 2007; 104(19):7803-8.
Ricci-Vitiani, L. et al., Identification and Expansion of Human Colon-Cancer-Initiating Cells. Nature. 2007; 445(7123):111-5.
Sampietro, J. et al., Crystal structure of a B-catenin/BCL9/Tcf4 complex. Mol Cell. 2006; 24:293-300.
Sharma, V. et al., Structure of isocitrate lyase, a persistence factor of *Mycobacterium tuberculosis*. Nat Struct Biol. 2000; 7(8):663-8.
Singh, S.K. et al., Identification of Human Brain Tumour Initiating Cells. Nature. 2004; 432(7015):396-401.
Smits, C. et al., Structural plasticity underpins promiscuous binding of the prosurvival protein AI. Structure. 2008; 16(5):818-29.
Takada, K. et al. Targeted disruption of the BCL9/l3-catenin complex inhibits oncogenic Wnt signaling. Sci Transl Med. 2012; 4: 148ra117 (19 pages).
Terradot, L. et al., Structures of two core subunits of the bacterial type IV secretion system, VirB8 from *Brucella suis* and ComB10 from Helicobacter pylori. Proc Natl Acad Sci USA. 2005; 102(12):4596-601.
Valenta, T. et al., Probing transcription-specific outputs of B-catenin in vivo. Genes Dev. 2011; 25(24):2631-43.
Wisniewski, J.A. et al., Structure-Based Design of 1,4-Dibenzoylpiperazines as B-Catenin-B-Cell Lymphoma 9 Protein-Protein Interaction Inhibitors. ACS Med Chem Lett. 2016; 7(5):508-13.
Yeung, J. et al., B-Catenin Mediates the Establishment and Drug Resistance of MLL Leukemic Stem Cells. Cancer Cell. 2010; 18(6):606-18.
Yu, al., B. et Rational design of small-molecule inhibitors for B-catenin/T-cell factor protein-protein interactions by bioisostere replacement. ACS Chem Biol. 2013; 8(3):524-9.
Zhang, M. et al., AlphaScreen Selectivity Assay for B-Catenin/B-Cell Lymphoma 9 Inhibitors. Anal Biochem. 2015; 469:43-53.
Zhao, J.J. et al., miR-30-5p functions as a tumor suppressor and novel therapeutic tool by targeting the oncogenic Wnt/B-catenin/BCL9 pathway. Cancer Res. 2014; 74:1801-13 (24 pages).
Zhao, X. et al., Structure of the Bcr-Abl oncoprotein oligomerization domain. Nat Struct Biol. 2002; 9(2):117-20.
Zheng, X. et al., Initiation of Wnt Signaling: Control of Wnt Coreceptor Lrp6 Phosphorylation/Activation via Frizzled, Dishevelled and Axin Functions. Development. 2008; 135(2):367-75 (20 pages).
International Search Report and Written Opinion mailed on Sep. 13, 2016 by the International Searching Authority for Patent Application No. PCT/US2016/027640, which was filed on Apr. 14, 2016 and published as WO 2016/168524 on Oct. 20, 2016 (Inventor—Ji et al.; Applicant—University of Utah Research Foundation) (9 pages).
International Preliminary Report on Patentability issued on Oct. 17, 2017 by the International Searching Authority for International Patent Application No. PCT/US2016/027640, which was filed on Apr. 14, 2016 and published as WO 2016/168524 on Oct. 20, 2016 (Inventor—Ji et al.; Applicant—University of Utah Research Foundation) (6 pages).
Preliminary Amendment filed on Oct. 13, 2017 with the U.S. Patent and Trademark Office for U.S. Appl. No. 15/566,568, filed Oct. 13, 2017 and published as US 2018/0092866 on Apr. 5, 2018 (Inventor—Ji et al.; Applicant—University of Utah Research Foundation) (4 pages).
Restriction Requirement issued on Apr. 23, 2018 by the U.S. Patent and Trademark Office for U.S. Appl. No. 15/566,568, filed Oct. 13, 2017 and published as US 2018/0092866 on Apr. 5, 2018 (Inventor—Ji et al.; Applicant—University of Utah Research Foundation) (9 pages).
Non-Final Office Action issued on Sep. 7, 2018 by the U.S. Patent and Trademark Office for U.S. Appl. No. 15/566,568, filed Oct. 13, 2017 and published as US 2018/0092866 on Apr. 5, 2018 (Inventor—Ji et al.; Applicant—University of Utah Research Foundation) (8 pages).
International Search Report and Written Opinion mailed on Jun. 19, 2017 by the International Searching Authority for Patent Application No. PCT/US2017/024130, which was filed on Mar. 24, 2017 and published as WO 2017/165839 on Sep. 28, 2017 (Inventor—Ji et al.; Applicant—University of Utah Research Foundation) (8 pages).
International Preliminary Report on Patentability issued on Sep. 25, 2018 by the International Searching Authority for Patent Application No. PCT/US2017/024130, which was filed on Mar. 24, 2017 and published as WO 2017/165839 on Sep. 28, 2017 (Inventor—Ji et al.; Applicant—University of Utah Research Foundation) (7 pages).
Final rejection was mailed on May 21, 2019 by the USPTO for U.S. Appl. No. 15/566,568, filed Oct. 13, 2017 and published as US2018-0092866 A1 on Apr. 5, 2018 (Inventor Haitao Ji) (9 Pages).

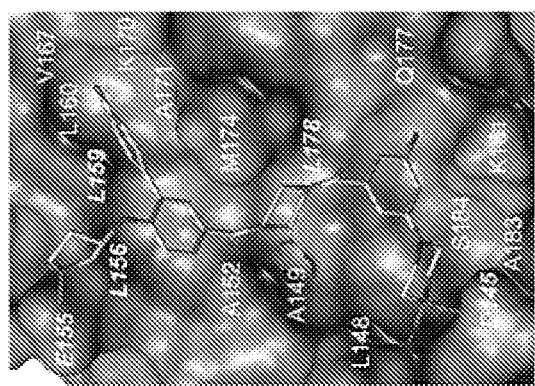
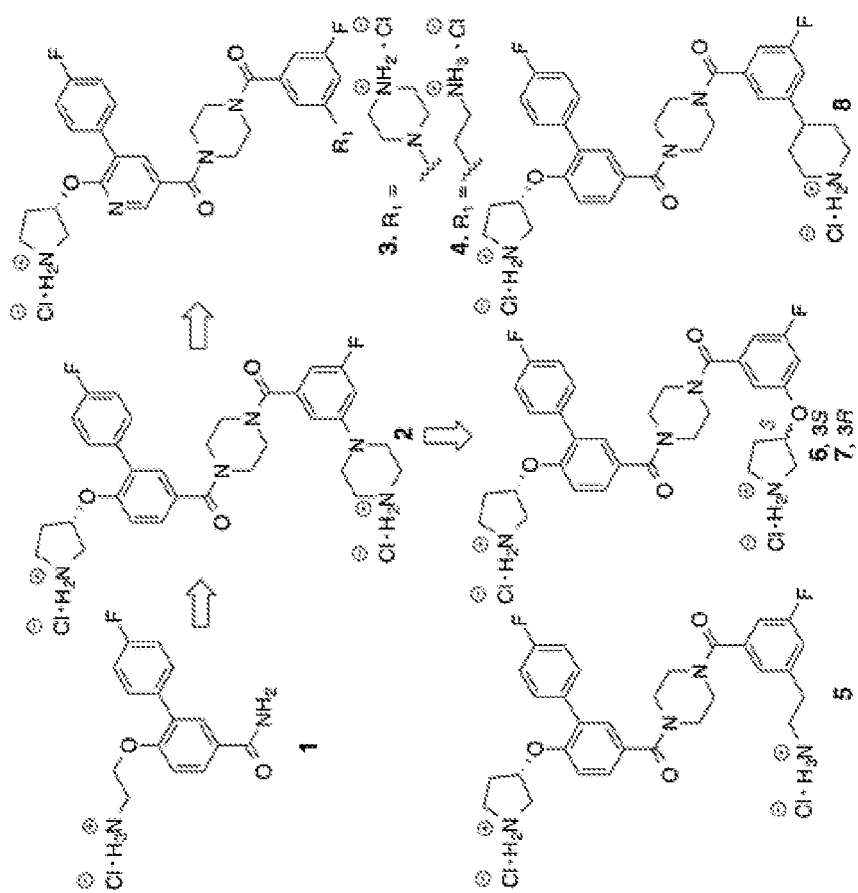
FIG. 4B
FIG. 4A

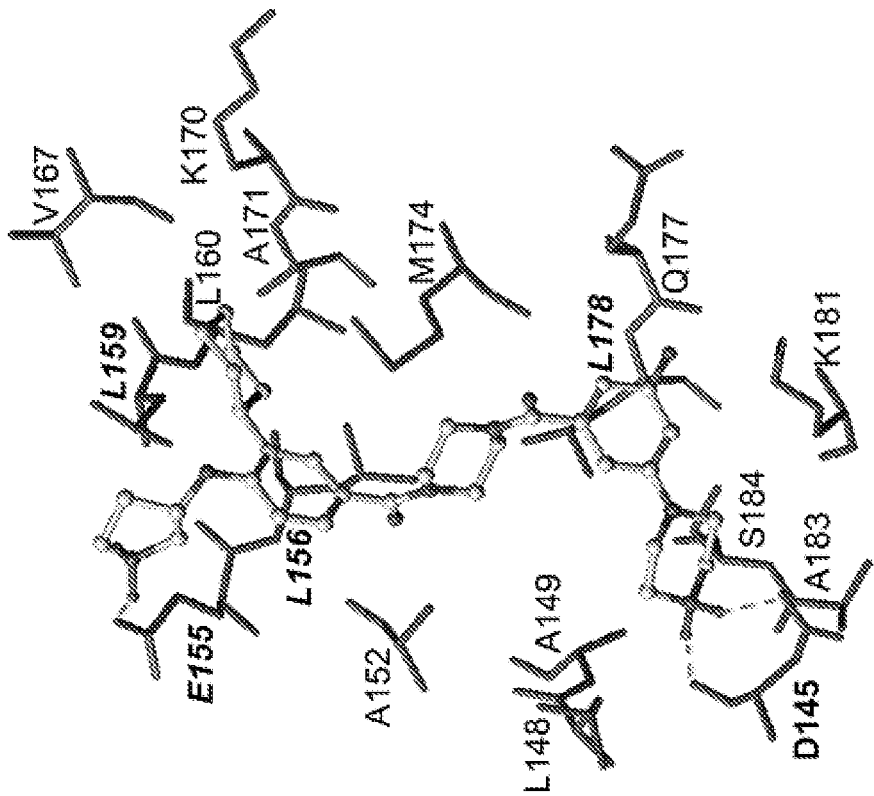
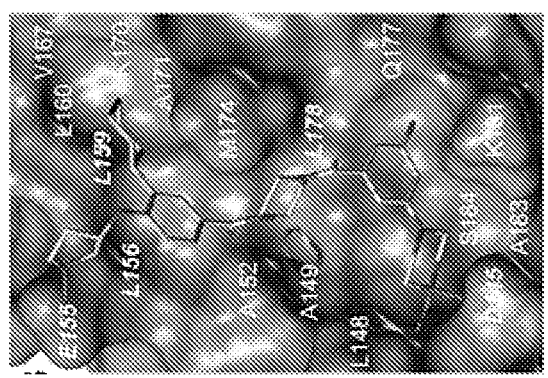
FIG. 6B
FIG. 6A

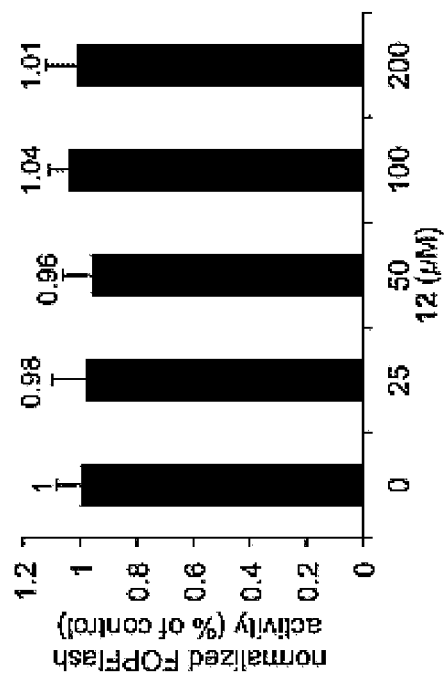
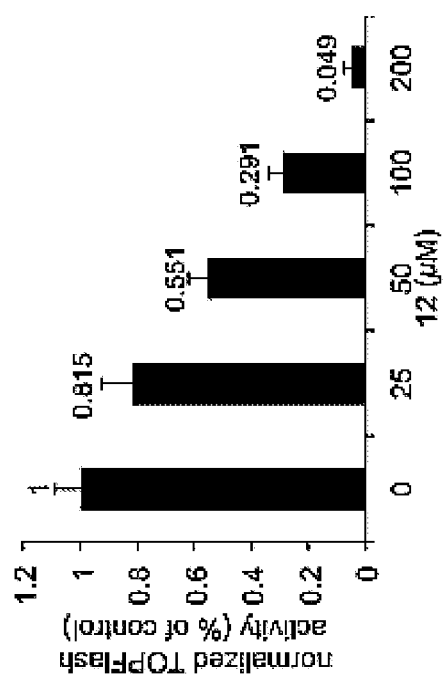
FIG. 12A
FIG. 12B

METHODS AND COMPOSITIONS OF 4-SUBSTITUTED BENZOYLPIPERAZINE-1-SUBSTITUTED CARBONYLS AS β-CATENIN/B-CELL LYMPHOMA 9 INHIBITORS

CROSS-REFERENCE TO RELATED APPLICATIONS

This application is a division of U.S. application Ser. No. 16/087,553, filed on Sep. 21, 2018, which is a U.S. National Phase of International Application No. PCT/US2017/024130, filed on Mar. 24, 2017, which claims priority to U.S. Application No. 62/313,604, filed on Mar. 25, 2016, each of which is incorporated herein by reference in its entirety.

STATEMENT REGARDING FEDERALLY SPONSORED RESEARCH

This invention was made with government support under Grant No. W81XWH-14-1-0083 awarded by the Army/MRMC. The government has certain rights in the invention.

BACKGROUND

The Wnt/β-catenin signaling pathway is instrumental in embryonic development, stem cell maintenance, and tissue homeostasis (Clevers et al. (2014) *Science* 346: 1248012). The protein β-catenin is the central hub of this pathway. In the absence of Wnt signaling, most intracellular β-catenin is complexed with cadherin to stabilize cell-cell junctions. Free cytosolic β-catenin enters a destruction complex that consists of adenomatous polyposis coli (APC), Axin, glycogen synthase kinase 3β, casein kinase 1α, and protein phosphatase 2A. This destruction complex phosphorylates β-catenin, which further leads to β-catenin ubiquitination and degradation. Wnt signaling is initiated extracellularly by Wnt proteins that bind to the membrane receptor proteins Frizzled and LRP 5/6 (Zeng et al. (2008) *Development* 135: 367-375). Upon binding, the β-catenin destruction complex is disrupted, and β-catenin is translocated to the cell nucleus, where β-catenin displaces the repressor protein groucho and binds T-cell factor (Tcf)/lymphoid enhancer-binding factor (Lef), B-cell lymphoma 9 (BCL9)/BCL9-like (B9L), CREB (cAMP response element-binding protein)-binding protein (CBP)/p300, etc. to activate the transcription of Wnt target genes (Mosimann et al. (2009) *Nature Rev. Mol. Cell Biol.* 10: 276-286).

Inactivating mutations of the β-catenin destruction complex, the epigenetic mutations of Wnt antagonist genes, or the autocrine/paracrine activation of Wnt proteins, Frizzled, and LRP5/6 allows β-catenin to escape degradation, translocate to the cell nucleus, bind with BCL9/B9L, etc., and initiate the transcription of Wnt target genes (Clevers and Nusse (2012) *Cell* 149: 1192-1205; Anastas and Moon (2013) *Nature Rev. Cancer* 13: 11-26). The unintended hyperactivation of canonical Wnt signaling causes many cancers and fibroses including idiopathic pulmonary fibrosis. Furthermore, the initiation, metastasis, and recurrence of cancers are believed driven by a subpopulation of cancer cells, called cancer stem cells (Singh et al. (2004) *Nature* 432: 396-401; O'Brien et al. (2007) *Nature* 445: 106-110; Ricci-Vitiani et al. (2007) *Nature* 445: 111-115). These cancer stem cells exhibit two distinct characteristics: the ability to self-renew and the ability to regenerate the phenotypic heterogeneity of the parental tumor. Canonical Wnt signaling is highly activated in cancer stem cells (Malanchi et al. (2008) *Nature* 452: 650-653; Yeung et al. (2010) *Cancer Cell* 18: 606-618). Significant efforts have been made to discover inhibitors for the key effectors of the canonical Wnt signaling pathway, but few drug-like hits were identified (Anastas and Moon (2013) *Nature Rev. Cancer* 13: 11-26; Hahne and Grossmann (2013) *Bioorg. Med. Chem.* 21: 4020-4026). One promising target is the β-catenin/BCL9 protein-protein interaction (PPI). BCL9 and its paralog B9L connect β-catenin with the chromatin remodeler pygo that is essential for Wnt signaling (Brembeck et al. (2011) *Gastroenterology* 141:1359-1370; Deka et al. (2010) *Cancer Res.* 70: 6619-6628). BCL9 and B9L were observed highly overexpressed in Wnt-dependent cancer cells (but not in normal tissues) (Brembeck et al. (2011) *Gastroenterology* 141:1359-1370; Adachi et al. (2004) *Cancer Res.* 64: 8496-8501; de la Roche et al. (2008) *BMC Cancer* 8: 199; Mani et al. (2009) *Cancer Res.* 69: 7577-7586). The knockdown of BCL9, B9L, and pygo (Adachi et al. (2004) *Cancer Res.* 64: 8496-8501; de la Roche et al. (2008) *BMC Cancer* 8: 199; Mani et al. (2009) *Cancer Res.* 69: 7577-7586; Brembeck et al. (2004) *Cancer Res.* 69: 7577-7586; Zhao et al. (2014) *Cancer Res.* 74: 1801-1813) or the use of dominant negative BCL9 or B9L (Adachi et al. (2004) *Cancer Res.* 64: 8496-8501; de la Roche et al. (2008) *BMC Cancer* 8: 199) inhibited the activity of canonical Wnt signaling in cell-based reporter assays, downregulated the transcription of Wnt target genes, inhibited cancer cell migration, and induced an epithelial-like phenotype in colon cancer and multiple myeloma cells. The knockdown of BCL9 also significantly enhanced the survival of xenograft mouse models of cancer by reducing cancer load, metastasis, and host angiogenesis (Mani et al. (2009) *Cancer Res.* 69: 7577-7586). The conditional ablation of BCL9 and B9L in mice reduced Wnt responsive genes that promote cancer stem cells and epithelial-to-mesenchymal transition (Brembeck et al. (2011) *Gastroenterology* 141:1359-1370; Deka et al. (2010) *Cancer Res.* 70: 6619-6628; Moor et al. (2015) *EBioMedicine* 2: 1932-1943). BCL9/B9L ablation in murine oncogenic intestinal organoids provoked differentiation and abrogated their tumorigenicity (Moor et al. (2015) *EBioMedicine* 2: 1932-1943). On the other hand, the conditional gene ablation of BCL9 and B9L showed normal cell lineage commitment and proliferation (Brembeck et al. (2011) *Gastroenterology* 141:1359-1370; Deka et al. (2010) *Cancer Res.* 70: 6619-6628), indicating the selective disruption of β-catenin/BCL9 interactions does not affect normal tissue homeostasis. Two other merits that make the β-catenin/BCL9 PPI appealing for inhibitor design are: (1) the binding site of β-catenin for BCL9 partially overlaps with that for cadherin but has no overlap with that for axin and APC; and (2) the interaction between β-catenin and BCL9 or B9L is relatively weak with a dissociation constant ($K_d$) of 0.465 µM (Sampietro et al. (2006) *Mol. Cell* 24: 293-300; Kawamoto et al. (2009) *Biochemistry* 48: 9534-9541; Zhang and Wisniewski (2015) *Anal. Biochem.* 469: 43-53).

Previous attempts to inhibit the β-catenin/BCL9 PPI have resulted in little to mild success; with one small-molecule inhibitor, carnosic acid, being identified from high-throughput screening (de la Roche et al. (2012) *Nature Commun.* 3: 680) and three different stapled α-helices being designed (Kawamoto et al. (2012) *J. Med. Chem.* 55: 1137-1146; Takada et al. (2012) *Sci. Transl. Med.* 4: 148ra117). The stapled α-helix, SAH-BCL9, was able to disrupt the β-catenin/Bcl9 PPI and suppressed tumor growth, angiogenesis, invasion, and metastasis in mouse xenograft models (Takada et al. (2012) *Sci. Transl. Med.* 4: 148ra117). MicroRNA miR-30-50p was also reported to downregulate BCL9 and Wnt transcriptional activity and reduce tumor burden and metastatic potential of multiple myeloma in vivo (Zhao et al. (2014) *Cancer Res.* 74: 1801-1813).

Despite advances in research directed to identifying inhibitors of the Wnt signaling pathway generally, and specifically inhibitors of β-catenin/BCL9 interactions, there remains a scarcity of compounds that are both potent, efficacious, and selective inhibitors of β-catenin/BCL9 interactions and also effective in the treatment of cancers and other diseases associated with uncontrolled cellular proliferation, e.g., fibrotic diseases, associated with β-catenin/BCL9 dysfunction. These needs and other needs are satisfied by the present invention.

SUMMARY

In accordance with the purpose(s) of the invention, as embodied and broadly described herein, the invention, in one aspect, relates to compounds useful as inhibitors of β-catenin/B-cell lymphoma 9 protein-protein interactions, methods of making same, pharmaceutical compositions comprising same, and methods of treating disorders, e.g., various tumors and cancers, associated with a β-catenin/B-cell lymphoma 9 protein-protein interaction dysfunction or a Wnt pathway dysregulation using same.

Disclosed are compounds having a structure represented by a formula:

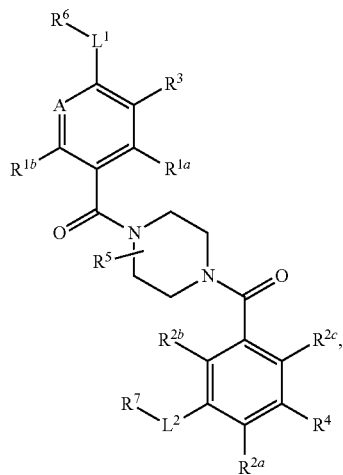

wherein A is $-N-$ or $-CR^8-$; wherein $R^8$ is hydrogen, halogen, C1-C3 alkyl, C1-C3 monohaloalkyl, or C1-C3 polyhaloalkyl; wherein $L^1$ is optionally present, and when present, is O, S, or NH; wherein $L^2$ is optionally present, and when present, is O, S, $NR^9$, or $-(CR^{10a}R^{10b})_n-$; wherein n is an integer having the value of 1, 2, or 3; wherein $R^9$ is hydrogen, C1-C3 alkyl, C1-C3 monohaloalkyl, or C1-C3 polyhaloalkyl; wherein each occurrence of $R^{10a}$ and $R^{10a}$ is independently hydrogen, C1-C3 alkyl, C1-C3 monohaloalkyl, or C1-C3 polyhaloalkyl; wherein each of $R^{1a}$ and $R^{1b}$ is independently hydrogen, halogen, C1-C3 alkyl, C1-C3 monohaloalkyl, or C1-C3 polyhaloalkyl; wherein each of $R^{2a}$, $R^{2b}$, and $R^{2c}$ is independently hydrogen, halogen, C1-C3 alkyl, C1-C3 monohaloalkyl, or C1-C3 polyhaloalkyl; wherein $R^3$ is $Cy^3$ or $Ar^1$; wherein $Cy^3$ is a C3-C8 cycloalkyl or a C2-C7 heterocycloalkyl; and wherein $Cy^3$ is substituted 0, 1, 2, or 3 groups independently selected from halogen, $-CN$, C1-C3 alkyl, C1-C3 monohaloalkyl, C1-C3 polyhaloalkyl, cyclopropyl, and $-CO_2H$; wherein $Ar^1$ is selected from aryl and heteroaryl, and wherein $Ar^1$ is substituted with 0, 1, 2, or 3 groups independently selected from halogen, $-CN$, C1-C3 alkyl, C1-C3 monohaloalkyl, C1-C3 polyhaloalkyl, cyclopropyl, and $-CO_2H$; wherein $R^4$ is hydrogen, halogen, C1-C3 alkyl, C1-C3 monohaloalkyl, or C1-C3 polyhaloalkyl; wherein each occurrence of $R^5$ is independently selected from hydrogen, C1-C8 alkyl, C1-C8 monohaloalkyl, or C1-C8 polyhaloalkyl; wherein $R^6$ is C1-C6 aminoalkyl, C1-C6 hydroxyalkyl, or $Cy^1$; and wherein $Cy^1$ is an amino C3-C8 cycloalkyl, a hydroxy C3-C8 cycloalkyl, or a C2-C7 heterocycloalkyl comprising at least one oxygen or nitrogen atom; and wherein $Cy^1$ is substituted 0, 1, 2, or 3 groups independently selected from halogen, C1-C4 alkyl, C1-C4 monohaloalkyl, and C1-C4 polyhaloalkyl; wherein $R^7$ is $H_2N-(C1-C6$ alkyl)-$(C=O)-$; $HO-(C1-C6$ alkyl)-$(C=O)-$; C1-C6 aminoalkyl, C1-C6 hydroxyalkyl, or $Cy^2$; and wherein $Cy^2$ is an amino C3-C8 cycloalkyl, a hydroxy C3-C8 cycloalkyl, or a C2-C7 heterocycloalkyl comprising at least one oxygen or nitrogen atom; and wherein $Cy^2$ is substituted 0, 1, 2, or 3 groups independently selected from halogen, C1-C4 alkyl, C1-C4 monohaloalkyl, and C1-C4 polyhaloalkyl; or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

Also disclosed are methods for the treatment of a disorder of uncontrolled cellular proliferation associated with a β-catenin/BCL9 dysfunction in a mammal comprising the step of administering to the mammal an effective amount of at least one disclosed compound, or a pharmaceutically acceptable salt thereof, or an effective amount of at least one disclosed pharmaceutical composition.

Also disclosed are methods for inhibiting protein-protein interactions of β-catenin and BCL9 in a mammal comprising the step of administering to the mammal an effective amount of at least one disclosed compound, or a pharmaceutically acceptable salt thereof, or an effective amount of at least one disclosed pharmaceutical composition.

Also disclosed are methods for inhibiting protein-protein interactions of β-catenin and BCL9 in at least one cell, comprising the step of contacting the at least one cell with an effective amount of at least one disclosed compound, or a pharmaceutically acceptable salt thereof, or an effective amount of at least one disclosed pharmaceutical composition.

Also disclosed are uses of at least one disclosed compound for inhibiting β-catenin/BCL9 activity.

Also disclosed are uses of at least one disclosed compound for administration to a subject; wherein the subject has a disorder of uncontrolled cellular proliferation.

Also disclosed are kits comprising at least one disclosed compound, or a pharmaceutically acceptable salt thereof, or at least one disclosed pharmaceutical composition; and one or more of:

(a) at least one agent known to increase BCL9 activity;
(b) at least one agent known to increase β-catenin activity;
(c) at least one agent known to decrease BCL9 activity;
(d) at least one agent known to decrease β-catenin activity;
(e) at least one agent known to treat a disease of uncontrolled cellular proliferation;
(f) instructions for treating a disorder associated uncontrolled cellular proliferation; or
(g) instructions for treating a disorder associated with a β-catenin/BCL9 dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 4A-C show representative data pertaining to the design of new β-catenin/BCL9 inhibitors. Specifically, the chemical structures of compounds 1-8 (4A) and a surface model (4B) and stick model (4C) of the AutoDock result of 1 with β-catenin (PDB id, 2GL7; Sampietro et al. (2006) *Mol. Cell* 24: 293-300) are shown.

FIG. 6A and FIG. 6B show representative AutoDock results of compound 10. Specifically, a surface model (6A) and a stick model (6B) are shown.

FIG. 12A-C show representative data pertaining to the effects of compound 12 and carnosic acid on the transactivation of the canonical Wnt signaling pathway. Specifically, TOPFlash (12A) and FOPFlash (12B) luciferase reporter assay results of compound 12 and TOPFlash luciferase assay results of carnosic acid (12C) are shown.

Figure 1A:
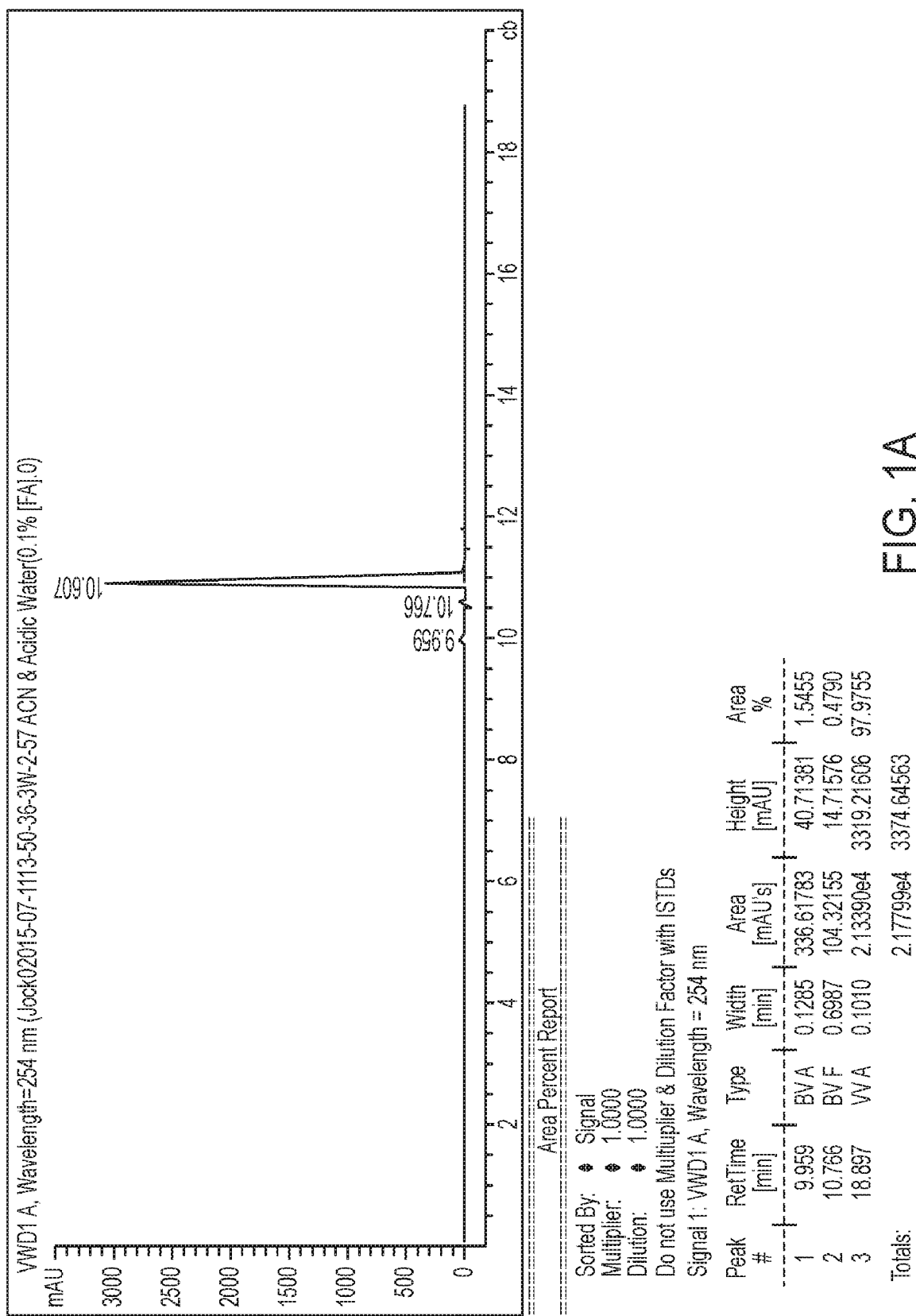
FIG. 1A and FIG. 1B show representative HPLC spectra of compound 2 run over a water/acetonitrile gradient (plus 0.1% TFA) (1A) and over a water/methanol gradient (plus 0.10% TFA (1B).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptenyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A'S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$", where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

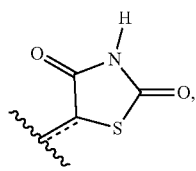

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

It is also appreciated that certain compounds described herein can be present as an equilibrium mixture of tautomers. For example, ketones with an α-hydrogen can exist in an equilibrium mixture of the keto form and the enol form.

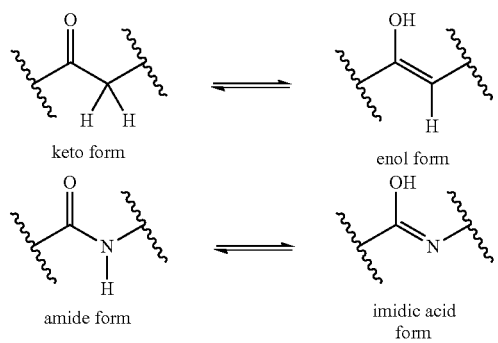

Likewise, amides with an N-hydrogen can exist in an equilibrium mixture of the amide form and the imidic acid form. As another example, tetrazoles can exist in two tautomeric forms, $N^{1}$-unsubstituted and $N^{2}$-unsubstituted, as shown below.

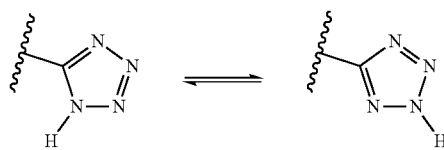 [SMILES: *c1nnn[nH]1 ; *c1nn[nH]n1]

Unless stated to the contrary, the invention includes all such possible tautomers.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

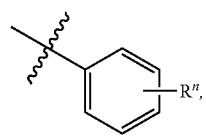

which is understood to be equivalent to a formula:

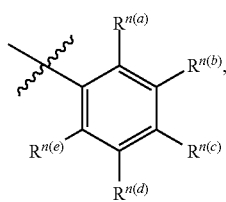

wherein n is typically an integer. That is, $R^{n}$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as inhibitors of β-catenin/BCL9 protein-protein interactions, and thus down-regulating Wnt signaling. In a further aspect, the compound selectively inhibits β-catenin/BCL9 interactions compared to 0-catenin/cadherin interactions. In a still further aspect, the compound inhibits Wnt signaling. In yet a further aspect, the compound inhibits transcription of at least one β-catenin target gene.

In a further aspect, the compound inhibits cell viability. In a still further aspect, the compound inhibits cell migration. In yet a further aspect, the compound inhibits angiogenesis. In an even further aspect, the compound inhibits tumor metastasis. In a still further aspect, the compound inhibits tumor progression.

In a further aspect, the compound exhibits inhibition with an $K_i$ of less than about $1.0 \times 10^{-4}$ M when determined in competitive inhibition assay. In a still further aspect, the compound exhibits inhibition with an $K_i$ of less than about $7.0 \times 10^{-5}$ M when determined in competitive inhibition assay. In yet a further aspect, the compound exhibits inhibition with an $K_i$ of less than about $5.0 \times 10^{-5}$ M when determined in competitive inhibition assay. In an even further aspect, the compound exhibits inhibition with an $K_i$ of less than about $2.5 \times 10^{-5}$ M when determined in competitive inhibition assay. In a still further aspect, the compound exhibits inhibition with an $K_i$ of less than about $1.0 \times 10^{-5}$ M when determined in competitive inhibition assay. In yet a further aspect, the compound exhibits inhibition with an $K_i$ of less than about $5.0 \times 10^{-6}$ M when determined in competitive inhibition assay.

In one aspect, the compounds of the invention are useful in the treatment of disorders, e.g., various tumors and cancers, associated with a β-catenin/BCL9 protein-protein interaction dysfunction or a Wnt pathway dysregulation using same, and other diseases in which β-catenin/BCL9 or the Wnt signaling pathway are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

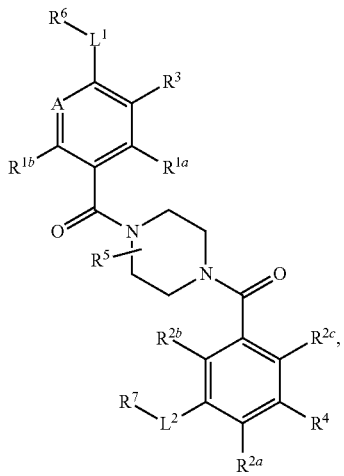

wherein A is —N— or —CR⁸—; wherein $R^8$ is hydrogen, halogen, C1-C3 alkyl, C1-C3 monohaloalkyl, or C1-C3 polyhaloalkyl; wherein $L^1$ is optionally present, and when present, is O, S, or NH; wherein $L^2$ is optionally present, and when present, is O, S, $NR^9$, or —$(CR^{10a}R^{10b})_n$—; wherein n is an integer having the value of 1, 2, or 3; wherein $R^9$ is hydrogen, C1-C3 alkyl, C1-C3 monohaloalkyl, or C1-C3 polyhaloalkyl; wherein each occurrence of $R^{10a}$ and $R^{10a}$ is independently hydrogen, C1-C3 alkyl, C1-C3 monohaloalkyl, or C1-C3 polyhaloalkyl; wherein each of $R^{1a}$ and $R^{1b}$ is independently hydrogen, halogen, C1-C3 alkyl, C1-C3 monohaloalkyl, or C1-C3 polyhaloalkyl; wherein each of $R^{2a}$, $R^{2b}$, and $R^{2c}$ is independently hydrogen, halogen, C1-C3 alkyl, C1-C3 monohaloalkyl, or C1-C3 polyhaloalkyl; wherein $R^3$ is $Cy^3$ or $Ar^1$; wherein $Cy^3$ is a C3-C8 cycloalkyl or a C2-C7 heterocycloalkyl; and wherein $Cy^3$ is substituted 0, 1, 2, or 3 groups independently selected from halogen, —CN, C1-C3 alkyl, C1-C3 monohaloalkyl, C1-C3 polyhaloalkyl, cyclopropyl, and —CO₂H; wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, cyclopropyl, and —CO₂H; wherein $R^4$ is hydrogen, halogen, C1-C3 alkyl, C1-C3 monohaloalkyl, or C1-C3 polyhaloalkyl; wherein each occurrence of $R^5$ is independently selected from hydrogen, C1-C8 alkyl, C1-C8 monohaloalkyl, or C1-C8 polyhaloalkyl; wherein $R^6$ is C1-C6 aminoalkyl, C1-C6 hydroxyalkyl, or $Cy^1$; and wherein $Cy^1$ is an amino C3-C8 cycloalkyl, a hydroxy C3-C8 cycloalkyl, or a C2-C7 heterocycloalkyl comprising at least one oxygen or nitrogen atom; and wherein $Cy^1$ is substituted 0, 1, 2, or 3 groups independently selected from halogen, C1-C4 alkyl, C1-C4 monohaloalkyl, and C1-C4 polyhaloalkyl; wherein $R^7$ is H₂N—(C1-C6 alkyl)-(C=O)—; HO—(C1-C6 alkyl)-(C=O)—; C1-C6 aminoalkyl, C1-C6 hydroxyalkyl, or $Cy^2$; and wherein $Cy^2$ is an amino C3-C8 cycloalkyl, a hydroxy C3-C8 cycloalkyl, or a C2-C7 heterocycloalkyl comprising at least one oxygen or nitrogen atom; and wherein $Cy^2$ is substituted 0, 1, 2, or 3 groups independently selected from halogen, C1-C4 alkyl, C1-C4 monohaloalkyl, and C1-C4 polyhaloalkyl; or a pharmaceutically acceptable salt thereof.

In view of the foregoing, one would appreciate that:

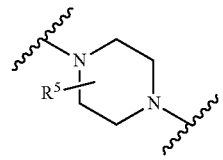

can also be expressed as:

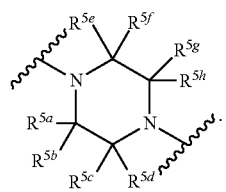

That is, $R^5$ is understood to represent eight independent substituents, $R^{5a}$, $R^{5b}$, $R^{5c}$, $R^{5d}$, $R^{5e}$, $R^{5f}$, $R^{5g}$, and $R^{5h}$. By "independent substituents," it is meant that each R substituent can be independently defined. For example, if in one instance $R^{5a}$ is hydrogen, then $R^{5b}$ is not necessarily hydrogen in that instance.

In a further aspect, the compound has a structure represented by a formula:

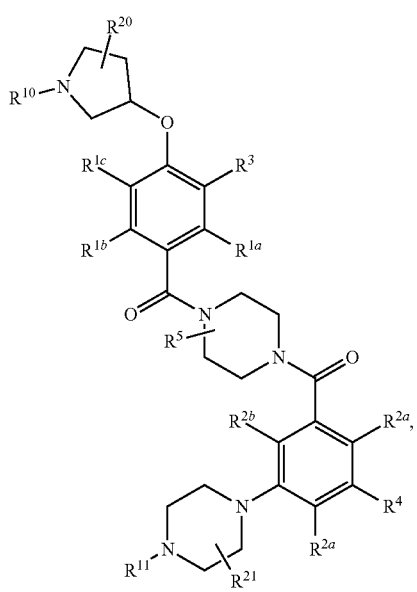

wherein $R^{10}$ is hydrogen, methyl, ethyl, propyl, or isopropyl; wherein $R^{11}$ is hydrogen, methyl, ethyl, propyl, or isopropyl; wherein each occurrence of $R^{20}$ is independently halogen, C1-C4 alkyl, C1-C4 monohaloalkyl, and C1-C4 polyhaloalkyl, provided that no more than two occurrences of $R^{20}$ are not hydrogen; and wherein each occurrence of $R^{21}$ is independently halogen, C1-C4 alkyl, C1-C4 monohaloalkyl, and C1-C4 polyhaloalkyl, provided that no more than two occurrences of $R^{21}$ are not hydrogen.

In view of the foregoing, one would appreciate that:

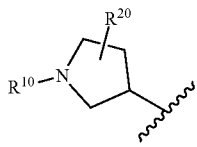

can also be expressed as:

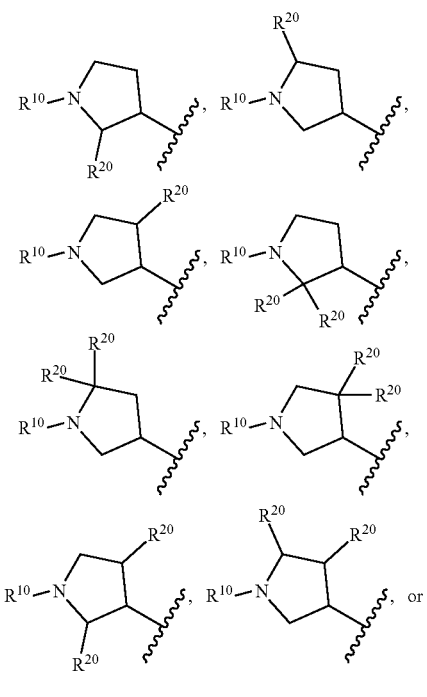

wherein each occurrence of $R^{20}$ is independently halogen, C1-C4 alkyl, C1-C4 monohaloalkyl, and C1-C4 polyhaloalkyl.

In view of the foregoing, one would further appreciate that:

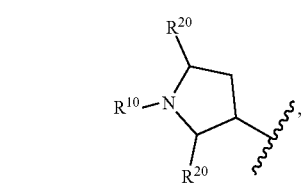

can also be expressed as:

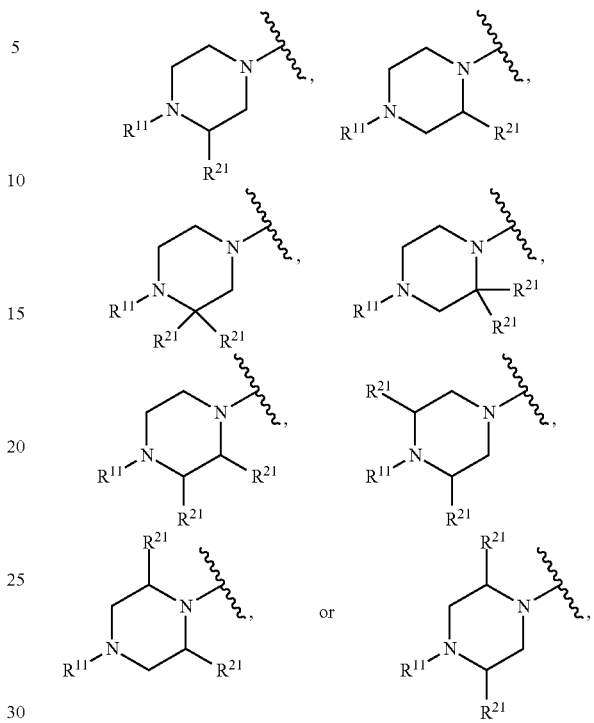

wherein each occurrence of $R^{21}$ is independently halogen, C1-C4 alkyl, C1-C4 monohaloalkyl, and C1-C4 polyhaloalkyl.

In a further aspect, the compound has a structure represented by a formula:

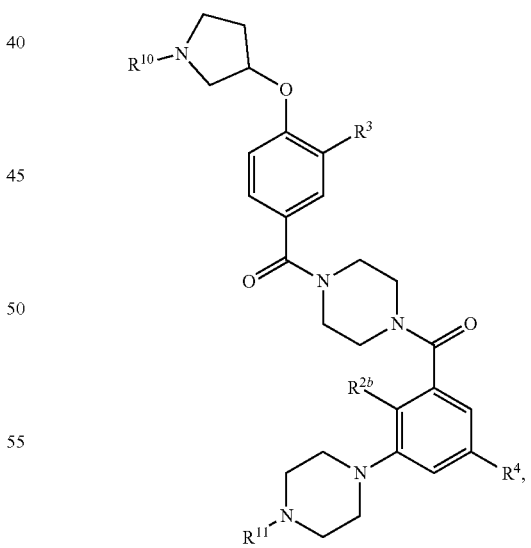

wherein $R^3$ is cyclohexyl or phenyl substituted 0, 1, 2, or 3 groups independently selected from halogen, —CN, C1-C3 alkyl, C1-C3 monohaloalkyl, C1-C3 polyhaloalkyl, cyclopropyl, and —CO$_2$H; wherein $R^4$ is —F, —Cl —Br, methyl, ethyl, —CFH$_2$, —CF$_2$H, or —CF$_3$; wherein $R^{10}$ is hydrogen, methyl, ethyl, propyl, or isopropyl; and wherein $R^{11}$ is hydrogen, methyl, ethyl, propyl, or isopropyl.

In a further aspect, the compound has a structure represented by a formula:

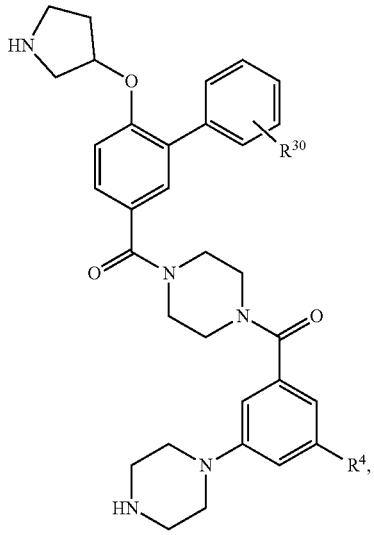

wherein $R^4$ is —F, —Cl —Br, methyl, ethyl, —CFH$_2$, —CF$_2$H, or —CF$_3$; and wherein each occurrence of $R^{30}$ is independently halogen, —CN, C1-C3 alkyl, C1-C3 monohaloalkyl, C1-C3 polyhaloalkyl, cyclopropyl, or —CO$_2$H, provided that no more than three occurrences of $R^{30}$ are not hydrogen.

In view of the foregoing, one would appreciate that:

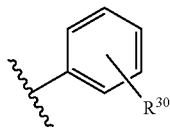

can also be expressed as:

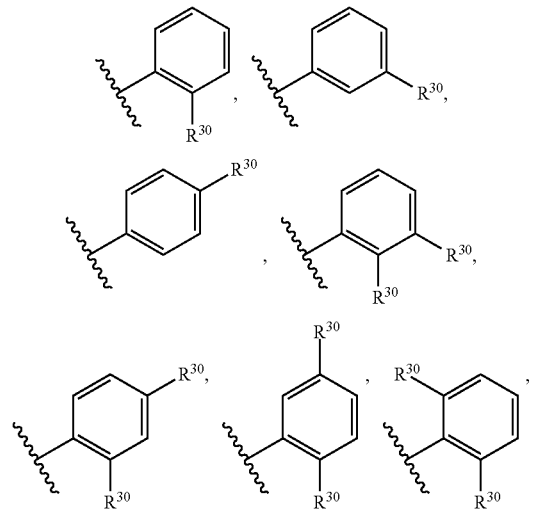

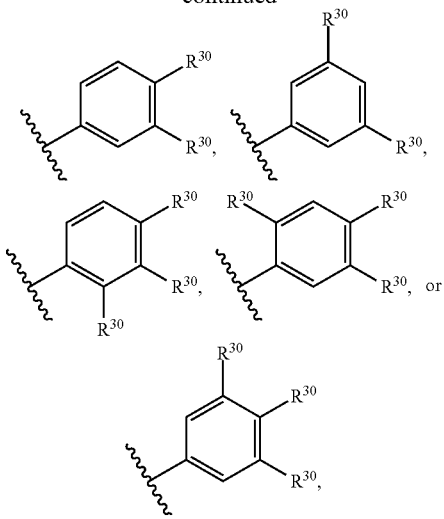

wherein each occurrence of $R^{30}$ is independently halogen, —CN, C1-C3 alkyl, C1-C3 monohaloalkyl, C1-C3 polyhaloalkyl, cyclopropyl, or —CO$_2$H.

In a further aspect, the compound has a structure represented by a formula:

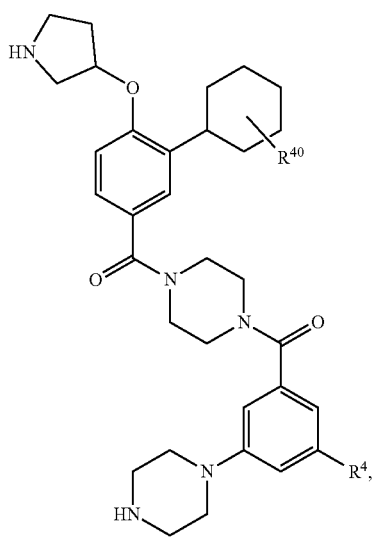

wherein $R^4$ is —F, —Cl —Br, methyl, ethyl, —CFH$_2$, —CF$_2$H, or —CF$_3$; and wherein each occurrence of $R^{40}$ is independently halogen, —CN, C1-C3 alkyl, C1-C3 monohaloalkyl, C1-C3 polyhaloalkyl, cyclopropyl, or —CO$_2$H, provided that no more than three occurrences of $R^{40}$ are not hydrogen.

In view of the foregoing, one would appreciate that:

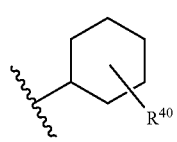

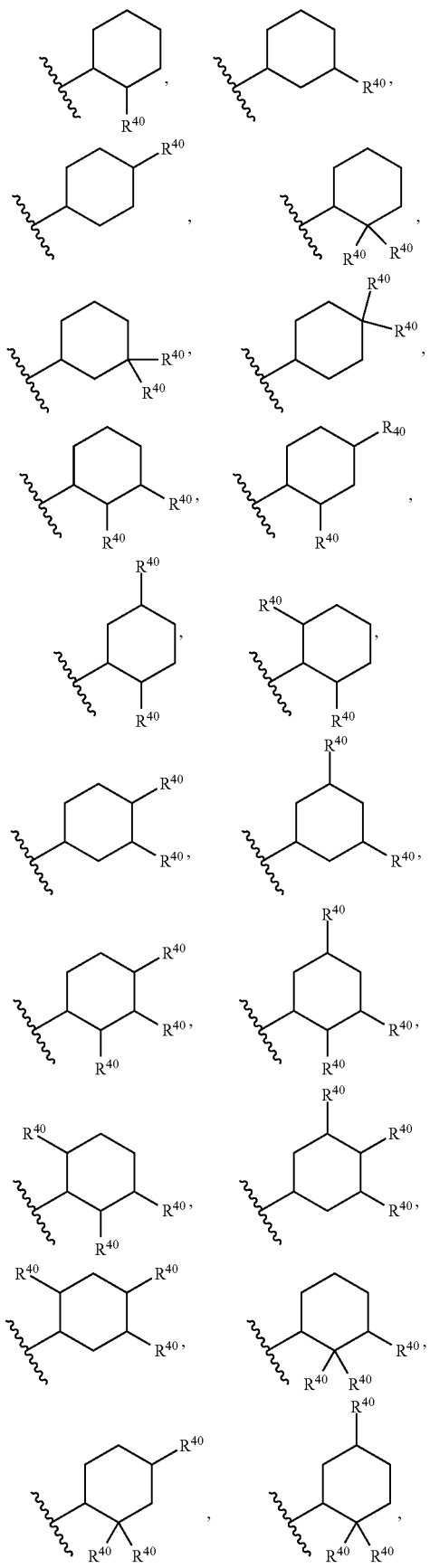

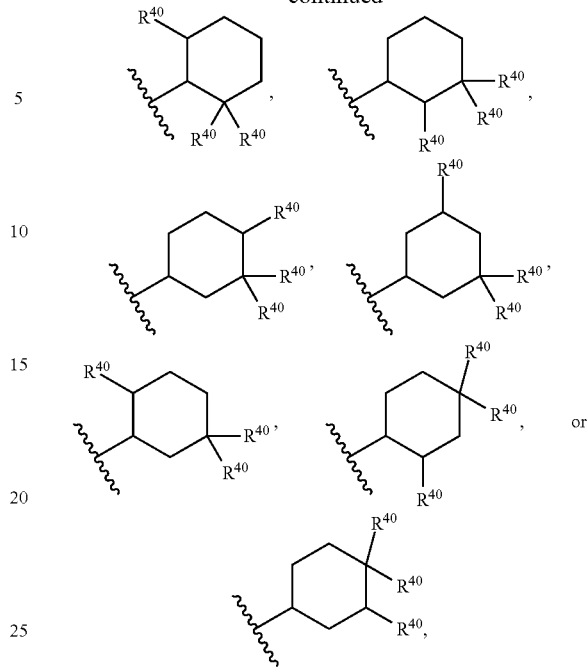

wherein each occurrence of $R^{40}$ is independently halogen, —CN, C1-C3 alkyl, C1-C3 monohaloalkyl, C1-C3 polyhaloalkyl, cyclopropyl, or —CO$_2$H.

In one aspect, n is an integer having the value of 1, 2, or 3. In a further aspect, n is an integer having the value of 1 or 2. In a still further aspect, n is an integer having the value of 2 or 3. In yet a further aspect, n is an integer having the value of 1 or 3. In an even further aspect, n is an integer having the value of 3. In a still further aspect, n is an integer having the value of 2. In yet a further aspect, n is an integer having the value of 1.

a. A Groups

In one aspect, A is selected from N and $CR^8$. In a further aspect, A is N. In a still further aspect, A is $CR^8$.

b. $L^1$ Groups

In one aspect, $L^1$ is optionally present, and when present, is O, S, or NH. In a further aspect, $L^1$ is not present.

In a further aspect, $L^1$ is optionally present, and when present, is O or S. In a still further aspect, $L^1$ is optionally present, and when present, is O or NH. In a yet further aspect, $L^1$ is optionally present, and when present, is S or NH. In an even further aspect, $L^1$ is optionally present, and when present, is O. In a still further aspect, $L^1$ is optionally present, and when present, is S. In a yet further aspect, $L^1$ is optionally present, and when present, is NH.

In a further aspect, $L^1$ is O, S, or NH. In a still further aspect, $L^1$ is O or S. In a yet further aspect, $L^1$ is O or NH. In an even further aspect, $L^1$ is S or NH. In a still further aspect, $L^1$ is O. In a yet further aspect, $L^1$ is S. In an even further aspect, $L^1$ is NH.

c. $L^2$ Groups

In one aspect, $L^2$ is optionally present, and when present, is O, S, $NR^9$, or —$(CR^{10a}R^{10b})$—. In a further aspect, $L^2$ is not present.

In a further aspect, $L^2$ is optionally present, and when present, is O, S, or $NR^9$. In a still further aspect, $L^2$ is optionally present, and when present, is O, $NR^9$, or —$(CR^{10a}R^{10b})_n$—. In a yet further aspect, $L^2$ is optionally present, and when present, is S, $NR^9$, or —$(CR^{10a}R^{10b})_n$—.

In an even further aspect, $L^2$ is optionally present, and when present, is O, S, or —$(CR^{10a}R^{10b})_n$—.

In a further aspect, $L^2$ is optionally present, and when present, is O or S. In a still further aspect, $L^2$ is optionally present, and when present, is O or $NR^9$. In a yet further aspect, $L^2$ is optionally present, and when present, is O or —$(CR^{10a}R^{10b})_n$—. In an even further aspect, $L^2$ is optionally present, and when present, is S or $NR^9$. In a still further aspect, $L^2$ is optionally present, and when present, is S or —$(CR^{10a}R^{10b})_n$—. In a yet further aspect, $L^2$ is optionally present, and when present, is $NR^9$ or —$(CR^{10a}R^{10b})_n$—.

In a further aspect, $L^2$ is optionally present, and when present, is O. In a yet further aspect, $L^2$ is optionally present, and when present, is S. In an even further aspect, $L^2$ is optionally present, and when present, is $NR^9$. In a still further aspect, $L^2$ is optionally present, and when present, is —$(CR^{10a}R^{10b})_n$—.

In various aspects, $L^2$ is O, S, $NR^9$, or —$(CR^{10a}R^{10b})_n$—.

In a further aspect, $L^2$ is O, S, or $NR^9$. In a still further aspect, $L^2$ is O, $NR^9$, or —$(CR^{10a}R^{10b})_n$—. In a yet further aspect, $L^2$ is S, $NR^9$, or —$(CR^{10a}R^{10b})_n$—. In an even further aspect, $L^2$ is O, S, or —$(CR^{10a}R^{10b})_n$—.

In a further aspect, $L^2$ is O or S. In a still further aspect, $L^2$ is O or $NR^9$. In a yet further aspect, $L^2$ is O or —$(CR^{10a}R^{10b})_n$—. In an even further aspect, $L^2$ is S or $NR^9$. In a still further aspect, $L^2$ is S or —$(CR^{10a}R^{10b})_n$—. In a yet further aspect, $L^2$ is $NR^9$ or —$(CR^{10a}R^{10b})_n$—.

In a further aspect, $L^2$ is O. In a yet further aspect, $L^2$ is S. In an even further aspect, $L^2$ is $NR^9$. In a still further aspect, $L^2$ is —$(CR^{10a}R^{10b})_n$—.

d. $R^{1a}$ and $R^{1b}$ Groups

In one aspect, each of $R^{1a}$ and $R^{1b}$, when present, is independently selected from hydrogen, halogen, C1-C3 alkyl, C1-C3 monohaloalkyl, and C1-C3 polyhaloalkyl. In a further aspect, each of $R^{1a}$ and $R^{1b}$, when present, is hydrogen.

In a further aspect, each of $R^{1a}$ and $R^{1b}$, when present, is independently selected from hydrogen and C1-C3 alkyl. In a still further aspect, each of $R^{1a}$ and $R^{1b}$, when present, is independently selected from hydrogen and C1-C3 monohaloalkyl. In yet a further aspect, each of $R^{1a}$ and $R^{1b}$, when present, is independently selected from hydrogen and C1-C3 polyhaloalkyl.

In a further aspect, each of Ra and $R^{1b}$, when present, is independently selected from hydrogen, halogen, and C1-C3 alkyl. In a still further aspect, each of $R^{1a}$ and $R^{1b}$, when present, is independently selected from hydrogen, halogen, and C1-C3 monohaloalkyl. In yet a further aspect, each of $R^{1a}$ and $R^{1b}$, when present, is independently selected from hydrogen, halogen, and C1-C3 polyhaloalkyl.

In a further aspect, each of $R^{1a}$ and $R^{1b}$, when present, is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, each of $R^{1a}$ and $R^{1b}$, when present, is independently selected from hydrogen, —F, —Cl, methyl, —$CH_2F$, —$CHF_2$, —$CF_3$, —$CHCl_2$, and —$CCl_3$. In yet a further aspect, each of $R^{1a}$ and $R^{1b}$, when present, is independently selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, each of $R^{1a}$ and $R^{1b}$, when present, is independently selected from hydrogen, methyl, —F, —$CH_2F$, —$CHF_2$, and —$CF_3$.

e. $R^{2a}$, $R^{2b}$, and $R^{2c}$ Groups

In one aspect, each of $R^{2a}$, $R^{2b}$, and $R^{2c}$, when present, is independently selected from hydrogen, halogen, C1-C3 alkyl, C1-C3 monohaloalkyl, and C1-C3 polyhaloalkyl. In a further aspect, each of $R^{2a}$, $R^{2b}$ and $R^{2c}$, when present, is hydrogen.

In a further aspect, each of $R^{2a}$, $R^{2b}$, and $R^{2c}$, when present, is independently selected from hydrogen and C1-C3 alkyl. In a still further aspect, each of $R^{2a}$, $R^{2b}$, and $R^{2c}$ when present, is independently selected from hydrogen and C1-C3 monohaloalkyl. In yet a further aspect, each of $R^{2a}$, $R^{2b}$, and $R^{2c}$, when present, is independently selected from hydrogen and C1-C3 polyhaloalkyl.

In a further aspect, each of $R^{2a}$, $R^{2b}$, and $R^{2c}$, when present, is independently selected from hydrogen, halogen, and C1-C3 alkyl. In a still further aspect, each of $R^{2a}$, $R^{2b}$ and $R^{2c}$, when present, is independently selected from hydrogen, halogen, and C1-C3 monohaloalkyl. In yet a further aspect, each of $R^{2a}$, $R^{2b}$, and $R^{2c}$, when present, is independently selected from hydrogen, halogen, and C1-C3 polyhaloalkyl.

In a further aspect, each of $R^{2a}$, $R^{2b}$, and $R^{2c}$, when present, is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, each of $R^{2a}$, $R^{2b}$, and $R^{2c}$, when present, is independently selected from hydrogen, —F, —Cl, methyl, —$CH_2F$, —$CHF_2$, —$CF_3$, —$CHCl_2$, and —$CCl_3$. In yet a further aspect, each of $R^{2a}$, $R^{2b}$, and $R^{2c}$, when present, is independently selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, each of $R^{2a}$, $R^{2b}$, and $R^{2c}$, when present, is independently selected from hydrogen, methyl, —F, —$CH_2F$, —$CHF_2$, and —$CF_3$.

f. $R^3$ Groups

In one aspect, $R^3$ is $Cy^3$ or $Ar^1$. In a further aspect, $R^3$ is $Cy^3$. In a still further aspect, $R^3$ is $Ar^1$.

In a further aspect, $R^3$ is cyclohexyl or phenyl substituted 0, 1, 2, or 3 groups independently selected from halogen, —CN, C1-C3 alkyl, C1-C3 monohaloalkyl, C1-C3 polyhaloalkyl, cyclopropyl, and —$CO_2H$. In a still further aspect, $R^3$ is cyclohexyl or phenyl substituted 0, 1, 2, or 3 groups independently selected from —F, —Cl, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, cyclopropyl, and —$CO_2H$. In a yet further aspect, $R^3$ is cyclohexyl or phenyl substituted 0, 1, 2, or 3 groups independently selected from —F, —Cl, methyl, —$CH_2F$, —$CH_2Cl$, —$CHF_2$, —$CF_3$, —$CHCl_2$, —$CCl_3$, cyclopropyl, and —$CO_2H$. In an even further aspect, $R^3$ is cyclohexyl or phenyl substituted 0, 1, 2, or 3 groups independently selected from —F, methyl, —$CH_2F$, —$CHF_2$, —$CF_3$, cyclopropyl, and —$CO_2H$.

In a further aspect, $R^3$ is cyclohexyl or phenyl substituted 0, 1, 2, or 3 groups independently selected from halogen, —CN, C1-C3 alkyl, C1-C3 monohaloalkyl, or C1-C3 polyhaloalkyl. In a still further aspect, $R^3$ is cyclohexyl or phenyl substituted 0, 1, 2, or 3 groups independently selected from —F, —Cl, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, or —$CH_2CCl_3$. In a yet further aspect, $R^3$ is cyclohexyl or phenyl substituted 0, 1, 2, or 3 groups independently selected from —F, —Cl, methyl, —$CH_2F$, —$CH_2Cl$, —$CHF_2$, —$CF_3$, —$CHCl_2$, or —$CCl_3$. In an even further aspect, $R^3$ is cyclohexyl or phenyl substituted 0, 1, 2, or 3 groups independently selected from —F, methyl, —$CH_2F$, —$CHF_2$, or —$CF_3$. In an even further aspect, $R^3$ is cyclohexyl or phenyl substituted 0, 1, 2, or 3 groups independently selected from —F, methyl, or —CF$_3$. In a still further aspect, R$^3$ is unsubstituted cyclohexyl or phenyl.

In a further aspect, R$^3$ is phenyl substituted 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, R$^3$ is phenyl substituted 0, 1, 2, or 3 groups independently selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, and —CO$_2$H. In a yet further aspect, R$^3$ is phenyl substituted 0, 1, 2, or 3 groups independently selected from —F, —Cl, methyl, —CH$_2$F, —CH$_2$Cl, —CHF$_2$, —CF$_3$, —CHCl$_2$, —CCl$_3$, cyclopropyl, and —CO$_2$H. In an even further aspect, R$^3$ is phenyl substituted 0, 1, 2, or 3 groups independently selected from —F, methyl, —CH$_2$F, —CHF$_2$, —CF$_3$, cyclopropyl, and —CO$_2$H.

In a further aspect, R$^3$ is phenyl substituted 0, 1, 2, or 3 groups independently selected from halogen, —CN, C1-C3 alkyl, C1-C3 monohaloalkyl, or C1-C3 polyhaloalkyl. In a still further aspect, R$^3$ is phenyl substituted 0, 1, 2, or 3 groups independently selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, or —CH$_2$CCl$_3$. In a yet further aspect, R$^3$ is phenyl substituted 0, 1, 2, or 3 groups independently selected from —F, —Cl, methyl, —CH$_2$F, —CH$_2$Cl, —CHF$_2$, —CF$_3$, —CHCl$_2$, or —CCl$_3$. In an even further aspect, R$^3$ is phenyl substituted 0, 1, 2, or 3 groups independently selected from —F, methyl, —CH$_2$F, —CHF$_2$, or —CF$_3$. In an even further aspect, R$^3$ is phenyl substituted 0, 1, 2, or 3 groups independently selected from —F, methyl, or —CF$_3$. In a still further aspect, R$^3$ is unsubstituted phenyl.

In a further aspect, R$^3$ is phenyl monosubstituted with a group selected from halogen, —CN, C1-C3 alkyl, C1-C3 monohaloalkyl, C1-C3 polyhaloalkyl, cyclopropyl, and —CO$_2$H. In a still further aspect, R$^3$ is phenyl monosubstituted with a group selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, and —CO$_2$H. In a yet further aspect, R$^3$ is phenyl monosubstituted with a group selected from —F, —Cl, methyl, —CH$_2$F, —CH$_2$Cl, —CHF$_2$, —CF$_3$, —CHCl$_2$, —CCl$_3$, cyclopropyl, and —CO$_2$H. In an even further aspect, R$^3$ is phenyl monosubstituted with a group selected from —F, methyl, —CH$_2$F, —CHF$_2$, —CF$_3$, cyclopropyl, and —CO$_2$H.

In a further aspect, R$^3$ is phenyl monosubstituted with a group selected from halogen, —CN, C1-C3 alkyl, C1-C3 monohaloalkyl, or C1-C3 polyhaloalkyl. In a still further aspect, R$^3$ is phenyl monosubstituted with a group selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, or —CH$_2$CCl$_3$. In a yet further aspect, R$^3$ is phenyl monosubstituted with a group selected from —F, —Cl, methyl, —CH$_2$F, —CH$_2$Cl, —CHF$_2$, —CF$_3$, —CHCl$_2$, or —CCl$_3$. In an even further aspect, R$^3$ is phenyl monosubstituted with a group selected from —F, methyl, —CH$_2$F, —CHF$_2$, or —CF$_3$. In an even further aspect, R$^3$ is phenyl monosubstituted with a group selected from —F, methyl, or —CF$_3$.

In a further aspect, R$^3$ is cyclohexyl substituted 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, R$^3$ is cyclohexyl substituted 0, 1, 2, or 3 groups independently selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, and —CO$_2$H. In a yet further aspect, R$^3$ is cyclohexyl substituted 0, 1, 2, or 3 groups independently selected from —F, —Cl, methyl, —CH$_2$F, —CH$_2$Cl, —CHF$_2$, —CF$_3$, —CHCl$_2$, —CCl$_3$, cyclopropyl, and —CO$_2$H. In an even further aspect, R$^3$ is cyclohexyl substituted 0, 1, 2, or 3 groups independently selected from —F, methyl, —CH$_2$F, —CHF$_2$, —CF$_3$, cyclopropyl, and —CO$_2$H.

In a further aspect, R$^3$ is cyclohexyl substituted 0, 1, 2, or 3 groups independently selected from halogen, —CN, C1-C3 alkyl, C1-C3 monohaloalkyl, or C1-C3 polyhaloalkyl. In a still further aspect, R$^3$ is cyclohexyl substituted 0, 1, 2, or 3 groups independently selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, or —CH$_2$CCl$_3$. In a yet further aspect, R$^3$ is cyclohexyl substituted 0, 1, 2, or 3 groups independently selected from —F, —Cl, methyl, —CH$_2$F, —CH$_2$Cl, —CHF$_2$, —CF$_3$, —CHCl$_2$, or —CCl$_3$. In an even further aspect, R$^3$ is cyclohexyl substituted 0, 1, 2, or 3 groups independently selected from —F, methyl, —CH$_2$F, —CHF$_2$, or —CF$_3$. In an even further aspect, R$^3$ is cyclohexyl substituted 0, 1, 2, or 3 groups independently selected from —F, methyl, or —CF$_3$. In a still further aspect, R$^3$ is unsubstituted cyclohexyl.

In a further aspect, R$^3$ is cyclohexyl monosubstituted with a group selected from halogen, —CN, C1-C3 alkyl, C1-C3 monohaloalkyl, C1-C3 polyhaloalkyl, cyclopropyl, and —CO$_2$H. In a still further aspect, R$^3$ is cyclohexyl monosubstituted with a group selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, and —CO$_2$H. In a yet further aspect, R$^3$ is cyclohexyl monosubstituted with a group selected from —F, —Cl, methyl, —CH$_2$F, —CH$_2$Cl, —CHF$_2$, —CF$_3$, —CHCl$_2$, —CCl$_3$, cyclopropyl, and —CO$_2$H. In an even further aspect, R$^3$ is cyclohexyl monosubstituted with a group selected from —F, methyl, —CH$_2$F, —CHF$_2$, —CF$_3$, cyclopropyl, and —CO$_2$H.

In a further aspect, R$^3$ is cyclohexyl monosubstituted with a group selected from halogen, —CN, C1-C3 alkyl, C1-C3 monohaloalkyl, or C1-C3 polyhaloalkyl. In a still further aspect, R$^3$ is cyclohexyl monosubstituted with a group selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, or —CH$_2$CCl$_3$. In a yet further aspect, R$^3$ is cyclohexyl monosubstituted with a group selected from —F, —Cl, methyl, —CH$_2$F, —CH$_2$Cl, —CHF$_2$, —CF$_3$, —CHCl$_2$, or —CCl$_3$. In an even further aspect, R$^3$ is cyclohexyl monosubstituted with a group selected from —F, methyl, —CH$_2$F, —CHF$_2$, or —CF$_3$. In an even further aspect, R$^3$ is cyclohexyl monosubstituted with a group selected from —F, methyl, or —CF$_3$.

g. R$^4$ Groups

In one aspect, R$^4$ is hydrogen, halogen, C1-C3 alkyl, C1-C3 monohaloalkyl, or C1-C3 polyhaloalkyl. In a further aspect, R$^4$ is hydrogen.

In a further aspect, R$^4$ is selected from hydrogen and C1-C3 alkyl. In a still further aspect, R$^4$ is selected from hydrogen and C1-C3 monohaloalkyl. In yet a further aspect, R$^4$ is selected from hydrogen and C1-C3 polyhaloalkyl.

In a further aspect, $R^4$ is selected from hydrogen, halogen, and C1-C3 alkyl. In a still further aspect, $R^4$ is selected from hydrogen, halogen, and C1-C3 monohaloalkyl. In yet a further aspect, $R^4$ is selected from hydrogen, halogen, and C1-C3 polyhaloalkyl.

In a further aspect, $R^4$ is selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^4$ is selected from hydrogen, —F, —Cl, methyl, —CH$_2$F, —CHF$_2$, —CF$_3$, —CHCl$_2$, and —CCl$_3$. In yet a further aspect, $R^4$ is selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, $R^4$ is selected from hydrogen, methyl, —F, —CH$_2$F, —CHF$_2$, and —CF$_3$.

In a further aspect, $R^4$ is —F, —Cl —Br, methyl, ethyl, —CFH$_2$, —CF$_2$H, or —CF$_3$.

In a further aspect, $R^4$ is —F, —Cl —Br, methyl, or —CF$_3$.

h. $R^5$ Groups

In one aspect, each occurrence of $R^5$ is independently selected from hydrogen, C1-C8 alkyl, C1-C8 monohaloalkyl, or C1-C8 polyhaloalkyl. In a further aspect, each occurrence of $R^5$ is hydrogen.

In a further aspect, each occurrence of $R^5$ is independently hydrogen, C1-C6 alkyl, C1-C6 haloalkyl, or C1-C6 polyhaloalkyl. In a further aspect, each occurrence of $R^5$ is independently hydrogenC1-C3 alkyl, C1-C3 haloalkyl, or C1-C3 polyhaloalkyl.

In a further aspect, each occurrence of $R^5$ is independently selected from hydrogen and C1-C3 alkyl. In a still further aspect, each occurrence of $R^5$ is independently selected from hydrogen and C1-C3 monohaloalkyl. In yet a further aspect, each occurrence of $R^5$ is independently selected from hydrogen and C1-C3 polyhaloalkyl.

In a further aspect, each occurrence of $R^5$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, each occurrence of $R^5$ is independently selected from hydrogen, methyl, —CH$_2$F, —CHF$_2$, —CF$_3$, —CHCl$_2$, and —CCl$_3$. In yet a further aspect, each occurrence of $R^5$ is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In an even further aspect, each occurrence of $R^5$ is independently selected from hydrogen, methyl, —CH$_2$F, —CHF$_2$, and —CF$_3$.

i. $R^6$ Groups

In one aspect, $R^6$ is C1-C6 aminoalkyl, C1-C6 hydroxyalkyl, or Cy$^1$; and Cy$^1$ is an amino C3-C8 cycloalkyl, a hydroxy C3-C8 cycloalkyl, or a C2-C7 heterocycloalkyl comprising at least one oxygen or nitrogen atom; and Cy$^1$ is substituted 0, 1, 2, or 3 groups independently selected from halogen, C1-C4 alkyl, C1-C4 monohaloalkyl, and C1-C4 polyhaloalkyl. In a further aspect, $R^6$ is Cy$^1$.

In a further aspect, $R^6$ is —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, —(CHNH$_2$)C(CH$_3$)$_3$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, or Cy$^1$. In a still further aspect, $R^6$ is —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, —(CHNH$_2$)CH(CH$_3$)$_2$, —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, or Cy$^1$. In a yet further aspect, $R^6$ is —CH$_2$NH$_2$, —(CH$_2$)$_2$NH$_2$, —(CHNH$_2$)CH$_3$, —CH$_2$OH, —(CH$_2$)$_2$OH, —(CHOH)CH$_3$, or Cy$^1$. In an even further aspect, $R^6$ is —CH$_2$NH$_2$, —CH$_2$OH, or Cy$^1$.

In a further aspect, $R^6$ is —CH$_2$NH$_2$, —(CH$_2$)$_2$NH$_2$, —(CH$_2$)$_3$NH$_2$, —(CH$_2$)$_4$NH$_2$, —(CH$_2$)SNH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, or —(CHNH$_2$)C(CH$_3$)$_3$. In a still further aspect, $R^6$ is —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, —(CHNH$_2$)CH(CH$_3$)$_2$, or —(CHNH$_2$)CH(CH$_3$)$_2$. In a yet further aspect, $R^6$ is —CH$_2$NH$_2$, —(CH$_2$)$_2$NH$_2$, —(CHNH$_2$)CH$_3$, —CH$_2$OH, —(CH$_2$)$_2$OH, or —(CHOH)CH$_3$. In an even further aspect, $R^6$ is —CH$_2$NH$_2$.

In a further aspect, $R^6$ is —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$ (CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, or —(CHOH)C(CH$_3$)$_3$. In a still further aspect, R$^6$ is —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, or Cy$^1$. In a yet further aspect, R$^6$ is —CH$_2$OH, —(CH$_2$)$_2$OH, or —(CHOH)CH$_3$. In an even further aspect, R$^6$ is —CH$_2$OH.

j. R$^7$ Groups

In one aspect, R$^7$ is H$_2$N—(C1-C6 alkyl)-(C=O)—; HO—(C1-C6 alkyl)-(C=O)—; C1-C6 aminoalkyl, C1-C6 hydroxyalkyl, or Cy$^2$; and wherein Cy$^2$ is an amino C3-C8 cycloalkyl, a hydroxy C3-C8 cycloalkyl, or a C2-C7 heterocycloalkyl comprising at least one oxygen or nitrogen atom; and wherein Cy$^2$ is substituted 0, 1, 2, or 3 groups independently selected from halogen, C1-C4 alkyl, C1-C4 monohaloalkyl, and C1-C4 polyhaloalkyl. In a further aspect, R$^7$ is Cy$^2$.

In a further aspect, R$^7$ is —(C=O)CH$_2$NH$_2$, —(C=O)(CH$_2$)$_2$NH$_2$, —(C=O)(CH$_2$)$_3$NH$_2$, —(C=O)(CH$_2$)$_4$NH$_2$, —(C=O)(CH$_2$)SNH$_2$, —(C=O)(CH$_2$)$_6$NH$_2$, —(C=O)(CHNH$_2$)CH$_3$, —(C=O)(CHNH$_2$)CH$_2$CH$_3$, —(C=O)(CHNH$_2$)(CH$_2$)$_2$CH$_3$, —(C=O)(CHNH$_2$)(CH$_2$)$_3$CH$_3$, —(C=O)(CHNH$_2$)(CH$_2$)$_4$CH$_3$, —(C=O)CH$_2$(CHNH$_2$)CH$_3$, —(C=O)CH$_2$(CHNH$_2$)CH$_2$CH$_3$, —(C=O)CH$_2$(CHNH$_2$)(CH$_2$)$_2$CH$_3$, —(C=O)CH$_2$(CHNH$_2$)(CH$_2$)$_3$CH$_3$, —(C=O)(CH$_2$)$_2$(CHNH$_2$)CH$_3$, —(C=O)(CH$_2$)$_3$(CHNH$_2$)CH$_3$, —(C=O)(CH$_2$)$_4$(CHNH$_2$)CH$_3$, —(C=O)(CHNH$_2$)CH(CH$_3$)$_2$, —(C=O)(CHNH$_2$)C(CH$_3$)$_3$, —(C=O)CH$_2$OH, —(C=O)(CH$_2$)$_2$OH, —(C=O)(CH$_2$)$_3$OH, —(C=O)(CH$_2$)$_4$OH, —(C=O)(CH$_2$)$_5$OH, —(C=O)(CH$_2$)$_6$OH, —(C=O)(CHOH)CH$_3$, —(C=O)(CHOH)CH$_2$CH$_3$, —(C=O)(CHOH)(CH$_2$)$_2$CH$_3$, —(C=O)(CHOH)(CH$_2$)$_3$CH$_3$, —(C=O)(CHOH)(CH$_2$)$_4$CH$_3$, —(C=O)CH$_2$(CHOH)CH$_3$, —(C=O)CH$_2$(CHOH)CH$_2$CH$_3$, —(C=O)CH$_2$(CHOH)(CH$_2$)$_2$CH$_3$, —(C=O)CH$_2$(CHOH)(CH$_2$)$_3$CH$_3$, —(C=O)(CH$_2$)$_2$(CHOH)CH$_3$, —(C=O)(CH$_2$)$_3$(CHOH)CH$_3$, —(C=O)(CH$_2$)$_4$(CHOH)CH$_3$, —(C=O)(CHOH)CH(CH$_3$)$_2$, —(C=O)(CHOH)C(CH$_3$)$_3$, or Cy$^2$. In a still further aspect, R$^7$ is —(C=O)CH$_2$NH$_2$, —(C=O)(CH$_2$)$_2$NH$_2$, —(C=O)(CH$_2$)$_3$NH$_2$, —(C=O)(CH$_2$)$_4$NH$_2$, —(C=O)(CHNH$_2$)CH$_3$, —(C=O)(CHNH$_2$)CH$_2$CH$_3$, —(C=O)(CHNH$_2$)(CH$_2$)$_2$CH$_3$, —(C=O)CH$_2$(CHNH$_2$)CH$_3$, —(C=O)CH$_2$(CHNH$_2$)CH$_2$CH$_3$, —(C=O)(CH$_2$)$_2$(CHNH$_2$)CH$_3$, —(C=O)(CHNH$_2$)CH(CH$_3$)$_2$, —(C=O)CH$_2$OH, —(C=O)(CH$_2$)$_2$OH, —(C=O)(CH$_2$)$_3$OH, —(C=O)(CH$_2$)$_4$OH, —(C=O)(CHOH)CH$_3$, —(C=O)(CHOH)CH$_2$CH$_3$, —(C=O)(CHOH)(CH$_2$)$_2$CH$_3$, —(C=O)CH$_2$(CHOH)CH$_3$, —(C=O)CH$_2$(CHOH)CH$_2$CH$_3$, —(C=O)(CH$_2$)$_2$(CHOH)CH$_3$, —(C=O)(CHOH)CH(CH$_3$)$_2$, or Cy$^2$. In a yet further aspect, R$^7$ is —(C=O)CH$_2$NH$_2$, —(C=O)(CH$_2$)$_2$NH$_2$, —(C=O)(CHNH$_2$)CH$_3$, —(C=O)CH$_2$OH, —(C=O)(CH$_2$)$_2$OH, —(C=O)(CHOH)CH$_3$, or Cy$^2$. In an even further aspect, R$^7$ is —(C=O)CH$_2$NH$_2$, —(C=O)CH$_2$OH, or Cy.

In a further aspect, R$^7$ is —(C=O)CH$_2$NH$_2$, —(C=O)(CH$_2$)$_2$NH$_2$, —(C=O)(CH$_2$)$_3$NH$_2$, —(C=O)(CH$_2$)$_4$NH$_2$, —(C=O)(CH$_2$)SNH$_2$, —(C=O)(CH$_2$)$_6$NH$_2$, —(C=O)(CHNH$_2$)CH$_3$, —(C=O)(CHNH$_2$)CH$_2$CH$_3$, —(C=O)(CHNH$_2$)(CH$_2$)$_2$CH$_3$, —(C=O)(CHNH$_2$)(CH$_2$)$_3$CH$_3$, —(C=O)(CHNH$_2$)(CH$_2$)$_4$CH$_3$, —(C=O)CH$_2$(CHNH$_2$)CH$_3$, —(C=O)CH$_2$(CHNH$_2$)CH$_2$CH$_3$, —(C=O)CH$_2$(CHNH$_2$)(CH$_2$)$_2$CH$_3$, —(C=O)CH$_2$(CHNH$_2$)(CH$_2$)$_3$CH$_3$, —(C=O)(CH$_2$)$_2$(CHNH$_2$)CH$_3$, —(C=O)(CH$_2$)$_3$(CHNH$_2$)CH$_3$, —(C=O)(CH$_2$)$_4$(CHNH$_2$)CH$_3$, —(C=O)(CHNH$_2$)CH(CH$_3$)$_2$, —(C=O)(CHNH$_2$)C(CH$_3$)$_3$, —(C=O)CH$_2$OH, —(C=O)(CH$_2$)$_2$OH, —(C=O)(CH$_2$)$_3$OH, —(C=O)(CH$_2$)$_4$OH, —(C=O)(CH$_2$)$_5$OH, —(C=O)(CH$_2$)$_6$OH, —(C=O)(CHOH)CH$_3$, —(C=O)(CHOH)CH$_2$CH$_3$, —(C=O)(CHOH)(CH$_2$)$_2$CH$_3$, —(C=O)(CHOH)(CH$_2$)$_3$CH$_3$, —(C=O)(CHOH)(CH$_2$)$_4$CH$_3$, —(C=O)CH$_2$(CHOH)CH$_3$, —(C=O)CH$_2$(CHOH)CH$_2$CH$_3$, —(C=O)CH$_2$(CHOH)(CH$_2$)$_2$CH$_3$, —(C=O)CH$_2$(CHOH)(CH$_2$)$_3$CH$_3$, —(C=O)(CH$_2$)$_2$(CHOH)CH$_3$, —(C=O)(CH$_2$)$_3$(CHOH)CH$_3$, —(C=O)(CH$_2$)$_4$(CHOH)CH$_3$, —(C=O)(CHOH)CH(CH$_3$)$_2$, or —(C=O)(CHOH)C(CH$_3$)$_3$. In a still further aspect, R$^7$ is —(C=O)CH$_2$NH$_2$, —(C=O)(CH$_2$)$_2$NH$_2$, —(C=O)(CH$_2$)$_3$NH$_2$, —(C=O)(CH$_2$)$_4$NH$_2$, —(C=O)(CHNH$_2$)CH$_3$, —(C=O)(CHNH$_2$)CH$_2$CH$_3$, —(C=O)(CHNH$_2$)(CH$_2$)$_2$CH$_3$, —(C=O)CH$_2$(CHNH$_2$)CH$_3$, —(C=O)CH$_2$(CHNH$_2$)CH$_2$CH$_3$, —(C=O)(CH$_2$)$_2$(CHNH$_2$)CH$_3$, —(C=O)(CHNH$_2$)CH(CH$_3$)$_2$, —(C=O)CH$_2$OH, —(C=O)(CH$_2$)$_2$OH, —(C=O)(CH$_2$)$_3$OH, —(C=O)(CH$_2$)$_4$OH, —(C=O)(CHOH)CH$_3$, —(C=O)(CHOH)CH$_2$CH$_3$, —(C=O)(CHOH)(CH$_2$)$_2$CH$_3$, —(C=O)CH$_2$(CHOH)CH$_3$, —(C=O)CH$_2$(CHOH)CH$_2$CH$_3$, —(C=O)(CH$_2$)$_2$(CHOH)CH$_3$, or —(C=O)(CHOH)CH(CH$_3$)$_2$. In a yet further aspect, R$^7$ is —(C=O)CH$_2$NH$_2$, —(C=O)(CH$_2$)$_2$NH$_2$, —(C=O)(CHNH$_2$)CH$_3$, —(C=O)CH$_2$OH, —(C=O)(CH$_2$)$_2$OH, or —(C=O)(CHOH)CH$_3$. In an even further aspect, R$^7$ is —(C=O)CH$_2$NH$_2$.

In a further aspect, R$^7$ is —(C=O)CH$_2$OH, —(C=O)(CH$_2$)$_2$OH, —(C=O)(CH$_2$)$_3$OH, —(C=O)(CH$_2$)$_4$OH, —(C=O)(CH$_2$)$_5$OH, —(C=O)(CH$_2$)$_6$OH, —(C=O)(CHOH)CH$_3$, —(C=O)(CHOH)CH$_2$CH$_3$, —(C=O)(CHOH)(CH$_2$)$_2$CH$_3$, —(C=O)(CHOH)(CH$_2$)$_3$CH$_3$, —(C=O)(CHOH)(CH$_2$)$_4$CH$_3$, —(C=O)CH$_2$(CHOH)CH$_3$, —(C=O)CH$_2$(CHOH)CH$_2$CH$_3$, —(C=O)CH$_2$(CHOH)(CH$_2$)$_2$CH$_3$, —(C=O)CH$_2$(CHOH)(CH$_2$)$_3$CH$_3$, —(C=O)(CH$_2$)$_2$(CHOH)CH$_3$, —(C=O)(CH$_2$)$_3$(CHOH)CH$_3$, —(C=O)(CH$_2$)$_4$(CHOH)CH$_3$, —(C=O)(CHOH)CH(CH$_3$)$_2$, or —(C=O)(CHOH)C(CH$_3$)$_3$. In a still further aspect, R$^7$ is —(C=O)CH$_2$OH, —(C=O)(CH$_2$)$_2$OH, —(C=O)(CH$_2$)$_3$OH, —(C=O)(CH$_2$)$_4$OH, —(C=O)(CHOH)CH$_3$, —(C=O)(CHOH)CH$_2$CH$_3$, —(C=O)(CHOH)(CH$_2$)$_2$CH$_3$, —(C=O)CH$_2$(CHOH)CH$_3$, —(C=O)CH$_2$(CHOH)CH$_2$CH$_3$, —(C=O)(CH$_2$)$_2$(CHOH)CH$_3$, —(C=O)(CHOH)CH(CH$_3$)$_2$, or Cy$^2$. In a yet further aspect, $R^7$ is —(C=O)CH$_2$OH, —(C=O)(CH$_2$)$_2$OH, or —(C=O)(CHOH)CH$_3$. In an even further aspect, $R^7$ is —(C=O)CH$_2$OH.

In a further aspect, $R^7$ is —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, —(CHNH$_2$)C(CH$_3$)$_3$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, or Cy$^2$. In a still further aspect, $R^7$ is —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, —(CHNH$_2$)CH(CH$_3$)$_2$, —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, or Cy$^2$. In a yet further aspect, $R^7$ is —CH$_2$NH$_2$, —(CH$_2$)$_2$NH$_2$, —(CHNH$_2$)CH$_3$, —CH$_2$OH, —(CH$_2$)$_2$OH, —(CHOH)CH$_3$, or Cy$^2$. In an even further aspect, $R^7$ is —CH$_2$NH$_2$, —CH$_2$OH, or Cy$^2$.

In a further aspect, $R^7$ is —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, —(CHNH$_2$)C(CH$_3$)$_3$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, or —(CHOH)C(CH$_3$)$_3$. In a still further aspect, $R^7$ is —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, —(CHNH$_2$)CH(CH$_3$)$_2$, —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, or —(CHOH)CH(CH$_3$)$_2$. In a yet further aspect, $R^7$ is —CH$_2$NH$_2$, —(CH$_2$)$_2$NH$_2$, —(CHNH$_2$)CH$_3$, —CH$_2$OH, —(CH$_2$)$_2$OH, or —(CHOH)CH$_3$. In an even further aspect, $R^7$ is —CH$_2$NH$_2$ or —CH$_2$OH.

In a further aspect, $R^7$ is —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, —(CH$_2$)$_3$(CHNH$_2$)CH$_3$, —(CHNH$_2$)CH(CH$_3$)$_2$, or —(CHNH$_2$)C(CH$_3$)$_3$. In a still further aspect, $R^7$ is —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, or —(CHNH$_2$)CH(CH$_3$)$_2$. In a yet further aspect, $R^7$ is —CH$_2$NH$_2$, —(CH$_2$)$_2$NH$_2$, —(CHNH$_2$)CH$_3$, —CH$_2$OH, —(CH$_2$)$_2$OH, or —(CHOH)CH$_3$. In an even further aspect, $R^7$ is —CH$_2$NH$_2$.

In a further aspect, $R^7$ is —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, or —(CHOH)C(CH$_3$)$_3$. In a still further aspect, $R^7$ is —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, or Cy$^2$. In a yet further aspect, $R^7$ is —CH$_2$OH, —(CH$_2$)$_2$OH, or —(CHOH)CH$_3$. In an even further aspect, $R^7$ is —CH$_2$OH.

k. $R^{10}$ Groups

In one aspect, $R^{10}$ is hydrogen, methyl, ethyl, propyl, or isopropyl. In a further aspect, $R^{10}$ is hydrogen.

In a further aspect, $R^{10}$ is hydrogen, methyl, or ethyl. In a still further aspect, $R^{10}$ is hydrogen or methyl. In a yet further aspect, $R^{10}$ is hydrogen, ethyl, propyl, or isopropyl. In an even further aspect, $R^{10}$ is hydrogen or ethyl. In a still further aspect, $R^{10}$ is hydrogen, propyl, or isopropyl. $R^{10}$ is hydrogen or propyl. In a yet further aspect, $R^{10}$ is hydrogen or isopropyl.

In a further aspect, $R^{10}$ is methyl or ethyl. In a still further aspect, $R^{10}$ is methyl. In a yet further aspect, $R^{10}$ is ethyl, propyl, or isopropyl. In an even further aspect, $R^{10}$ is ethyl. In a still further aspect, $R^{10}$ is propyl or isopropyl. $R^{10}$ is propyl. In a yet further aspect, $R^{10}$ is isopropyl.

l. $R^{11}$ Groups

In one aspect, $R^{11}$ is hydrogen, methyl, ethyl, propyl, or isopropyl. In a further aspect, $R^{11}$ is hydrogen.

In a further aspect, $R^{11}$ is hydrogen, methyl, or ethyl. In a still further aspect, $R^{11}$ is hydrogen or methyl. In a yet further aspect, $R^{11}$ is hydrogen, ethyl, propyl, or isopropyl. In an even further aspect, $R^{11}$ is hydrogen or ethyl. In a still further aspect, $R^{11}$ is hydrogen, propyl, or isopropyl. $R^{11}$ is hydrogen or propyl. In a yet further aspect, $R^{11}$ is hydrogen or isopropyl.

In a further aspect, $R^{11}$ is methyl or ethyl. In a still further aspect, $R^{11}$ is methyl. In a yet further aspect, $R^{11}$ is ethyl, propyl, or isopropyl. In an even further aspect, $R^{11}$ is ethyl. In a still further aspect, $R^{11}$ is propyl or isopropyl. $R^{11}$ is propyl. In a yet further aspect, $R^{11}$ is isopropyl.

m. $R^{20}$ Groups

In one aspect, each occurrence of $R^{20}$ is independently hydrogen, halogen, C1-C4 alkyl, C1-C4 monohaloalkyl, or C1-C4 polyhaloalkyl, provided that no more than two occurrences of $R^{20}$ are not hydrogen.

In a further aspect, each occurrence of $R^{20}$ is independently hydrogen, halogen, C1-C3 alkyl, C1-C3 monohaloalkyl, or C1-C3 polyhaloalkyl, provided that no more than two occurrences of $R^{20}$ are not hydrogen. In a further aspect, each occurrence of $R^{20}$ is hydrogen.

In a further aspect, each occurrence of $R^{20}$ is independently hydrogen or C1-C3 alkyl, provided that no more than two occurrences of $R^{20}$ are not hydrogen. In a still further aspect, each occurrence of $R^{20}$ is independently hydrogen or C1-C3 monohaloalkyl, provided that no more than two occurrences of $R^{20}$ are not hydrogen. In yet a further aspect, each occurrence of $R^{20}$ is independently hydrogen or C1-C3 polyhaloalkyl.

In a further aspect, each occurrence of $R^{20}$ is independently selected from hydrogen, halogen and C1-C3 alkyl, provided that no more than two occurrences of $R^{20}$ are not hydrogen. In a still further aspect, each occurrence of $R^{20}$ is independently selected from hydrogen, halogen and C1-C3 monohaloalkyl, provided that no more than two occurrences of $R^{20}$ are not hydrogen. In yet a further aspect, each occurrence of $R^{20}$ is independently selected from hydrogen, halogen and C1-C3 polyhaloalkyl.

In a further aspect, each occurrence of $R^{20}$ is independently selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$, provided that no more than two occurrences of $R^{20}$ are not hydrogen. In a still further aspect, each occurrence of $R^{20}$ is independently selected from hydrogen, —F, —Cl, methyl, —CH$_2$F, —CHF$_2$, —CF$_3$, —CHCl$_2$, and —CCl$_3$, provided that no more than two occurrences of $R^{20}$ are not hydrogen. In yet a further aspect, each occurrence of $R^{20}$ is independently selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$, provided that no more than two occurrences of $R^{20}$ are not hydrogen. In an even further aspect, each occurrence of $R^{20}$ is independently selected from hydrogen, methyl, —F, —CH$_2$F, —CHF$_2$, and —CF$_3$, provided that no more than two occurrences of $R^{20}$ are not hydrogen.

In a further aspect, each occurrence of $R^{20}$ is independently hydrogen, —F, —Cl—Br, methyl, ethyl, —CFH$_2$, —CF$_2$H, or —CF$_3$, provided that no more than two occurrences of $R^{20}$ are not hydrogen.

In a further aspect, each occurrence of $R^{20}$ is independently hydrogen, —F, —Cl—Br, methyl, or —CF$_3$, provided that no more than two occurrences of $R^{20}$ are not hydrogen.

n. $R^{21}$ Groups

In one aspect, each occurrence of $R^{21}$ is independently hydrogen, halogen, C1-C4 alkyl, C1-C4 monohaloalkyl, and C1-C4 polyhaloalkyl, provided that no more than two occurrences of $R^{21}$ are not hydrogen.

In a further aspect, each occurrence of $R^{21}$ is independently hydrogen, halogen, C1-C3 alkyl, C1-C3 monohaloalkyl, or C1-C3 polyhaloalkyl, provided that no more than two occurrences of $R^{21}$ are not hydrogen. In a further aspect, each occurrence of $R^{21}$ is hydrogen.

In a further aspect, each occurrence of $R^{21}$ is independently hydrogen or C1-C3 alkyl, provided that no more than two occurrences of $R^{21}$ are not hydrogen. In a still further aspect, each occurrence of $R^{21}$ is independently hydrogen or C1-C3 monohaloalkyl, provided that no more than two occurrences of $R^{21}$ are not hydrogen. In yet a further aspect, each occurrence of $R^{21}$ is independently hydrogen or C1-C3 polyhaloalkyl.

In a further aspect, each occurrence of $R^{21}$ is independently selected from hydrogen, halogen and C1-C3 alkyl, provided that no more than two occurrences of $R^{21}$ are not hydrogen. In a still further aspect, each occurrence of $R^{21}$ is independently selected from hydrogen, halogen and C1-C3 monohaloalkyl, provided that no more than two occurrences of $R^2$ are not hydrogen. In yet a further aspect, each occurrence of $R^{21}$ is independently selected from hydrogen, halogen and C1-C3 polyhaloalkyl.

In a further aspect, each occurrence of $R^{21}$ is independently selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$, provided that no more than two occurrences of $R^{21}$ are not hydrogen. In a still further aspect, each occurrence of $R^{21}$ is independently selected from hydrogen, —F, —Cl, methyl, —CH$_2$F, —CHF$_2$, —CF$_3$, —CHCl$_2$, and —CCl$_3$, provided that no more than two occurrences of $R^{21}$ are not hydrogen. In yet a further aspect, each occurrence of $R^{21}$ is independently selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$, provided that no more than two occurrences of $R^{21}$ are not hydrogen. In an even further aspect, each occurrence of $R^{21}$ is independently selected from hydrogen, methyl, —F, —CH$_2$F, —CHF$_2$, and —CF$_3$, provided that no more than two occurrences of $R^{21}$ are not hydrogen.

In a further aspect, each occurrence of $R^{21}$ is independently hydrogen, —F, —Cl—Br, methyl, ethyl, —CFH$_2$, —CF$_2$H, or —CF$_3$, provided that no more than two occurrences of $R^2$ are not hydrogen.

In a further aspect, each occurrence of $R^{21}$ is independently hydrogen, —F, —Cl—Br, methyl, or —CF$_3$, provided that no more than two occurrences of $R^{21}$ are not hydrogen.

o. $R^{30}$ Groups

In one aspect, each occurrence of $R^{30}$ is independently selected from hydrogen, halogen, —CN, C1-C3 alkyl, C1-C3 monohaloalkyl, C1-C3 polyhaloalkyl, cyclopropyl, and —CO$_2$H, provided that no more than three occurrences of $R^{30}$ are not hydrogen. In a further aspect, each occurrence of $R^{30}$ is hydrogen.

In a further aspect, each occurrence of $R^{30}$ is independently hydrogen or C1-C3 alkyl, provided that no more than three occurrences of $R^{30}$ are not hydrogen. In a still further aspect, each occurrence of $R^{30}$ is independently hydrogen or C1-C3 monohaloalkyl, provided that no more than three occurrences of $R^{30}$ are not hydrogen. In yet a further aspect, each occurrence of $R^{30}$ is independently hydrogen or C1-C3 polyhaloalkyl.

In a further aspect, each occurrence of $R^{30}$ is independently selected from hydrogen, halogen and C1-C3 alkyl, provided that no more than three occurrences of $R^{30}$ are not hydrogen. In a still further aspect, each occurrence of $R^{30}$ is independently selected from hydrogen, halogen and C1-C3 monohaloalkyl, provided that no more than three occurrences of $R^{30}$ are not hydrogen. In yet a further aspect, each occurrence of $R^{30}$ is independently selected from hydrogen, halogen and C1-C3 polyhaloalkyl.

In a further aspect, each occurrence of $R^{30}$ is independently selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, or —CO$_2$H, provided that no more than three occurrences of $R^{30}$ are not hydrogen. In a still further aspect, each occurrence of $R^{30}$ is independently selected from hydrogen, —F, —Cl, methyl, —CH$_2$F, —CHF$_2$, —CF$_3$, —CHCl$_2$, —CCl$_3$, cyclopropyl, or —CO$_2$H, provided that no more than three occurrences of $R^{30}$ are not hydrogen. In yet a further aspect, each occurrence of $R^{30}$ is independently selected from hydrogen, methyl, ethyl, —F, —CH$_2$F, —CH$_2$CH$_2$F, —CHF$_2$, —CF$_3$, —CH$_2$CHF$_2$, —CH$_2$CF$_3$, cyclopropyl, or —CO$_2$H, provided that no more than three occurrences of $R^{30}$ are not hydrogen. In an even further aspect, each occurrence of $R^{30}$ is independently selected from hydrogen, methyl, —F, —$CH_2F$, —$CHF_2$, —$CF_3$, cyclopropyl, or —$CO_2H$, provided that no more than three occurrences of $R^{30}$ are not hydrogen.

In a further aspect, each occurrence of $R^{30}$ is independently hydrogen, —F, —Cl—Br, methyl, ethyl, —$CFH_2$, —$CF_2H$, —$CF_3$, cyclopropyl, or —$CO_2H$, provided that no more than three occurrences of $R^{30}$ are not hydrogen.

In a further aspect, each occurrence of $R^{30}$ is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$, provided that no more than three occurrences of $R^{30}$ are not hydrogen. In a still further aspect, each occurrence of $R^{30}$ is independently selected from hydrogen, —F, —Cl, methyl, —$CH_2F$, —$CHF_2$, —$CF_3$, —$CHCl_2$, and —$CCl_3$, provided that no more than three occurrences of $R^{30}$ are not hydrogen. In yet a further aspect, each occurrence of $R^{30}$ is independently selected from hydrogen, methyl, ethyl, —F, —$CH_2F$, —$CH_2CH_2F$, —$CHF_2$, —$CF_3$, —$CH_2CHF_2$, and —$CH_2CF_3$, provided that no more than three occurrences of $R^{30}$ are not hydrogen. In an even further aspect, each occurrence of $R^{30}$ is independently selected from hydrogen, methyl, —F, —$CH_2F$, —$CHF_2$, and —$CF_3$, provided that no more than three occurrences of $R^{30}$ are not hydrogen.

In a further aspect, each occurrence of $R^{30}$ is independently hydrogen, —F, —Cl—Br, methyl, ethyl, —$CFH_2$, —$CF_2H$, or —$CF_3$, provided that no more than three occurrences of $R^{30}$ are not hydrogen.

In a further aspect, each occurrence of $R^{30}$ is independently hydrogen, —F, —Cl—Br, methyl, or —$CF_3$, provided that no more than three occurrences of $R^{30}$ are not hydrogen.

p. $R^{40}$ Groups

In one aspect, each occurrence of $R^{40}$ is independently selected from hydrogen, halogen, —CN, C1-C3 alkyl, C1-C3 monohaloalkyl, C1-C3 polyhaloalkyl, cyclopropyl, and —$CO_2H$; provided that no more than three occurrences of $R^{40}$ are not hydrogen. In a further aspect, each occurrence of $R^{40}$ is hydrogen.

In a further aspect, each occurrence of $R^{40}$ is independently hydrogen or C1-C3 alkyl, provided that no more than three occurrences of $R^{40}$ are not hydrogen. In a still further aspect, each occurrence of $R^{40}$ is independently hydrogen or C1-C3 monohaloalkyl, provided that no more than three occurrences of $R^{40}$ are not hydrogen. In yet a further aspect, each occurrence of $R^{40}$ is independently hydrogen or C1-C3 polyhaloalkyl.

In a further aspect, each occurrence of $R^{40}$ is independently selected from hydrogen, halogen and C1-C3 alkyl, provided that no more than three occurrences of $R^{40}$ are not hydrogen. In a still further aspect, each occurrence of $R^{40}$ is independently selected from hydrogen, halogen and C1-C3 monohaloalkyl, provided that no more than three occurrences of $R^{40}$ are not hydrogen. In yet a further aspect, each occurrence of $R^{40}$ is independently selected from hydrogen, halogen and C1-C3 polyhaloalkyl.

In a further aspect, each occurrence of $R^{40}$ is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, cyclopropyl, or —$CO_2H$, provided that no more than three occurrences of $R^{40}$ are not hydrogen. In a still further aspect, each occurrence of $R^{40}$ is independently selected from hydrogen, —F, —Cl, methyl, —$CH_2F$, —$CHF_2$, —$CF_3$, —$CHCl_2$, —$CCl_3$, cyclopropyl, or —$CO_2H$, provided that no more than three occurrences of $R^{40}$ are not hydrogen. In yet a further aspect, each occurrence of $R^{40}$ is independently selected from hydrogen, methyl, ethyl, —F, —$CH_2F$, —$CH_2CH_2F$, —$CHF_2$, —$CF_3$, —$CH_2CHF_2$, —$CH_2CF_3$, cyclopropyl, or —$CO_2H$, provided that no more than three occurrences of $R^{40}$ are not hydrogen. In an even further aspect, each occurrence of $R^{40}$ is independently selected from hydrogen, methyl, —F, —$CH_2F$, —$CHF_2$, —$CF_3$, cyclopropyl, or —$CO_2H$, provided that no more than three occurrences of $R^{40}$ are not hydrogen.

In a further aspect, each occurrence of $R^{40}$ is independently hydrogen, —F, —Cl—Br, methyl, ethyl, —$CFH_2$, —$CF_2H$, —$CF_3$, cyclopropyl, or —$CO_2H$, provided that no more than three occurrences of $R^{40}$ are not hydrogen.

In a further aspect, each occurrence of $R^{40}$ is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$, provided that no more than three occurrences of $R^{40}$ are not hydrogen. In a still further aspect, each occurrence of $R^{40}$ is independently selected from hydrogen, —F, —Cl, methyl, —$CH_2F$, —$CHF_2$, —$CF_3$, —$CHCl_2$, and —$CCl_3$, provided that no more than three occurrences of $R^{40}$ are not hydrogen. In yet a further aspect, each occurrence of $R^{40}$ is independently selected from hydrogen, methyl, ethyl, —F, —$CH_2F$, —$CH_2CH_2F$, —$CHF_2$, —$CF_3$, —$CH_2CHF_2$, and —$CH_2CF_3$, provided that no more than three occurrences of $R^{40}$ are not hydrogen. In an even further aspect, each occurrence of $R^{40}$ is independently selected from hydrogen, methyl, —F, —$CH_2F$, —$CHF_2$, and —$CF_3$, provided that no more than three occurrences of $R^{40}$ are not hydrogen.

In a further aspect, each occurrence of $R^{40}$ is independently hydrogen, —F, —Cl—Br, methyl, ethyl, —$CFH_2$, —$CF_2H$, or —$CF_3$, provided that no more than three occurrences of $R^{40}$ are not hydrogen.

In a further aspect, each occurrence of $R^{40}$ is independently hydrogen, —F, —Cl—Br, methyl, or —$CF_3$, provided that no more than three occurrences of $R^{40}$ are not hydrogen.

q. $Cy^1$ Groups

In one aspect, $Cy^1$, when present, is an amino C3-C8 cycloalkyl, a hydroxy C3-C8 cycloalkyl, or a C2-C7 heterocycloalkyl comprising at least one oxygen or nitrogen atom; and wherein $Cy^1$ is substituted 0, 1, 2, or 3 groups independently selected from halogen, C1-C4 alkyl, C1-C4 monohaloalkyl, and C1-C4 polyhaloalkyl.

In a further aspect, $Cy^1$ has a structure represented by a formula:

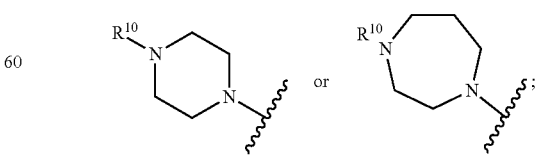

and wherein $R^{10}$ is hydrogen, methyl, ethyl, propyl, or isopropyl.

In a further aspect, Cy¹ has a structure represented by a formula:

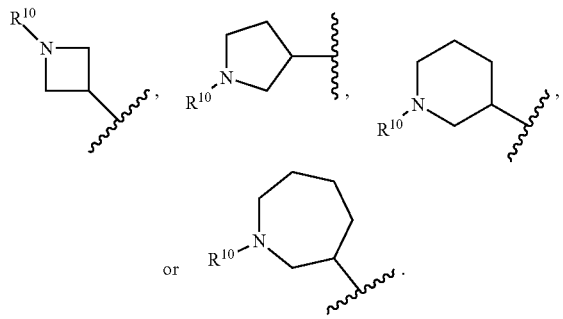

In a further aspect, Cy¹ has a structure represented by a formula:

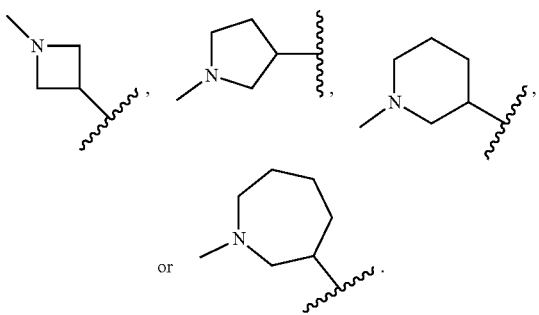

a further aspect, Cy¹ has a structure represented by a formula:

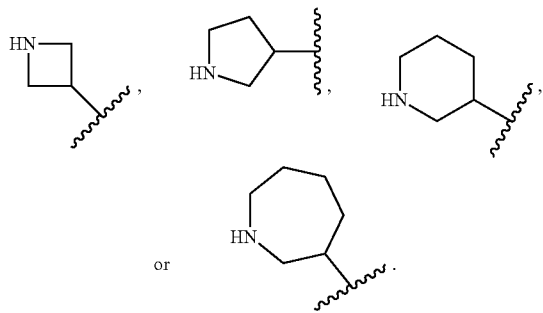

r. Cy² Groups

In one aspect, Cy², when present, is an amino C3-C8 cycloalkyl, a hydroxy C3-C8 cycloalkyl, or a C2-C7 heterocycloalkyl comprising at least one oxygen or nitrogen atom; and wherein Cy² is substituted 0, 1, 2, or 3 groups independently selected from halogen, C1-C4 alkyl, C1-C4 monohaloalkyl, and C1-C4 polyhaloalkyl.

In a further aspect, Cy², when present, is a C2-C7 heterocycloalkyl comprising at least one oxygen or nitrogen atom, and wherein Cy² is substituted with 0, 1, or 2 groups independently selected from halogen, C1-C4 alkyl, C1-C4 monohaloalkyl, and C1-C4 polyhaloalkyl. In a still further aspect, Cy², when present, is a C2-C7 heterocycloalkyl comprising at least one oxygen or nitrogen atom, and wherein Cy² is substituted with 0 or 1 group selected from halogen, C1-C4 alkyl, C1-C4 monohaloalkyl, and C1-C4 polyhaloalkyl. In yet a further aspect, Cy², when present, is a C2-C7 heterocycloalkyl comprising at least one oxygen or nitrogen atom, and wherein Cy² is monosubstituted with a group selected from halogen, C1-C4 alkyl, C1-C4 monohaloalkyl, and C1-C4 polyhaloalkyl. In an even further aspect, Cy², when present, is an unsubstituted C2-C7 heterocycloalkyl comprising at least one oxygen or nitrogen atom.

In a further aspect, Cy², when present, is a C2-C6 heterocycloalkyl comprising at least one oxygen or nitrogen atom, and wherein Cy² is substituted with 0, 1, 2, or 3 groups independently selected from halogen, C1-C4 alkyl, C1-C4 monohaloalkyl, and C1-C4 polyhaloalkyl. In a still further aspect, Cy², when present, is a C2-C6 heterocycloalkyl comprising at least one oxygen or nitrogen atom, and wherein Cy² is substituted with 0, 1, or 2 groups independently selected from halogen, C1-C4 alkyl, C1-C4 monohaloalkyl, and C1-C4 polyhaloalkyl. In yet a further aspect, Cy², when present, is a C2-C6 heterocycloalkyl comprising at least one oxygen or nitrogen atom, and wherein Cy² is substituted with 0 or 1 group selected from halogen, C1-C4 alkyl, C1-C4 monohaloalkyl, and C1-C4 polyhaloalkyl. In an even further aspect, Cy², when present, is a C2-C6 heterocycloalkyl comprising at least one oxygen or nitrogen atom, and wherein Cy² is monosubstituted with a group selected from halogen, C1-C4 alkyl, C1-C4 monohaloalkyl, and C1-C4 polyhaloalkyl. In a still further aspect, Cy², when present, is an unsubstituted C2-C6 heterocycloalkyl comprising at least one oxygen or nitrogen atom.

In a further aspect, Cy², when present, is a C2-C5 heterocycloalkyl comprising at least one oxygen or nitrogen atom, and wherein Cy² is substituted with 0, 1, 2, or 3 groups independently selected from halogen, C1-C4 alkyl, C1-C4 monohaloalkyl, and C1-C4 polyhaloalkyl. In a still further aspect, Cy², when present, is a C2-C5 heterocycloalkyl comprising at least one oxygen or nitrogen atom, and wherein Cy² is substituted with 0, 1, or 2 groups independently selected from halogen, C1-C4 alkyl, C1-C4 monohaloalkyl, and C1-C4 polyhaloalkyl. In yet a further aspect, Cy², when present, is a C2-C5 heterocycloalkyl comprising at least one oxygen or nitrogen atom, and wherein Cy² is substituted with 0 or 1 group selected from halogen, C1-C4 alkyl, C1-C4 monohaloalkyl, and C1-C4 polyhaloalkyl. In an even further aspect, Cy², when present, is a C2-C5 heterocycloalkyl comprising at least one oxygen or nitrogen atom, and wherein Cy² is monosubstituted with a group selected from halogen, C1-C4 alkyl, C1-C4 monohaloalkyl, and C1-C4 polyhaloalkyl. In a still further aspect, Cy², when present, is an unsubstituted C2-C5 heterocycloalkyl comprising at least one oxygen or nitrogen atom.

In a further aspect, Cy², when present, is a C2-C4 heterocycloalkyl comprising at least one oxygen or nitrogen atom, and wherein Cy² is substituted with 0, 1, 2, or 3 groups independently selected from halogen, C1-C4 alkyl, C1-C4 monohaloalkyl, and C1-C4 polyhaloalkyl. In a still further aspect, Cy², when present, is a C2-C4 heterocycloalkyl comprising at least one oxygen or nitrogen atom, and wherein Cy² is substituted with 0, 1, or 2 groups independently selected from halogen, C1-C4 alkyl, C1-C4 monohaloalkyl, and C1-C4 polyhaloalkyl. In yet a further aspect, Cy², when present, is a C2-C4 heterocycloalkyl comprising at least one oxygen or nitrogen atom, and wherein Cy² is substituted with 0 or 1 group selected from halogen, C1-C4 alkyl, C1-C4 monohaloalkyl, and C1-C4 polyhaloalkyl. In an even further aspect, Cy², when present, is a C2-C4 heterocycloalkyl comprising at least one oxygen or nitrogen atom, and wherein Cy² is monosubstituted with a group selected from halogen, C1-C4 alkyl, C1-C4 monohaloalkyl, and C1-C4 polyhaloalkyl. In a still further aspect, $Cy^2$, when present, is an unsubstituted C2-C4 heterocycloalkyl comprising at least one oxygen or nitrogen atom.

In a further aspect, $Cy^2$, when present, is a C4 heterocycloalkyl comprising at least one oxygen or nitrogen atom, and wherein $Cy^2$ is substituted with 0, 1, 2, or 3 groups independently selected from halogen, C1-C4 alkyl, C1-C4 monohaloalkyl, and C1-C4 polyhaloalkyl. In a still further aspect, $Cy^2$, when present, is a C4 heterocycloalkyl comprising at least one oxygen or nitrogen atom, and wherein $Cy^2$ is substituted with 0, 1, or 2 groups independently selected from halogen, C1-C4 alkyl, C1-C4 monohaloalkyl, and C1-C4 polyhaloalkyl. In yet a further aspect, $Cy^2$, when present, is a C4 heterocycloalkyl comprising at least one oxygen or nitrogen atom, and wherein $Cy^2$ is substituted with 0 or 1 group selected from halogen, C1-C4 alkyl, C1-C4 monohaloalkyl, and C1-C4 polyhaloalkyl. In an even further aspect, $Cy^2$, when present, is a C4 heterocycloalkyl comprising at least one oxygen or nitrogen atom, and wherein $Cy^2$ is monosubstituted with a group selected from halogen, C1-C4 alkyl, C1-C4 monohaloalkyl, and C1-C4 polyhaloalkyl. In a still further aspect, $Cy^2$, when present, is an unsubstituted C4 heterocycloalkyl comprising at least one oxygen or nitrogen atom.

In a further aspect, $Cy^2$, when present, is pyrrolidinyl substituted with 0, 1, 2, or 3 groups independently selected from halogen, C1-C4 alkyl, C1-C4 monohaloalkyl, and C1-C4 polyhaloalkyl. In a still further aspect, $Cy^2$, when present, is pyrrolidinyl substituted with 0, 1, or 2 groups independently selected from halogen, C1-C4 alkyl, C1-C4 monohaloalkyl, and C1-C4 polyhaloalkyl. In yet a further aspect, $Cy^2$, when present, is pyrrolidinyl substituted with 0 or 1 group selected from halogen, C1-C4 alkyl, C1-C4 monohaloalkyl, and C1-C4 polyhaloalkyl. In an even further aspect, $Cy^2$, when present, is pyrrolidinyl monosubstituted with a group selected from halogen, C1-C4 alkyl, C1-C4 monohaloalkyl, and C1-C4 polyhaloalkyl. In a still further aspect, $Cy^2$, when present, is an unsubstituted pyrrolidinyl.

In a further aspect, $Cy^2$, when present, is pyrrolidinyl substituted with 0, 1, 2, or 3 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $Cy^2$, when present, is pyrrolidinyl substituted with 0, 1, or 2 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $Cy^2$, when present, is pyrrolidinyl substituted with 0 or 1 group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In an even further aspect, $Cy^2$, when present, is pyrrolidinyl monosubstituted with a group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$.

In a further aspect, $Cy^2$, when present, is pyrrolidinyl substituted with 0, 1, 2, or 3 groups independently selected from —F, —Cl, methyl, —$CH_2F$, —$CH_2Cl$, —$CHF_2$, —$CF_3$, —$CHCl_2$, and —$CCl_3$. In a still further aspect, $Cy^2$, when present, is pyrrolidinyl substituted with 0, 1, or 2 groups independently selected from —F, —Cl, methyl, —$CH_2F$, —$CH_2Cl$, —$CHF_2$, —$CF_3$, —$CHCl_2$, and —$CCl_3$. In yet a further aspect, $Cy^2$, when present, is pyrrolidinyl substituted with 0 or 1 group selected from —F, —Cl, methyl, —$CH_2F$, —$CH_2Cl$, —$CHF_2$, —$CF_3$, —$CHCl_2$, and —$CCl_3$. In an even further aspect, $Cy^2$, when present, is pyrrolidinyl monosubstituted with a group selected from —F, —Cl, methyl, —$CH_2F$, —$CH_2Cl$, —$CHF_2$, —$CF_3$, —$CHCl_2$, and —$CCl_3$.

In a further aspect, $Cy^2$, when present, is pyrrolidinyl substituted with 0, 1, 2, or 3 groups independently selected from —F, methyl, —$CH_2F$, —$CHF_2$, and —$CF_3$. In a still further aspect, $Cy^2$, when present, is pyrrolidinyl substituted with 0, 1, or 2 groups independently selected from —F, methyl, —$CH_2F$, —$CHF_2$, and —$CF_3$. In yet a further aspect, $Cy^2$, when present, is pyrrolidinyl substituted with 0 or 1 group selected from —F, methyl, —$CH_2F$, —$CHF_2$, and —$CF_3$. In an even further aspect, $Cy^2$, when present, is pyrrolidinyl monosubstituted with a group selected from —F, methyl, —$CH_2F$, —$CHF_2$, and —$CF_3$.

In a further aspect, $Cy^2$ has a structure represented by a formula:

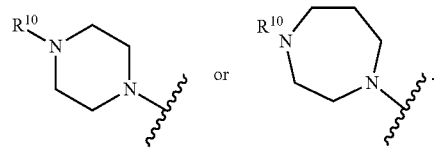

In a further aspect, $Cy^2$ has a structure represented by a formula:

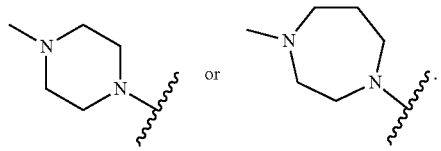

In a further aspect, $Cy^2$ has a structure represented by a formula:

s. $Cy^3$ Groups

In one aspect, $Cy^3$, when present, is a C3-C8 cycloalkyl or a C2-C7 heterocycloalkyl comprising at least one oxygen or nitrogen atom, and wherein $Cy^3$ is substituted with 0, 1, 2, or 3 groups independently selected from halogen, C1-C4 alkyl, C1-C4 monohaloalkyl, and C1-C4 polyhaloalkyl.

In a further aspect, $Cy^3$, when present, is a C2-C7 heterocycloalkyl comprising at least one oxygen or nitrogen atom, and wherein $Cy^3$ is substituted with 0, 1, or 2 groups independently selected from halogen, C1-C4 alkyl, C1-C4 monohaloalkyl, and C1-C4 polyhaloalkyl. In a still further aspect, $Cy^3$, when present, is a C2-C7 heterocycloalkyl comprising at least one oxygen or nitrogen atom, and wherein $Cy^3$ is substituted with 0 or 1 group selected from halogen, C1-C4 alkyl, C1-C4 monohaloalkyl, and C1-C4 polyhaloalkyl. In yet a further aspect, $Cy^3$, when present, is a C2-C7 heterocycloalkyl comprising at least one oxygen or nitrogen atom, and wherein $Cy^3$ is monosubstituted with a group selected from halogen, C1-C4 alkyl, C1-C4 monohaloalkyl, and C1-C4 polyhaloalkyl. In an even further aspect, $Cy^3$, when present, is an unsubstituted C2-C7 heterocycloalkyl comprising at least one oxygen or nitrogen atom.

In a further aspect, $Cy^3$, when present, is a C2-C6 heterocycloalkyl comprising at least one oxygen or nitrogen atom, and wherein $Cy^3$ is substituted with 0, 1, 2, or 3 groups independently selected from halogen, C1-C4 alkyl, C1-C4 monohaloalkyl, and C1-C4 polyhaloalkyl. In a still further aspect, $Cy^3$, when present, is a C2-C6 heterocycloalkyl comprising at least one oxygen or nitrogen atom, and wherein $Cy^3$ is substituted with 0, 1, or 2 groups independently selected from halogen, C1-C4 alkyl, C1-C4 monohaloalkyl, and C1-C4 polyhaloalkyl. In yet a further aspect, $Cy^3$, when present, is a C2-C6 heterocycloalkyl comprising at least one oxygen or nitrogen atom, and wherein $Cy^3$ is substituted with 0 or 1 group selected from halogen, C1-C4 alkyl, C1-C4 monohaloalkyl, and C1-C4 polyhaloalkyl. In an even further aspect, $Cy^3$, when present, is a C2-C6 heterocycloalkyl comprising at least one oxygen or nitrogen atom, and wherein $Cy^3$ is monosubstituted with a group selected from halogen, C1-C4 alkyl, C1-C4 monohaloalkyl, and C1-C4 polyhaloalkyl. In a still further aspect, $Cy^3$, when present, is an unsubstituted C2-C6 heterocycloalkyl comprising at least one oxygen or nitrogen atom.

In a further aspect, $Cy^3$, when present, is a C2-C5 heterocycloalkyl comprising at least one oxygen or nitrogen atom, and wherein $Cy^3$ is substituted with 0, 1, 2, or 3 groups independently selected from halogen, C1-C4 alkyl, C1-C4 monohaloalkyl, and C1-C4 polyhaloalkyl. In a still further aspect, $Cy^3$, when present, is a C2-C5 heterocycloalkyl comprising at least one oxygen or nitrogen atom, and wherein $Cy^3$ is substituted with 0, 1, or 2 groups independently selected from halogen, C1-C4 alkyl, C1-C4 monohaloalkyl, and C1-C4 polyhaloalkyl. In yet a further aspect, $Cy^3$, when present, is a C2-C5 heterocycloalkyl comprising at least one oxygen or nitrogen atom, and wherein $Cy^3$ is substituted with 0 or 1 group selected from halogen, C1-C4 alkyl, C1-C4 monohaloalkyl, and C1-C4 polyhaloalkyl. In an even further aspect, $Cy^3$, when present, is a C2-C5 heterocycloalkyl comprising at least one oxygen or nitrogen atom, and wherein $Cy^3$ is monosubstituted with a group selected from halogen, C1-C4 alkyl, C1-C4 monohaloalkyl, and C1-C4 polyhaloalkyl. In a still further aspect, $Cy^3$, when present, is an unsubstituted C2-C5 heterocycloalkyl comprising at least one oxygen or nitrogen atom.

In a further aspect, $Cy^3$, when present, is a C2-C4 heterocycloalkyl comprising at least one oxygen or nitrogen atom, and wherein $Cy^3$ is substituted with 0, 1, 2, or 3 groups independently selected from halogen, C1-C4 alkyl, C1-C4 monohaloalkyl, and C1-C4 polyhaloalkyl. In a still further aspect, $Cy^3$, when present, is a C2-C4 heterocycloalkyl comprising at least one oxygen or nitrogen atom, and wherein $Cy^3$ is substituted with 0, 1, or 2 groups independently selected from halogen, C1-C4 alkyl, C1-C4 monohaloalkyl, and C1-C4 polyhaloalkyl. In yet a further aspect, $Cy^3$, when present, is a C2-C4 heterocycloalkyl comprising at least one oxygen or nitrogen atom, and wherein $Cy^3$ is substituted with 0 or 1 group selected from halogen, C1-C4 alkyl, C1-C4 monohaloalkyl, and C1-C4 polyhaloalkyl. In an even further aspect, $Cy^3$, when present, is a C2-C4 heterocycloalkyl comprising at least one oxygen or nitrogen atom, and wherein $Cy^3$ is monosubstituted with a group selected from halogen, C1-C4 alkyl, C1-C4 monohaloalkyl, and C1-C4 polyhaloalkyl. In a still further aspect, $Cy^3$, when present, is an unsubstituted C2-C4 heterocycloalkyl comprising at least one oxygen or nitrogen atom.

In a further aspect, $Cy^3$, when present, is a C4 heterocycloalkyl comprising at least one oxygen or nitrogen atom, and wherein $Cy^3$ is substituted with 0, 1, 2, or 3 groups independently selected from halogen, C1-C4 alkyl, C1-C4 monohaloalkyl, and C1-C4 polyhaloalkyl. In a still further aspect, $Cy^3$, when present, is a C4 heterocycloalkyl comprising at least one oxygen or nitrogen atom, and wherein $Cy^3$ is substituted with 0, 1, or 2 groups independently selected from halogen, C1-C4 alkyl, C1-C4 monohaloalkyl, and C1-C4 polyhaloalkyl. In yet a further aspect, $Cy^3$, when present, is a C4 heterocycloalkyl comprising at least one oxygen or nitrogen atom, and wherein $Cy^3$ is substituted with 0 or 1 group selected from halogen, C1-C4 alkyl, C1-C4 monohaloalkyl, and C1-C4 polyhaloalkyl. In an even further aspect, $Cy^3$, when present, is a C4 heterocycloalkyl comprising at least one oxygen or nitrogen atom, and wherein $Cy^3$ is monosubstituted with a group selected from halogen, C1-C4 alkyl, C1-C4 monohaloalkyl, and C1-C4 polyhaloalkyl. In a still further aspect, $Cy^3$, when present, is an unsubstituted C4 heterocycloalkyl comprising at least one oxygen or nitrogen atom.

In a further aspect, $Cy^3$, when present, is pyrrolidinyl substituted with 0, 1, 2, or 3 groups independently selected from halogen, C1-C4 alkyl, C1-C4 monohaloalkyl, and C1-C4 polyhaloalkyl. In a still further aspect, $Cy^3$, when present, is pyrrolidinyl substituted with 0, 1, or 2 groups independently selected from halogen, C1-C4 alkyl, C1-C4 monohaloalkyl, and C1-C4 polyhaloalkyl. In yet a further aspect, $Cy^3$, when present, is pyrrolidinyl substituted with 0 or 1 group selected from halogen, C1-C4 alkyl, C1-C4 monohaloalkyl, and C1-C4 polyhaloalkyl. In an even further aspect, $Cy^3$, when present, is pyrrolidinyl monosubstituted with a group selected from halogen, C1-C4 alkyl, C1-C4 monohaloalkyl, and C1-C4 polyhaloalkyl. In a still further aspect, $Cy^3$, when present, is an unsubstituted pyrrolidinyl.

In a further aspect, $Cy^3$, when present, is pyrrolidinyl substituted with 0, 1, 2, or 3 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $Cy^3$, when present, is pyrrolidinyl substituted with 0, 1, or 2 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $Cy^3$, when present, is pyrrolidinyl substituted with 0 or 1 group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In an even further aspect, $Cy^3$, when present, is pyrrolidinyl monosubstituted with a group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$.

In a further aspect, $Cy^3$, when present, is pyrrolidinyl substituted with 0, 1, 2, or 3 groups independently selected from —F, —Cl, methyl, —$CH_2F$, —$CH_2Cl$, —$CHF_2$, —$CF_3$, —$CHCl_2$, and —$CCl_3$. In a still further aspect, $Cy^3$, when present, is pyrrolidinyl substituted with 0, 1, or 2 groups independently selected from —F, —Cl, methyl, —$CH_2F$, —$CH_2Cl$, —$CHF_2$, —$CF_3$, —$CHCl_2$, and —$CCl_3$. In yet a further aspect, $Cy^3$, when present, is pyrrolidinyl substituted with 0 or 1 group selected from —F, —Cl, methyl, —$CH_2F$, —$CH_2Cl$, —$CHF_2$, —$CF_3$, —$CHCl_2$, and —CCl$_3$. In an even further aspect, Cy$^3$, when present, is pyrrolidinyl monosubstituted with a group selected from —F, —Cl, methyl, —CH$_2$F, —CH$_2$Cl, —CHF$_2$, —CF$_3$, —CHCl$_2$, and —CCl$_3$.

In a further aspect, Cy$^3$, when present, is pyrrolidinyl substituted with 0, 1, 2, or 3 groups independently selected from —F, methyl, —CH$_2$F, —CHF$_2$, and —CF$_3$. In a still further aspect, Cy$^3$, when present, is pyrrolidinyl substituted with 0, 1, or 2 groups independently selected from —F, methyl, —CH$_2$F, —CHF$_2$, and —CF$_3$. In yet a further aspect, Cy$^3$, when present, is pyrrolidinyl substituted with 0 or 1 group selected from —F, methyl, —CH$_2$F, —CHF$_2$, and —CF$_3$. In an even further aspect, Cy$^3$, when present, is pyrrolidinyl monosubstituted with a group selected from —F, methyl, —CH$_2$F, —CHF$_2$, and —CF$_3$.

In a further aspect, Cy$^3$ has a structure represented by a formula:

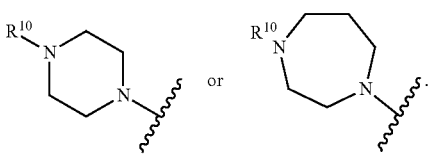

In a further aspect, Cy$^3$ has a structure represented by a formula:

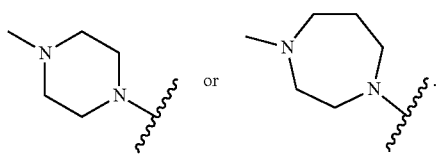

In a further aspect, Cy$^3$ has a structure represented by a formula:

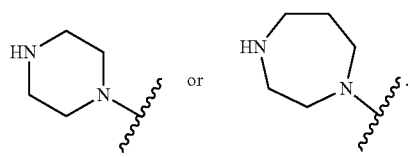 [SMILES: *N1CCNCC1 ; *N1CCCNCC1]

t. Ar$^1$ Groups

In one aspect, Ar$^1$ is selected from aryl and heteroaryl, and wherein Ar$^1$ is substituted with 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a further aspect, Ar$^1$ is unsubstituted.

In a further aspect, Ar$^1$ is selected from aryl and heteroaryl, and wherein Ar$^1$ is substituted with 0, 1, or 2 groups independently selected from halogen, —CN, C1-C3 alkyl, C1-C3 monohaloalkyl, C1-C3 polyhaloalkyl, cyclopropyl, and —CO$_2$H. In a still further aspect, Ar$^1$ is selected from aryl and heteroaryl, and wherein Ar$^1$ is substituted with 0 or 1 group selected from halogen, —CN, C1-C3 alkyl, C1-C3 monohaloalkyl, C1-C3 polyhaloalkyl, cyclopropyl, and —CO$_2$H. In yet a further aspect, Ar$^1$ is selected from aryl and heteroaryl, and wherein Ar$^1$ is monosubstituted with a group selected from halogen, —CN, C1-C3 alkyl, C1-C3 monohaloalkyl, C1-C3 polyhaloalkyl, cyclopropyl, and —CO$_2$H. In an even further aspect, Ar$^1$ is selected from aryl and heteroaryl, and wherein Ar$^1$ is unsubstituted.

In a further aspect, Ar$^1$ is selected from phenyl, naphthyl, pyridinyl, pyrimidinyl, pyridazinyl, and pyrazinyl, and wherein Ar$^1$ is substituted with 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, Ar$^1$ is selected from phenyl, naphthyl, pyridinyl, pyrimidinyl, pyridazinyl, and pyrazinyl, and wherein Ar$^1$ is substituted with 0, 1, or 2 groups independently selected from halogen, —CN, C1-C3 alkyl, C1-C3 monohaloalkyl, C1-C3 polyhaloalkyl, cyclopropyl, and —CO$_2$H. In yet a further aspect, Ar$^1$ is selected from phenyl, naphthyl, pyridinyl, pyrimidinyl, pyridazinyl, and pyrazinyl, and wherein Ar$^1$ is substituted with 0 or 1 group selected from halogen, —CN, C1-C3 alkyl, C1-C3 monohaloalkyl, C1-C3 polyhaloalkyl, cyclopropyl, and —CO$_2$H. In an even further aspect, Ar$^1$ is selected from phenyl, naphthyl, pyridinyl, pyrimidinyl, pyridazinyl, and pyrazinyl, and wherein Ar$^1$ is monosubstituted with a group selected from halogen, —CN, C1-C3 alkyl, C1-C3 monohaloalkyl, C1-C3 polyhaloalkyl, cyclopropyl, and —CO$_2$H. In a still further aspect, Ar$^1$ is selected from phenyl, naphthyl, pyridinyl, pyrimidinyl, pyridazinyl, and pyrazinyl, and wherein Ar$^1$ is unsubstituted.

In a further aspect, Ar$^1$ is selected from phenyl and pyridinyl, and wherein Ar$^1$ is substituted with 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, Ar$^1$ is selected from phenyl and pyridinyl, and wherein Ar$^1$ is substituted with 0, 1, or 2 groups independently selected from halogen, —CN, C1-C3 alkyl, C1-C3 monohaloalkyl, C1-C3 polyhaloalkyl, cyclopropyl, and —CO$_2$H. In yet a further aspect, Ar$^1$ is selected from phenyl and pyridinyl, and wherein Ar$^1$ is substituted with 0 or 1 group selected from halogen, —CN, C1-C3 alkyl, C1-C3 monohaloalkyl, C1-C3 polyhaloalkyl, cyclopropyl, and —CO$_2$H. In an even further aspect, Ar$^1$ is selected from phenyl and pyridinyl, and wherein Ar$^1$ is monosubstituted with a group selected from halogen, —CN, C1-C3 alkyl, C1-C3 monohaloalkyl, C1-C3 polyhaloalkyl, cyclopropyl, and —CO$_2$H. In a still further aspect, Ar$^1$ is selected from phenyl and pyridinyl, and wherein Ar$^1$ is unsubstituted.

In a further aspect, Ar$^1$ is phenyl substituted with 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, Ar$^1$ is phenyl substituted with 0, 1, or 2 groups independently selected from halogen, —CN, C1-C3 alkyl, C1-C3 monohaloalkyl, C1-C3 polyhaloalkyl, cyclopropyl, and —CO$_2$H. In yet a further aspect, Ar$^1$ is phenyl substituted with 0 or 1 group selected from halogen, —CN, C1-C3 alkyl, C1-C3 monohaloalkyl, C1-C3 polyhaloalkyl, cyclopropyl, and —CO$_2$H. In an even further aspect, Ar$^1$ is phenyl monosubstituted with a group selected from halogen, —CN, C1-C3 alkyl, C1-C3 monohaloalkyl, C1-C3 polyhaloalkyl, cyclopropyl, and —CO$_2$H. In a still further aspect, Ar$^1$ is unsubstituted phenyl.

In a further aspect, Ar$^1$ is pyridinyl substituted with 0, 1, 2, or 3 groups independently selected from halogen, —CN, C1-C3 alkyl, C1-C3 monohaloalkyl, C1-C3 polyhaloalkyl, cyclopropyl, and —CO$_2$H. In a still further aspect, Ar$^1$ is pyridinyl substituted with 0, 1, or 2 groups independently selected from halogen, —CN, C1-C3 alkyl, C1-C3 monohaloalkyl, C1-C3 polyhaloalkyl, cyclopropyl, and —CO$_2$H. In yet a further aspect, Ar$^1$ is pyridinyl substituted with 0 or 1 group selected from halogen, —CN, C1-C3 alkyl, C1-C3 monohaloalkyl, C1-C3 polyhaloalkyl, cyclopropyl, and —CO$_2$H. In an even further aspect, Ar$^1$ is pyridinyl monosubstituted with a group selected from halogen, —CN, C1-C3 alkyl, C1-C3 monohaloalkyl, C1-C3 polyhaloalkyl, cyclopropyl, and —CO$_2$H. In a still further aspect, Ar$^1$ is unsubstituted pyridinyl.

In a further aspect, Ar$^1$ is selected from phenyl and pyridinyl, and wherein Ar$^1$ is substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In a still further aspect, Ar$^1$ is selected from phenyl and pyridinyl, and wherein Ar$^1$ is substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In yet a further aspect, Ar$^1$ is selected from phenyl and pyridinyl, and wherein Ar$^1$ is substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In an even further aspect, Ar$^1$ is selected from phenyl and pyridinyl, and wherein Ar$^1$ is monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H.

In a further aspect, Ar$^1$ is phenyl substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In a still further aspect, Ar$^1$ is phenyl substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In yet a further aspect, Ar$^1$ is phenyl substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In an even further aspect, Ar$^1$ is phenyl monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H.

In a further aspect, Ar$^1$ is pyridinyl substituted with 0, 1, 2, or 3 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In a still further aspect, Ar$^1$ is pyridinyl substituted with 0, 1, or 2 groups independently selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In yet a further aspect, Ar$^1$ is pyridinyl substituted with 0 or 1 group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H. In an even further aspect, Ar$^1$ is pyridinyl monosubstituted with a group selected from halogen, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$. and —CO$_2$H.

2. Example Compounds

In one aspect, a compound can be present as:

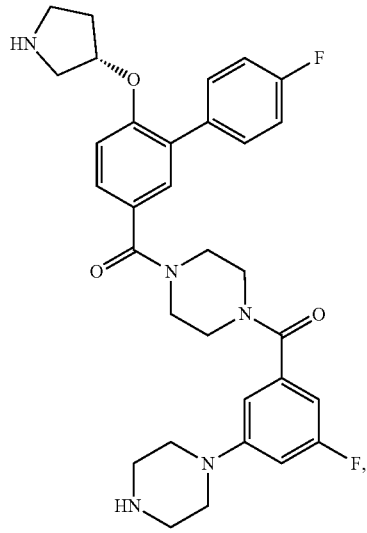

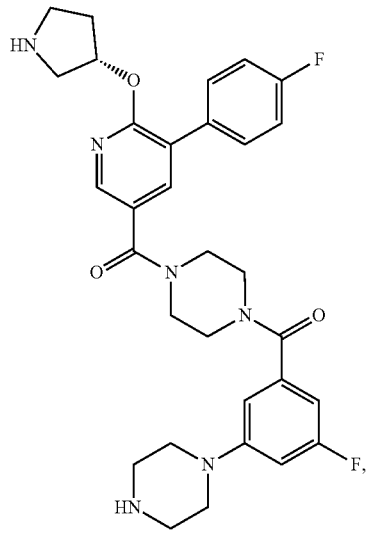

51
-continued
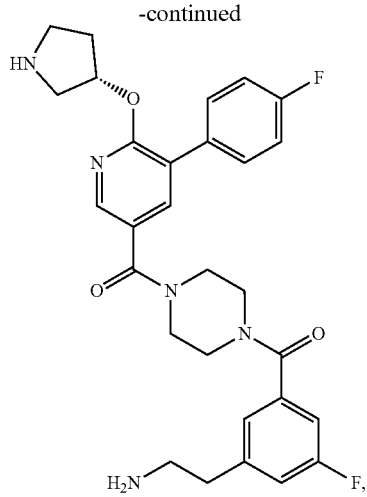
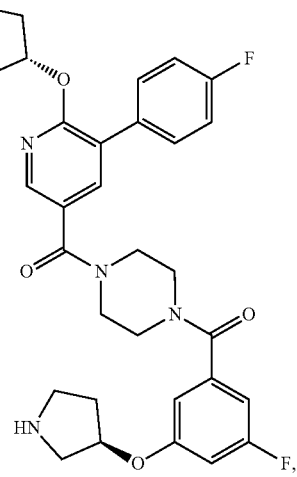
52
-continued
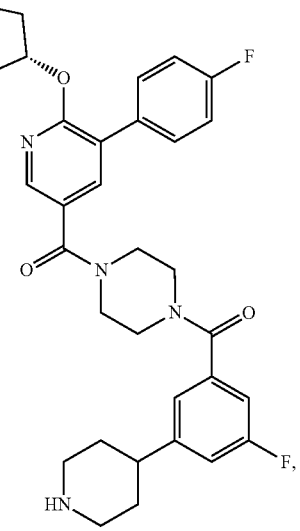
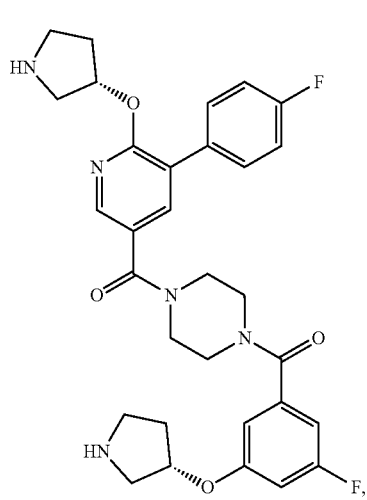
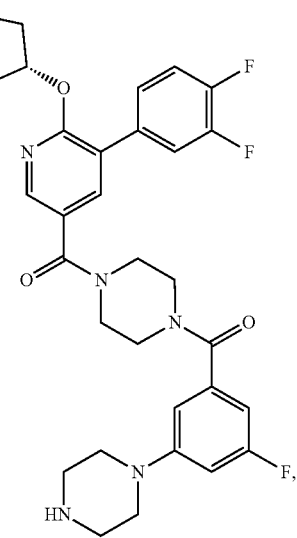

53
-continued
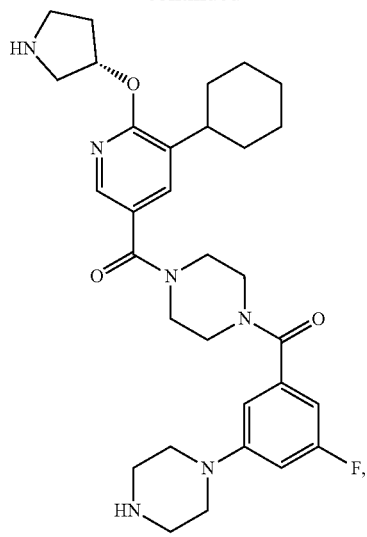
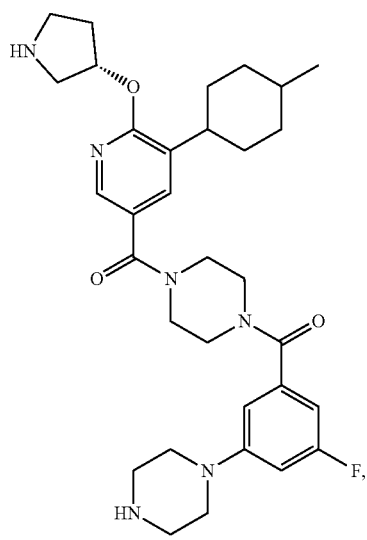
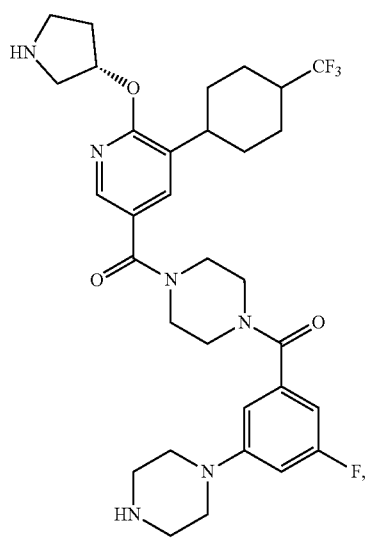
54
-continued
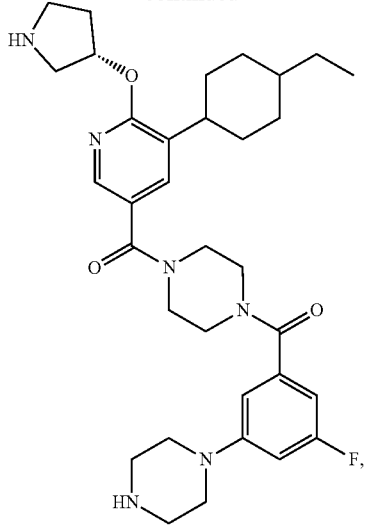
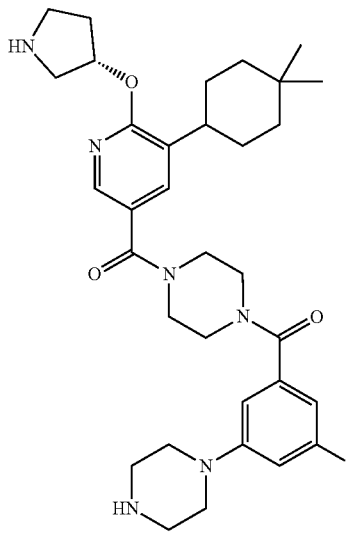
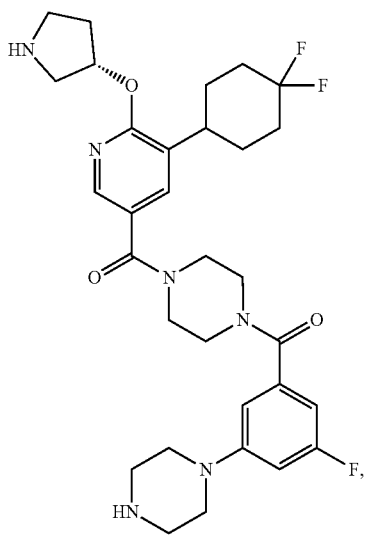

55
-continued
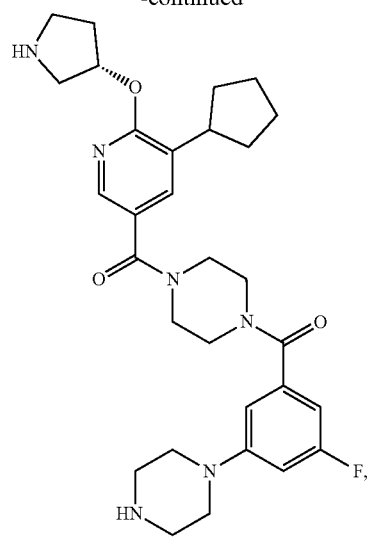
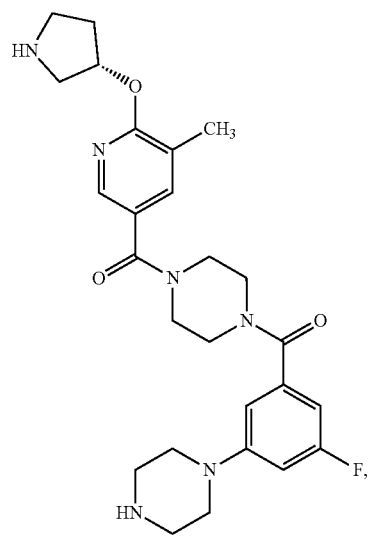
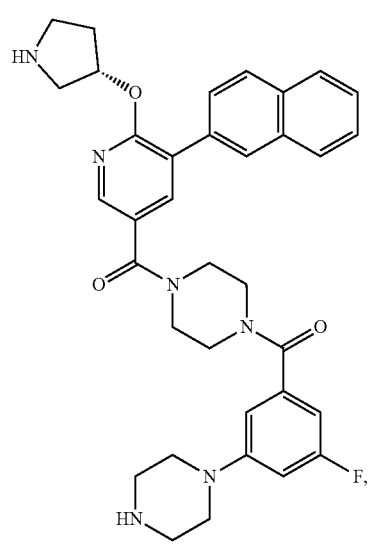
56
-continued
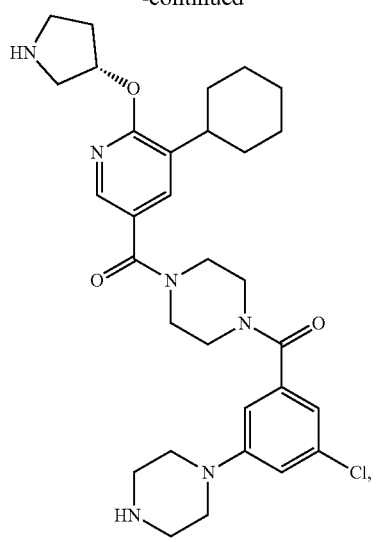
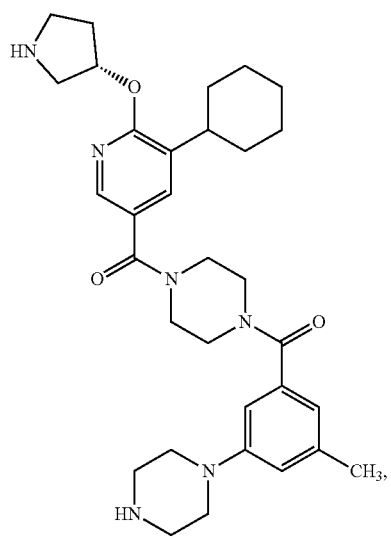
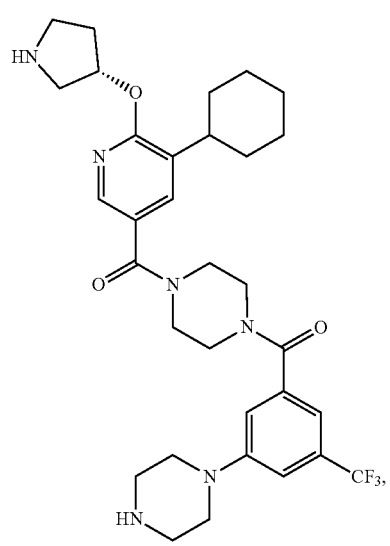

57
-continued
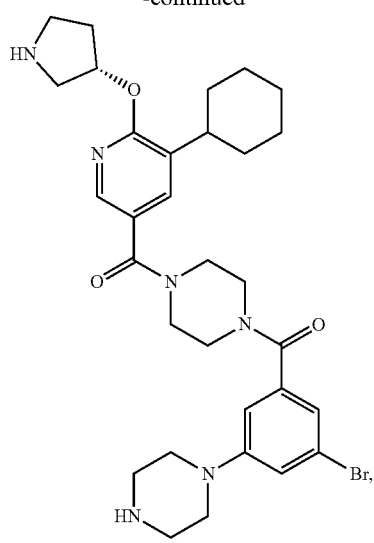
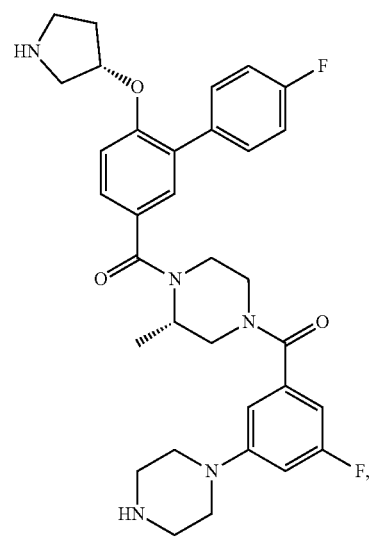
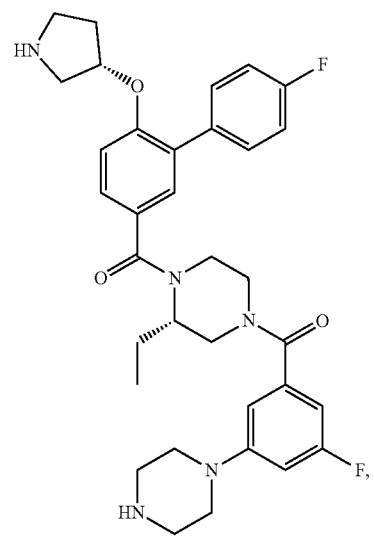
58
-continued
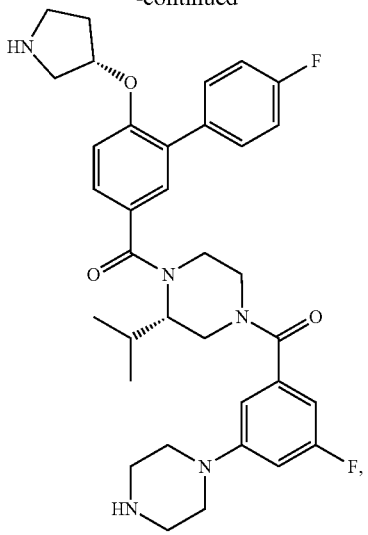
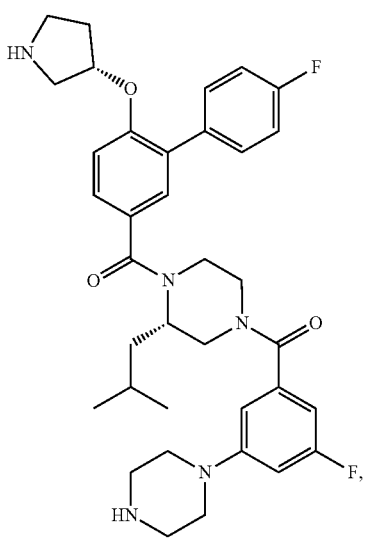
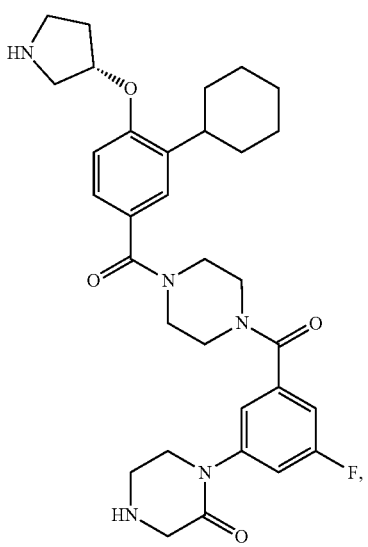

59
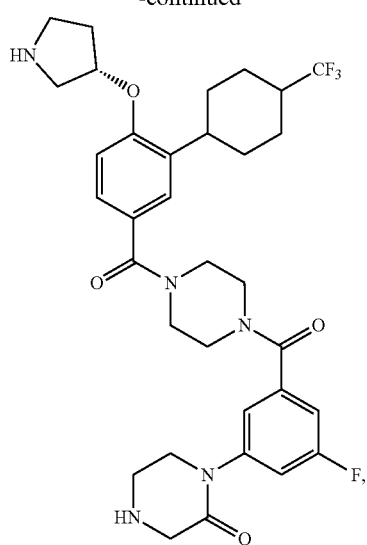
60
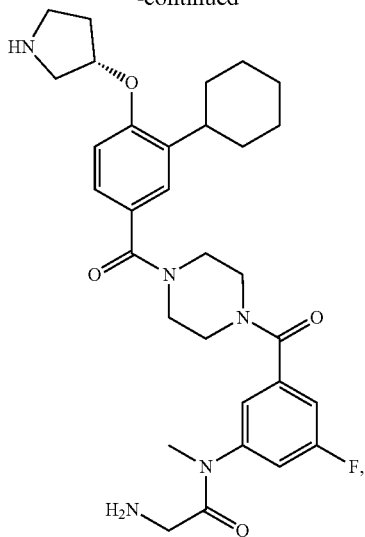
or a pharmaceutically acceptable salt thereof, or a subgroup thereof.

C. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of β-catenin/BCL9 protein-protein interactions an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting β-catenin/BCL9 protein-protein interactions (e.g., treatment of one or more disorders of uncontrolled cellular proliferation associated with β-catenin/BCL9 protein-protein interaction dysfunction or Wnt dysregulation) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

In a further aspect, the pharmaceutical composition further comprises a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the pharmaceutical composition further comprises a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent, or a pharmaceutically acceptable salt thereof. In yet a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In yet a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In an even further aspect, the mTor inhibitor agent is selected from one or more of the group consisting of everolimus, sirolimus, and temsirolimus, or a pharmaceutically acceptable salt thereof.

It is understood that the disclosed pharmaceutical compositions can be prepared from the disclosed compounds. It is also understood that the disclosed pharmaceutical compositions can be employed in the disclosed methods of using.

D. METHODS OF MAKING THE COMPOUNDS

In one aspect, the invention relates to methods of making N-(3-(pyrimidin-4-yl)phenyl)acrylamide analogs useful as inhibitors of β-catenin/B-cell lymphoma 9 protein-protein interactions. The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

1. Route I

In one aspect, N-(3-(pyrimidin-4-yl)phenyl)acrylamide intermediates can be prepared as shown below.

SCHEME 1A.

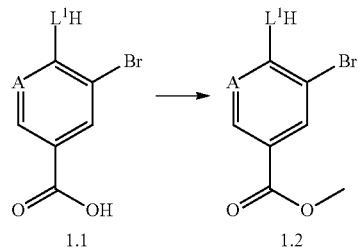

Compounds are represented in generic form, with substituents as noted in compound descriptions elsewhere herein. A more specific example is set forth below.

SCHEME 1B.

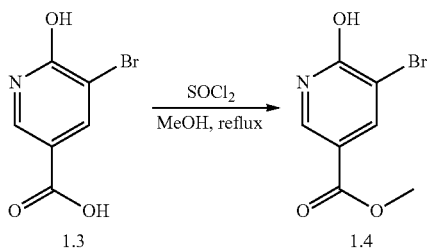

In one aspect, the synthesis of N-(3-(pyrimidin-4-yl) phenyl)acrylamide intermediates can begin with a carboxylic acid. Carboxylic acids are commercially available or readily prepared by one skilled in the art. Thus, compounds of type 1.2, and similar compounds, can be prepared according to reaction Scheme 1B above. Compounds of type 1.4 can be prepared by a alkylation reaction of an appropriate carboxylic acid derivative, e.g., 1.3 as shown above. The alkylation reaction is carried out in the presence of an appropriate activating agent, e.g., thionyl chloride as shown above, and an appropriate alcohol, e.g., methanol. As can be appreciated by one skilled in the art, the above reaction provides an example of a generalized approach wherein compounds similar in structure to the specific reactants above (compounds similar to compounds of type 1.1), can be substituted in the reaction to provide substituted N-(3-(pyrimidin-4-yl)phenyl)acrylamide intermediates similar to Formula 1.2.

2. Route II

In one aspect, N-(3-(pyrimidin-4-yl)phenyl)acrylamide intermediates can be prepared as shown below.

SCHEME 2A.

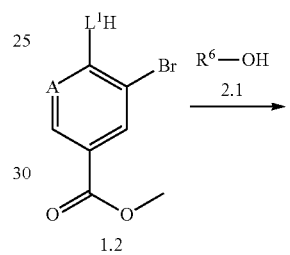

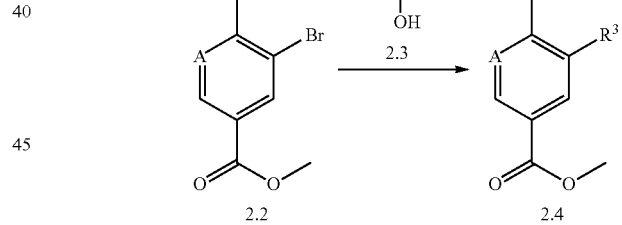

Compounds are represented in generic form, with substituents as noted in compound descriptions elsewhere herein. A more specific example is set forth below.

SCHEME 2B.

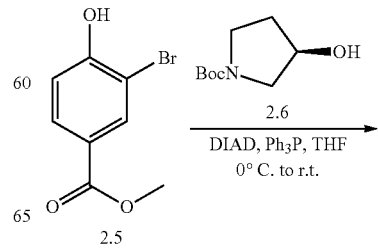

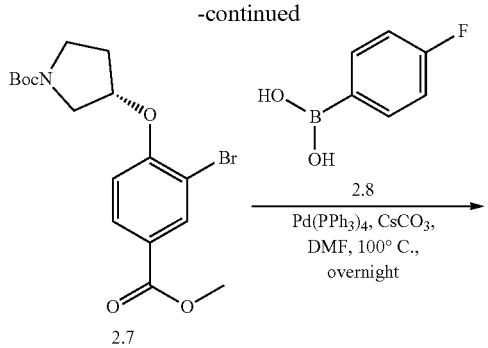

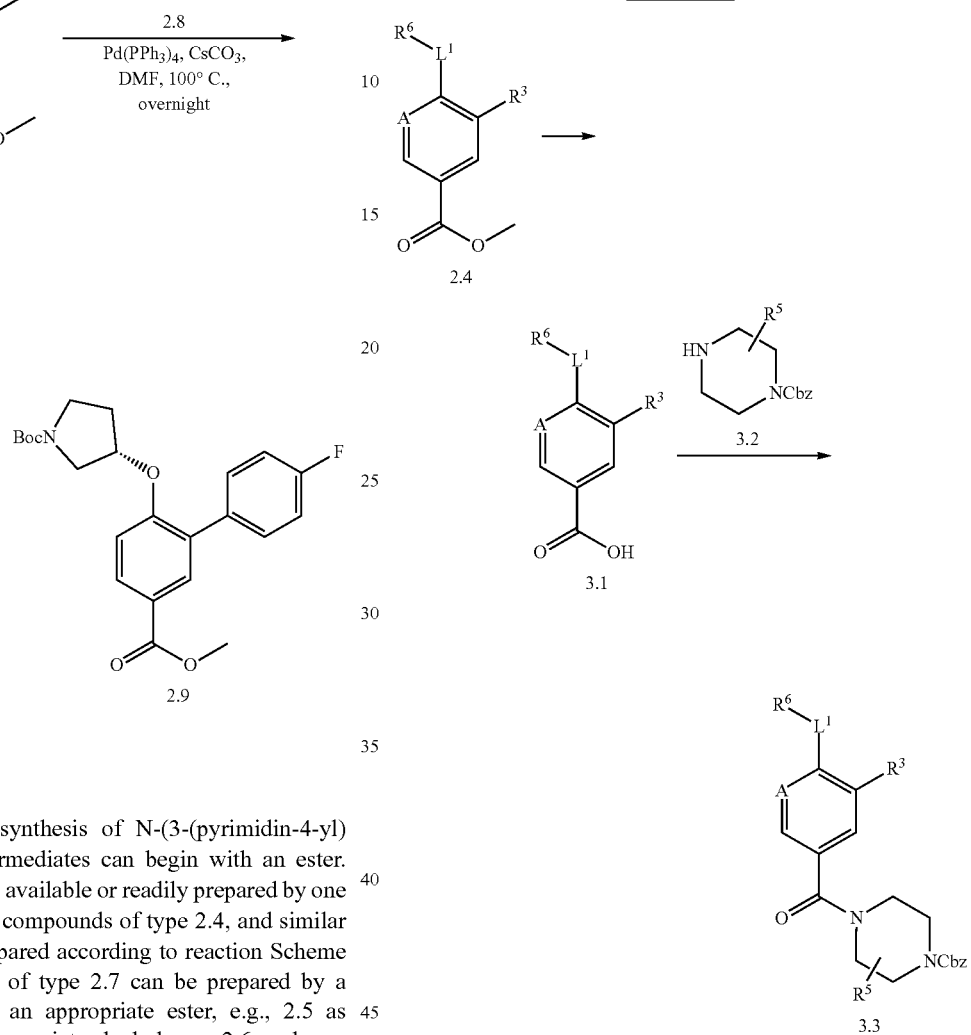

3. Route III

In one aspect, N-(3-(pyrimidin-4-yl)phenyl)acrylamide intermediates can be prepared as shown below.

SCHEME 3A.

In one aspect, the synthesis of N-(3-(pyrimidin-4-yl)phenyl)acrylamide intermediates can begin with an ester. Esters are commercially available or readily prepared by one skilled in the art. Thus, compounds of type 2.4, and similar compounds, can be prepared according to reaction Scheme 3B above. Compounds of type 2.7 can be prepared by a Mitsonobu reaction of an appropriate ester, e.g., 2.5 as shown above, and an appropriate alcohol, e.g., 2.6 as shown above. The Mitsonobu reaction is carried out in the presence of an appropriate electrophile, e.g., diethyl azodicarboxylate (DIAD) as shown above, and an appropriate nucleophile, e.g., triphenylphosphine, in an appropriate solvent, e.g., tetrahydrofuran. Compounds of type 2.9 can be prepared by a coupling reaction of an appropriate halide, e.g., 2.7 as shown above, and an appropriate boride, e.g., 2.8 as shown above. The coupling reaction is carried out in the presence of an appropriate catalyst, e.g., tetrakis(triphenylphosphine) palladium as shown above, and an appropriate base, e.g., cesium carbonate, in an appropriate solvent, e.g., dimethylformamide, at an appropriate temperature, e.g., 100° C. As can be appreciated by one skilled in the art, the above reaction provides an example of a generalized approach wherein compounds similar in structure to the specific reactants above (compounds similar to compounds of type 1.2, 2.1, 2.2, and 2.3), can be substituted in the reaction to provide substituted N-(3-(pyrimidin-4-yl)phenyl)acrylamide intermediates similar to Formula 2.4.

Compounds are represented in generic form, with substituents as noted in compound descriptions elsewhere herein. A more specific example is set forth below.

SCHEME 3B.

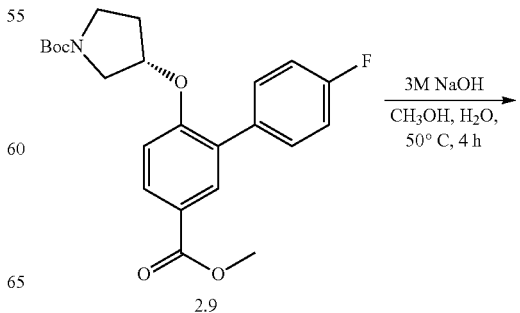

-continued

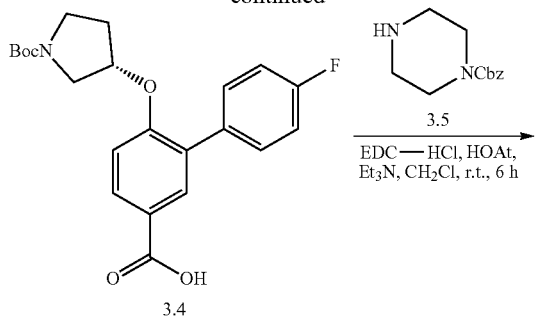

3.4

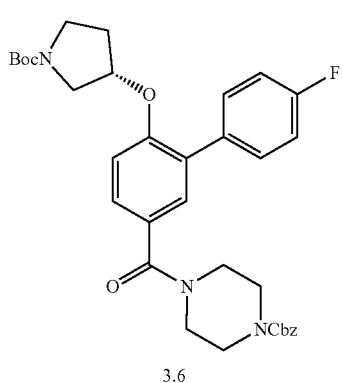

3.6

In one aspect, the synthesis of N-(3-(pyrimidin-4-yl)phenyl)acrylamide intermediates can begin with an ester. Thus, compounds of type 3.3, and similar compounds, can be prepared according to reaction Scheme 3B above. Compounds of type 3.4 can be prepared by reduction of an appropriate ester derivative, e.g., 2.9 as shown above. The reduction is carried out in the presence of an appropriate base, e.g., 3 M sodium hydroxide as shown above, in an appropriate protic solvent, e.g., methanol, at an appropriate temperature, e.g., 50° C., for an appropriate period of time, e.g., 4 hours. Compounds of type 3.6 can be prepared by a coupling reaction of an appropriate carboxylic acid derivative, e.g., 3.4 as shown above, and an appropriate amine, e.g., 3.5 as shown above. The coupling reaction is carried out in the presence of an appropriate coupling agent, e.g., 1-ethyl-3-(3-dimethylaminopropyl)carbodiimide hydrochloride as shown above, an appropriate additive, e.g., 3-hydroxytriazolo[4,5-b]pyridine, and an appropriate base, e.g., triethylamine, in an appropriate solvent, e.g., dichloromethane, at an appropriate temperature, e.g., room temperature, for an appropriate period of time, e.g., 6 hours. As can be appreciated by one skilled in the art, the above reaction provides an example of a generalized approach wherein compounds similar in structure to the specific reactants above (compounds similar to compounds of type 2.4, 3.1, and 3.2), can be substituted in the reaction to provide substituted N-(3-(pyrimidin-4-yl)phenyl)acrylamide intermediates similar to Formula 3.3.

4. Route IV

In one aspect, N-(3-(pyrimidin-4-yl)phenyl)acrylamide intermediates can be prepared as shown below.

SCHEME 4A.

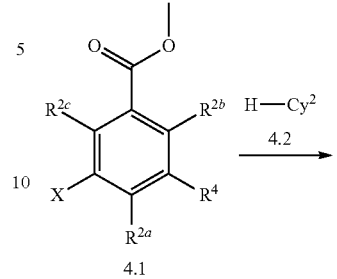

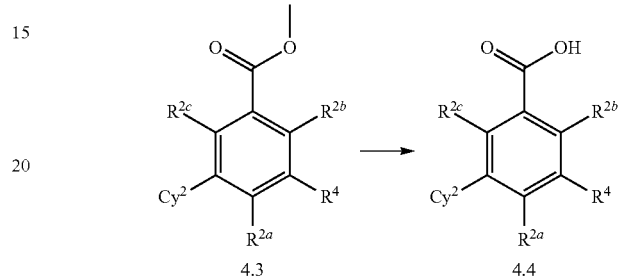

Compounds are represented in generic form, with substituents as noted in compound descriptions elsewhere herein. A more specific example is set forth below.

SCHEME 4B.

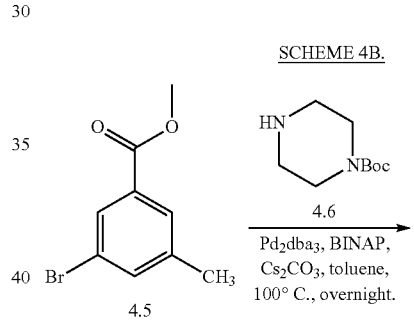

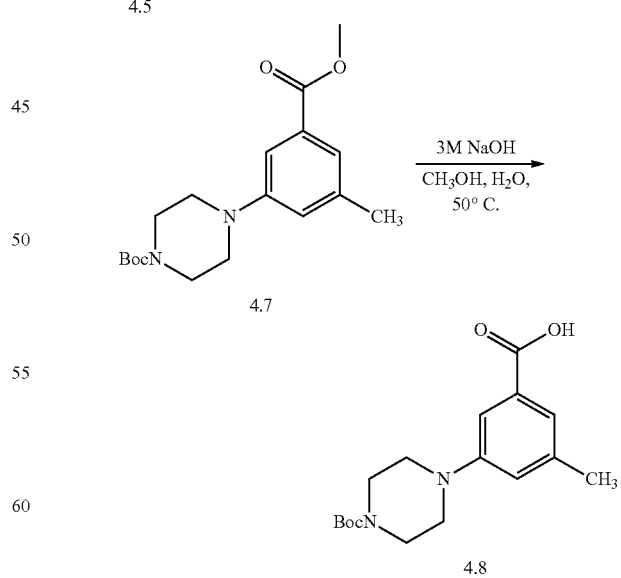

In one aspect, the synthesis of N-(3-(pyrimidin-4-yl)phenyl)acrylamide intermediates can begin with a halide. Thus, compounds of type 4.4, and similar compounds, can be prepared according to reaction Scheme 4B above. Compounds of type 4.7 can be prepared by a coupling reaction of an appropriate halide derivative, e.g., 4.5 as shown above, and an appropriate amine, e.g., 4.6 as shown above. The coupling reaction is carried out in the presence of an appropriate catalyst, e.g., tris(dibenzylideneacetone)palladium as shown above, an appropriate ligand, e.g., 2,2'-bis(diphenylphosphino)-1,1'-binaphthyl (BINAP), and an appropriate base, e.g., cesium carbonate, in an appropriate solvent, e.g., toluene, at an appropriate temperature, e.g., 100° C. Compounds of type 4.8 can be prepared by reduction of an appropriate ester derivative, e.g., 4.7 as shown above. The reduction is carried out in the presence of an appropriate base, e.g., 3 M sodium hydroxide as shown above, in an appropriate protic solvent, e.g., methanol, at an appropriate temperature, e.g., 50° C. As can be appreciated by one skilled in the art, the above reaction provides an example of a generalized approach wherein compounds similar in structure to the specific reactants above (compounds similar to compounds of type 4.1, 4.2, and 4.3), can be substituted in the reaction to provide substituted N-(3-(pyrimidin-4-yl)phenyl)acrylamide intermediates similar to Formula 4.4.

5. Route V

In one aspect, N-(3-(pyrimidin-4-yl)phenyl)acrylamide intermediates can be prepared as shown below.

SCHEME 5A.

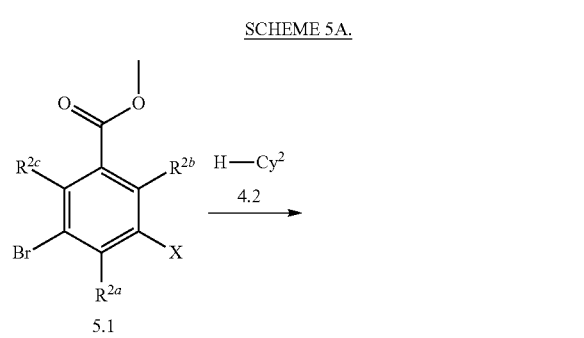

5.1

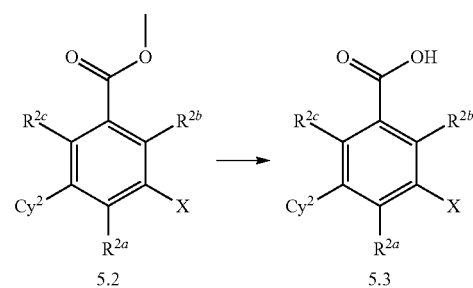

5.2      5.3

Compounds are represented in generic form, with substituents as noted in compound descriptions elsewhere herein. A more specific example is set forth below.

SCHEME 5B.

[Structure 5.4: methyl 3-bromo-5-fluorobenzoate]

5.5 [Boc-piperazinone]

CuI
N,N'-dimethylethylenediamine,
CsF, toluene,
115° C.

[Structure 5.6]

1M NaOH
THF:MeOH
0° C. to r.t.

[Structure 5.7]

In one aspect, the synthesis of N-(3-(pyrimidin-4-yl)phenyl)acrylamide intermediates can begin with a halide. Thus, compounds of type 5.3, and similar compounds, can be prepared according to reaction Scheme 5B above. Compounds of type 5.6 can be prepared by a coupling reaction of an appropriate halide derivative, e.g., 5.4 as shown above, and an appropriate amine, e.g., 5.5 as shown above. The coupling reaction is carried out in the presence of an appropriate catalyst, e.g., copper iodide as shown above, an appropriate ligand, e.g., N,N'-dimethylethylenediamine, and an appropriate salt, e.g., cesium fluoride, in an appropriate solvent, e.g., toluene, at an appropriate temperature, e.g., 115° C. Compounds of type 5.7 can be prepared by reduction of an appropriate ester derivative, e.g., 5.6 as shown above. The reduction is carried out in the presence of an appropriate base, e.g., 1 M sodium hydroxide as shown above, in an appropriate solvent(s), e.g., tetrahydrofuran and methanol. As can be appreciated by one skilled in the art, the above reaction provides an example of a generalized approach wherein compounds similar in structure to the specific reactants above (compounds similar to compounds of type 4.2, 5.1, and 5.2), can be substituted in the reaction to provide substituted of N-(3-(pyrimidin-4-yl)phenyl)acrylamide intermediates similar to Formula 5.3.

6. Route VI

In one aspect, N-(3-(pyrimidin-4-yl)phenyl)acrylamide intermediates can be prepared as shown below.

SCHEME 6A.

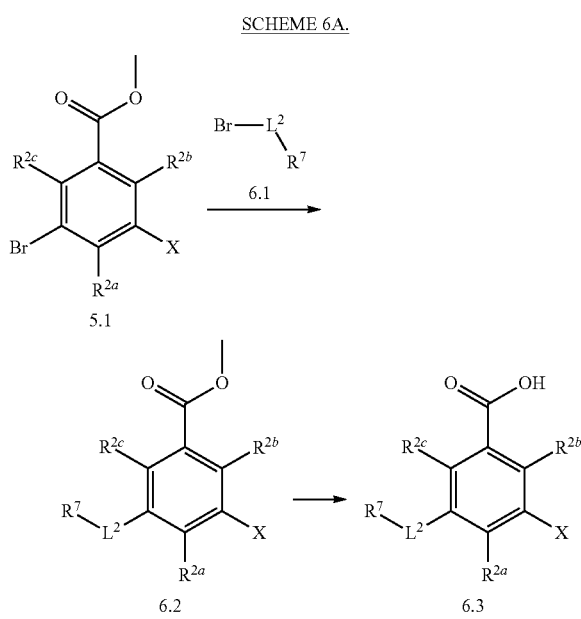

Compounds are represented in generic form, with substituents as noted in compound descriptions elsewhere herein. A more specific example is set forth below.

SCHEME 6B.

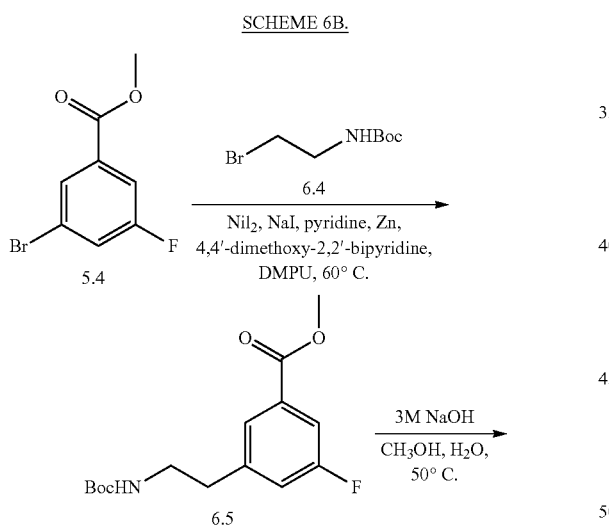

In one aspect, the synthesis of N-(3-(pyrimidin-4-yl) phenyl)acrylamide intermediates can begin with a halide. Thus, compounds of type 6.5, and similar compounds, can be prepared according to reaction Scheme 6B above. Compounds of type 6.5 can be prepared by a coupling reaction of an appropriate halide derivative, e.g., 5.4 as shown above, and an appropriate amine, e.g., 6.4 as shown above. The coupling reaction is carried out in the presence of an appropriate catalyst, e.g., nickel (II) iodide as shown above, an appropriate ligand, e.g., 4,4'-dimethoxy-2,2'-bipyridine, an appropriate metal, e.g., Zn metal, an appropriate salt, e.g., sodium iodide, and an appropriate base, e.g., pyridine, in an appropriate solvent, e.g., 1,3-dimethyl-3,4,5,6-tetrahydro-2 (1H)-pyrimidinone (DMPU), at an appropriate temperature, e.g., 60° C. Compounds of type 6.6 can be prepared by reduction of an appropriate ester derivative, e.g., 6.5 as shown above. The reduction is carried out in the presence of an appropriate base, e.g., 3 M sodium hydroxide as shown above, in an appropriate solvent, e.g., methanol, at an appropriate temperature, e.g., 50° C. As can be appreciated by one skilled in the art, the above reaction provides an example of a generalized approach wherein compounds similar in structure to the specific reactants above (compounds similar to compounds of type 5.1, 6.1, and 6.2), can be substituted in the reaction to provide substituted of N-(3-(pyrimidin-4-yl)phenyl)acrylamide intermediates similar to Formula 6.3.

7. Route VII

In one aspect, N-(3-(pyrimidin-4-yl)phenyl)acrylamide analogs can be prepared as shown below.

SCHEME 7A.

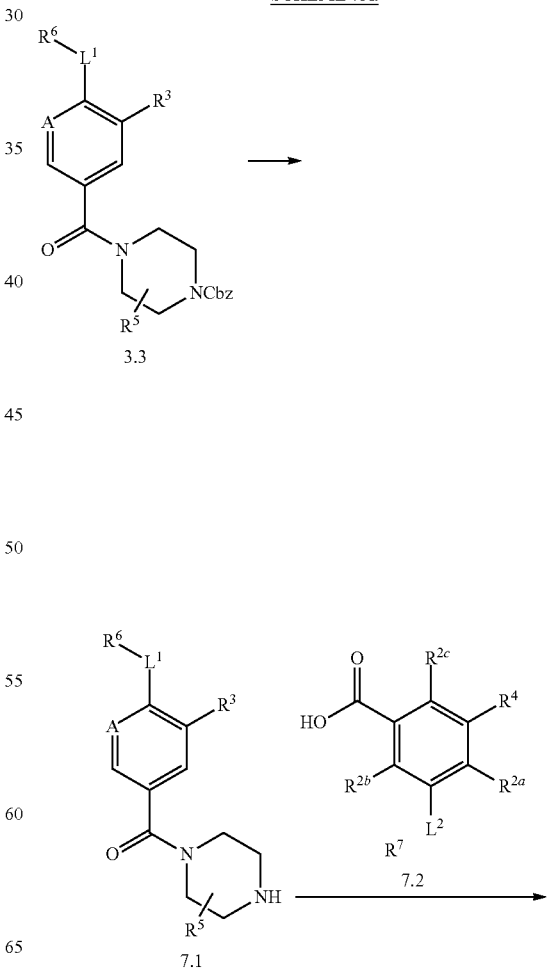

75

-continued

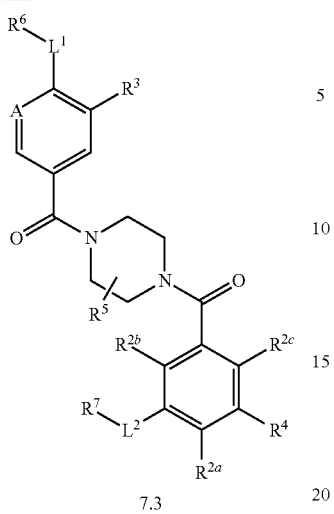

7.3

Compounds are represented in generic form, with substituents as noted in compound descriptions elsewhere herein. A more specific example is set forth below.

SCHEME 7B.

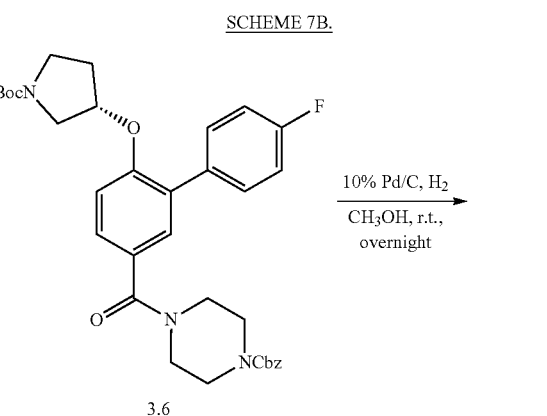

76

-continued

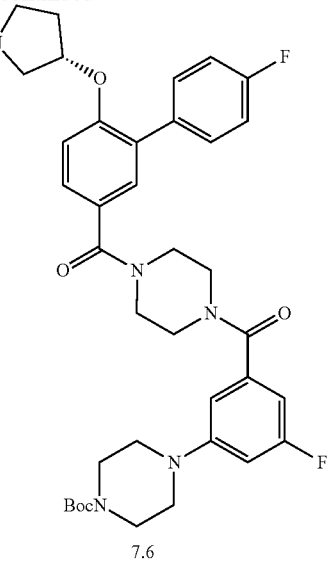

7.6

In one aspect, the synthesis of N-(3-(pyrimidin-4-yl)phenyl)acrylamide analogs can begin with a protected amine. Thus, compounds of type 7.3, and similar compounds, can be prepared according to reaction Scheme 7B above. Compounds of type 7.4 can be prepared by hydrogenation of an appropriate amine, e.g., 3.6 as shown above. The hydrogenation is carried out in the presence of an appropriate catalyst, e.g., 10% palladium on carbon as shown above, and an appropriate hydrogen source, e.g., hydrogen gas, in an appropriate protic solvent, e.g., methanol. Compounds of type 7.6 can be prepared by a coupling reaction of an appropriate amine, e.g., 7.4 as shown above, and an appropriate carboxylic acid, e.g., 7.5 as shown above. The coupling reaction is carried out in the presence of an appropriate coupling agent, e.g., 1-ethyl-3-(3-dimethylaminopropyl)carbodiimide hydrochloride as shown above, an appropriate additive, e.g., 3-hydroxytriazolo[4,5-b]pyridine, and an appropriate base, e.g., triethylamine, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 3.3, 7.1, and 7.2), can be substituted in the reaction to provide substituted N-(3-(pyrimidin-4-yl)phenyl)acrylamide analogs similar to Formula 7.3.

8. Route VIII

In one aspect, N-(3-(pyrimidin-4-yl)phenyl)acrylamide analogs can be prepared as shown below.

SCHEME 8A.

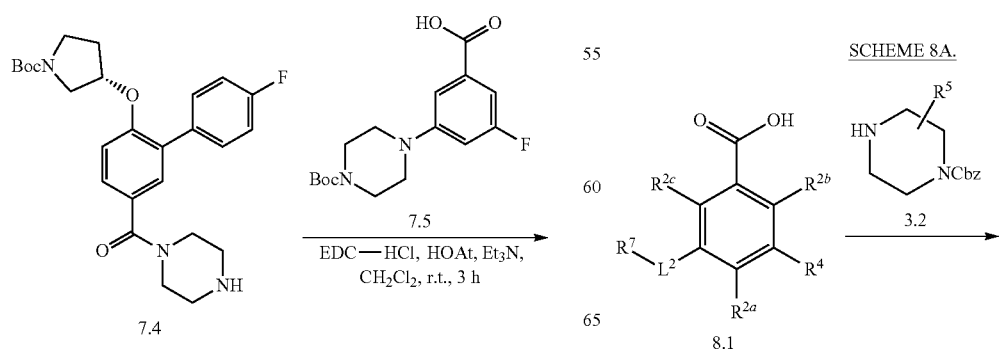

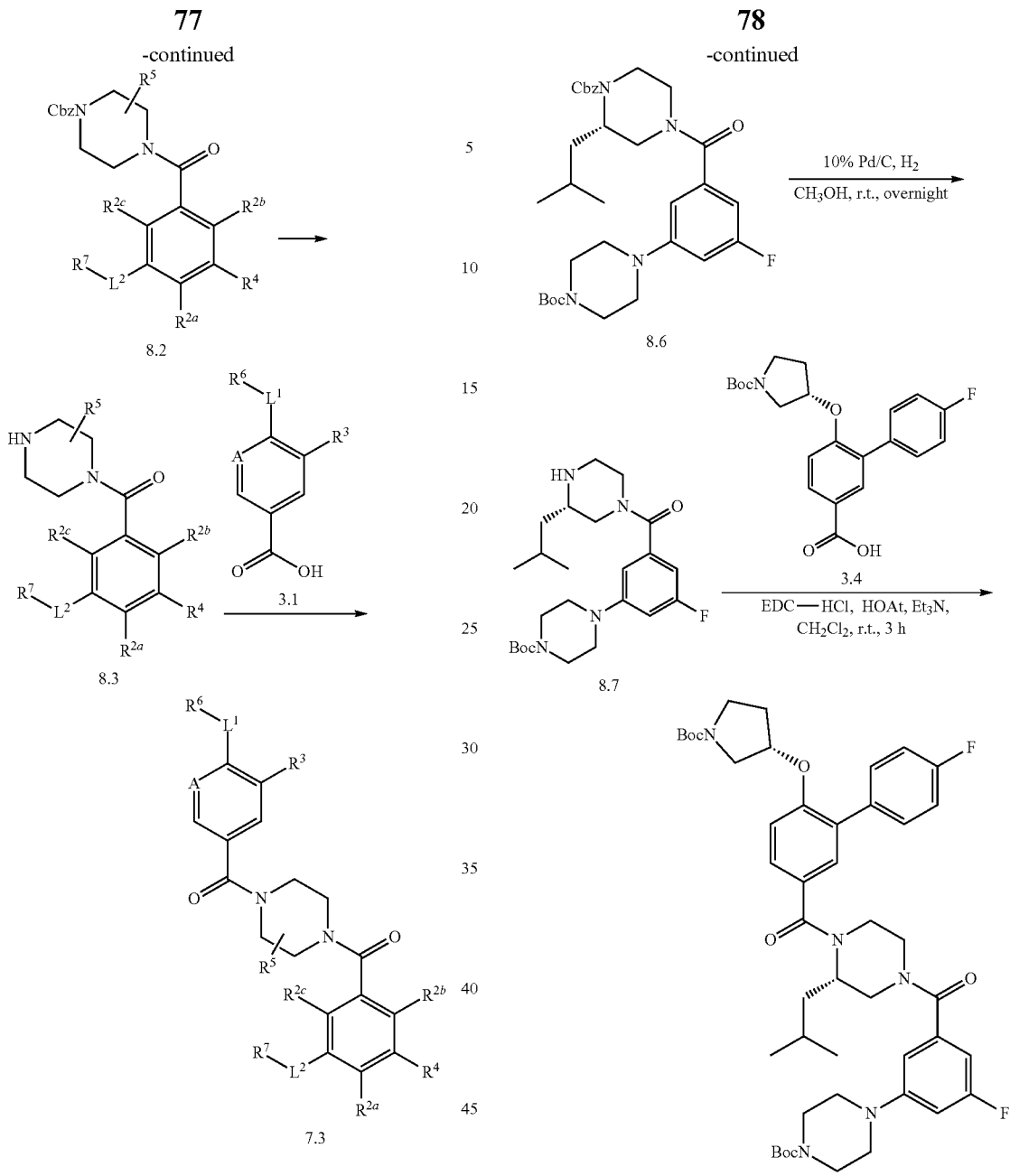

Compounds are represented in generic form, with substituents as noted in compound descriptions elsewhere herein. A more specific example is set forth below.

SCHEME 8B.

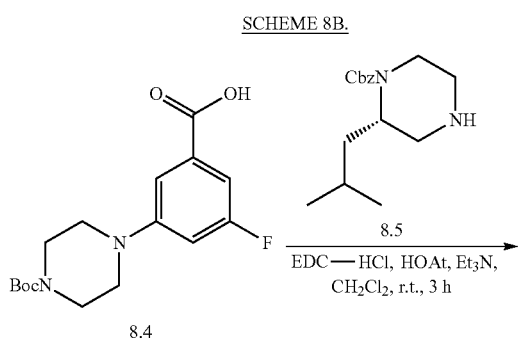

In one aspect, the synthesis of N-(3-(pyrimidin-4-yl)phenyl)acrylamide analogs can begin with a carboxylic acid. Thus, compounds of type 7.3, and similar compounds, can be prepared according to reaction Scheme 7B above. Compounds of type 8.6 can be prepared by a coupling reaction of an appropriate carboxylic acid, e.g., 8.4 as shown above, and an appropriate amine, e.g., 8.5 as shown above. The coupling reaction is carried out in the presence of an appropriate coupling agent, e.g., 1-ethyl-3-(3-dimethylaminopropyl)carbodiimide hydrochloride as shown above, an appropriate additive, e.g., 3-hydroxytriazolo[4,5-b]pyridine, and an appropriate base, e.g., triethylamine, in an appropriate solvent, e.g., dichloromethane, for an appropriate period of time, e.g., 3 hours. Compounds of type 8.7 can be prepared by hydrogenation of an appropriate amine, e.g., 8.6 as shown above. The hydrogenation is carried out in the presence of an appropriate catalyst, e.g., 10% palladium on carbon as shown above, and an appropriate hydrogen source, e.g., hydrogen gas, in an appropriate protic solvent, e.g., methanol. Compounds of type 8.8 can be prepared by a coupling reaction of an appropriate amine, e.g., 3.4 as shown above, and an appropriate carboxylic acid, e.g., 3.4 as shown above. The coupling reaction is carried out in the presence of an appropriate coupling agent, e.g., 1-ethyl-3-(3-dimethylaminopropyl)carbodiimide hydrochloride as shown above, an appropriate additive, e.g., 3-hydroxytriazolo[4,5-b]pyridine, and an appropriate base, e.g., triethylamine, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 3.1, 3.2, 8.1, 8.2, and 8.3), can be substituted in the reaction to provide substituted N-(3-(pyrimidin-4-yl)phenyl)acrylamide analogs similar to Formula 7.3.

9. Route IX

In one aspect, N-(3-(pyrimidin-4-yl)phenyl)acrylamide analogs can be prepared as shown below.

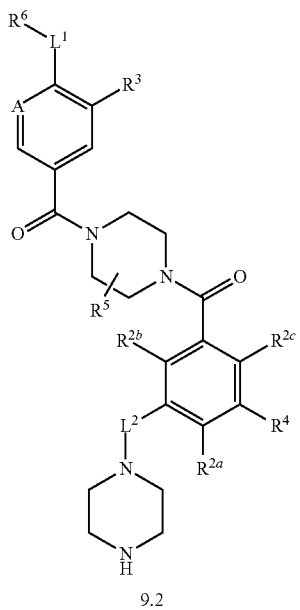

Compounds are represented in generic form, with substituents as noted in compound descriptions elsewhere herein. A more specific example is set forth below.

SCHEME 9A.

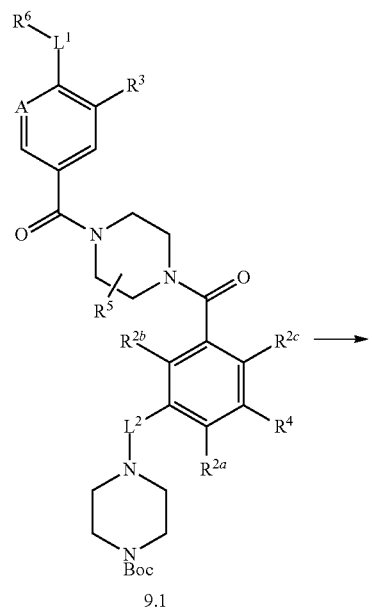

SCHEME 9B.

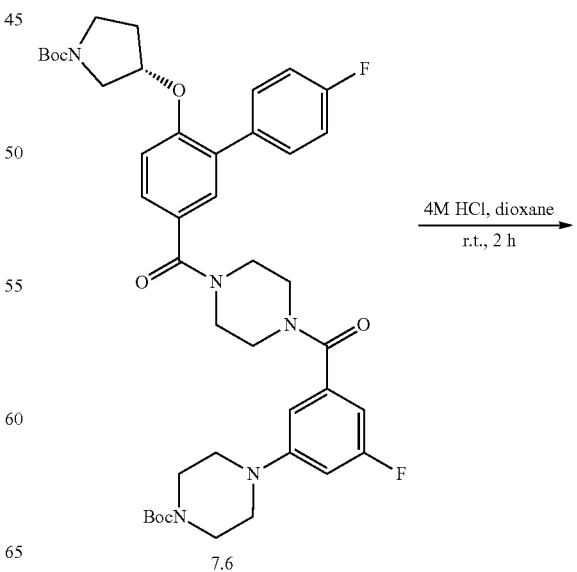

-continued

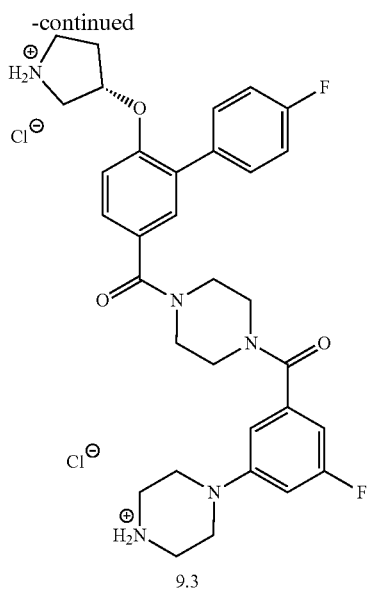

9.3

In one aspect, the synthesis of N-(3-(pyrimidin-4-yl) phenyl)acrylamide analogs can begin with a protected amine. Thus, compounds of type 9.2, and similar compounds, can be prepared according to reaction Scheme 9B above. Compounds of type 9.3 can be prepared by deprotection of an appropriate amine derivative, e.g., 7.6 as shown above. The deprotection is carried out in the presence of an appropriate acid, e.g., 4 M hydrochloric acid, in an appropriate solvent, e.g., dioxane, for an appropriate period of time, e.g., 2 hours. As can be appreciated by one skilled in the art, the above reaction provides an example of a generalized approach wherein compounds similar in structure to the specific reactants above (compounds similar to compounds of type 9.1), can be substituted in the reaction to provide substituted N-(3-(pyrimidin-4-yl)phenyl)acrylamide analogs similar to Formula 9.2.

E. METHODS OF USING THE COMPOUNDS AND COMPOSITIONS

The pharmaceutical compositions and methods of the present invention can further comprise other therapeutically active compounds as noted herein which are usually applied in the treatment of the above mentioned pathological conditions.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

1. Treatment Methods

The compounds disclosed herein are useful for treating, preventing, ameliorating, controlling or reducing the risk of a variety of disorders wherein the patient or subject would benefit from inhibition or negative modulation of β-catenin/BCL9 protein-protein interaction. In one aspect, a treatment can include selective inhibition of β-catenin/BCL9 protein-protein interaction to an extent effective to effect downregulation of Wnt pathway signaling activity. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which β-catenin/BCL9 protein-protein interaction inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a disorder characterized by fibrosis, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein β-catenin/BCL9 protein-protein interaction inhibition would be predicted to have a therapeutic effect, such as disorders of uncontrolled cellular proliferation (e.g. tumors and cancers) and disorders characterized by fibrosis (e.g. polycystic kidney disease), by administering one or more disclosed compounds or products.

The compounds disclosed herein are useful for treating, preventing, ameliorating, controlling or reducing the risk of a variety of disorders of uncontrolled cellular proliferation. In one aspect, the disorder of uncontrolled cellular proliferation is associated with dysregulation of the Wnt signaling pathway. In a further aspect, the Wnt signaling pathway dysregulation is associated with a β-catenin/BCL9 protein-protein interaction dysfunction.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders associated with β-catenin/BCL9 protein-protein interaction dysfunction include a disorder of uncontrolled cellular proliferation. In a still further aspect, the disorder is cancer. In yet a further aspect, the cancer is a sarcoma. In an even further aspect, the cancer is a carcinoma. In a still further aspect, the cancer is a hematological cancer. In a yet further aspect, the cancer is a solid tumor.

It is understood that cancer refers to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopericytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from a ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopericytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In a further aspect, the cancer is treatment-resistant. In a still further aspect, the cancer is resistant to treatment with the at least one chemotherapeutic agent. In yet a further aspect, the cancer is resistant to treatment with the at least one hormone therapy agent.

In various aspects, disorders associated with a β-catenin/BCL9 protein-protein interaction dysfunction include disorders characterized by fibrosis. In a further aspect, the fibrotic disease is selected from pulmonary fibrosis, liver fibrosis, and polycystic kidney disease.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a β-catenin/BCL9 protein-protein interaction inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Adminstration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1;1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents. In a further aspect, the anti-cancer therapeutic agent is selected from 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225 Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™ Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™ Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Oraprel®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™ Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject compounds can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225 Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™ Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™ Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In another aspect, the subject compound can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225 Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™ Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™ Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In the treatment of conditions which require inhibition or negative modulation of β-catenin/BCL9 protein-protein interaction, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating β-catenin/BCL9 protein-protein interaction in at least one cell, comprising the step of contacting the at least one cell with at least one compound of the invention, in an amount effective to negatively modulate β-catenin/BCL9 protein-protein interaction in the at least one cell. In a further aspect, the cell is mammalian, for example human. In a further aspect, the cell has been isolated from a subject prior to the contacting step. In a further aspect, contacting is via administration to a subject.

In various aspects, disclosed are methods for the treatment of a disorder of uncontrolled cellular proliferation associated with a β-catenin/BCL9 dysfunction in a mammal comprising the step of administering to the mammal an effective amount of at least one disclosed compound, or a disclosed pharmaceutical composition.

Also disclosed are methods for the treatment of a disorder of uncontrolled cellular proliferation associated with a β-catenin/BCL9 protein-protein interaction dysfunction in a mammal comprising the step of administering to the mammal an effective amount of at least one disclosed compound, or a disclosed pharmaceutical composition.

Also disclosed are methods for inhibiting β-catenin/BCL9 protein-protein interactions in a mammal comprising the step of administering to the mammal an effective amount of at least one disclosed compound, or a disclosed pharmaceutical composition.

Also disclosed are methods for down-regulation of the Wnt pathway in a mammal comprising the step of administering to the mammal an effective amount of at least one disclosed compound, or a disclosed pharmaceutical composition.

Also disclosed are methods for inhibiting protein-protein interactions of β-catenin and BCL9 in a mammal comprising the step of administering to the mammal an effective amount of at least disclosed one compound, or a pharmaceutically acceptable salt thereof, or an effective amount of a disclosed pharmaceutical composition.

In a further aspect, the effective amount is a therapeutically effective amount. In a still further aspect, the effective amount is a prophylactically effective amount.

In a further aspect, the mammal is a human. In a still further aspect, the mammal has been diagnosed with a need for treatment of the disorder prior to the administering step. In yet a further aspect, the mammal has been diagnosed with a need for inhibiting protein-protein interactions of β-catenin and BCL9 activity prior to the administering step. In an even further aspect, the method further comprises the step of identifying a mammal in need of treatment of the disorder. In a still further aspect, the method further comprises the step of identifying a mammal in need for inhibiting protein-protein interactions of β-catenin and BCL9. In yet a further aspect, inhibiting protein-protein interactions of β-catenin and BCL9 is associated with treating a cancer.

In a further aspect, the mammal is human; and wherein the human has been identified to have a 1q21 chromosomal abnormality.

In a further aspect, the mammal is human; and wherein the step of identifying the human in need of treatment of the disorder comprises the steps of: (a) obtaining a sample from the human; wherein the sample comprises cells suspected of being associated with the disorder of uncontrolled cellular proliferation; (b) determining if the sample comprises cells with a 1q21 chromosomal abnormality; and (c) administering to the human the compound when the sample is positive for a 1q21 chromosomal abnormality.

Also disclosed are methods for inhibiting β-catenin/BCL9 protein-protein interactions in at least one cell comprising the step comprising the step of contacting the cell with an effective amount of at least one disclosed compound or a disclosed pharmaceutical composition.

In a further aspect, the cell is mammalian. In a still further aspect, the cell is human. In yet a further aspect, the cell has been isolated from a mammal prior to the contacting step. In an even further aspect, contacting is via administration to a mammal. In a still further aspect, the mammal has been diagnosed with a need for inhibiting protein-protein interactions of β-catenin and BCL9 prior to the administering step. In yet a further aspect, the mammal has been diagnosed with a need for treatment of a disorder related to protein-protein interactions of β-catenin and BCL9 prior to the administering step. In an even further aspect, the disorder is a disorder of uncontrolled cellular proliferation. In a still further aspect, the disorder of uncontrolled cellular proliferation is a cancer.

2. Manufacture of a Medicament

In one aspect, the invention relates to a method for the manufacture of a medicament for inhibition of β-catenin/BCL9 protein-protein interaction in a mammal comprising combining a therapeutically effective amount of a disclosed compound or product of a disclosed method with a pharmaceutically acceptable carrier or diluent. In a further aspect, the invention relates to a method for the manufacture of a medicament for inhibition of the Wnt signaling pathway in a mammal comprising combining a therapeutically effective amount of a disclosed compound or product of a disclosed method with a pharmaceutically acceptable carrier or diluent.

3. Use of Compounds

In one aspect, the invention relates to the use of a disclosed compound or a disclosed pharmaceutical composition.

In a further aspect, the invention relates to the use of at least one disclosed compound for inhibiting β-catenin/BCL9 activity.

In a further aspect, the invention relates to the use of at least one disclosed compound for administration to a subject; wherein the subject has a disorder of uncontrolled cellular proliferation.

In a further aspect, the compound of the use is a disclosed compound or a product of a disclosed method of making a compound.

In a still further aspect, the use is therapeutic treatment of a mammal. In a yet further aspect, the mammal is human.

In a further aspect, the use is inhibition of β-catenin/BCL9 protein-protein interactions. In a still further aspect, the use is inhibition of the Wnt signaling pathway. In a still further aspect, the need for inhibition of β-catenin/BCL9 protein-protein interactions is associated with treatment of a disorder of uncontrolled cellular proliferation. In a yet further aspect, inhibition of the Wnt signaling pathway treats a disorder of uncontrolled cellular proliferation.

In a further aspect, the disorder of uncontrolled cellular proliferation is a cancer. In an even further aspect, cancer is a leukemia. In a still further aspect, the cancer is a myeloma. In a yet further aspect, cancer is a solid tumor. In an even further aspect, the cancer is a lymphoma.

In a further aspect, the cancer is selected from the cancer is selected from cancers of the blood, brain, prostate, genitourinary tract, gastrointestinal tract, colon, rectum, breast, livery, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspect, the cancer is a cancer of the liver. In a still further aspect, the cancer is a cancer of the prostate. In a yet further aspect, the cancer is a cancer of the colon or rectum.

In a further aspect, the disorder is characterized by fibrosis. In a yet further aspect, the fibrotic disorder is selected from pulmonary fibrosis, liver fibrosis, and polycystic kidney disease.

4. Kits

In one aspect, the invention relates to a kit comprising at least one disclosed compound, or a disclosed pharmaceutical composition, and one or more of.
  (a) at least one agent known to increase BCL9 activity;
  (b) at least one agent known to increase β-catenin activity;
  (c) at least one agent known to decrease BCL9 activity;
  (d) at least one agent known to decrease β-catenin activity;
  (e) at least one agent known to treat a disease of uncontrolled cellular proliferation;
  (f) instructions for treating a disorder associated uncontrolled cellular proliferation; or
  (g) instructions for treating a disorder associated with a β-catenin/BCL9 dysfunction.

In a further aspect, the compound of the kit is a disclosed compound or a product of a disclosed method of making a compound.

In a further aspect, the at least one compound and the at least one agent are co-formulated. In a still further aspect, the at least one compound or the at least one product and the at least one agent are co-packaged.

In a further aspect, the at least one agent is a hormone therapy agent. In a yet further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a yet further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, sirolimus, and temsirolimus, or a pharmaceutically acceptable salt, hydrate, solvate, or polymorph thereof.

In a further aspect, the disorder of uncontrolled cellular proliferation is associated with a β-catenin/BCL9 protein-protein interaction dysfunction. In a still further aspect, the disorder of uncontrolled cellular proliferation is a cancer. In an even further aspect, cancer is a leukemia. In a still further aspect, the cancer is a sarcoma. In a yet further aspect, cancer is a solid tumor. In an even further aspect, the cancer is a lymphoma. In a still further aspect, the cancer is selected from chronic lymphocytic leukemia, small lymphocytic lymphoma, B-cell non-Hodgkin lymphoma, and large B-cell lymphoma. In a yet further aspect, the cancer is selected from cancers of the blood, brain, genitourinary tract, gastrointestinal tract, colon, rectum, breast, livery, kidney, lymphatic system, stomach, lung, pancreas, and skin. In an even further aspect, the cancer is selected from a cancer of the lung and liver. In a still further aspect, the cancer is selected from a cancer of the breast, ovary, testes and prostate. In a yet further aspect, the cancer is a cancer of the breast. In various aspect, the cancer is a cancer of the ovary. In a still further aspect, the cancer is a cancer of the prostate. In a yet further aspect, the cancer is a cancer of the testes.

In a further aspect, the instructions further comprise providing the compound in connection with a surgical procedure. In a still further aspect, the instructions provide that surgery is performed prior to the administering of at least one compound. In yet a further aspect, the instructions provide that surgery is performed after the administering of at least one compound. In an even further aspect, the instructions provide that the administering of at least one compound is to effect presurgical debulking of a tumor. In a still further aspect, the instructions provide that the administering of at least one compound is to effect presurgical debulking of a tumor.

In a further aspect, the instructions further comprise providing the compound in connection with radiotherapy. In a still further aspect, the instructions provide that radiotherapy is performed prior to the administering of at least one compound. In yet a further aspect, the instructions provide that radiotherapy is performed after the step of the administering of at least one compound. In an even further aspect, the instructions provide that radiotherapy is performed at about the same time as the step of the administering of at least one compound.

In a further aspect, the instructions further comprise providing the compound in connection with at least one agent that is a chemotherapeutic agent.

5. Non-Medical Uses

Also provided are the uses of the disclosed compounds and products as pharmacological tools in the development and standardization of in vitro and in vivo test systems for the evaluation of the effects of inhibitors of β-catenin/BCL9 protein-protein interactions in laboratory animals such as cats, dogs, rabbits, monkeys, rats and mice, as part of the search for new therapeutic agents that inhibit β-catenin/BCL9 protein-protein interactions.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Chemistry Methods, Reagents, and Materials

All reagents were purchased from Aldrich and Acros Organics and used without further purification unless stated otherwise. Organic solution was concentrated under reduced pressure on a Büchi rotary evaporator using an isopropyl alcohol-dry ice bath. Thin-layer chromatography (TLC) was carried out on 0.25 mm pre-coated silica gel 60 F254 plates (SiliCycle Inc. Candida), and the compounds were visualized with a UV-visible lamp at 254 nM. Further visualization was achieved by staining with iodine. Column chromatography was performed with SilicaFlash@ F60 (230-400 mesh) and commercial solvents. H NMR and $^{13}$C NMR spectra were recorded on a Varian VXR-500 (500 MHz), a Varian Inova-400 (400 MHz), or a Varian Unity-300 (300 MHz) spectrometer (125.7 MHz, 100 MHz, and 75 MHz for $^{13}$C NMR spectra, respectively) in CDCl$_3$, d$^4$-methanol and D$_2$O. Chemical shifts were reported as values in parts per million (ppm), and the reference resonance peaks were set at 7.26 ppm (CHCl$_3$), 3.31 ppm (CD$_2$HOD), and 4.80 ppm (HOD) for the $^1$H NMR spectra and 77.23 ppm (CDCl$_3$) and 49.00 ppm (CD$_3$OD) for the $^{13}$C NMR spectra. Low-resolution (LRMS) were determined on a Micromass Quattro II mass spectrometer with an ESI source. High-resolution mass spectra (HRMS) was recorded on Waters LCT Premier XE TOF with Acquity Classic UPLC.

2. Preparation of Compound 27

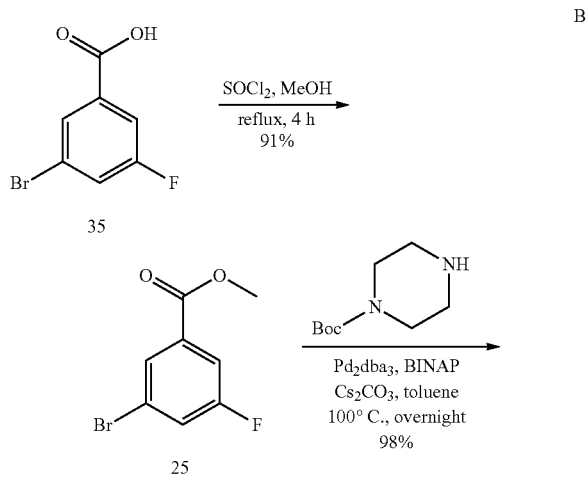

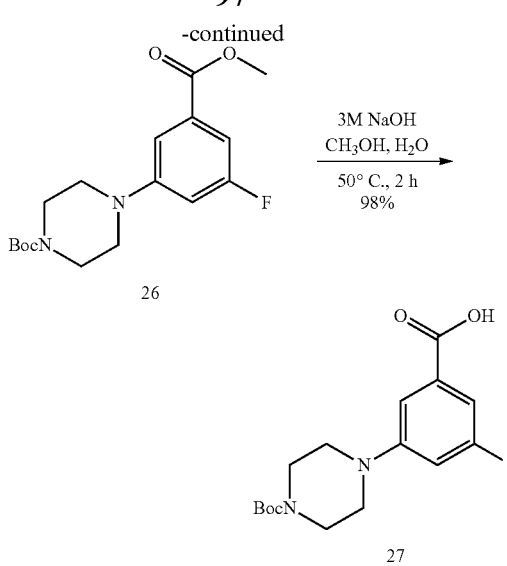

Hz), 154.60, 152.50 (d, J=9.8 Hz), 132.40 (d, J=9.6 Hz), 112.62 (d, J=2.3 Hz), 107.17 (d, J=23.8 Hz), 107.04 (d, J=25.3 Hz), 80.12, 52.35, 48.51, 28.39.

c. Preparation of 3-(4-(tert-butoxycarbonyl)piperazin-1-yl)-5-fluorobenzoic Acid (27)

The synthesis of compound 27 followed the same procedure as for compound 32 to afford white solid (0.0779 g, 98% yield). $^1$H NMR (300 MHz, CD$_3$OD): δ ppm 7.41 (s, 1H), 7.12 (d, 1H, J=8.6 Hz), 6.92 (td, 1H, J=2.1, 11.9 Hz), 3.57 (t, 4H, J=5.0 Hz), 3.21 (t, 4H, J=5.1 Hz), 1.48 (s, 9H). $^{13}$C NMR (125 MHz, CDCl$_3$): δ ppm 170.67, 163.43 (d, J=245.0 Hz), 154.71, 152.47 (d, J=9.8 Hz), 131.68 (d, J=10.0 Hz), 113.08 (d, J=2.1 Hz), 107.79 (d, J=25.6 Hz), 107.72 (d, J=23.9 Hz), 80.34, 48.48, 28.38.

3. Preparation of Compound 2 a. Preparation of Methyl 3-bromo-5-fluorobenzoate (25)

To an ice cold stirred solution of 3-bromo-5-fluorobenzoic acid (4.13 g, 18.9 mmol) in anhydrous methanol (40 mL) was added thionyl chloride (2.05 mL, 28.2 mmol) dropwise. The reaction mixture was allowed to stir for 15 min and then heated to reflux. Upon completion (1 h) the solvent was removed under reduced pressure, and the residue was taken into EtOAc (150 mL). The organic solution was washed with water (2×150 mL), brine (150 mL) and dried over MgSO$_4$. The solids were filtered, and solvent removed under reduced pressure to yield compound 25 (4.00 g, 91% yield) as brown liquid. $^1$H NMR (300 MHz, CDCl$_3$): δ ppm 7.95-7.93 (m, 1H), 7.64 (ddd, 1H, J=1.4, 2.4, 8.8 Hz), 7.41 (td, 1H, J=2.1, 7.8 Hz), 3.92 (s, 3H). $^{13}$C NMR (75 MHz, CDCl$_3$): δ ppm 164.59 (d, J=3.1 Hz), 162.25 (d, J=251.9 Hz), 133.36 (d, J=8.0 Hz), 128.54 (d, J=3.3 Hz), 123.38 (d, J=24.5 Hz), 122.60 (d, J=9.2 Hz), 115.48 (d, J=23.1 Hz), 52.66.

b. Preparation of tert-Butyl 4-(3-fluoro-5-(methoxycarbonyl)phenyl)piperazine-1-carboxylate (26)

To a solution of 25 (0.117 g, 0.432 mmol) in dry toluene (25 mL) under anhydrous conditions was added N-Boc-piperazine (0.109 g, 0.585 mmol), tris (dibenzylideneacetone) dipalladium (0) (Pd$_2$(dba)$_3$) (0.0217 g, 0.0237 mmol), 2,2'-bis (diphenylphosphino)-1,1'-binapthyl (BINAP) (0.0551 g, 0.0886 mmol) and Cs$_2$CO$_3$ (0.1981 g, 0.608 mmol). The mixture was heated to 90° C. in a pressurized flask and stirred for 20 h. The solvent was then removed under reduced pressure, and the residue was taken into EtOAc (100 mL). The organic solution was washed with water (2×50 mL) and brine (50 mL), dried over MgSO$_4$, solids filtered, and solvent removed under reduced pressure. The residue was purified by column chromatography (silica gel, hexanes:EtOAc=9:1) to yield 26 (0.143 g, 98% yield) as white solid. $^1$H NMR (300 MHz, CDCl$_3$): δ ppm 7.37 (dd, 1H, J=1.3, 2.3 Hz), 7.18 (ddd, 1H, J=1.3, 2.3, 8.6 Hz), 6.75 (td, 1H, J=2.4, 11.6 Hz), 3.90 (s, 3H), 3.58 (t, 4H, J=5.1 Hz), 3.19 (t, 4H, J=5.1 Hz), 1.48 (s, 9H). $^{13}$C NMR (125 MHz, CDCl$_3$): δ ppm 166.27 (d, J=3.71 Hz), 163.44 (d, J=244.5

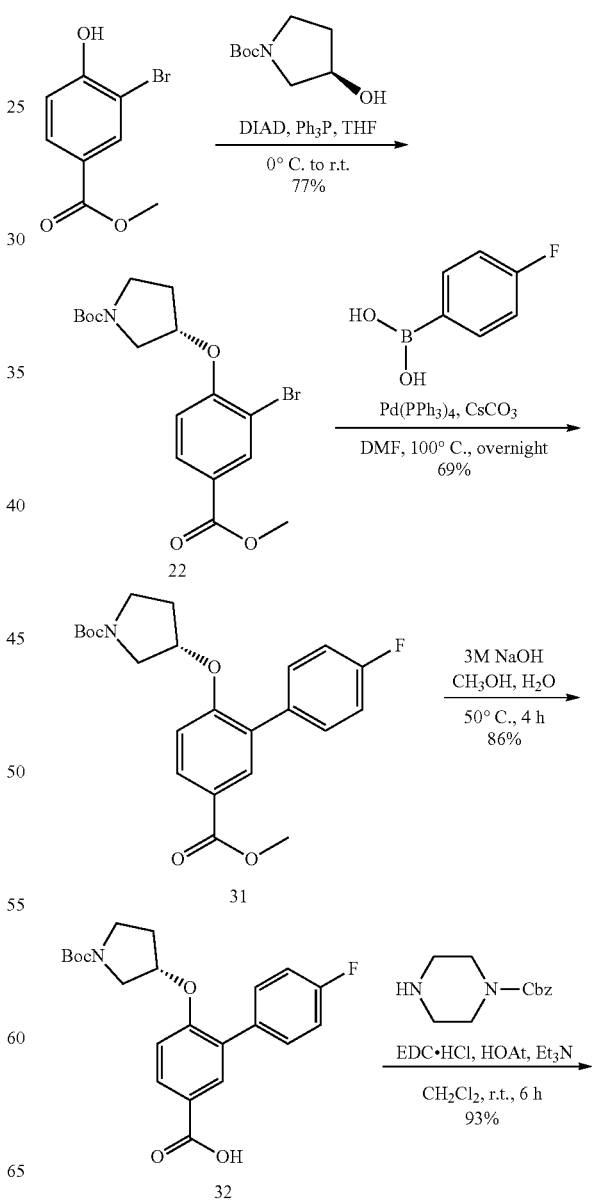

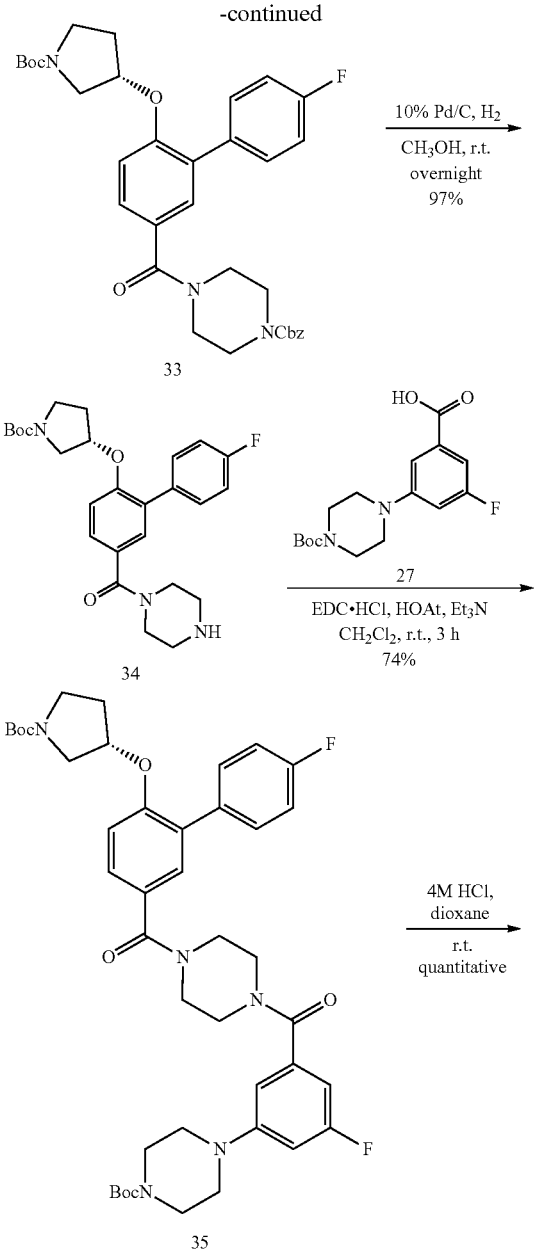

a. Preparation of tert-Butyl (S)-3-(2-bromo-4-(methoxycarbonyl)phenoxy)pyrrolidine-1-carboxylate (22)

To a solution of methyl 3-bromo-4-hydroxybenzoate (0.626 g, 2.70 mmol) in dry THF (35 mL) under anhydrous conditions was added (R)-tert-butyl 3-hydroxypyrrolidine-1-carboxylate (0.505 g, 2.70 mmol) and triphenyl phosphine (1.43 g, 5.39 mmol). The reaction mixture was then cooled in an ice bath, and DIAD (1.12 g, 5.56 mmol) dissolved in THF (10 mL) was added dropwise. The reaction mixture was stirred for 1 h at room temperature under argon. Upon completion the reaction was diluted with ethyl acetate (100 mL). The organic layer was washed with water (2×50 mL), brine (50 mL), dried over MgSO$_4$, solids filtered, and the solvent removed under reduced pressure. The residue was then purified by column chromatography (silica gel, hexa-nes:EtOAc=5:1) to yield 22 (0.837 g, 77% yield) as white solid. $^1$H NMR (500 MHz, CDCl$_3$): δ (ppm 8.22 (s, 1H), 7.93 (d, J=8.0 Hz, 1H), 6.85 (d, J=8.0 Hz, 1H), 5.00-4.98 (m, 1H), 3.88 (s, 3H), 3.63-3.56 (m, 4H), 2.23-2.13 (m, 2H), 1.45 (s, 9H). $^{13}$C NMR (125 MHz, CDCl$_3$): δ (ppm 165.67, 157.47, 143.72, 135.31, 130.41, 124.36, 113.33, 79.76, 79.74, 78.32, 52.29, 51.57, 51.22, 44.25, 43.84, 31.85, 31.02, 28.60. MS (ESI) m/z=400.6 [M+H]$^+$.

b. Preparation of tert-Butyl (S)-3-((4'-fluoro-5-(methoxycarbonyl)-[1,1'-biphenyl]-2-yl)oxy)pyrrolidine-1-carboxylate (31)

To a solution of 22 (1.00 g, 2.50 mmol) in dry DMF (50 mL) under anhydrous conditions was added (4-fluorophenyl) boronic acid (0.574 g, 4.10 mmol), Pd(PPh$_3$)$_4$ (0.254 g, 0.220 mmol), and Cs$_2$CO$_3$ (2.41 g, 7.40 mmol). The mixture was heated to 100° C. under argon and stirred for 20 h. The solvent was then removed under reduced pressure, and the residue was taken into EtOAc (100 mL). The organic solution was washed with water (2×50 mL) and brine (50 mL), dried over MgSO$_4$, solids filtered, and solvent removed under reduced pressure. The residue was purified by column chromatography (silica gel, hexanes:EtOAc=5:1) to yield 31 (0.71 g, 69% yield) as white solid. $^1$H NMR (500 MHz, CDCl$_3$): δ ppm 8.00 (d, 2H, J=6.8 Hz), 7.43 (dd, 2H, J=5.6, 8.2 Hz), 7.08 (t, 2H, J=8.5 Hz), 6.94 (d, 1H, J=9.0 Hz), 4.97-4.95 (m, 1H), 3.90 (s, 3H), 3.66-3.29 (m, 4H), 2.11-2.08 (m, 2H), 1.44 (s, 9H). $^{13}$C NMR (125 MHz, CDCl$_3$): δ ppm 166.77, 163.29, 161.33, 157.67, 154.61, 132.81, 131.17, 131.11, 130.69, 123.46, 115.15, 115.02, 113.14, 112.85, 79.77, 52.16, 51.60, 51.24, 51.23, 51.21, 44.23, 44.21, 44.20, 43.92, 43.89, 31.70, 30.98, 30.97, 28.61. MS (ESI) m/z=416.7 [M+H]$^+$.

c. Preparation of (S)-6-((1-(tert-butoxycarbonyl)pyrrolidin-3-yl)oxy)-4'-fluoro-[1,1'-biphenyl]-3-carboxylic Acid (32)

To a solution of 31 (1.12 g, 2.70 mmol) in MeOH (10 mL) was added 6 M NaOH (10 mL), and the reaction was allowed to stir at room temperature for 6 h. MeOH was then removed under reduced pressure. The remaining aqueous solution was acidified with 12 M HCl to pH=2. The product was extracted with CH$_2$Cl$_2$ (50 mL) and the organics washed with water (2×50 mL), brine (50 mL), dried over MgSO$_4$, solids filtered, and solvent removed under reduced pressure to yield 32 (0.94 g, 86% yield) as white solid. $^1$H NMR (500 MHz, CDCl$_3$): δ ppm 8.07-8.04 (m, 2H), 7.46-7.42 (m, 2H), 7.09 (t, J=8.3 Hz, 2H), 6.97 (d, J=9.5 Hz, 1H), 5.00-4.97 (m, 1H), 3.69-3.30 (m, 4H), 2.14-2.12 (m, 2H), 1.45 (s, 9H). $^{13}$C NMR (125 MHz, CDCl$_3$): δ ppm 171.39, 171.24, 163.33, 161.35, 158.29, 158.22, 154.83, 154.62, 133.41, 133.32, 131.38, 131.17, 131.14, 130.93, 130.87, 122.65, 115.23, 115.09, 114.92, 113.09, 112.75, 79.98, 77.26, 76.48, 51.63, 51.19, 44.26, 43.91, 31.67, 30.92, 28.59.

d. Preparation of Benzyl (S)-4-(6-((1-(tert-butoxycarbonyl)pyrrolidin-3-yl)oxy)-4'-fluoro-[1,1'-biphenyl]-3-carbonyl)piperazine-1-carboxylate (33)

To a solution of 32 (0.681 g, 1.70 mmol) in anhydrous CH$_2$Cl$_2$ (50 mL) was added benzyl piperazine-1-carboxylate (0.374 g, 1.70 mmol), triethylamine (0.8 mL, 6 mmol), EDC-HCl (0.644 g, 3.36 mmol), and HOAt (0.230 g, 1.70 mmol). The mixture was then stirred at room temperature for 4 h. The mixture was diluted with CH$_2$Cl$_2$ (50 mL) and the organic solution was washed with water (2×50 mL), brine (50 mL), dried over MgSO₄, solids filtered, and solvent removed under reduced pressure. The residue was then purified by column chromatography (silica gel, hexanes:EtOAc=3:1) to yield white solid (0.930 g, 93% yield). $^1$H NMR (500 MHz, CDCl₃): δ ppm 7.41-7.29 (m, 9H), 7.08-7.04 (m, 2H), 6.94 (d, 1H, J=6.9 Hz), 5.14 (s, 2H), 4.90-4.88 (m, 1H), 3.65-3.20 (m, 12H), 2.09-2.03 (m, 2H), 1.43 (s, 9H). $^{13}$C NMR (125 MHz, CDCl₃): δ ppm 173.10, 171.02, 170.10, 162.08 (d, J=245.6 Hz), 155.10, 155.02, 154.99, 154.45, 154.27, 136.19, 133.11, 133.01, 131.11, 130.89, 130.86, 130.22, 128.43, 128.20 (d, J=4.8 Hz), 128.08, 127.89, 114.93 (d, J=20.9 Hz), 114.80 (d, J=20.9 Hz), 113.74, 113.46, 79.53, 79.46, 77.14, 76.26, 67.38, 60.26, 51.34, 50.85, 44.05, 43.64, 31.41, 30.64, 28.36, 20.92, 20.57, 14.08.

e. Preparation of tert-Butyl (S)-3-((4'-fluoro-5-(piperazine-1-carbonyl)-[1,1'-biphenyl]-2-yl)oxy)pyrrolidine-1-carboxylate (34)

To a solution of 33 (0.927 g, 0.154 mmol) in MeOH (20 mL) under argon was added 10% Pd on activated carbon (0.012 g). The argon was evacuated and exchanged with H₂ gas three times and the reaction was allowed to stir under H₂ for 3 h. The reaction mixture was filtered through celite, and the solvent removed under reduced pressure to yield 34 (0.699 g, 97% yield) as off-white solid. $^1$H NMR (300 MHz, CDCl₃): δ ppm 7.38-7.30 (m, 4H), 7.01 (t, 2H, J=8.4 Hz), 6.90 (d, 1H, J=8.1 Hz), 4.86-4.83 (m, 1H), 3.61-3.17 (m, 8H), 2.85-2.79 (m, 4H), 2.02-1.98 (m, 2H), 1.37 (s, 9H). $^{13}$C NMR (125 MHz, CDCl₃): δ (ppm 169.77, 161.78 (d, J=247.3 Hz), 154.64, 154.54, 154.32, 154.17, 132.98 (d, J=9.3 Hz), 130.80, 130.70, 130.65, 129.90, 129.86, 128.46, 127.59, 114.64 (d, J=21.7 Hz), 114.53 (d, J=21.3 Hz), 113.61, 113.33, 79.37, 79.30, 76.89, 76.09, 51.16, 50.66, 49.69, 45.72, 43.81, 43.42, 31.12, 30.39, 28.11.

f. Preparation of tert-Butyl (S)-4-(3-(4-(6-((1-(tert-butoxycarbonyl)pyrrolidin-3-yl)oxy)-4'-fluoro-[1,1'-biphenyl]-3-carbonyl)piperazine-1-carbonyl)-5-fluorophenyl)piperazine-1-carboxylate (35)

To a solution of 34 (0.066 g, 0.14 mmol) in anhydrous CH₂Cl₂ (50 mL) was added 27 (0.046 g, 0.14 mmol), triethylamine (0.066 mL, 0.494 mmol), EDC·HCl (0.053 g, 0.28 mmol), and HOAt (0.019 g, 0.14 mmol). The mixture was then stirred at room temperature for 4 h. The mixture was diluted with CH₂Cl₂ (50 mL), and the organic solution was washed with water (2×50 mL), brine (50 mL), dried over MgSO₄, solids filtered, and solvent removed under reduced pressure. The residue was then purified by column chromatography (silica gel, CH₂Cl₂:MeOH=98:2) to yield 35 as white solid (0.0811 g, 74% yield). $^1$H NMR (500 MHz, CD₃OD): δ (ppm 7.46-7.44 (m, 4H), 7.18 (t, 1H, J=6.5 Hz), 7.11 (t, 2H, J=8.8 Hz), 6.91-6.79 (m, 2H), 5.08-5.06 (m, 1H), 3.78-3.40 (m, 16H), 3.21 (t, 4H, J=4.5 Hz), 2.12-2.09 (m, 2H), 1.48 (s, 9H), 1.43 (s, 9H). $^{13}$C NMR (125 MHz, CD₃OD): δ (ppm 172.37, 171.71 (d, J=2.9 Hz), 165.02 (d, J=244.3 Hz), 163.61 (d, J=245.6 Hz), 156.73, 156.44, 156.38 156.32, 154.59 (d, J=10.3 Hz), 138.9 (d, J=9.3 Hz), 134.92, 132.71, 132.46, 132.40, 132.34, 131.40 (d, J=6.7 Hz), 129.44, 129.31 (d, J=15.9 Hz), 115.92 (d, J=21.7 Hz), 115.87 (d, J=21.7 Hz), 115.56, 115.41, 110.89 (d, J=2.2 Hz), 105.16 (d, J=24.1 Hz), 104.95 (d, J=25.7 Hz), 81.48, 81.14, 81.05, 78.59, 78.05, 52.70, 52.20, 49.33, 45.34, 44.98, 40.23, 34.79, 32.22, 31.64, 31.49, 30.13, 28.80, 28.71.

g. Preparation of (S)-(4-(3-fluoro-5-(piperazin-1-yl)benzoyl)piperazin-1-yl) (4'-fluoro-6-(pyrrolidin-3-yloxy)-[1,1'-biphenyl]-3-yl)methanone Hydrochloride (2)

To compound 35 (0.080 g, 0.103 mmol) under anhydrous conditions was added 4 M HCl in dioxane (10 mL), and the mixture was stirred at room temperature for 1 h. The solvent was then removed under reduced pressure. The product was dissolved in DI water (20 mL) and the aqueous layer was washed with ethyl acetate (3×20 mL). The resulting aqueous solution was frozen and lyophilized to yield 2 (0.0664 g, quantitative yield) as white solid. $^1$H NMR (500 MHz, d⁶-DMSO): δ (ppm 9.20 (brs, 2H), 8.99 (brs, 2H), 7.61-7.57 (m, 2H), 7.43 (dd, 1H, J=1.5, 8.5 Hz), 7.37 (s, 1H), 7.24-7.18 (m, 3H), 6.90 (d, 1H, J=12.0 Hz), 6.80 (s, 1H), 6.65 (d, 1H, J=8.0 Hz), 5.18-5.12 (m, 1H), 3.66-3.06 (m, 20H), 2.21-2.13 (m, 1H), 2.07-2.02 (m, 1H); $^{13}$C NMR (125 MHz, CD₃OD): δ (ppm 171.03, 170.27, 163.79 (d, J=244.4 Hz), 162.55 (d, J=243.5 Hz), 155.06, 152.41, 152.33, 138.06, 137.98, 133.58, 131.38, 131.26, 130.48, 128.74, 128.37, 114.95 (d, J=21.3 Hz), 114.10, 110.23, 105.18 (d, J=23.5 Hz), 104.39 (d, J=25.8 Hz), 76.85, 50.62, 48.38-47.36 (m, 4C), 45.58, 44.42, 43.31, 30.95; HRMS (ESI) m/z calculated for C₃₂H₃₅F₂N₅O₃(M+H)⁺=576.2781, found 576.2786.

4. Preparation of Compound 44

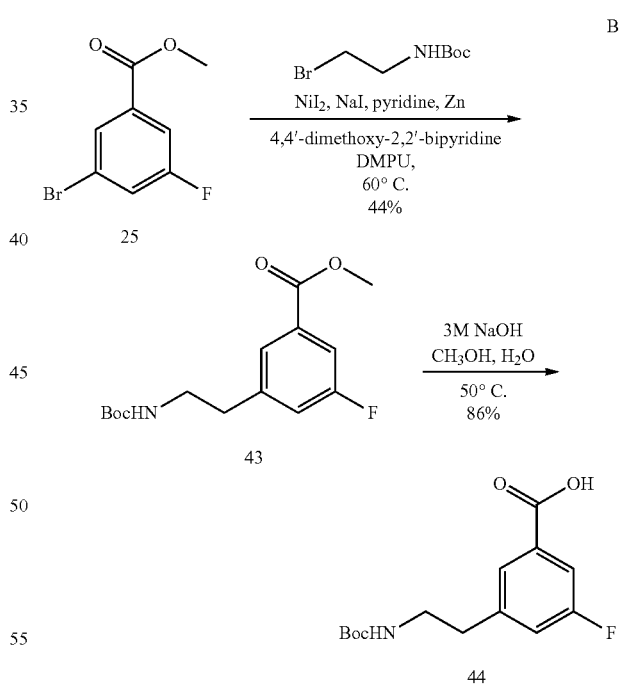

a. Preparation of methyl 3-(2-((tert-butoxycarbonyl)amino)ethyl)-5-fluorobenzoate (43)

To a solution of 25 (1.52 g, 6.52 mmol) in dry DMPU (22 mL) was added NiI₂ (0.176 g, 0.563 mmol), 4,4'-dimethoxy-2,2'-bipyridine (0.125 g, 0.578 mmol), NaI (0.212 g, 1.41 mmol), pyridine (0.06 mL, 0.7 mmol), tert-butyl (2-bromoethyl) carbamate (2.49 g, 11.1 mmol), and zinc (0.734 g, 11.2 mmol). The reaction mixture was stirred and heated to 60° C. for 6 h, then allowed to cool. The reaction mixture was purified directly by column chromatography (silica gel, hexane:EtOAc=4:1) to afford 43 (0.844 g, 44% yield) as white solid. $^1$H NMR (300 MHz, CDCl$_3$): δ (ppm 7.66 (t, 1H, J=1.4 Hz), 7.56 (ddd, 1H, J=1.5, 2.5, 9.0 Hz), 7.12-7.07 (m, 1H), 4.61 (bs, 1H), 3.91 (s, 3H), 3.38 (q, 2H, J=6.6 Hz), 2.84 (t, 2H, J=7.0 Hz), 1.42 (s, 9H). $^{13}$C NMR (75 MHz, CDCl$_3$): δ (ppm 165.92 (d, J=3.1 Hz), 162.54 (d, J=247.1 Hz), 155.74, 141.88 (d, J=7.2 Hz), 132.21 (d, J=8.0 Hz), 125.67 (d, J=2.7 Hz), 120.33 (d, J=21.23 Hz), 114.52 (d, J=23.2 Hz), 79.46, 52.35, 41.41, 35.86, 28.31.

b. Preparation of 3-(2-((tert-butoxycarbonyl)amino)ethyl)-5-fluorobenzoic Acid (44)

To a solution of 43 (0.144 g, 0.484 mmol) in MeOH (10 mL) was added 6 M NaOH (10 mL) and the reaction stirred at room temperature for 6 h. MeOH was then removed under reduced pressure. The remaining aqueous solution was acidified with 12 M HCl to pH=2. The product was then extracted with CH$_2$Cl$_2$ (50 mL) and the organics washed with water (2×50 mL), brine (50 mL), dried over MgSO$_4$, solids filtered, and solvent removed under reduced pressure to yield 44 (0.118 g, 86% yield) as white solid. $^1$H NMR (500 MHz, CD$_3$OD): δ (ppm 7.71 (s, 1H), 7.52 (d, 1H, J=9.0 Hz), 7.21 (d, 1H, J=9.2 Hz), 3.39 (t, 2H, J=7.0 Hz), 2.83 (t, 2H, J=7.0 Hz), 1.39 (s, 9H). $^{13}$C NMR (125 MHz, CD$_3$OD): δ (ppm 168.54 (d, J=2.5 Hz), 163.99 (d, J=245.2 Hz), 158.42, 144.04 (d, J=7.5 Hz), 134.22 (d, J=8.1 Hz), 127.31 (d, J=2.4 Hz), 121.27 (d, J=21.5 Hz), 115.12 (d, J=23.2 Hz), 80.08, 42.45, 36.75, 28.76.

5. Preparation of Compounds 3 and 4

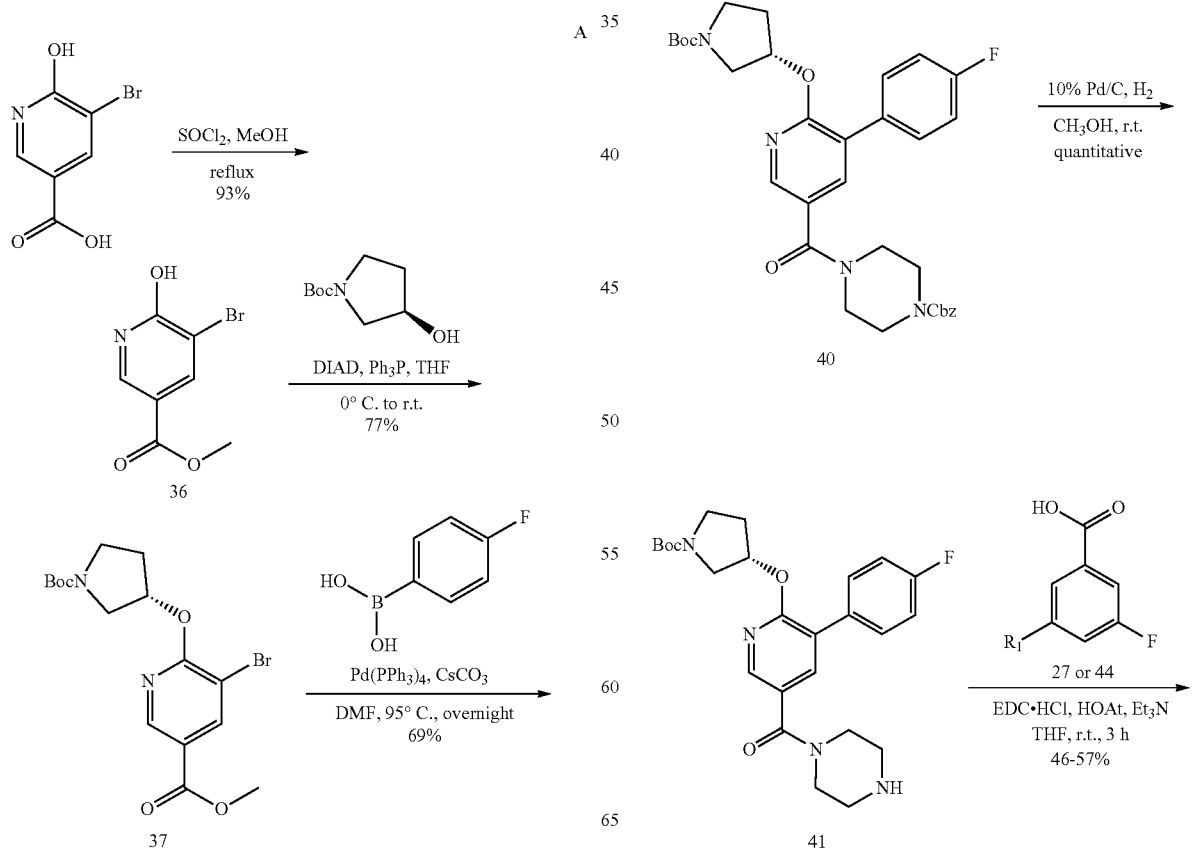

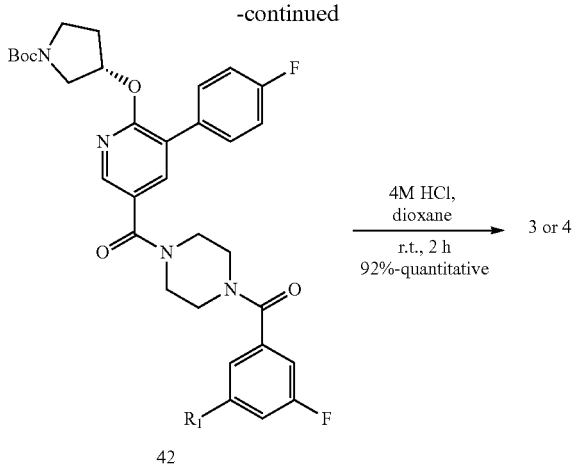

a. Preparation of methyl 5-bromo-6-hydroxynicotinate (36)

To an ice cold stirred solution of 5-bromo-6-hydroxy nicotinic acid (2.03 g, 9.31 mmol) in anhydrous methanol (40 mL) was added thionyl chloride (1.01 mL, 13.9 mmol) dropwise. The reaction mixture was allowed to stir for 15 min and then heated to reflux. Upon completion (1 h) the solvent was removed under reduced pressure, and the residue was taken into EtOAc (150 mL). The organic solution was washed with water (2×150 mL), brine (150 mL), and dried over MgSO$_4$. The solids were filtered, and solvent removed under reduced pressure to yield compound 36 (2.01 g, 93% yield) as off-white solid. $^1$H NMR (500 MHz, CD$_3$OD): δ (ppm 12.65 (s, 1H), 8.11 (d, 1H, J=2.3 Hz), 8.04 (d, 1H, J=2.3 Hz), 3.73 (s, 3H). $^{13}$C NMR (125 MHz, CD$_3$OD): δ (ppm 172.94, 168.07, 150.22, 149.46, 124.33, 118.41, 61.60.

b. Preparation of methyl (S)-5-bromo-6-((1-(tert-butoxycarbonyl)pyrrolidin-3-yl)oxy)nicotinate (37)

To a solution of 36 (0.626 g, 2.70 mmol) in dry THF (35 mL) under anhydrous conditions was added (R)-tert-butyl 3-hydroxypyrrolidine-1-carboxylate (0.505 g, 2.70 mmol) and triphenyl phosphine (1.43 g, 5.39 mmol). The reaction mixture was then cooled in an ice bath, and DIAD (1.12 g, 5.56 mmol) dissolved in THF (10 mL) was added dropwise. The reaction mixture was stirred for 1 h at room temperature under argon. Upon completion the reaction was diluted with ethyl acetate (100 mL). The organic layer was washed with water (2×50 ml), brine (50 mL), dried over MgSO$_4$, solids filtered, and the solvent removed under reduced pressure. The residue was then purified by column chromatography (silica gel, hexanes:EtOAc=7:1) to yield 37 (0.837 g, 77% yield) as white solid. $^1$H NMR (500 MHz, CDCl$_3$): δ ppm 8.70 (d, 1H, J=2.0 Hz), 8.38 (d, 1H, J=2.1 Hz), 5.64-5.62 (m, 1H), 3.91 (s, 3H), 3.72-3.69 (m, 1H), 3.59-3.52 (m, 3H), 2.21-2.17 (m, 2H), 1.46 (s, 9H). $^{13}$C NMR (125 MHz, CDCl$_3$): δ ppm 164.65, 161.64, 154.51, 147.88, 142.55, 121.08, 107.19, 79.47, 72.19, 52.30, 51.65, 44.02, 28.49.

c. Preparation of methyl (S)-6-((1-(tert-butoxycarbonyl) pyrrolidin-3-yl)oxy)-5-(4-fluorophenyl) nicotinate (38)

The synthesis of compound 38 followed the same procedure as for compound 31. Column chromatography (silica gel, hexanes:EtOAc=5:1) afforded white solid (0.147 g, 69% yield). $^1$H NMR (500 MHz, CDCl$_3$): δ ppm 8.74 (s, 1H), 8.16 (s, 1H), 7.48-7.45 (m, 2H), 7.09-7.06 (m, 2H), 5.69-5.66 (m, 1H), 3.90 (s, 3H), 3.68-3.30 (m, 4H), 2.13-2.11 (m, 2H), 1.42 (s, 9H). $^{13}$C NMR (125 MHz, CDCl$_3$): δ ppm 165.76, 162.49 (d, J=247.9 Hz), 162.06, 154.56, 142.28, 139.46, 130.72 (d, J=8.2 Hz), 123.57, 120.34, 115.27 (d, J=22.0 Hz), 79.46, 52.15, 28.47.

d. Preparation of (S)-6-((1-(tert-butoxycarbonyl) pyrrolidin-3-yl)oxy)-5-(4-fluorophenyl)nicotinic Acid (39)

The synthesis of compound 39 followed the same procedure as for compound 32 (except solvent CH$_3$OH was replaced by THF) to afford white solid (0.130 g, 94% yield). $^1$H NMR (500 MHz, CD$_3$OD): δ ppm 8.74 (d, 1H, J=2.2 Hz), 8.18 (s, 1H), 7.52 (dd, 2H, J=5.6 Hz, J=8.0 Hz), 7.13 (t, 2H, J=8.7 Hz), 5.72-5.69 (m, 1H), 3.65-3.48 (m, 3H), 3.40-3.35 (m, 1H), 2.23-2.13 (m, 2H), 1.44 (s, 4.5H), 1.42 (s, 4.5H). $^{13}$C NMR (125 MHz, CD$_3$OD): δ (ppm 168.20, 163.95 (d, J=246.4 Hz), 163.36, 156.56, 156.54, 149.60, 140.79, 133.02, 132.13 (d, J=8.2 Hz), 124.97, 122.32, 116.20 (d, J=21.8 Hz), 116.17 (d, J=21.9 Hz), 81.66, 81.11, 77.31, 76.61, 53.28, 52.81, 45.53, 45.10, 32.39, 31.17, 28.79.

e. Preparation of Benzyl (S)-4-(6-((1-(tert-butoxycarbonyl)pyrrolidin-3-yl)oxy)-5-(4-fluorophenyl) nicotinoyl)piperazine-1-carboxylate (40)

The synthesis of compound 40 followed the same procedure as for compound 33. Column chromatography (silica gel, hexanes:EtOAc=1:1) afforded white solid (0.168 g, 87% yield). $^1$H NMR (500 MHz, CDCl$_3$): δ (ppm 8.19 (d, 1H, J=7.8 Hz), 7.68 (s, 1H), 7.46-7.44 (m, 2H), 7.34-7.28 (m, 5H), 7.09-7.05 (m, 2H), 5.64-5.61 (m, 1H), 5.13 (s, 2H), 3.64-3.33 (m, 12H), 2.14-2.11 (m, 2H), 1.44 (s, 4.5H), 1.43 (s, 4.5H). $^{13}$C NMR (125 MHz, CDCl$_3$): δ (ppm 167.97, 162.39 (d, J=250.0 Hz), 160.16, 154.94, 154.52, 154.40, 144.59, 138.04, 136.15, 131.24, 131.13, 130.57 (d, J=8.15 Hz), 128.42, 128.06, 127.88, 124.80, 123.88, 115.23 (d, J=20.6 Hz), 115.12 (d, J=21.4 Hz), 79.30, 75.55, 74.69, 67.39, 60.21, 51.84, 51.23, 44.24, 43.80, 31.82, 30.72, 28.36.

f. Preparation of tert-butyl (S)-3-((3-(4-fluorophenyl)-5-(piperazine-1-carbonyl)pyridin-2-yl)oxy)pyrrolidine-1-carboxylate (41)

To a solution of 40 (0.119 g, 0.197 mmol) in MeOH (20 mL) under argon was added 10% Pd on activated carbon (0.0132 g). The argon was evacuated and exchanged with H$_2$ gas three times, and the reaction was allowed to stir under H$_2$ for 3 h. The reaction mixture was filtered through celite, and the solvent removed under reduced pressure to yield 41 (0.0994 g, quantitative yield) as off-white solid. $^1$H NMR (500 MHz, CD$_3$OD): δ (ppm 8.24 (s, 1H), 7.79 (s, 1H), 7.56 (dd, 2H, J=5.6, 8.1 Hz), 7.15 (t, 2H, J=8.6 Hz), 5.69-5.67 (m, 1H), 3.71-3.35 (m, 8H), 2.88-2.83 (m, 4H), 2.21-2.14 (m, 2H), 1.45 (s, 4H), 1.43 (s, 5H). $^{13}$C NMR (125 MHz, CD$_3$OD): δ (ppm 169.82, 163.06 (d, J=246.50 Hz), 161.50, 156.53, 156.51, 145.98, 139.30, 133.04, 132.21 (d, J=8.2 Hz), 126.75, 125.22, 116.19 (d, J=21.9 Hz), 116.16 (d, J=21.6 Hz), 81.10, 81.04, 77.01, 76.30, 53.28, 52.81, 46.53, 45.54, 45.11, 44.33, 32.38, 31.66, 28.80.

g. Preparation of tert-butyl (S)-4-(3-(4-(6-((1-(tert-butoxycarbonyl)pyrrolidin-3-yl)oxy)-5-(4-fluorophenyl)nicotinoyl)piperazine-1-carbonyl)-5-fluorophenyl)piperazine-1-carboxylate (42A)

The synthesis of compound 42a followed the same procedure as for compound 35 (except solvent anhydrous CH$_2$Cl$_2$ was replaced by anhydrous THF). Column chromatography (silica gel, CH$_2$Cl$_2$:MeOH=99:1) afforded white solid (0.0497 g, 46% yield). $^1$H NMR (300 MHz, CDCl$_3$): δ (ppm 8.20 (d, 1H, J=2.6 Hz), 7.69 (s, 1H), 7.45 (d, 2H, J=5.5 Hz), 7.08 (t, 2H, J=8.4 Hz), 6.68 (s, 1H), 6.60 (td, 1H, J=2.1, 12.1 Hz), 6.51 (d, 1H, J=7.8 Hz), 5.62-5.60 (m, 1H), 3.77-3.33 (m, 16H), 3.16 (t, 4H, J=5.0 Hz), 2.17-2.10 (m, 2H), 1.46 (s, 9H), 1.43 (s, 9H). $^{13}$C NMR (125 MHz, CDCl$_3$): δ ppm 169.59 (d, 1H, J=2.0 Hz), 168.14, 163.38 (d, J=246.2 Hz), 162.44 (d, J=246.9 Hz), 160.33, 160.31, 154.61, 154.50, 152.95 (d, J=10.1 Hz), 144.69, 138.11, 137.29 (d, J=9.1 Hz), 131.21, 131.10, 130.62 (d, J=8.15 Hz), 124.57, 124.04, 115.33 (d, J=21.5 Hz), 115.22 (d, J=21.4 Hz), 109.73 (d, J=1.5 Hz), 104.30 (d, J=23.3 Hz), 103.96 (d, J=25.4 Hz), 80.12, 79.44, 79.41, 75.66, 74.81, 51.90, 51.85, 48.19, 44.29, 43.85, 31.44, 30.79, 28.42, 28.32.

h. Preparation of tert-butyl (S)-3-((5-(4-(3-(2-((tert-butoxycarbonyl)amino)ethyl)-5-fluorobenzoyl)piperazine-1-carbonyl)-3-(4-fluorophenyl)pyridin-2-yl)oxy)pyrrolidine-1-carboxylate (42B)

The synthesis of compound 42b followed the same procedure as for compound 35 (except solvent anhydrous CH$_2$Cl$_2$ was replaced by anhydrous THF). Column chromatography (silica gel, hexanes:EtOAc=1:4) afforded white solid (0.0877 g, 57% yield). $^1$H NMR (500 MHz, CDCl$_3$): δ (ppm 8.21 (s, 1H), 7.70 (s, 1H), 7.46 (dd, 2H, J=5.5, 7.8 Hz), 7.09 (t, 2H, J=8.3 Hz), 7.03 (s, 1H), 6.97 (d, 2H, J=8.3 Hz), 5.65-5.62 (m, 1H), 4.60 (bs, 1H), 3.80-3.40 (m, 14H), 2.81 (t, 2H, J=6.9 Hz), 2.15-2.12 (m, 2H), 1.44 (s, 9H), 1.40 (s, 9H). $^{13}$C NMR (125 MHz, CDCl$_3$): δ (ppm 169.12, 168.16, 162.56 (d, J=249.0 Hz), 162.51 (d, J=247.1 Hz), 160.38, 155.73, 154.63, 144.75, 142.57 (d, J=7.7 Hz), 138.15, 137.08 (d, J=6.6 Hz), 130.66 (d, J=8.2 Hz), 124.62, 124.08, 123.03 (d, J=1.5 Hz), 117.51 (d, J=20.8 Hz), 115.37, 115.35 (d, J=22.1 Hz), 112.31 (d, J=22.9 Hz), 79.43, 75.70, 74.86, 51.94, 51.63, 47.47, 44.33, 44.32, 42.42, 41.29, 36.00, 31.48, 30.85, 28.46, 28.32.

i. Preparation of (S)-(4-(3-fluoro-5-(piperazin-1-yl)benzoyl)piperazin-1-yl) (5-(4-fluorophenyl)-6-(pyrrolidin-3-yloxy)pyridin-3-yl)methanone Hydrochloride (3)

The synthesis of compound 3 followed the same procedure as for compound 2 to afford white solid (0.0431 g, quantitative yield). $^1$H NMR (500 MHz, d$^6$-DMSO): δ (ppm 9.17 (brs, 2H), 8.94 (brs, 2H), 8.26 (s, 1H), 7.84 (s, 1H), 7.73-7.70 (m, 2H), 7.29-7.25 (m, 2H), 6.91 (d, 1H, J=13.0 Hz), 6.81 (s, 1H), 6.66 (d, 1H, J=8.5 Hz), 5.65-5.63 (m, 1H), 3.70-3.18 (m, 20H), 2.26-2.21 (m, 1H), 2.15-2.10 (m, 1H); $^{13}$C NMR (125 MHz, CD$_3$OD) δ (ppm 170.23, 168.81, 163.80 (d, J=244.4 Hz), 162.89 (d, J=245.1 Hz), 159.92, 152.42, 152.34, 144.85, 138.55, 138.04, 137.97, 131.59, 131.28, 125.86, 124.11, 115.18 (d, J=21.3 Hz), 110.21, 105.16 (d, J=23.5 Hz), 104.38 (d, J=25.8 Hz), 74.99, 50.97, 48.39-47.37 (m, 4C), 45.55, 44.59, 43.28, 30.92. HRMS (ESI) m/z calculated for C$_{31}$H$_{34}$F$_2$N$_6$O$_3$ (M+H)$^+$=577.2733, found 577.2741.

j. Preparation of (S)-(4-(3-(2-aminoethyl)-5-fluorobenzoyl)piperazin-1-yl) (5-(4-fluorophenyl)-6-(pyrrolidin-3-yloxy)pyridin-3-yl)methanone Hydrochloride (4)

The synthesis of compound 4 followed the same procedure as for compound 2 to afford white solid (0.0667 g, 92% yield). $^1$H NMR (500 MHz, d$^6$-DMSO) δ ppm 9.51 (brs, 3H), 8.27 (s, 1H), 8.08 (brs, 2H), 7.84 (s, 1H), 7.74-7.71 (m, 2H), 7.27-7.24 (m, 3H), 7.16-7.13 (m, 2H), 7.20-7.16 (m, 1H), 5.74-5.78 (m, 1H), 3.68-3.16 (m, 12H), 3.06 (t, 2H, J=7.0 Hz), 2.93 (t, 2H, J=7.0 Hz), 2.24-2.18 (m, 1H), 2.13-2.10 (m, 1H); $^{13}$C NMR (125 MHz, D$_2$O) δ ppm 171.04, 169.68, 163.61, 161.65, 159.82, 144.55, 140.63, 140.57, 138.75, 136.56, 131.32, 131.27, 131.06, 124.98, 124.47, 123.31, 118.05 (d, J=21.3 Hz), 115.62 (d, J=22.0 Hz), 112.96 (d, J=24.4 Hz), 75.21, 50.91, 47.78, 47.14, 44.58, 42.76, 42.13, 40.25, 32.58, 30.74. HRMS (ESI) m/z calculated for C$_{29}$H$_{31}$F$_2$N$_5$O$_3$(M+H)$^+$=536.2468, found 536.2470.

6. Preparation of Compound 48

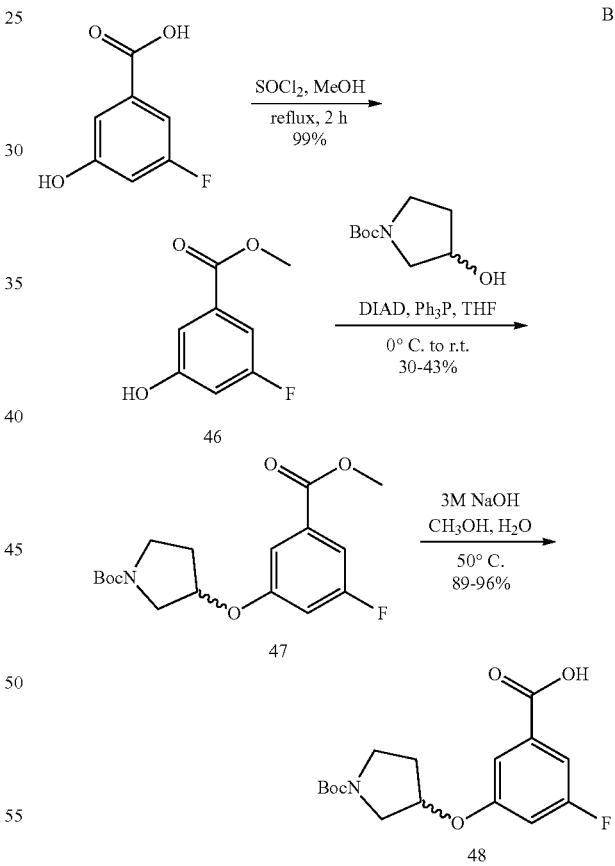

a. Preparation of methyl 3-fluoro-5-hydroxybenzoate (46)

The synthesis of compound 46 followed the same procedure as for compound 25 to afford brown liquid (2.35 g, 99% yield). $^1$H NMR (500 MHz, CD$_3$OD): δ (ppm 7.23 (s, 1H), 7.13 (ddd, 1H, J=1.3, 2.1, 9.1 Hz), 6.73 (td, 1H, J=2.3, 10.4 Hz), 3.39 (s, 3H). $^{13}$C NMR (125 MHz, CD$_3$OD): δ (ppm 167.43 (d, J=3.7 Hz), 164.76 (d, J=243.9 Hz), 160.57 (d, J=11.5 Hz), 133.88 (d, J=9.9 Hz), 113.48 (d, J=2.7 Hz), 108.22 (d, J=24.3 Hz), 107.92 (d, J=24.0 Hz), 52.87.

b. Preparation of tert-butyl (S)-3-(3-fluoro-5-(methoxycarbonyl)phenoxy)pyrrolidine-1-carboxylate (47A)

The synthesis of compound 47a followed the same procedure as for compound 22. Column chromatography (silica gel, hexanes:EtOAc=95:5) afforded white solid (0.141 g, 30%). ¹H NMR (500 MHz, CDCl₃): δ (ppm 7.32-7.30 (m, 2H), 6.76 (td, 1H, J=2.3, 10.0 Hz), 4.92-4.89 (m, 1H), 3.890 (s, 3H), 3.61-3.45 (m, 4H), 2.18-2.12 (m, 2H), 1.45 (s, 9H). ¹³C NMR (125 MHz, CDCl₃): δ 165.66 (d, J=3.6 Hz), 163.17 (d, J=246.8 Hz), 158.31 (d, J=11.0 Hz), 154.36, 132.73 (d, J=9.5 Hz), 111.71 (d, J=2.8 Hz), 109.30 (d, J=23.6 Hz), 108.05 (d, J=24.5 Hz), 79.54, 76.27, 52.39, 51.43, 51.21, 43.91, 43.63, 31.33, 30.61, 28.43.

c. Preparation of tert-butyl (R)-3-(3-fluoro-5-(methoxycarbonyl)phenoxy)pyrrolidine-1-carboxylate (47B)

The synthesis of compound 47b followed the same procedure as for compound 22. Column chromatography (silica gel, hexanes:EtOAc=95:5) afforded yellow oil (0.254 g, 43% yield). ¹H NMR (500 MHz, CDCl₃): δ (ppm 7.25-7.22 (m, 2H), 6.71 (d, 1H, J=10.0 Hz), 4.87-4.84 (m, 1H), 3.83 (s, 3H), 3.57-3.39 (m, 4H), 2.11-2.03 (m, 2H), 1.45 (s, 9H). ¹³C NMR (125 MHz, CDCl₃): δ (ppm 165.45 (d, J=3.4 Hz), 162.98 (d, J=246.7 Hz), 158.15 (d, J=10.9 Hz), 154.24, 154.15, 132.50 (d, J=9.4 Hz), 111.57, 109.06 (d, J=23.1 Hz), 107.83 (d, J=24.8 Hz), 79.35, 79.32, 76.93, 76.07, 52.39, 51.31, 50.99, 43.78, 43.45, 31.16, 30.39, 28.25.

d. Preparation of (S)-3-((1-(tert-butoxycarbonyl)pyrrolidin-3-yl)oxy)-5-fluorobenzoic Acid (48A)

The synthesis of compound 48a followed the same procedure as for compound 27 to afford white solid (0.125 g, 96% yield). ¹H NMR (500 MHz, CDCl₃): δ (ppm 11.33 (brs, 1H), 7.40-7.36 (m, 2H), 6.81 (d, 1H, J=4.5 Hz), 4.94-4.92 (m, 1H), 3.68-3.48 (m, 4H), 2.17-2.12 (m, 2H), 1.47 (s, 9H). ¹³C NMR (125 MHz, CDCl₃): δ (ppm 169.50, 163.46 (d, J=242.4 Hz), 158.35 (d, J=10.9 Hz), 154.79, 154.67, 132.33 (d, J=9.2 Hz), 112.07, 109.86 (d, J=24.3 Hz), 108.73 (d, J=24.9 Hz), 80.05, 77.10, 76.29, 51.55, 51.21, 44.05, 43.69, 31.36, 30.60, 28.70.

e. Preparation of (R)-3-((1-(tert-butoxycarbonyl)pyrrolidin-3-yl)oxy)-5-fluorobenzoic Acid (48B)

The synthesis of compound 48b followed the same procedure as for compound 27 to afford white solid (0.419 g, 89% yield). ¹H NMR (300 MHz, CD₃OD): δ (ppm 7.37 (s, 1H), 7.30 (d, 1H, J=8.0 Hz), 6.96 (td, 1H, J=2.4, 10.4 Hz), 5.07-5.04 (m, 1H), 3.66-3.43 (m, 4H), 2.19-2.17 (m, 2H), 1.46 (d, 9H, J=4.1 Hz). ¹³C NMR (125 MHz, CD₃OD): δ (ppm 168.10 (d, J=3.4 Hz), 164.70 (d, J=245.3 Hz), 159.93 (d, J=11.0 Hz), 156.44, 156.36, 135.01 (d, J=9.3 Hz), 113.48 (d, J=2.6 Hz), 110.01 (d, J=23.2 Hz), 108.62 (d, J=24.6 Hz), 81.18, 81.16, 78.51, 77.73, 52.74, 52.36, 45.29, 44.86, 32.12, 31.39, 28.78.

7. Preparation of Compound 49

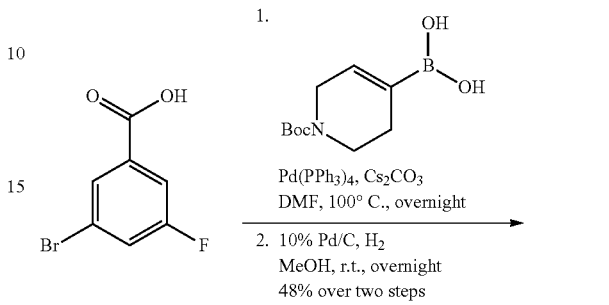

To a solution of 3-bromo-5-fluoroboronic acid (0.410 g, 1.87 mmol), in dry DMF (40 mL) under anhydrous conditions was added tert-butyl 4-(4,4,5,5-tetramethyl-1,3,2-dioxaborolan-2-yl)-3,6-dihydropyridine-1(2H)-carboxylate (0.878 g, 2.84 mmol), Pd(PPh₃)₄ (0.325 g, 0.281 mmol), and K₂CO₃ (0.785 g, 5.68 mmol). The mixture was heated to 100° C. under argon and stirred for 20 h. The solvent was then removed under reduced pressure, and the residue was taken into EtOAc (100 mL). The organic solution was washed with water (2×50 mL) and brine (50 mL), dried over MgSO₄, solids filtered, and solvent removed under reduced pressure. The residue was purified by column chromatography (silica gel, hexanes:EtOAc:acetic acid=9:1:0.25) to yield white solid (0.419 g, 1.30 mmol). A portion of this solid (0.0845 g, 0.262 mmol) was dissolved in MeOH (20 mL). The air was evacuated and exchanged with argon three times and 10% Pd on activated carbon (0.017 g) was added. The argon was evacuated and exchanged with the H₂ gas three times and the reaction was allowed to stir under H₂ for 12 h. The mixture was filtered through celite and the solvent removed under reduced pressure to yield 49 (0.0584 g, 48% overall yield) as off-white solid. ¹H NMR (500 MHz, CD₃OD): δ ppm 7.72-7.70 (m, 1H), 7.52 (ddd, 1H, J=1.4, 2.4, 9.0 Hz), 7.24 (td, 1H, J=2.0, 9.7 Hz), 4.21 (m, 2H), 2.87-2.78 (m, 3H) 1.84 (m, 2H), 1.58 (dq, 2H, J=4.3, 12.7 Hz), 1.47 (s, 9H). ¹³C NMR (125 MHz, CD₃OD): δ ppm 168.51 (d, J=3.1 Hz), 164.14 (d, J=245.3 Hz), 156.51, 150.42 (d, J=6.9 Hz), 134.43 (d, J=7.8 Hz), 125.1 (d, J=2.6 Hz), 119.28 (d, J=21.8 Hz), 115.19 (d, J=23.2 Hz), 81.14, 43.35, 43.34, 34.04, 28.76.

8. Preparation of Compounds 5-8

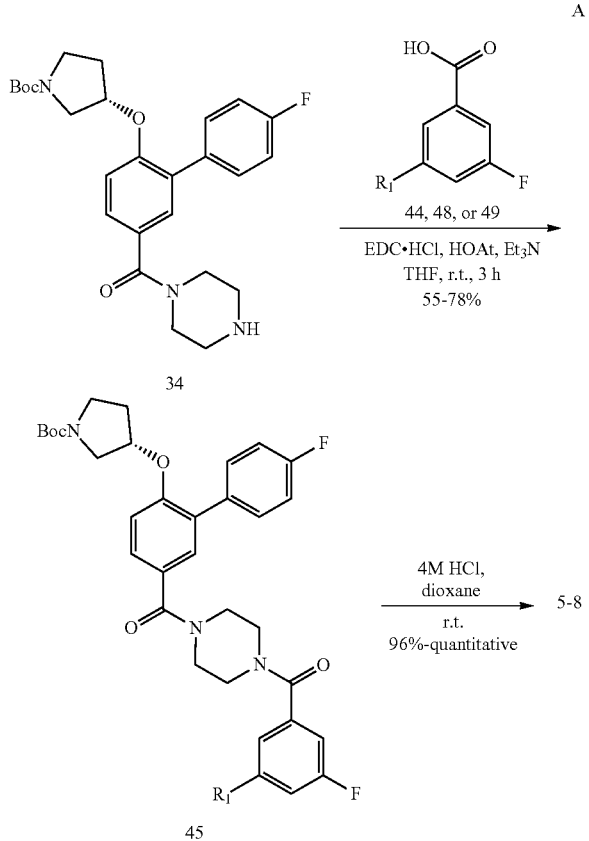

a. Preparation of tert-butyl (S)-3-((5-(4-(3-(2-((tert-butoxycarbonyl)amino)ethyl)-5-fluorobenzoyl)piperazine-1-carbonyl)-4'-fluoro-[1,1'-biphenyl]-2-yl)oxy)pyrrolidine-1-carboxylate (45A)

The synthesis of compound 45a followed the same procedure as for compound 35. Column chromatography (silica gel, 100% EtOAc) afforded white solid (0.0752 g, 55% yield). $^1$H NMR (500 MHz, CDCl$_3$): δ ppm 7.41-7.38 (m, 4H), 7.07 (t, 2H, J=7.7 Hz), 7.02 (s, 1H), 6.98-6.94 (m, 3H), 4.91-4.89 (m, 1H), 4.58 (bs, 1H), 3.78-3.20 (m, 14H), 2.81, (t, 2H, J=6.5 Hz), 2.11-2.07 (m, 2H), 1.44 (s, 9H), 1.41 (s, 9H). $^{13}$C NMR (125 MHz, CDCl$_3$): δ ppm 172.91, 171.03 (d, J=2.1 Hz), 170.12, 169.04, 163.45, 162.46 (d, J=248.9 Hz), 162.05 (d, J=247.5 Hz), 155.72, 155.22, 155.10, 154.44, 154.26, 142.50 (d, J=7.5 Hz), 137.09 (d, J=6.9 Hz), 133.00 (d, J=11.7 Hz), 131.8, 131.00, 130.89, 130.83, 130.27, 127.92, 122.94, 117.35 (d, J=21.03 Hz), 114.96 (d, J=21.7 Hz), 114.83 (d, J=21.3 Hz), 113.77, 113.47, 112.27 (d, J=23.1 Hz), 79.53, 79.46, 79.31, 77.14, 76.28, 60.27, 51.35, 50.84, 44.00, 43.63, 41.21, 35.87, 31.41, 30.63, 28.36, 28.24.

b. Preparation of tert-butyl (S)-3-(3-(4-(6-(((S)-1-(tert-butoxycarbonyl)pyrrolidin-3-yl)oxy)-4'-fluoro-[1,1'-biphenyl]-3-carbonyl)piperazine-1-carbonyl)-5-fluorophenoxy)pyrrolidine-1-carboxylate (45B)

The synthesis of compound 45b followed the same procedure as for compound 35. Column chromatography (silica gel, CH$_2$Cl$_2$:MeOH=99:1) afforded white solid (0.0656 g, 61% yield). $^1$H NMR (300 MHz, CDCl$_3$): δ ppm 7.41-7.36 (m, 4H), 7.05, (t, 2H, J=8.2 Hz), 6.94 (d, 1H, J=8.5 Hz), 6.69-6.67 (m, 2H), 6.62 (d, 1H, J=10.8 Hz), 4.91-4.89 (m, 1H), 4.86-4.83 (m, 1H), 3.74-3.21 (m, 16H), 2.14-2.05 (m, 4H) 1.44 (s, 18H). $^{13}$C NMR (125 MHz, CD$_3$OD): δ ppm 172.34, 170.89 (J=2.8 Hz), 164.88 (d, J=246.8 Hz), 163.60 (d, J=245.6 Hz), 160.30 (d, J=11.1 Hz), 156.72, 156.42, 156.41, 156.36, 156.29, 139.36 (d, J=9.2 Hz), 134.91, 132.68, 132.45, 132.39, 132.33, 131.40 (d, J=6.8 Hz), 129.44, 129.30 (d, J=15.8 Hz), 115.91 (d, J=21.6 Hz), 115.86 (d, J=21.6 Hz), 115.54, 115.14, 111.26, 107.62 (d, J=23.7 Hz), 105.61 (d, J=25.1 Hz), 81.14, 81.03, 78.59, 78.52, 78.04, 77.76, 54.87, 52.76, 52.72, 52.36, 52.20, 45.34, 45.29, 44.97, 44.88, 32.22, 32.14, 31.49, 31.39, 28.80.

c. Preparation of tert-butyl (R)-3-(3-(4-(6-(((S)-1-(tert-butoxycarbonyl)pyrrolidin-3-yl)oxy)-4'-fluoro-[1,1'-biphenyl]-3-carbonyl)piperazine-1-carbonyl)-5-fluorophenoxy)pyrrolidine-1-carboxylate (45C)

The synthesis of compound 45c followed the same procedure as for compound 35. Column chromatography (silica gel, CH$_2$Cl$_2$:MeOH=99:1) afforded white solid (0.0788 g, 78% yield). $^1$H NMR (500 MHz, CDCl$_3$): δ ppm 7.39-7.36 (m, 4H), 7.06-7.02 (m, 2H), 6.94-6.93 (m, 1H), 6.69-6.67 (m, 2H), 6.62 (d, 1H, J=10.0 Hz), 4.90-4.88 (m, 1H), 4.85-4.83 (m, 1H), 3.74-3.21 (m, 16H), 2.14-2.02 (m, 4H), 1.44 (s, 18H). $^{13}$C NMR (125 MHz, CDCl$_3$): δ ppm 174.10, 171.05, 170.19, 168.84 (d, J=2.4 Hz), 163.19 (d, J=249.2 Hz), 162.07 (d, J=247.0 Hz), 158.70 (d, J=10.7 Hz), 155.25, 155.13, 154.48, 154.42, 154.29, 137.63 (d, J=10.7 Hz), 132.99 (d, J=10.7 Hz), 131.21, 131.03, 130.83, 130.27, 127.94, 114.97 (d, J=21.0 Hz), 114.84 (d, J=21.3 Hz), 113.47, 110.00, 106.59 (d, J=23.2 Hz), 104.39 (d, J=24.29 Hz), 79.60, 79.52, 77.20, 77.15, 76.29, 76.17, 60.29, 51.42, 51.37, 51.06, 50.84, 44.02, 43.90, 43.65, 43.54, 31.42, 31.29, 30.64, 30.52, 28.38.

d. Preparation of tert-butyl (S)-4-(3-(4-(6-((1-(tert-butoxycarbonyl)pyrrolidin-3-yl)oxy)-4'-fluoro-[1,1'-biphenyl]-3-carbonyl)piperazine-1-carbonyl)-5-fluorophenyl)piperidine-1-carboxylate (45D)

The synthesis of compound 45d followed the same procedure as for compound 35. Column chromatography (silica gel, CH$_2$Cl$_2$:MeOH=99:1) afforded white solid (0.0848 g, 71% yield). $^1$H NMR (500 MHz, CDCl$_3$): δ ppm 7.39-7.36 (m, 4H), 7.08-7.04 (m, 2H), 7.02 (s, 1H), 6.97-6.93 (m, 3H), 4.91-4.88 (m, 1H), 4.27-4.17 (m, 2H), 3.76-3.21 (m, 12H), 2.79-2.76 (m, 2H), 2.65 (t, 1H, J=12.1 Hz), 2.09-2.04 (m, 2H), 1.81-1.79 (m, 2H), 1.58-1.52 (m, 2H), 1.46 (s, 9H), 1.43 (s, 4.5H), 1.42 (s, 4.5H). $^{13}$C NMR (125 MHz, CDCl$_3$): δ δ ppm 170.17, 169.19, 162.56 (d, J=248.4 Hz), 162.09 (d, J=244.5 Hz), 155.26, 155.12, 154.62, 154.47, 154.27, 149.26 (d, J=7.3 Hz), 137.07 (d, J=6.9 Hz), 133.07, 132.96, 131.23, 132.05, 130.90, 130.84, 130.30, 127.95 (d, J=5.3 Hz), 121.14, 115.39 (d, J=22.3 Hz), 114.86 (d, J=21.1 Hz), 113.76, 113.49, 112.07 (d, J=22.9 Hz) 79.56, 79.49, 77.20, 76.27, 60.29, 51.37, 50.83, 44.03, 43.65, 42.34, 32.81, 31.46, 30.83, 30.67, 29.60, 28.37.

e. Preparation of (S)-(4-(3-(2-aminoethyl)-5-fluorobenzoyl)piperazin-1-yl) (4'-fluoro-6-(pyrrolidin-3-yloxy)-[1,1'-biphenyl]-3-yl) methanone Hydrochloride (5)

The synthesis of compound 5 followed the same procedure as for compound 2 to afford white solid (0.0593 g, 96% yield). $^1$H NMR (500 MHz, d$^6$-DMSO): δ ppm 9.47 (brs, 2H), 8.03 (brs, 2H), 7.60 (d, 1H, J=8.0 Hz), 7.59 (d, 1H, J=8.0 Hz), 7.43 (d, 1H, J=8.5 Hz), 7.37 (s, 1H), 7.26-7.15 (m, 6H), 5.18-5.13 (m, 1H), 3.65-3.26 (m, 12H), 3.07 (t, 2H, J=7.2 Hz), 2.92 (t, 2H, J=7.4 Hz), 2.17-2.12 (m, 2H), 2.06-2.02 (m, 2H); $^{13}$C NMR (125 MHz, CD$_3$OD): δ ppm 171.04, 169.77, 162.97 (d, J=245.9 Hz), 162.56 (d, J=244.3 Hz), 155.08, 140.71 (d, J=7.5 Hz), 137.90 (d, J=6.9 Hz), 133.59, 133.56, 131.43, 131.37, 131.28, 130.49, 128.73, 128.40, 123.45 (d, J=2.4 Hz), 117.43 (d, J=22.0 Hz), 114.96 (d, J=21.3 Hz), 114.15, 112.92 (d, J=22.8 Hz), 76.87, 50.63, 48.38-47.36 (m, 4C), 44.44, 40.28, 32.82, 30.97. HRMS (ESI) m/z calculated for C$_{30}$H$_{32}$F$_2$N$_4$O$_3$(M+H)$^+$=535.2515, found 535.2522.

f. Preparation of (4-(3-fluoro-5-(((S)-pyrrolidin-3-yl)oxy)benzoyl)piperazin-1-yl) (4'-fluoro-6-(((S)-pyrrolidin-3-yl)oxy)-[1,1'-biphenyl]-3-yl)methanone Hydrochloride (6)

The synthesis of compound 6 followed the same procedure as for compound 2 to afford white solid (0.0531 g, 97% yield). $^1$H NMR (500 MHz, d$^6$-DMSO): δ (ppm 9.20 (brs, 4H), 7.61-7.57 (m, 2H), 7.43 (d, 1H, J=8.5 Hz), 7.37 (s, 1H), 7.23 (t, 2H, J=9.0 Hz), 7.19 (d, 1H, J=8.5 Hz), 6.97 (d, 1H, J=10.5 Hz), 6.89 (d, 1H, J=8.5 Hz), 6.83 (s, 1H), 5.20-5.14 (m, 2H), 3.66-3.06 (m, 16H), 2.23-2.02 (m, 4H). $^{13}$C NMR (125 MHz, CD$_3$OD): δ ppm 171.01, 169.54, 163.64 (d, J=245.9 Hz), 162.54 (d, J=244.3 Hz), 158.37, 158.28, 155.08, 138.38, 138.32, 133.58, 131.46, 131.32 (d, J=19 Hz), 130.50, 128.69, 128.42, 114.97 (d, J=22.0 Hz), 114.14, 110.37, 107.18 (d, J=23.5 Hz), 104.87 (d, J=25.9 Hz), 76.86, 76.54, 50.71, 50.62, 48.40-47.38 (m, 4C), 44.45, 44.10, 31.00, 30.50. HRMS (ESI) m/z calculated for C$_{32}$H$_{34}$F$_2$N$_4$O$_4$(M+H)$^+$=577.2621, found 577.2626.

g. Preparation of (4-(3-fluoro-5-(((R)-pyrrolidin-3-yl)oxy)benzoyl)piperazin-1-yl) (4'-fluoro-6-(((S)-pyrrolidin-3-yl)oxy)-[1,1'-biphenyl]-3-yl)methanone Hydrochloride (7)

The synthesis of compound 7 followed the same procedure as for compound 2 to afford white solid (0.0682 g, quantitative yield). $^1$H NMR (500 MHz, d$^6$-DMSO): δ (ppm 9.43 (brs, 4H), 7.61-7.58 (m, 2H), 7.43 (d, 1H, J=8.5 Hz), 7.37 (s, 1H), 7.23 (t, 2H, J=9.0 Hz), 7.19 (d, 1H, J=8.5 Hz), 6.98 (d, 1H, J=10.5 Hz), 6.89 (d, 1H, J=8.5 Hz), 6.83 (s, 1H), 5.21-5.14 (m, 2H), 3.69-3.08 (m, 16H), 2.23-2.02 (m, 4H). $^{13}$C NMR (125 MHz, CD$_3$OD): δ (ppm 171.00, 169.53, 163.64 (d, J=245.9 Hz), 162.54 (d, J=244.4 Hz), 158.37, 158.28, 155.07, 138.40, 138.32, 133.56, 131.45, 131.31 (d, J=20.5 Hz), 130.48, 128.71, 128.40, 114.97 (d, J=22.0 Hz), 114.12, 110.35, 107.16 (d, J=22.8 Hz), 104.86 (d, J=24.4 Hz), 76.85, 76.52, 51.68, 50.69, 48.41-47.39 (m, 4C), 44.44, 44.08, 30.98, 30.49. HRMS (ESI) m/z calculated for C$_{32}$H$_{34}$F$_2$N$_4$O$_4$(M+H)$^+$=577.2621, found 577.2636.

h. Preparation of (S)-(4-(3-fluoro-5-(piperidin-4-yl)benzoyl)piperazin-1-yl) (4'-fluoro-6-(pyrrolidin-3-yloxy)-[1,1'-biphenyl]-3-yl) methanone Hydrochloride (8)

The synthesis of compound 8 followed the same procedure as for compound 2 to afford white solid (0.0685 g, 97% yield). $^1$H NMR (500 MHz, d$^6$-DMSO): δ (ppm 9.44 (brs, 2H), 8.93 (brs, 2H), 7.61-7.58 (m, 2H), 7.43 (d, 1H, J=8.5 Hz), 7.37 (s, 1H), 7.22 (t, 2H, J=9.0 Hz), 7.19 (d, 1H, J=8.5 Hz), 7.17-7.14 (m, 2H), 7.11 (s, 1H), 5.17-5.13 (m, 1H), 3.66-2.83 (m, 16H), 2.19-1.80 (m, 6H). $^{13}$C NMR (125 MHz, D$_2$O): δ ppm 171.87, 171.03, 162.60 (d, J=242.9 Hz), 162.23 (d, J=243.6 Hz), 154.74, 148.19, 136.34, 133.02, 131.44, 131.37, 130.00, 128.57, 127.75, 121.34, 115.95, (d, J=22.0 Hz), 115.36 (d, J=21.3 Hz), 114.56, 112.32 (d, J=22 Hz), 76.79, 50.59, 47.82, 47.64, 47.25, 47.05, 44.38, 44.30, 42.60, 42.11, 39.02, 30.51, 29.20. HRMS (ESI) m/z calculated for C$_{33}$H$_{36}$F$_2$N$_4$O$_3$(M+H)$^+$=575.2828, found 575.2842.

9. Preparation of Compound 29

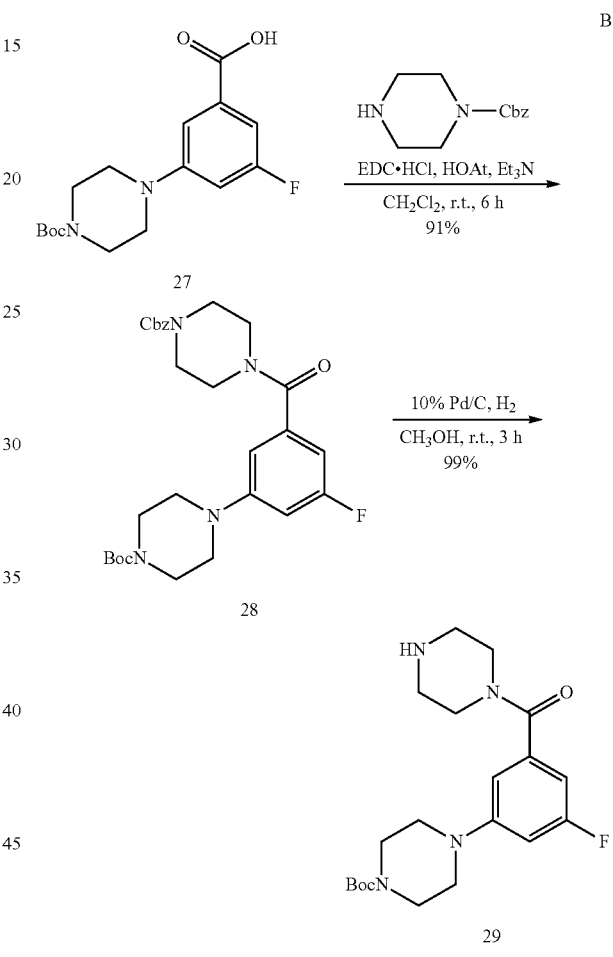

a. Preparation of Benzyl 4-(3-(4-(tert-butoxycarbonyl)piperazin-1-yl)-5-fluorobenzoyl)piperazine-1-carboxylate (28)

The synthesis of compound 28 followed the same procedure as for compound 33. Column chromatography (silica gel, hexanes:acetone=70:30) afforded yellow solid (0.873 g, 91% yield). $^1$H NMR (500 MHz, CDCl$_3$): δ (ppm 7.29-7.24 (m, 5H), 6.63 (s, 1H), 6.57 (td, 1H, J=2.0, 11.9 Hz), 6.46 (d, 1H, J=7.7 Hz), 5.09 (s, 2H), 3.66-3.54 (m, 12H), 3.11 (t, 4H, J=5.0 Hz), 1.42 (s, 9H). $^{13}$C NMR (125 MHz, CDCl$_3$): δ (ppm 169.26 (d, J=2.8 Hz), 163.17 (d, J=245.8 Hz), 154.79, 154.27, 152.70 (d, J=10.1 Hz), 137.5 (d, J=8.9 Hz), 136.07, 128.28, 127.92, 127.73, 109.51 (d, J=2.1 Hz), 104.09 (d, J=23.5 Hz), 103.59 (d, J=25.1 Hz), 79.78, 67.19, 47.99, 28.12.

b. Preparation of tert-butyl 4-(3-fluoro-5-(piperazine-1-carbonyl)phenyl)piperazine-1-carboxylate (29)

The synthesis of compound 29 followed the same procedure as for compound 34 to afford off-white solid (0.644 g, 99% yield). $^1$H NMR (500 MHz, CD$_3$OD): δ (ppm 6.77-6.74 (m, 2H), 6.55 (d, J=7.3 Hz), 3.77-3.71 (m, 2H), 3.52-3.43 (m, 6H), 3.18-3.16 (m, 4H), 2.96-2.88 (m, 4H), 1.44 (s, 9H). $^{13}$C NMR (125 MHz, CD$_3$OD): δ (ppm 171.19, 164.87 (d, J=244.1 Hz), 156.12, 154.43 (d, J=10.3 Hz), 138.96 (d, J=9.1 Hz), 110.73 (d, J=1.6 Hz), 104.95 (d, J=23.8 Hz), 104.67 (d, J=25.5 Hz), 81.26, 49.20, 28.76.

10. Preparation of Compounds 24, 51, and 52

7.31-7.26 (m, 1H), 7.19-7.16 (m, 2H), 6.97 (d, 1H, J=8.7 Hz), 5.03-5.00 (m, 1H), 3.71-3.33 (m, 4H), 2.16-2.12 (m, 2H), 1.46 (s, 9H). $^{13}$C NMR (125 MHz, d$^6$-DMSO/CDCl$_3$): δ 8 ppm 171.12, 170.88, 158.18, 158.03, 154.96, 154.62, 150.92, 150.90, 148.96, 148.94, 148.93, 148.85, 148.83, 134.23, 133.19, 131.80, 129.74, 129.68, 125.60, 122.73, 118.65, 118.51, 117.00, 116.86, 112.98, 112.81, 80.18, 76.50, 51.63, 51.13, 44.29, 43.87, 31.69, 30.89, 28.55.

c. Preparation of (S)-3-bromo-4-((1-(tert-butoxycarbonyl) pyrrolidin-3-yl)oxy)benzoic Acid (23)

The synthesis of compound 23 followed the same procedure as for compound 32 to afford white solid (0.941 g, 93%

A

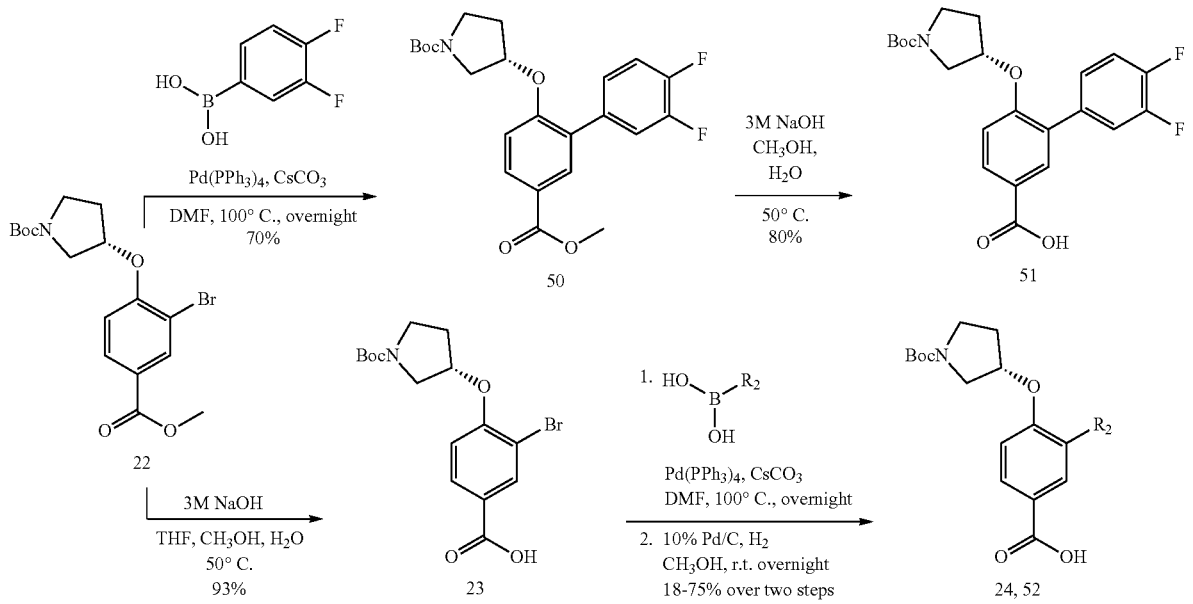

a. Preparation of tert-butyl (S)-3-((3',4'-difluoro-5-(methoxycarbonyl)-[1,1'-biphenyl]-2-yl)oxy)pyrrolidine-1-carboxylate (50)

The synthesis of compound 50 followed the same procedure as for compound 31. Column chromatography (silica gel, hexanes:EtOAc=5:1) afforded white solid (0.38 g, 70% yield). $^1$H NMR (500 MHz, CDCl$_3$): δ (ppm 7.99 (d, 2H, J=9.0 Hz), 7.29 (d, 1H, J=8.1 Hz), 7.16 (d, 2H, J=3.5 Hz), 6.94 (d, 1H, J=8.4 Hz), 4.98-4.96 (m, 1H), 3.89 (s, 3H), 3.66-3.31 (m, 4H), 2.11-2.09 (m, 2H), 1.44 (s, 9H). $^{13}$C NMR (125 MHz, CDCl$_3$): δ (ppm 166.57, 157.44, 154.45, 150.84, 148.87, 132.64, 131.12, 129.65, 125.62, 125.59, 125.57, 125.54, 123.47, 118.63, 118.58, 118.56, 118.48, 118.45, 118.42, 117.00, 116.97, 116.89, 116.83, 113.01, 112.81, 79.86, 76.47, 52.18, 51.58, 51.12, 44.22, 43.83, 31.69, 30.88, 30.87, 28.53. MS (ESI) m/z=434.6 [M+H]$^+$.

b. Preparation of (S)-6-((1-(tert-butoxycarbonyl) pyrrolidin-3-yl)oxy)-3',4'-difluoro-[1,1'-biphenyl]-3-carboxylic Acid (51)

The synthesis of compound 51 followed the same procedure as for compound 32 to afford white solid (0.51 g, 80%). $^1$H NMR (500 MHz, CDCl$_3$): δ (ppm 8.10-8.02 (m, 2H), yield). $^1$H NMR (300 MHz, CDCl$_3$): δ (ppm 8.29 (d, 1H, J=4.7 Hz), 8.01 (t, 1H, J=8.9 Hz), 6.88 (d, 1H, J=8.6 Hz), 5.03-5.01 (m, 1H), 3.70-3.56 (m, 4H), 2.30-2.13 (m, 2H), 1.47 (s, 9H). $^{13}$C NMR (125 MHz, CDCl$_3$): δ (ppm 169.84, 157.90, 154.76, 154.49, 135.77, 130.93, 123.49, 113.12, 112.98, 79.94, 78.18, 51.45, 51.07, 44.15, 43.72, 31.67, 30.87, 28.45.

d. Preparation of (S)-4-((1-(tert-butoxycarbonyl) pyrrolidin-3-yl)oxy)-3-cyclohexylbenzoic Acid (24A)

The synthesis of compound 24a followed the same procedure as for compound 49. Column chromatography (silica gel, hexanes:acetone:AcOH=88:10:2) afforded off-white solid (0.173 g, 75% yield). $^1$H NMR (500 MHz, CD$_3$OD): δ (ppm 7.87-7.84 (m, 2H), 6.96 (d, 1H, J=8.0 Hz), 5.10-5.08 (m, 1H), 3.61-3.45 (m, 4H), 2.85 (t, 1H, J=9.8 Hz), 2.20-2.16 (m, 2H), 1.82-1.73 (m, 6H), 1.45 (s, 4.5H), 1.42, (s, 4.5H), 1.38-1.25 (m, 4H). $^{13}$C NMR (125 MHz, CD$_3$OD): δ (ppm 170.58, 159.11, 156.50, 156.39, 137.98, 137.89, 130.21, 129.73, 125.00, 124.90, 113.13, 113.10, 81.08, 81.04, 77.77, 76.94, 52.76, 52.28, 45.52, 45.12, 38.91, 38.85, 34.32, 34.29, 33.82, 33.72, 32.38, 31.69, 28.82, 28.29, 28.23, 28.19, 28.16, 27.43.

e. Preparation of (S)-4-((1-(tert-butoxycarbonyl)pyrrolidin-3-yl)oxy)-3-(4-(trifluoromethyl)cyclohexyl)benzoic Acid (24B)

The synthesis of compound 24b followed the same procedure as for compound 49. Column chromatography (silica gel, hexanes:acetone:AcOH=88:10:2) afforded white solid (0.0983 g, 41% yield). $^1$H NMR (300 MHz, CD$_3$OD): δ (ppm 7.89-7.86 (m, 2H), 7.01-6.97 (m, 1H), 5.13-5.10 (m, 1H), 3.59-3.42 (m, 4H), 2.98-2.81 (m, 1H), 2.44-2.36 (m, 1H), 2.22-2.18 (m, 2H), 2.05-1.98 (m, 4H), 1.81-1.66 (m, 4H), 1.46 (m, 4.5H), 1.43 (m, 4.5H). $^{13}$C NMR (75 MHz, CD$_3$OD): δ (ppm 175.31, 169.94, 159.52, 159.35, 156.49, 156.44, 13662, 136.54, 136.51, 132.16, 130.69, 130.66, 130.12, 129.70, 129.63, 128.44, 124.50, 124.36, 124.30, 113.29, 113.15, 81.17, 81.13, 77.89, 77.82, 77.12, 52.76, 52.32, 45.52, 45.13, 38.37, 38.03, 37.43, 26.66, 25.08, 25.01, 20.88.

f. Preparation of (S)-4-((1-(tert-butoxycarbonyl)pyrrolidin-3-yl)oxy)-3-(4-methylcyclohexyl)benzoic Acid (52A)

The synthesis of compound 52a followed the same procedure as for compound 49. Column chromatography (silica gel, hexanes:acetone:AcOH=88:10:2) afforded white solid (0.0763 g, 36% yield). $^1$H NMR (500 MHz, CDCl$_3$): δ (ppm 7.88-7.79 (m, 2H), 6.64-6.60 (m, 1H), 4.87-4.83 (m, 1H), 3.61-3.43 (m, 4H), 2.72-2.67 (m, 1H), 2.12-2.03 (m, 2H), 1.67-1.56 (m, 4H), 1.48-1.42 (m, 11H), 1.36-1.20 (m, 3H), 0.93 (d, 3H, J=6.1 Hz). $^{13}$C NMR (75 MHz, CD$_3$OD): δ (ppm 172.17, 158.67, 156.52, 156.46, 137.61, 137.53, 130.00, 129.68, 127.03, 126.85, 113.07, 113.04, 81.08, 81.05, 77.74, 76.92, 52.81, 52.33, 45.55, 45.16, 39.46, 39.42, 38.60, 37.02, 33.87, 33.46, 32.38, 31.69, 28.80, 28.56, 28.21, 27.73, 27.67, 23.19, 18.40.

g. Preparation of (S)-4-((1-(tert-butoxycarbonyl)pyrrolidin-3-yl)oxy)-3-(4-ethylcyclohexyl)benzoic Acid (52B)

The synthesis of compound 52b followed the same procedure as for compound 49. Column chromatography (silica gel, hexanes:acetone:AcOH=88:10:2) afforded white solid (0.111 g, 45% yield). $^1$H NMR (500 MHz, CD$_3$OD): δ (ppm 7.90-7.86 (m, 1H), 7.85-7.82 (m, 1H), 6.96-6.93 (m, 1H), 5.10-5.08 (m, 1H), 3.61-3.48 (m, 4H), 2.88-2.79 (m, 1H), 2.20-2.16 (m, 2H), 1.87-1.62 (m, 6H), 1.56-1.48 (m, 2H), 1.46 (s, 4.5H), 1.43 (s, 4.5H), 1.29-1.17 (m, 2H), 1.07-1.00 (m, 1H), 0.93-0.89 (m, 3H). $^{13}$C NMR (125 MHz, CD$_3$OD): δ ppm 172.26, 158.66, 158.62, 156.52, 156.50, 156.44, 156.42, 137.61, 137.53, 130.05, 129.99, 129.67, 129.64, 127.12, 127.09, 126.92, 113.06, 81.06, 81.01, 77.75, 76.91, 52.78, 52.32, 45.55, 45.15, 40.62, 39.49, 39.22, 39.13, 39.00, 36.07, 34.68, 34.60, 34.57, 34.54, 34.52, 34.16, 34.08, 33.65, 33.57, 32.40, 32.38, 31.72, 31.68, 31.40, 31.30, 31.21, 31.19, 31.16, 30.75, 29.60, 28.81, 28.56, 28.48, 28.05, 27.91, 25.14, 12.82, 11.93.

h. Preparation of (S)-4-((1-(tert-butoxycarbonyl)pyrrolidin-3-yl)oxy)-3-(4,4-dimethylcyclohexyl)benzoic Acid (52C)

The synthesis of compound 52c followed the same procedure as for compound 49. Column chromatography (silica gel, hexanes:acetone:AcOH=85:15:2) afforded white solid (0.164 g, 58% yield). $^1$H NMR (500 MHz, CDCl$_3$): δ (ppm 7.88-7.81 (m, 2H), 6.64-6.64 (m, 1H), 4.88-4.85 (m, 1H), 3.64-3.41 (m, 4H), 2.63 (t, 1H, J=10.3 Hz), 2.14-2.05 (m, 2H), 1.62-1.50 (m, 4H), 1.46 (s, 4.5H), 1.44 (s, 4.5H), 1.41 (m, 2H), 1.25 (t, 2H, J=12.3 Hz), 0.90 (s, 3H), 0.88 (s, 3H). $^{13}$C NMR (125 MHz, CDCl$_3$): δ (ppm 172.35, 157.63, 154.48, 154.40, 135.87, 135.77, 129.25, 129.11, 124.58, 124.47, 110.98, 79.54, 79.44, 76.16, 75.30, 51.60, 51.29, 44.13, 43.78, 39.75, 38.36, 38.23, 33.05, 31.41, 30.75, 29.77, 28.40, 28.21, 28.07, 28.00, 24.25.

i. Preparation of (S)-4-((1-(tert-butoxycarbonyl)pyrrolidin-3-yl)oxy)-3-(4,4-difluorocyclohexyl)benzoic Acid (52D)

The synthesis of compound 52d followed the same procedure as for compound 49. Column chromatography (silica gel, hexanes:acetone:AcOH=88:10:2) afforded white solid (0.0486 g, 18% yield). $^1$H NMR (500 MHz, CD$_3$OD): δ (ppm 7.88-7.87 (m, 1H), 7.84-7.81 (m, 1H), 6.95-6.92 (m, 1H), 5.12-5.10 (m, 1H), 3.60-3.50 (m, 4H), 2.98-2.94 (m, 1H), 2.24-2.20 (m, 2H), 2.15-2.10 (m, 2H), 1.86-1.81 (m, 6H), 1.47 (s, 4.5H), 1.43 (s, 4.5H). $^{13}$C NMR (125 MHz, CD$_3$OD): δ (ppm 180.27, 175.29, 157.42, 157.35, 156.56, 156.52, 134.67, 134.65, 134.54, 131.55, 130.03, 129.63, 129.59, 129.63, 129.59, 124.40, 112.95, 81.13, 81.09, 77.68, 76.99, 52.74, 52.34, 45.85, 45.18, 37.70, 37.57, 35.36, 32.44, 31.72, 30.05, 29.97, 29.90, 28.82, 28.76, 24.14.

j. Preparation of (S)-4-((1-(tert-butoxycarbonyl)pyrrolidin-3-yl)oxy)-3-cyclopentylbenzoic Acid (52E)

The synthesis of compound 52e followed the same procedure as for compound 49. Column chromatography (silica gel, hexanes:acetone:AcOH=88:10:2) afforded white solid (0.152 g, 68% yield). $^1$H NMR (500 MHz, CDCl$_3$): δ (ppm 7.87-7.81 (m, 2H), 6.66-6.62 (m, 1H), 4.89-4.85 (m, 1H), 3.65-3.41 (m, 4H), 3.14-3.11 (m, 1H), 2.14-2.11 (m, 1H), 2.08-2.04 (m, 1H), 1.90-1.86 (m, 2H), 1.69-1.66 (m, 2H), 1.59-1.50 (m, 2H), 1.51-1.48 (m, 2H), 1.46 (s, 4.5H), 1.44 (s, 4.5H). $^{13}$C NMR (125 MHz, CDCl$_3$): δ (ppm 172.32, 158.08, 154.54, 154.46, 134.73, 134.57, 129.23, 129.18, 124.40, 124.24, 110.88, 79.56, 79.47, 76.22, 75.36, 51.66, 51.40, 44.12, 43.78, 39.43, 32.49, 32.36, 32.30, 31.35, 30.84, 30.70, 28.40, 25.40, 24.75.

11. Preparation of Compounds 9-17

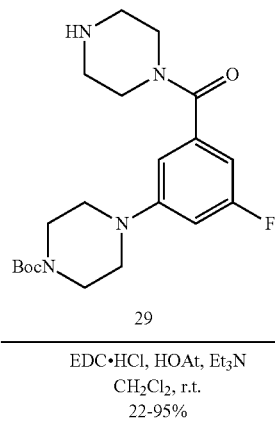

24, 51, 52 $\xrightarrow{\text{EDC·HCl, HOAt, Et}_3\text{N}}_{\substack{\text{CH}_2\text{Cl}_2, \text{r.t.} \\ 22-95\%}}$ -continued

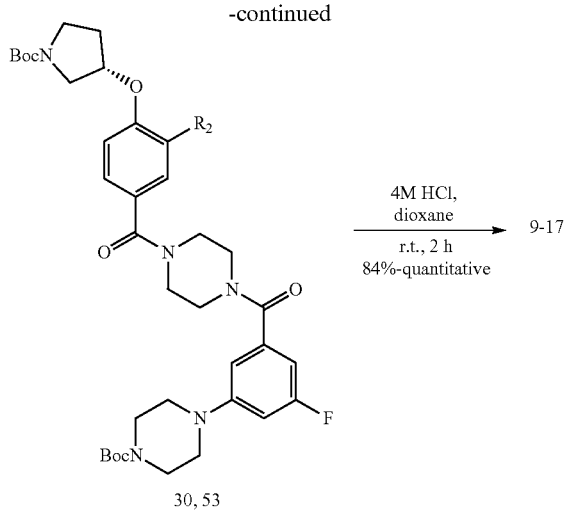

4M HCl, dioxane
r.t., 2 h
84%-quantitative
→ 9-17

30, 53 a. Preparation of tert-butyl (S)-4-(3-(4-(4-((1-(tert-butoxycarbonyl)pyrrolidin-3-yl)oxy)-3-cyclohexyl-benzoyl)piperazine-1-carbonyl)-5-fluorophenyl)piperazine-1-carboxylate (30A)

The synthesis of compound 30a followed the same procedure as for compound 35. Column chromatography (silica gel, hexanes:acetone=70:30) afforded white solid (0.0494 g, 21% yield). $^1$H NMR (500 MHz, CDCl$_3$): δ (ppm 7.25-7.20 (m, 2H), 6.78 (d, 1H, J=7.8 Hz), 6.68 (s, 1H), 6.60 (d, 1H, J=11.8 Hz), 6.52 (d, 1H, J=7.2 Hz), 4.94-4.92 (m, 1H), 3.77-3.46 (m, 16H), 3.17-3.15 (m, 4H), 2.86-2.81 (m, 1H), 2.22-2.18 (m, 1H), 2.14-2.09 (m, 1H), 1.80-1.72 (m, 6H), 1.46 (s, 9H), 1.44 (s, 9H), 1.38-1.28 (m, 4H). $^{13}$C NMR (125 MHz, CDCl$_3$): δ (ppm 170.91, 169.58, 163.39 (d, J=246.0 Hz), 155.64, 155.52, 154.53, 154.51, 154.37, 152.93 (d, J=10.1 Hz), 137.52 (d, J=8.3 Hz), 137.33 (d, J=11.0 Hz), 127.22, 126.50, 126.09, 126.0, 111.83, 109.75, 104.36 (d, J=23.2 Hz), 103.9 (d, J=23.2 Hz), 80.09, 79.50, 79.42, 76.46, 75.36, 53.77, 51.45, 50.96, 48.22, 44.18, 43.82, 37.31, 37.22, 33.08, 33.03, 32.80, 32.59, 31.68, 31.67, 31.63, 30.92, 29.21, 28.41, 28.33, 26.94, 26.88, 26.22.

b. Preparation of tert-butyl (S)-4-(3-(4-(4-((1-(tert-butoxycarbonyl)pyrrolidin-3-yl)oxy)-3-(4-(trifluoromethyl)cyclohexyl)benzoyl)piperazine-1-carbonyl)-5-fluorophenyl)piperazine-1-carboxylate (30B)

The synthesis of compound 30b followed the same procedure as for compound 35. Column chromatography (silica gel, hexanes:acetone=70:30) afforded white solid (0.0997 g, 68% yield). $^1$H NMR (500 MHz, CDCl$_3$): δ (ppm 7.25-7.22 (m, 2H), 6.80-6.77 (m, 1H), 6.67-6.66 (m, 1H), 6.61-6.58 (m, 1H), 6.51-6.50 (m, 1H), 4.94-4.92 (m, 1H), 3.73-3.45 (m, 16H), 3.16-3.14 (m, 4H), 2.93-2.90 (m, 1H), 2.33-2.28 (m, 1H), 2.19-2.10 (m, 2H), 2.03-1.98 (m, 3H), 1.92-1.87 (m, 1H), 1.76-1.63 (m, 4H), 1.45 (s, 9H), 1.43 (s, 9H). $^{13}$C NMR (125 MHz, CDCl$_3$): δ (ppm 170.66, 169.50, 163.35 (d, J=246.0 Hz), 155.61, 154.46, 154.32, 152.85 (d, J=9.5 Hz), 137.46 (d, J=8.9 Hz), 135.74, 135.59, 129.69, 127.46, 127.24, 126.78, 126.51, 126.44, 111.90, 111.83, 109.72, 104.37 (d, J=22.9 Hz), 103.88 (d, J=25.2 Hz), 80.05, 80.03, 79.53, 79.45, 76.48, 75.46, 51.41, 51.02, 48.21, 44.10, 43.75, 36.85, 36.63, 36.47, 35.57, 35.55, 31.50, 30.90, 30.81, 29.56, 29.16, 28.36, 28.27, 27.54, 27.35, 27.24, 25.25, 23.84, 20.92, 14.08.

c. Preparation of tert-butyl (S)-4-(3-(4-(6-((1-(tert-butoxycarbonyl)pyrrolidin-3-yl)oxy)-3',4'-difluoro-[1,1'-biphenyl]-3-carbonyl)piperazine-1-carbonyl)-5-fluorophenyl)piperazine-1-carboxylate (53A)

The synthesis of compound 53a followed the same procedure as for compound 35. Column chromatography (silica gel, hexanes:acetone=70:30) afforded white solid (0.144 g, 69% yield). $^1$H NMR (500 MHz, CDCl$_3$): δ (ppm 7.37-7.33 (m, 2H), 7.25-7.20 (m, 1H), 7.15-7.10 (m, 2H), 6.92 (d, 1H, J=8.1 Hz), 6.64 (s, 1H), 6.57 (d, 1H, J=11.5 Hz), 6.47 (d, 1H, J=7.4 Hz), 4.91-4.88 (m, 1H), 3.77-3.24 (m, 16H), 3.14-3.11 (m, 4H), 2.08-2.04 (m, 2H), 1.42 (s, 9H), 1.40 (s, 5H), 1.39 (s, 4H). $^{13}$C NMR (125 MHz, CDCl$_3$): δ (ppm 169.84, 169.44 (d, J=2.4 Hz), 163.26 (d, J=246.11 Hz), 155.05, 154.86, 154.38, 154.12, 152.81 (d, J=10.1 Hz), 150.62, 150.59, 150.49, 148.72, 148.62, 148.50, 137.31 (d, J=8.6 Hz), 133.94, 133.79, 130.13, 129.87, 129.68, 128.32, 128.29, 127.92, 125.23, 118.30, 118.25, 118.23, 118.16, 118.11, 118.08, 116.81, 116.76, 116.67, 116.63, 113.44, 113.32, 109.58, 104.16 (d, J=23.4 Hz), 103.77 (d, J=25.5 Hz), 79.96, 79.48, 77.20, 77.17, 76.13, 69.30, 53.72, 51.26, 50.67, 48.06, 43.95, 43.51, 31.58, 31.36, 30.73, 30.52, 29.09, 28.23, 28.20.

d. Preparation of tert-butyl (S)-4-(3-(4-(4-((1-(tert-butoxycarbonyl)pyrrolidin-3-yl)oxy)-3-(4-methylcyclohexyl)benzoyl)piperazine-1-carbonyl)-5-fluorophenyl)piperazine-1-carboxylate (53B)

The synthesis of compound 53b followed the same procedure as for compound 35. Column chromatography (silica gel, hexanes:acetone=70:30) afforded white solid (0.0313 g, 22% yield). $^1$H NMR (300 MHz, CDCl$_3$): δ (ppm 7.30-7.28 (m, 1H), 7.24-7.19 (m, 1H), 6.80-6.77 (m, 1H), 6.70-6.68 (m, 1H), 6.64-6.59 (m, 1H), 6.55-6.52 (m, 1H), 4.95-4.93 (m, 1H), 3.78-3.48 (m, 16H), 3.17 (t, 4H, J=4.7 Hz), 2.83-2.78 (m, 1H), 2.21-2.10 (m, 2H), 1.99-1.95 (m, 1H), 1.80-1.52 (m, 6H), 1.47 (s, 9H), 1.45 (s, 9H), 1.32-1.25 (m, 2H), 1.01 (d, 3H, J=7.2 Hz). $^{13}$C NMR (75 MHz, CDCl$_3$): δ (ppm 170.99, 169.64, 163.42 (d, J=245.9 Hz), 155.81, 155.69, 154.56, 152.96 (d, J=10.0 Hz), 137.53 (d, J=8.5 Hz), 137.31, 127.15, 126.86, 126.11, 111.78, 109.82 (d, J=2.3 Hz), 104.45 (d, J=23.8 Hz), 103.98 (d, J=25.7 Hz), 80.17, 79.56, 79.50, 53.73, 48.28, 37.69, 32.53, 32.15, 31.73, 30.93, 29.67, 29.23, 28.45, 28.37, 27.00, 26.56, 22.62, 17.90.

e. Preparation of tert-butyl (S)-4-(3-(4-(4-((1-(tert-butoxycarbonyl)pyrrolidin-3-yl)oxy)-3-(4-ethylcyclohexyl)benzoyl)piperazine-1-carbonyl)-5-fluorophenyl)piperazine-1-carboxylate (53C)

The synthesis of compound 53c followed the same procedure as for compound 35. Column chromatography (silica gel, hexanes:acetone=70:30) afforded white solid (0.120 g, 58% yield). $^1$H NMR (500 MHz, CDCl$_3$): δ (ppm 7.23-7.16 (m, 2H), 6.75-6.73 (m, 1H), 6.65-6.64 (m, 1H), 6.58-6.56 (m, 1H), 6.49-6.48 (m, 1H), 4.91-4.89 (m, 1H), 3.71-3.45 (m, 16H), 3.14-3.12 (m, 4H), 2.82-2.75 (m, 1H), 2.17-2.05 (m, 2H), 1.80-1.47 (m, 6H), 1.43 (s, 9H), 1.40 (s, 9H), 1.36-1.19 (m, 5H), 0.84 (t, 3H, J=7.4 Hz). $^{13}$C NMR (125 MHz, CDCl$_3$): δ (ppm 170.80, 169.45, 163.28 (d, J=246.2

Hz), 155.63, 155.52, 154.39, 152.76 (d, J=10.3 Hz), 137.44 (d, J=9.1 Hz), 127.06, 126.68, 126.34, 125.94, 111.69, 109.68, 104.32 (d, J=23.1 Hz), 103.83 (d, J=25.2 Hz), 79.97, 79.37, 79.29, 76.34, 75.26, 53.73, 51.36, 50.87, 48.15, 44.09, 43.71, 39.05, 37.46, 37.31, 37.22, 34.30, 33.01, 32.69, 31.60, 31.51, 30.79, 30.76, 29.93, 29.81, 29.11, 28.31, 28.22, 27.16, 26.90, 26.71, 23.89, 12.20, 11.36.

f. Preparation of tert-butyl (S)-4-(3-(4-(4-((1-(tert-butoxycarbonyl)pyrrolidin-3-yl)oxy)-3-(4,4-dimethylcyclohexyl)benzoyl)piperazine-1-carbonyl)-5-fluorophenyl)piperazine-1-carboxylate (53D)

The synthesis of compound 53d followed the same procedure as for compound 35. Column chromatography (silica gel, hexanes:acetone=70:30) afforded white solid (0.0884 g, 44% yield). $^1$H NMR (500 MHz, CDCl$_3$): δ (ppm 7.27 (s, 1H), 7.23-7.18 (m, 1H), 6.76 (d, 1H, J=8.3 Hz), 6.67 (s, 1H), 6.59 (d, 1H, 11.6 Hz), 6.51 (d, 1H, 7.5 Hz), 4.93-4.91 (m, 1H), 3.74-3.45 (m, 16H), 3.16-3.14 (m, 4H), 2.74-2.68 (m, 1H), 2.21-2.15 (m, 1H), 2.12-2.07 (m, 1H), 1.57-1.52 (m, 4H), 1.45 (s, 9H), 1.43 (s, 11H), 1.32-1.26 (m, 2H), 0.92 (s, 6H). $^{13}$C NMR (125 MHz, CDCl$_3$): δ (ppm 171.03, 169.65, 163.35 (d, J=246.0 Hz), 155.82, 155.72, 154.58, 154.53, 154.42, 152.88 (d, J=10.1 Hz), 137.34 (d, J=8.7 Hz), 137.00, 126.96, 126.69, 126.08, 126.01, 111.69, 109.74 (d, J=1.6 Hz), 104.33 (d, J=23.7 Hz), 103.91 (d, J=25.1 Hz), 80.16, 79.62, 79.54, 76.34, 75.36, 51.49, 50.99, 48.17, 44.18, 43.78, 39.71, 39.67, 39.62, 37.88, 37.82, 32.97, 31.55, 30.81, 29.80, 28.50, 28.44, 28.38, 28.29, 28.18, 28.13, 24.20.

g. Preparation of tert-butyl (S)-4-(3-(4-(4-((1-(tert-butoxycarbonyl)pyrrolidin-3-yl)oxy)-3-(4,4-difluorocyclohexyl)benzoyl)piperazine-1-carbonyl)-5-fluorophenyl)piperazine-1-carboxylate (53E)

The synthesis of compound 53e followed the same procedure as for compound 35. Column chromatography (silica gel, hexanes:acetone=70:30) afforded white solid (0.0530 g, 61% yield). $^1$H NMR (500 MHz, CDCl$_3$): δ (ppm 7.28-7.23 (m, 2H), 6.81-6.80 (m, 1H), 6.70-6.68 (m, 1H), 6.63-6.60 (m, 1H), 6.53-6.52 (m, 1H), 4.97-4.95 (m, 1H), 3.77-3.46 (m, 16H), 3.18-3.16 (m, 4H), 2.94-2.89 (m, 1H), 2.20-2.15 (m, 4H), 1.89-1.70 (m, 6H), 1.47 (s, 9H), 1.45 (s, 9H). $^{13}$C NMR (125 MHz, CDCl$_3$): δ (ppm 170.56, 169.58, 163.40 (d, J=246.2 Hz), 155.58, 154.52, 152.89 (d, J=10.3 Hz), 137.49 (d, J=8.2 Hz), 134.55, 127.44, 126.76, 126.74, 126.72, 126.68, 126.59, 126.57, 111.88, 109.82, 104.45 (d, J=23.4 Hz), 103.99 (d, J=24.8 Hz), 80.14, 79.68, 79.63, 53.75, 51.45, 50.97, 48.29, 44.17, 43.80, 35.92, 35.65, 34.31, 34.10, 33.93, 31.70, 31.64, 30.89, 29.22, 28.62, 28.53, 28.43, 28.35.

h. Preparation of tert-butyl (S)-4-(3-(4-(4-((1-(tert-butoxycarbonyl)pyrrolidin-3-yl)oxy)-3-cyclopentyl-benzoyl)piperazine-1-carbonyl)-5-fluorophenyl)piperazine-1-carboxylate (53F)

The synthesis of compound 53f followed the same procedure as for compound 35. Column chromatography (silica gel, hexanes:acetone=70:30) afforded white solid (0.0742 g, 41% yield). $^1$H NMR (500 MHz, CDCl$_3$): δ (ppm 7.28 (s, 1H), 7.23-7.19 (m, 1H), 6.77 (d, 1H, J=8.3 Hz), 6.68 (s, 1H), 6.60 (d, J=11.8 Hz), 6.52 (d, J=7.5 Hz), 4.95-4.93 (m, 1H), 3.75-3.45 (m, 16H), 3.23-3.19 (m, 1H), 3.17-3.15 (m, 4H), 2.23-2.16 (m, 1H), 2.13-2.09 (m, 1H), 1.98-1.93 (m, 2H), 1.75-1.71 (m, 2H), 1.66-1.62 (m, 2H), 1.55-1.49 (m, 2H), 1.46 (s, 9H), 1.44 (s, 9H). $^{13}$C NMR (125 MHz, D$_2$O): δ ppm 170.89, 169.57 (d, J=2.5 Hz), 163.39 (d, J=246.0 Hz), 156.27, 156.21, 154.56, 154.51, 154.41, 152.93 (d, J=10.1 Hz), 137.51 (d, J=8.1 Hz), 135.90, 135.77, 127.00, 126.76, 126.06, 126.04, 126.02, 111.54, 109.75 (d, J=1.9 Hz), 104.36 (d, J=23.6 Hz), 103.91 (d, J=25.3 Hz), 80.10, 79.53, 79.45, 76.39, 75.39, 51.59, 51.15, 48.23, 44.18, 43.79, 39.44, 39.35, 32.60, 32.54, 32.32, 31.51, 30.78, 28.42, 28.33, 25.46.

i. Preparation of tert-butyl (S)-4-(3-(4-(4-((1-(tert-butoxycarbonyl)pyrrolidin-3-yl)oxy)-3-methylbenzoyl)piperazine-1-carbonyl)-5-fluorophenyl)piperazine-1-carboxylate (53G)

The synthesis of compound 53g followed the same procedure as for compound 35. Column chromatography (silica gel, hexanes:acetone=70:30) afforded white solid (0.2507 g, 81% yield). $^1$H NMR (500 MHz, CDCl$_3$): δ (ppm 7.15-7.11 (m, 2H), 6.70-6.68 (m, 1H), 6.61-6.59 (m, 1H), 6.54-6.51 (m, 1H), 6.45-6.43 (m, 1H), 4.85-4.83 (m, 1H), 3.66-3.44 (m, 16H), 3.10-3.07 (m, 4H), 2.09 (s, 3H), 1.38 (s, 9H), 1.37 (s, 9H). $^{13}$C NMR (125 MHz, CDCl$_3$): δ (ppm 170.34, 169.24 (d, J=2.7 Hz), 163.15 (d, J=246.0 Hz), 156.40, 154.23, 152.64 (d, J=10.1 Hz), 137.36 (d, J=8.8 Hz), 129.99, 127.78, 126.90, 126.02, 111.39, 109.44 (d, J=1.5 Hz), 104.05 (d, J=23.3 Hz), 103.57 (d, J=25.1 Hz), 79.74, 79.14, 76.35, 75.47, 51.35, 50.95, 47.94, 43.88, 43.49, 31.35, 30.57, 28.18, 28.09.

j. Preparation of (S)-(4-(3',4'-difluoro-6-(pyrrolidin-3-yloxy)-[1,1'-biphenyl]-3-carbonyl)piperazin-1-yl)(3-fluoro-5-(piperazin-1-yl)phenyl)methanone Hydrochloride (9)

The synthesis of compound 9 followed the same procedure as for compound 2 to afford white solid (0.116 g, 97% yield). $^1$H NMR (500 MHz, d$^6$-DMSO): δ (ppm 9.45 (brs, 2H), 9.28 (brs, 2H), 7.68-7.64 (m, 2H), 7.48-7.39 (m, 3H), 7.20 (d, 1H, J=8.5 Hz), 6.90 (d, 1H, J=12.5 Hz), 6.80 (s, 1H), 6.65 (d, 1H, J=8.0 Hz), 5.18-5.15 (m, 1H), 3.64-3.09 (m, 20H), 2.21-2.03 (m, 2H), 7.41 (d, 1H, J=7.4 Hz), 7.13-7.10 (m, 4H), 7.00 (s, 1H), 6.76-6.72 (m, 2H), 6.44 (s, 1H), 5.15-5.11 (m, 1H), 3.69-3.12 (m, 20H), 2.24-2.16 (m, 1H), 2.09-2.04 (m, 1H). $^{13}$C NMR (125 MHz, D$_2$O): δ ppm 171.43, 170.81, 163.60 (d, J=244.4 Hz), 154.66, 150.45, 148.50, 136.92, 136.85, 134.06, 129.76, 129.16, 127.73, 126.25, 118.27, 118.13, 117.26, 117.13, 114.35, 110.56, 105.34, 76.63, 50.45, 45.64, 44.42, 43.05, 42.76, 30.45, 29.60. HRMS (ESI) m/z calculated for C$_{32}$H$_{34}$F$_3$N$_5$O$_3$(M+H)$^+$=594.2687, found 594.2698.

k. Preparation of (S)-(4-(3-cyclohexyl-4-(pyrrolidin-3-yloxy)benzoyl)piperazin-1-yl) (3-fluoro-5-(piperazin-1-yl)phenyl) methanone Hydrochloride (10)

The synthesis of compound 10 followed the same procedure as for compound 2 to afford white solid (0.0392 g, 98% yield). $^1$H NMR (500 MHz, d$^6$-DMSO): δ (ppm 9.34 (brs, 4H), 7.24-7.22 (m, 2H), 7.00 (d, 1H, J=9.0 Hz), 6.90 (d, 1H, J=12.5 Hz), 6.80 (s, 1H), 6.64 (d, 1H, J=8.5 Hz), 5.18-5.14 (m, 1H), 3.62-2.85 (m, 20H), 2.90-2.85 (m, 1H), 2.19-1.20 (m, 12H). $^{13}$C NMR (75 MHz, D$_2$O): δ ppm 172.71, 171.23, 163.38 (d, J=243.2 Hz), 155.12 (d, J=16.8 Hz), 151.97, 137.68, 136.77 (d, J=15.0 Hz), 127.07, 126.46, 126.34, 112.69, 110.65, 105.80, 105.43, 75.91, 50.74, 47.76, 47.17, 45.85, 44.47, 42.99, 42.69, 42.11, 36.56, 32.97, 30.66, 26.59, 25.94. HRMS (ESI) m/z calculated for $C_{32}H_{43}FN_5O_3$ $(M+H)^+$=564.3344, found 564.3348.

l. Preparation of (S)-(4-(3-cyclopentyl-4-(pyrrolidin-3-yloxy)benzoyl)piperazin-1-yl) (3-fluoro-5-(piperazin-1-yl)phenyl) methanone Hydrochloride (11)

The synthesis of compound 11 followed the same procedure as for compound 2 to afford white solid (0.0661 g, quantitative yield, trans:cis=2:1). Major isomer: $^1$H NMR (500 MHz, d$^6$-DMSO): δ (ppm 9.47 (brs, 2H), 9.22 (brs, 2H), 7.28-7.22 (m 2H), 7.00 (d, 1H, J=8.5 Hz), 6.90 (d, 1H, J=12.5 Hz), 6.80 (s, 1H), 6.65 (d, 1H, J=8.0 Hz), 5.18-5.15 (m, 1H), 3.72-3.16 (m, 20H), 2.90-2.82 (m, 1H) 2.20-1.07 (m, 11H), 1.00 (d, 1H, J=7.0 Hz). $^{13}$C NMR (75 MHz, D$_2$O): δ ppm 172.67, 171.15, 163.23 (d, J=244.9 Hz), 155.02, 151.79, 151.71, 137.44, 136.63, 136.56, 126.96, 126.89, 126.47, 116.24, 126.07, 112.53, 110.46, 75.73, 50.57, 47.74, 44.15, 46.89, 45.69, 44.31, 42.80, 42.58, 36.40, 36.09, 365.03, 32.62, 32.55, 31.88, 31.55, 30.47, 26.77, 26.70, 21.97. HRMS (ESI) m/z calculated for $C_{31}H_{40}FN_5O_3$ $(M+H)^+$=550.3188, found 550.3208.

m. Preparation of (S)-(4-(3-fluoro-5-(piperazin-1-yl) benzoyl)piperazin-1-yl) (3-(4-methylcyclohexyl)-4-(pyrrolidin-3-yloxy)phenyl)methanone Hydrochloride (12)

The synthesis of compound 12 followed the same procedure as for compound 2 to afford white solid (0.0252 g, quantitative yield). $^1$H NMR (500 MHz, d$^6$-DMSO): δ (ppm 9.40 (brs, 2H), 9.06 (brs, 2H), 7.28-7.21 (m, 2H), 7.02 (d, 1H, J=8.0 Hz), 6.91 (d, 1H, J=12.5 Hz), 6.80 (s, 1H), 6.65 (d, 1H, J=8.5 Hz), 5.21-5.16 (m 2H), 3.66-3.00 (m, 21H), 2.22-1.42 (m, 11H). $^{13}$C NMR (125 MHz, D$_2$O): δ ppm 172.21, 170.73, 163.18 (d, J=242.9 Hz), 155.19 (d, J=12.4 Hz), 151.74 (d, J=10.1 Hz), 151.94 (d, J=10.5 Hz), 151.91 (d, J=10.4 Hz), 136.80 (d, J=9.5 Hz), 126.94 (d, J=23.8 Hz), 126.86 (d, J=15.1 Hz), 126.02, 112.66, 110.43, 105.13, 75.70, 50.58, 50.53, 47.75, 47.78, 45.50, 44.33, 42.89, 41.92, 35.61, 30.58, 27.46, 27.32, 24.83, 23.03. HRMS (ESI) m/z calculated for $C_{33}H_{44}FN_5O_3(M+H)^+$=578.3547, found 578.3510.

n. Preparation of (S)-(4-(3-fluoro-5-(piperazin-1-yl) benzoyl)piperazin-1-yl) (4-(pyrrolidin-3-yloxy)-3-(4-(trifluoromethyl)cyclohexyl)phenyl)methanone Hydrochloride (13)

The synthesis of compound 13 followed the same procedure as for compound 2 to afford white solid (0.0767 g, 92% yield). $^1$H NMR (500 MHz, d$^6$-DMSO): δ (ppm 9.41 (brs, 2H), 9.18 (brs, 2H), 7.26-7.22 (m, 2H), 7.00 (d, 1H, J=8.5 Hz), 6.90 (d, 1H, J=12.0 Hz), 6.80 (s, 1H), 6.65 (d, 1H, J=8.0 Hz), 5.18-5.15 (m, 1H), 3.70-2.81 (m, 21H), 2.21-1.10 (m, 13H); 0.86 (t, 3H, J=7.5 Hz). $^{13}$C NMR (125 MHz, D$_2$O): δ ppm 171.93, 170.44, 163.09 (d, J=242.9 Hz), 155.17, 152.10, 152.02, 136.87, 136.32, 127.05, 126.98, 125.55, 112.76, 110.47, 104.79, 75.61, 50.41, 45.38, 44.28, 42.89, 39.24, 36.43, 36.21, 34.51, 32.86, 32.70, 30.68, 29.78, 29.63, 27.31, 27.14, 24.08, 12.13, 11.37. HRMS (ESI) m/z calculated for $C_{33}H_{41}F_4N_5O_3(M+H)^+$=632.3224, found 632.3235.

o. Preparation of (S)-(4-(3-(4-ethylcyclohexyl)-4-(pyrrolidin-3-yloxy)benzoyl)piperazin-1-yl) (3-fluoro-5-(piperazin-1-yl)phenyl) methanone Hydrochloride (14)

The synthesis of compound 14 followed the same procedure as for compound 2 to afford white solid (0.0836 g, 84% yield). $^1$H NMR (500 MHz, d$^6$-DMSO): δ (ppm 9.22 (brs, 2H), 8.89 (brs, 2H), 7.28 (s, 1H), 7.24 (d, 1H, J=8.5 Hz), 7.00 (d, 1H, J=8.5 Hz), 6.91 (d, 1H, J=12.5 Hz), 6.80 (s, 1H), 6.65 (d, 1H, J=8.5 Hz), 5.18-5.14 (m, 1H), 3.65-3.18 (m, 20H), 2.81-2.75 (m, 1H), 2.22-2.09 (m, 2H), 1.57-1.30 (m, 8H), 0.95 (s, 3H), 0.93 (s, 3H). $^{13}$C NMR (125 MHz, D$_2$O): δ ppm 172.23, 170.72 163.25, 155.33, 152.19, 152.06, 136.88, 136.76, 136.54, 127.06, 126.89, 126.79, 112.78, 110.63, 105.03, 75.72, 50.55, 45.59, 44.41, 42.99, 36.37, 36.77, 32.93, 30.79, 30.40, 30.13, 29.88, 29.88, 29.54, 28.56, 24.24. HRMS (ESI) m/z calculated for $C_{33}H_{46}FN_5O_3$ $(M+H)^+$=592.3663, found 592.3667.

p. Preparation of (S)-(4-(3-(4,4-dimethylcyclohexyl)-4-(pyrrolidin-3-yloxy)benzoyl)piperazin-1-yl) (3-fluoro-5-(piperazin-1-yl)phenyl)methanone Hydrochloride (15)

The synthesis of compound 15 followed the same procedure as for compound 2 to afford white solid (0.0720 g, 97% yield). $^1$H NMR (500 MHz, d$^6$-DMSO): δ (ppm 9.72 (brs, 1H), 9.46 (brs, 1H), 9.18 (brs, 2H), 7.27 (d, 1H, J=8.5 Hz), 7.23 (s, 1H), 7.04 (d, 1H, J=8.5 Hz), 6.90 (d, 1H, J=12.5 Hz), 6.80 (s, 1H), 6.64 (d, 1H, J=8.0 Hz), 5.23-5.19 (m, 1H), 3.72-3.08 (m, 21H), 2.49-1.54 (m, 10H). $^{13}$C NMR (125 MHz, D$_2$O): δ ppm 172.58, 171.19, 163.30 (d, J=243.9 Hz), 155.17, 151.81 (d, J=10.5 Hz), 136.71 (d, J=9.5 Hz), 134.92, 127.01, 126.64, 126.19, 112.48, 110.50, 105.93 (d, J=21.9 Hz), 105.49 (d, J=25.6 Hz), 75.79, 50.66, 45.74, 44.37, 42.87, 34.56, 33.50, 33.31 (t, J=24.8 Hz), 33.12, 30.51, 28.35 (t, J=10.4 Hz). HRMS (ESI) m/z calculated for $C_{34}H_{47}FN_5O_3(M+H)^+$=592.3657, found 592.3674.

q. Preparation of (S)-(4-(3-(4,4-difluorocyclohexyl)-4-(pyrrolidin-3-yloxy)benzoyl)piperazin-1-yl) (3-fluoro-5-(piperazin-1-yl)phenyl)methanone Hydrochloride (16)

The synthesis of compound 16 followed the same procedure as for compound 2 to afford white solid (0.0512 g, 84% yield). $^1$H NMR (500 MHz, d$^6$-DMSO): δ (ppm 9.30 (brs, 2H), 9.02 (brs, 2H), 7.25 (s, 1H), 7.24 (d, 1H, J=8.5 Hz), 7.00 (d, 1H, J=8.5 Hz), 6.91 (d, 1H, J=12.5 Hz), 6.80 (s, 1H), 6.65 (d, 1H, J=8.5 Hz), 5.20-5.16 (m, 1H), 3.63-3.17 (m, 21H), 2.20-1.46 (m, 10H). $^{13}$C NMR (125 MHz, D$_2$O): δ ppm 172.64, 171.16, 163.01 (d, J==243.6 Hz), 155.74, 152.01, 151.87, 136.84, 136.29, 126.89, 126.42, 112.51, 110.63, 75.83, 50.75, 47.77, 47.19, 46.93, 45.78, 44.43, 42.99, 42.62, 42.08, 38.49, 32.77, 32.66, 30.59, 30.36, 25.15. HRMS (ESI) m/z calculated for $C_{32}H_{40}F_3N_5O_3(M+H)^+$=600.3162, found 600.3168.

r. Preparation of (S)-(4-(3-fluoro-5-(piperazin-1-yl) benzoyl)piperazin-1-yl) (3-methyl-4-(pyrrolidin-3-yloxy)phenyl)methanone Hydrochloride (17)

The synthesis of compound 17 followed the same procedure as for compound 2 to afford white solid (0.189 g, 92% yield). $^1$H NMR (500 MHz, d$^6$-DMSO): δ (ppm 9.47 (brs, 2H), 9.23 (brs, 2H), 7.24-7.22 (m, 2H), 7.00 (d, 1H, J=8.5

Hz), 6.90 (d, 1H, J=8.5 Hz), 6.80 (s, 1H), 6.64 (d, 1H, J=7.5 Hz), 5.20-5.17 (m, 1H), 3.61-3.16 (m, 20H), 2.19-2.09 (m, 5H). $^{13}$C NMR (125 MHz, D$_2$O): δ ppm 172.29, 170.83, 163.15 (d, J=242.9 Hz), 155.90, 155.54, 136.67, 129.84, 128.23, 126.60, 126.36, 112.26, 110.42, 105.77 (d, J=20.7 Hz), 105.29 (d, J=24.8 Hz), 75.62, 50.64, 47.56, 46.94, 45.62, 44.09, 42.80, 42.48, 41.85, 30.23, 15.39. HRMS (ESI) m/z calculated for C$_{27}$H$_{34}$FN$_5$O$_3$(M+H)$^+$=496.2724, found 496.2731.

12. Preparation of Compounds 18-21 a. Preparation of Benzyl (S)-4-(4-((1-(tert-butoxycarbonyl) pyrrolidin-3-yl)oxy)-3-cyclohexylbenzoyl) piperazine-1-carboxylate (54)

The synthesis of compound 54 followed the same procedure as for compound 33. Column chromatography (silica gel, hexanes:EtOAc=3:1) afforded white solid (0.800 g, 73% yield). $^1$H NMR (500 MHz, CDCl$_3$): δ (ppm 7.34-7.28 (m, 5H), 7.23-7.18 (m, 2H), 6.77 (d, 1H, J=8.3 Hz), 5.13 (s, 2H), 4.93-4.91 (m, 1H), 3.66-3.48 (m, 12H), 2.83 (t, 1H, J=9.4

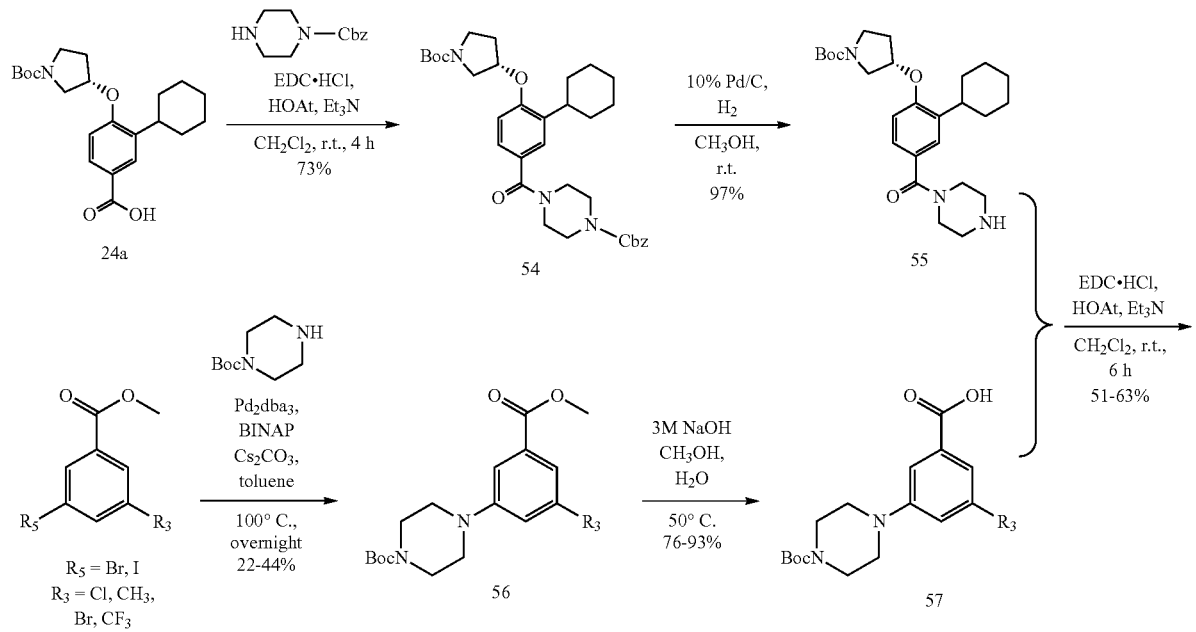

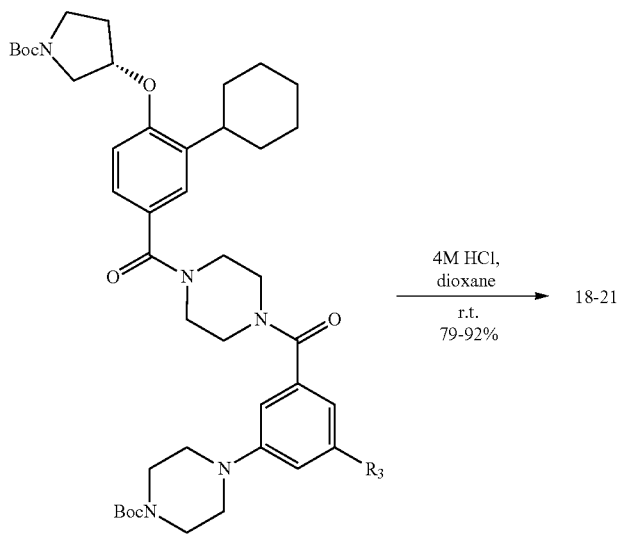

Hz), 2.22-2.16 (m, 1H), 2.12-2.08 (m, 1H), 1.80-1.71 (m, 6H), 1.44 (s, 4.5H), 1.44 (s, 4.5H), 1.38-1.19 (m, 4H). $^{13}$C NMR (125 MHz, CDCl$_3$): δ (ppm 170.79, 155.43, 155.02, 154.46, 154.31, 137.22, 137.12, 136.23, 128.40, 128.04, 127.86, 127.44, 126.39, 125.97, 125.91, 111.80, 111.72, 79.40, 79.33, 76.37, 75.27, 67.30, 51.38, 50.94, 44.12, 43.77, 37.24, 37.14, 34.51, 32.96, 32.71, 32.53, 31.54, 31.43, 30.85, 28.34, 26.82, 26.15, 25.13, 22.50.

b. Preparation of tert-butyl (S)-3-(2-cyclohexyl-4-(piperazine-1-carbonyl)phenoxy)pyrrolidine-1-carboxylate (55)

The synthesis of compound 55 followed the same procedure as for compound 34 to afford off-white solid (0.58 g, 97% yield). $^1$H NMR (500 MHz, CDCl$_3$): δ (ppm 7.23-7.21 (m, 2H), 6.79 (d, 1H, J=8.4 Hz), 4.95-4.93 (m, 1H), 4.00-3.96 (m, 4H), 3.66-3.47 (m, 4H), 3.25-3.20 (m, 4H), 2.84 (t, 1H, J=10.0 Hz), 2.23-2.18 (m, 1H), 2.15-2.11 (m, 1H), 1.81-1.72 (m, 6H), 1.45 (s, 9H), 1.39-1.21 (m, 4H). $^{13}$C NMR (125 MHz, CDCl$_3$): δ ppm 170.90, 155.96, 154.60, 154.41, 137.66, 137.59, 126.57, 126.28, 126.21, 126.02, 125.97, 111.91, 79.61, 79.54, 76.53, 75.40, 51.51, 50.99, 44.21, 43.83, 43.51, 37.34, 37.27, 33.10, 33.02, 32.81, 32.56, 31.65, 30.94, 28.44, 26.94, 26.87, 26.19.

c. Preparation of tert-butyl 4-(3-chloro-5-(methoxycarbonyl)phenyl)piperazine-1-carboxylate (56A)

The synthesis of compound 56a followed the same procedure as for compound 26 except using methyl 3-bromo-5-chlorobenzoate. Column chromatography (silica gel, hexanes:EtOAc=9:1) afforded white solid (0.951 g, 41% yield). $^1$H NMR (500 MHz, CDCl$_3$): δ (ppm 7.46-7.45 (m, 1H), 7.44-7.43 (m, 1H), 7.02-7.00 (m, 1H), 3.89 (s, 3H), 3.57-3.54 (m, 4H), 3.19-3.17 (m, 4H), 1.47 (s, 9H). $^{13}$C NMR (125 MHz, CDCl$_3$): δ ppm 166.12, 154.55, 151.93, 135.11, 132.14, 120.43, 120.37, 119.93, 115.24, 115.18, 80.06, 52.38, 52.30, 48.53, 28.36.

d. Preparation of tert-butyl 4-(3-(methoxycarbonyl)-5-methylphenyl)piperazine-1-carboxylate (56B)

The synthesis of compound 56b followed the same procedure as for compound 26 using methyl 3-bromo-5-methylbenzoate. Column chromatography (silica gel, hexanes:EtOAc=9:1) afforded white solid (0.246 g, 40% yield). $^1$H NMR (300 MHz, CDCl$_3$): δ (ppm 7.39-7.38 (m, 1H), 7.37-7.36 (m, 1H), 6.92-6.91 (m, 1H), 3.87 (s, 3H), 3.57 (t, 4H, J=5.1 Hz), 3.15 (t, 4H, J=5.0 Hz), 2.34 (s, 3H), 1.47 (s, 9H). $^{13}$C NMR (75 MHz, CDCl$_3$): δ (ppm 167.32, 154.60, 151.19, 138.95, 130.76, 121.98, 121.72, 114.49, 79.86, 51.99, 49.18, 28.33, 21.53.

e. Preparation of tert-butyl 4-(3-(methoxycarbonyl)-5-(trifluoromethyl)phenyl)piperazine-1-carboxylate (56C)

The synthesis of compound 56c followed the same procedure as for compound 26 using methyl 3-bromo-5-trifluoromethylbenzoate. Column chromatography (silica gel, hexanes:EtOAc=9:1) afforded white solid (0.680 g, 44% yield). $^1$H NMR (300 MHz, CDCl$_3$): δ (ppm 7.70-7.68 (m, 2H), 7.23-7.22 (m, 1H), 3.89 (s, 3H), 3.57 (t, 4H, J=5.2 Hz), 3.21 (t, 4H, J=5.1 Hz), 1.45 (s, 9H). $^{13}$C NMR (125 MHz, CDCl$_3$): δ (ppm 165.94, 154.46, 151.32, 131.72, 131.71 (q, J=32.4 Hz), 123.67 (q, J=272.8 Hz), 119.74, 119.68, 119.53, 116.95, 116.16, 80.01, 52.50, 52.38, 52.27, 52.16, 48.42, 28.28.

f. Preparation of tert-butyl 4-(3-bromo-5-(methoxycarbonyl)phenyl)piperazine-1-carboxylate (56D)

The synthesis of compound 56d followed the same procedure as for compound 26 using methyl 3-bromo-5-iodobenzoate. Column chromatography (silica gel, hexanes:EtOAc=9:1) afforded white solid (0.103 g, 22% yield). $^1$H NMR (500 MHz, CDCl$_3$): δ (ppm 7.63-7.62 (m, 1H), 7.49-7.48 (m, 1H), 7.18-7.17 (m, 1H), 3.90 (s, 3H), 3.57 (t, 4H, J=5.0 Hz), 3.18 (m, 4H), 1.48 (s, 9H). $^{13}$C NMR (125 MHz, CDCl$_3$): δ (ppm 166.00, 154.57, 152.07, 132.35, 123.37, 123.11, 122.89, 115.72, 80.09, 52.37, 48.57, 28.38.

g. Preparation of 3-(4-(tert-butoxycarbonyl)piperazin-1-yl)-5-chlorobenzoic Acid (57A)

The synthesis of compound 57a followed the same procedure as for compound 32 to afford white solid (0.197 g, 90% yield). $^1$H NMR (300 MHz, CDCl$_3$): δ (ppm 7.54-7.53 (m, 1H), 7.50-7.49 (m, 1H), 7.07-7.05 (m, 1H), 3.59 (t, 4H, J=5.0 Hz), 3.21 (t, 4H, J=4.9 Hz), 1.48 (s, 9H). $^{13}$C NMR (125 MHz, CDCl$_3$): δ (ppm 170.50, 154.71, 151.96, 135.27, 131.50, 120.99, 120.91, 120.66, 115.69, 115.61, 80.35, 48.50, 28.37.

h. Preparation of 3-(4-(tert-butoxycarbonyl)piperazin-1-yl)-5-methylbenzoic Acid (57B)

The synthesis of compound 57b followed the same procedure as for compound 32 to afford white solid (0.179 g, 76% yield). $^1$H NMR (500 MHz, CDCl$_3$): δ (ppm 7.47-7.46 (m, 1H), 7.45-7.44 (m, 1H), 6.98-6.97 (m, 1H), 3.60-3.58 (m, 4H), 3.18-3.16 (m, 4H), 2.36 (s, 3H), 1.48 (s, 9H). $^{13}$C NMR (125 MHz, CDCl$_3$): δ (ppm 171.81, 154.73, 151.21, 139.11, 130.18, 122.65, 122.51, 115.02, 80.07, 49.21, 28.36, 21.53.

i. Preparation of 3-(4-(tert-butoxycarbonyl)piperazin-1-yl)-5-(trifluoromethyl)benzoic Acid (57C)

The synthesis of compound 57c followed the same procedure as for compound 32 to afford white solid (0.609 g, 93% yield). $^1$H NMR (500 MHz, CDCl$_3$): δ (ppm 7.82-7.81 (m, 1H), 7.78-7.77 (m, 1H), 7.31-7.30 (m, 1H), 3.63 (t, 4H, J=4.8 Hz), 3.28-3.26 (m, 4H), 1.49 (s, 9H). $^{13}$C NMR (125 MHz, CDCl$_3$): δ (ppm 170.16, 154.74, 151.42, 131.99 (q, J=32.5 Hz), 131.20, 123.67 (q, J=272.8 Hz), 120.11, 117.61, 116.91, 80.47, 48.45, 28.36.

j. Preparation of 3-bromo-5-(4-(tert-butoxycarbonyl)piperazin-1-yl)benzoic Acid (57D)

The synthesis of compound 57d followed the same procedure as for compound 32 to afford white solid (0.0816 g, 82% yield). $^1$H NMR (500 MHz, CDCl$_3$): δ (ppm 7.70-7.69 (m, 1H), 7.55 (dd, 1H, J=1.3, 2.3 Hz), 7.24-7.23 (m, 1H), 3.60 (t, 4H, J=4.9 Hz), 3.22-3.20 (m, 4H), 1.49 (s, 9H). $^{13}$C NMR (125 MHz, CDCl$_3$): δ ppm 170.41, 154.68, 152.12, 131.57, 123.90, 123.64, 123.23, 116.14, 80.31, 48.53, 28.40.

k. Preparation of tert-butyl (S)-4-(3-(4-(4-((1-(tert-butoxycarbonyl)pyrrolidin-3-yl)oxy)-3-cyclohexylbenzoyl)piperazine-1-carbonyl)-5-chlorophenyl) piperazine-1-carboxylate (58A)

The synthesis of compound 58a followed the same procedure as for compound 35. Column chromatography (silica gel, hexanes:acetone=70:30) afforded white solid (0.0998 g, 58% yield). $^1$H NMR (500 MHz, CDCl$_3$): δ (ppm 7.23-7.19 (m, 2H), 6.89-6.88 (m, 1H), 6.79-6.76 (m, 3H), 4.93-4.91 (m, 1H), 3.74-3.46 (m, 16H), 3.16-3.14 (m, 4H), 2.84-2.81 (m, 1H), 2.21-2.17 (m, 1H), 2.13-2.09 (m, 1H), 1.79-1.71 (m, 6H), 1.45 (s, 9H), 1.43 (s, 9H), 1.38-1.30 (m, 4H). $^{13}$C NMR (125 MHz, CDCl$_3$): δ (ppm 170.88, 169.33, 155.60, 155.48, 154.47, 154.32, 152.17, 137.37, 137.26, 135.27, 127.18, 127.14, 126.48, 126.04, 125.98, 117.33, 116.98, 112.45, 111.81, 80.07, 79.46, 79.38, 76.44, 75.34, 51.43, 50.95, 48.29, 44.17, 43.80, 37.29, 37.21, 34.56, 33.06, 32.78, 32.57, 31.61, 31.48, 30.90, 29.59, 28.39, 28.31, 26.86, 26.20, 25.18, 22.55, 20.61, 14.03.

l. Preparation of tert-butyl (S)-4-(3-(4-(4-((1-(tert-butoxycarbonyl)pyrrolidin-3-yl)oxy)-3-cyclohexylbenzoyl)piperazine-1-carbonyl)-5-methylphenyl) piperazine-1-carboxylate (58B)

The synthesis of compound 58b followed the same procedure as for compound 35. Column chromatography (silica gel, hexanes:acetone=70:30) afforded white solid (0.0880 g, 51% yield). $^1$H NMR (500 MHz, CDCl$_3$): δ (ppm 7.25-7.19 (m, 2H), 6.79-6.76 (m, 2H), 6.73-6.72 (m, 1H), 6.68-6.67 (m, 1H), 4.94-4.92 (m, 1H), 3.76-3.46 (m, 16H), 3.14-3.11 (m, 4H), 2.86-2.81 (m, 1H), 2.31 (s, 3H), 2.22-2.18 (m, 1H), 2.13-2.09 (m, 1H), 1.86-1.72 (m, 6H), 1.46 (s, 9H), 1.44 (s, 9H), 1.38-1.28 (m, 4H). $^{13}$C NMR (125 MHz, CDCl$_3$): δ δ ppm 170.90, 155.59, 155.47, 154.58, 154.53, 154.37, 151.29, 139.36, 137.35, 137.24, 136.11, 127.34, 126.50, 126.03, 118.97, 118.51, 111.92, 111.83, 79.93, 79.48, 79.41, 76.46, 75.37, 51.45, 50.99, 49.05, 44.18, 43.82, 37.31, 37.22, 34.58, 33.06, 32.80, 32.60, 31.63, 31.50, 30.93, 28.41, 28.34, 26.88, 26.22, 21.65.

m. Preparation of tert-butyl (S)-4-(3-(4-(4-((1-(tert-butoxycarbonyl)pyrrolidin-3-yl)oxy)-3-cyclohexylbenzoyl)piperazine-1-carbonyl)-5-(trifluoromethyl) phenyl)piperazine-1-carboxylate (58C)

The synthesis of compound 58c followed the same procedure as for compound 35. Column chromatography (silica gel, hexanes:acetone=70:30) afforded white solid (0.144 g, 65% yield). $^1$H NMR (500 MHz, CDCl$_3$): δ (ppm 7.23-7.17 (m, 2H), 7.11-7.10 (m, 1H), 7.05-7.03 (m, 2H), 6.77-6.74 (m, 2H), 4.92-4.90 (m, 1H), 3.74-3.42 (m, 16H), 3.20-3.18 (m, 4H), 2.84-2.79 (m, 1H), 2.20-2.15 (m, 1H), 2.12-2.07 (m, 1H), 1.77-1.69 (m, 6H), 1.44 (s, 9H), 1.42 (s, 9H), 1.37-1.31 (m, 4H). $^{13}$C NMR (125 MHz, CDCl$_3$): δ (ppm 170.84, 169.28, 155.59, 155.45, 154.45, 154.39, 154.28, 151.44, 137.30, 137.22, 136.94, 131.82, (q, J=32.3 Hz), 127.09, 126.42, 126.00, 125.94, 123.55 (q, J=272.8 Hz), 117.04, 113.87, 113.42, 111.76, 80.04, 79.38, 79.32, 76.39, 75.29, 51.38, 50.87, 48.17, 44.11, 43.73, 37.24, 37.17, 34.50, 34.35, 33.00, 32.96, 32.71, 32.48, 31.56, 31.41, 30.83, 29.13, 28.32, 28.23, 26.86, 26.80, 26.74, 26.14, 25.11.

n. Preparation of tert-butyl (S)-4-(3-bromo-5-(4-(4-((1-(tert-butoxycarbonyl)pyrrolidin-3-yl)oxy)-3-cyclohexylbenzoyl)piperazine-1-carbonyl)phenyl) piperazine-1-carboxylate (58D)

The synthesis of compound 58d followed the same procedure as for compound 35. Column chromatography (silica gel, hexanes:acetone=70:30) afforded white solid (0.0845 g, 63% yield). $^1$H NMR (500 MHz, CDCl$_3$): δ (ppm 7.19-7.14 (m, 2H), 7.00-6.98 (m, 1H), 6.89-6.87 (m, 1H), 6.77-6.76 (m, 1H), 6.73-6.71 (m, 1H), 4.88-4.86 (m, 1H), 3.68-3.43 (m, 16H), 3.11-3.08 (m, 4H), 2.79-2.75 (m, 1H), 2.16-2.11 (m, 1H), 2.09-2.04 (m, 1H), 1.75-1.66 (m, 6H), 1.40 (s, 9H), 1.38 (s, 9H), 1.33-1.21 (m, 4H). $^{13}$C NMR (125 MHz, CDCl$_3$): δ (ppm 170.92, 169.19, 155.63, 154.49, 152.26, 137.62, 137.35, 127.18, 126.51, 126.04, 123.33, 120.23, 119.96, 112.96, 111.84, 80.10, 79.45, 76.45, 75.36, 53.77, 51.44, 50.97, 48.31, 44.18, 43.80, 37.29, 37.24, 33.03, 32.77, 32.59, 31.65, 30.90, 29.19, 28.39, 28.30, 26.88, 26.19.

o. Preparation of (S)-(4-(3-chloro-5-(piperazin-1-yl) benzoyl)piperazin-1-yl) (3-cyclohexyl-4-(pyrrolidin-3-yloxy)phenyl) methanone Hydrochloride (18)

The synthesis of compound 18 followed the same procedure as for compound 2 to afford white solid (0.0752 g, 92% yield). $^1$H NMR (300 MHz, d$^6$-DMSO): δ (ppm 9.49 (brs, 2H), 9.23 (brs, 2H), 7.24-7.22 (m, 2H), 7.10 (s, 1H), 7.00 (d, 1H, J=9.0 HZ), 6.92 (s, 1H), 6.85 (s, 1H), 5.19-5.15 (m, 1H), 3.68-3.16 (m, 20H), 2.90-2.86 (m, 1H), 2.20-2.06 (m, 2H), 1.76-1.18 (m, 10H). $^{13}$C NMR (125 MHz, D$_2$O): δ ppm 172.15, 170.37, 154.89, 151.11, 136.52, 134.80, 126.65, 126.34, 125.80, 117.83, 113.06, 112.41, 75.51, 50.36, 47.46, 47.05, 45.34, 44.09, 42.73, 42.28, 41.84, 36.21, 32.75, 32.69, 30.41, 26.32, 25.80. HRMS (ESI) m/z calculated for C$_{32}$H$_{42}$ClN$_5$O$_3$(M+H)$^+$=580.3054, found 580.3060.

p. Preparation of (S)-(4-(3-cyclohexyl-4-(pyrrolidin-3-yloxy)benzoyl)piperazin-1-yl) (3-methyl-5-(piperazin-1-yl)phenyl) methanone Hydrochloride (19)

The synthesis of compound 19 followed the same procedure as for compound 2 to afford peach solid (0.0648 g, 90% yield). $^1$H NMR (500 MHz, d$^6$-DMSO): δ (ppm 9.44 (brs, 2H), 9.12 (brs, 2H), 7.24-7.22 (m, 2H), 7.00 (d, 1H, J=9.0 Hz), 6.88 (s, 1H), 6.76 (s, 1H), 6.67 (s, 1H), 5.19-5.15 (m, 1H), 3.69-3.17 (m, 20H), 2.90-2.85 (m, 1H), 2.27 (s, 3H), 2.21-2.10 (m, 2H), 1.77-1.20 (m, 10H). $^{13}$C NMR (125 MHz, D$_2$O): δ ppm 172.29, 172.09, 154.98, 149.27, 140.68, 137.28, 135.22, 126.87, 126.32, 126.07, 120.83, 119.95, 112.63, 112.53, 75.67, 50.52, 46.70, 44.28, 42.84, 36.40, 32.82, 32.75, 30.50, 26.42, 26.38, 25.81, 20.64, 13.22. HRMS (ESI) m/z calculated for C$_{32}$H$_{45}$N$_5$O$_3$ (M+H)$^+$ =560.3601, found 560.3604.

q. Preparation of (S)-(4-(3-cyclohexyl-4-(pyrrolidin-3-yloxy)benzoyl)piperazin-1-yl) (3-(piperazin-1-yl)-5-(trifluoromethyl)phenyl)methanone Hydrochloride (20)

The synthesis of compound 20 followed the same procedure as for compound 2 to afford white solid (0.103 g, 85% yield). $^1$H NMR (500 MHz, d$^6$-DMSO): δ (ppm 9.49 (brs, 2H), 9.26 (brs, 2H), 7.31 (s, 1H), 7.25-7.23 (m, 3H), 7.12 (s, 1H), 7.00 (d, 1H, J=9.0 Hz), 5.18-5.15 (m, 1H), 3.69-3.18 (m, 20H), 2.90-2.86 (m, 1H), 2.19-02.12 (m, 2H), 1.76-1.17 (m, 10H). $^{13}$C NMR (125 MHz, D$_2$O): δ ppm 172.13, 170.34, 154.99, 150.67, 136.83, 136.42, 131.22 (d, J=28.5 Hz), 126.90 (d, J=8.5 Hz), 126.53, 125.65, 123.68 (d, J=271.4 Hz), 120.42, 117.89, 114.43, 112.67, 75.61, 50.45, 47.56, 46.99, 45.32, 44.23, 42.88, 42.33, 41.88, 36.28, 32.81, 32.72, 30.51, 26.39, 26.36, 25.84. HRMS (ESI) m/z calculated for $C_{33}H_{42}F_3N_5O_3(M+H)^+=614.3318$, found 614.3319.

r. Preparation of (S)-(4-(3-bromo-5-(piperazin-1-yl)benzoyl)piperazin-1-yl) (3-cyclohexyl-4-(pyrrolidin-3-yloxy)phenyl) methanone Hydrochloride (21)

The synthesis of compound 21 followed the same procedure as for compound 2 to afford white solid (0.0546 g, 79% yield). $^1$H NMR (500 MHz, d$^6$-DMSO): δ (ppm 9.58 (brs, 2H), 9.30 (brs, 2H), 7.24-7.22 (m, 3H), 7.00 (d, 1H, J=9.0 Hz), 6.97-6.96 (m, 2H), 5.15-5.19 (m, 1H), 3.69-3.15 (m, 20H), 2.90-2.86 (m, 1H), 2.19-2.12 (m, 2H), 1.76-1.17 (m, 10H). $^{13}$C NMR (125 MHz, D$_2$O): δ ppm 172.27, 170.32, 154.99, 151.27, 137.14, 136.87, 126.85, 126.42, 126.06, 122.98, 120.87, 113.58, 112.62, 75.69, 71.52, 70.66, 60.24, 50.52, 45.48, 44.28, 43.19, 42.84, 36.36, 32.88, 32.81, 30.52, 26.46, 26.41, 25.89. HRMS (ESI) m/z calculated for $C_{32}H_{42}BrN_5O_3(M+H)^+=624.2549$, found 624.2551.

13. Preparation of Compounds 62-64

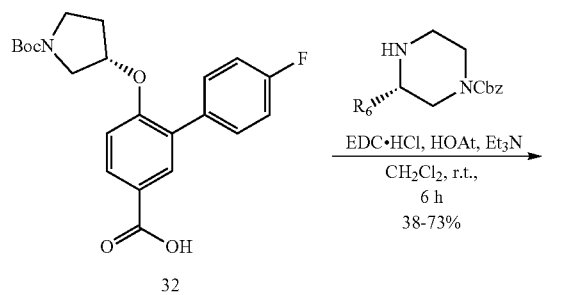

32

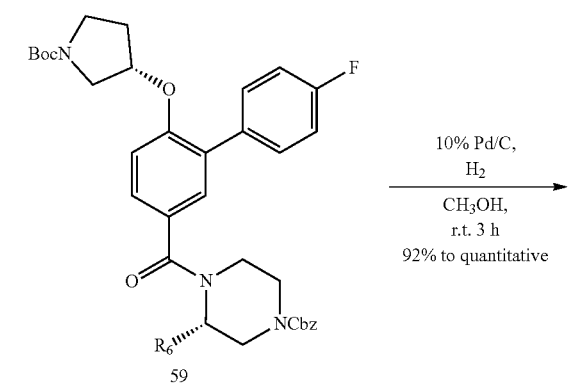

59

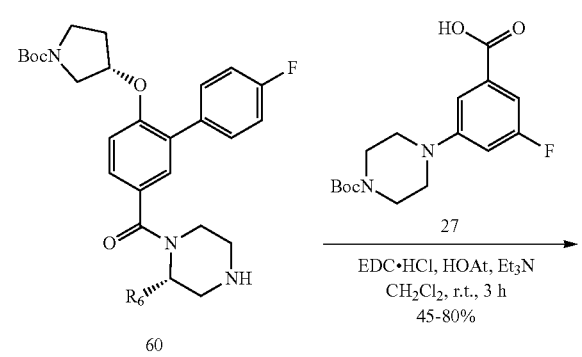

60

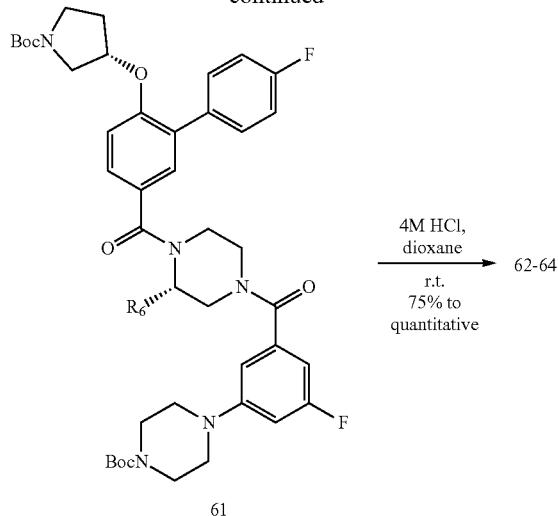

61 a. Preparation of Benzyl (S)-4-(6-(((S)-1-(tert-butoxycarbonyl)pyrrolidin-3-yl)oxy)-4'-fluoro-[1,1'-biphenyl]-3-carbonyl)-3-methylpiperazine-1-carboxylate (59A)

The synthesis of compound 59a followed the same procedure as for compound 33 to afford a white solid (0.153 g, 67% yield). $^1$HNMR (300 MHz, CDCl$_3$): δ (ppm 7.40 (dd, 2H, J=5.7 Hz, J=8.4 Hz), 7.35-7.30 (m, 7H), 7.06 (t, 2H, J=8.3 Hz), 6.94 (d, 1H, J=8.7 Hz), 5.15 (s, 1H), 5.14 (s, 1H), 4.91-4.88 (m, 1H), 4.62-4.44 (m, 1H), 4.20-3.93 (m, 3H), 3.67-2.88 (m, 7H), 2.09-2.05 (m, 2H), 1.45 (s, 9H), 1.25 (d, 3H, J=5.1 Hz). $^{13}$CNMR (125 MHz, CDCl$_3$): δ ppm 170.11, 162.10 (d, J=247.0 Hz), 155.55, 154.95, 154.82, 154.46, 154.27, 136.30, 133.17 (d, J=3.4 Hz), 133.04 (d, J=2.4 Hz), 131.22, 131.05, 130.91, 130.85, 130.81, 129.77 (d, J=11.9 Hz), 128.93, 128.87, 128.45, 128.07, 127.83, 127.40, 114.95 (d, J=21.0 Hz), 114.82 (d, J=21.3 Hz), 113.83, 113.60, 79.50, 79.44, 77.15, 76.27, 67.36, 51.35, 50.86, 44.02, 43.65, 34.56, 31.48, 31.44, 30.66, 28.38, 26.81, 25.18, 22.55, 15.44, 14.03.

b. Preparation of Benzyl (S)-4-(6-(((S)-1-(tert-butoxycarbonyl)pyrrolidin-3-yl)oxy)-4'-fluoro-[1,1'-biphenyl]-3-carbonyl)-3-ethylpiperazine-1-carboxylate (59B)

The synthesis of compound 59b followed the same procedure as for compound 33 to afford a white solid (0.130 g, 73% yield). $^1$HNMR (500 MHz, CDCl$_3$): δ ppm 7.39 (dd, 2H, J=8.6 Hz), 7.34-7.29 (m, 7H), 7.06 (dd, 1H, J=7.9 Hz, J=14.2 Hz), 6.93 (d, 1H, J=8.5 Hz), 5.18 (s, 0.3H), 5.15 (s, 0.7H), 5.12 (s, 0.7H), 5.10 (s, 0.3H), 4.90-4.88 (m, 1H), 4.15-4.08 (m, 2H), 3.65-3.21 (m, 5H), 3.07-2.75 (m, 3H), 2.10-2.02 (m, 2H), 1.68-1.59 (m, 2H), 1.44 (s, 4.5H), 1.43 (s, 4.5H), 0.96-0.82 (m, 4H). $^{13}$CNMR (125 MHz, CDCl$_3$): δ ppm 170.4, 162.04 (d, J=247.0), 155.46, 154.87, 154.77, 154.45, 154.26, 136.28, 133.17, 133.07, 131.26, 131.02, 1130.89, 130.84, 129.96, 129.88, 129.01, 128.44, 128.08, 127.87, 127.58, 127.39, 114.96 (d, J=20.2 Hz), 114.82 (d, J=21.1 Hz), 113.73, 113.62, 79.50, 79.43, 77.14, 76.28, 67.36, 51.34, 50.86, 44.02, 43.65, 41.26, 35.83, 34.56, 31.48, 31.44, 30.67, 28.38, 26.80, 25.17, 22.54, 21.67, 21.39, 20.61, 14.04, 14.02, 10.34 c. Preparation of Benzyl (S)-4-(6-(((S)-1-(tert-butoxycarbonyl)pyrrolidin-3-yl)oxy)-4'-fluoro-[1,1'-biphenyl]-3-carbonyl)-3-isopropylpiperazine-1-carboxylate (59C)

The synthesis of compound 59c followed the same procedure as for compound 33 to afford a white solid (0.0887 g, 38% yield). $^1$HNMR (500 MHz, CDCl$_3$): δ ppm 7.40 (dd, 2H, J=5.6 Hz, J=8.4 Hz), 7.34-7.28 (m, 7H), 7.09-7.04 (m, 2H), 6.93 (d, 1H, J=8.3 Hz), 5.19 (s, 0.3H), 5.16 (s, 0.7H), 5.11 (s, 0.7H), 5.09 (s, 0.3H), 4.90-4.88 (m, 1H), 4.48-3.99 (m, 3H), 3.69-3.62 (m, 1H), 3.53-3.34 (m, 4H), 3.27-3.22 (m, 1H), 3.02-2.95 (m, 2H), 2.10-2.03 (m, 3H), 1.45 (s, 4.5H), 1.43 (s, 4.5H), 1.00-0.78 (m, 6H). (125 MHz, CDCl$_3$): δ ppm 170.07, 162.13 (d, J=246.7 Hz), 162.06 (d, J=246.03 Hz), 155.34, 154.84, 154.80, 154.77, 154.46, 154.29, 136.24, 133.18, 133.08, 130.94, 130.88, 130.83, 130.08, 129.91, 129.45, 128.13, 128.01, 127.34, 115.07, 114.92, 114.76, 113.79, 113.63, 79.53, 79.47, 77.15, 76.32, 67.45, 54.85, 51.35, 50.89, 44.73, 44.03, 43.67, 43.33, 37.28, 34.58, 31.50, 31.47, 30.70, 29.61, 28.40, 26.82, 25.47, 25.19, 22.57, 20.09, 19.90, 18.86, 18.62, 14.05.

d. Preparation of tert-butyl (S)-3-((4'-fluoro-5-((S)-2-methylpiperazine-1-carbonyl)-[1,1'-biphenyl]-2-yl)oxy)pyrrolidine-1-carboxylate (60A)

The synthesis of compound 60a followed the same procedure as for compound 34 to afford an off-white solid (0.109 g, 92% yield). $^1$HNMR (500 MHz, CD$_3$OD): δ ppm 7.40-7.35 (m, 4H), 7.16-7.13 (m, 1H), 7.05 (t, 2H, J=8.0 Hz), 5.04-5.01 (m, 1H), 4.50-4.45 (m, 1H), 4.03-3.96 (m, 1H), 3.49-2.94 (m, 8H), 2.82 (t, 1H, J=11.5 Hz), 2.06-2.02 (m, 2H), 1.38 (s, 4.5H), 1.36 (s, 4.5H), 1.34 (d, 3H, J=6.9 Hz). $^{13}$CNMR (125 MHz, CD$_3$OD): δ ppm 172.31, 163.55 (d, J=245.5 Hz), 156.51, 156.38, 156.32, 134.90 (d, J=3.2 Hz), 132.71, 132.50, 132.42, 132.36, 132.30, 130.88 (d, J=7.9 Hz), 129.79, 129.68, 128.91, 115.89 (d, J=21.5 Hz), 115.84 (d, J=21.5 Hz), 115.65, 115.25, 81.06, 80.97, 78.58, 78.03, 52.69, 52.18, 49.52, 45.65, 45.32, 44.95, 32.19, 31.47, 28.80, 15.65.

e. Preparation of tert-butyl (S)-3-((5-((S)-2-ethylpiperazine-1-carbonyl)-4'-fluoro-[1,1'-biphenyl]-2-yl)oxy)pyrrolidine-1-carboxylate (60B)

The synthesis of compound 60b followed the same procedure as for compound 34 to afford an off-white solid (0.108 g, quantitative yield). $^1$HNMR (500 MHz, CDCl$_3$): δ ppm 7.37-3.35 (m, 2H), 7.31-7.29 (m, 2H), 7.05-7.01 (m, 2H), 5.97 (bs, 1H), 4.87-4.85 (m, 1H), 3.61-2.80 (m, 11H), 2.06-2.00 (m, 3H), 1.80-1.75 (m, 1H), 1.40 (s, 4.5H), 1.39 (s, 4.5H), 0.89-0.85 (m, 3H). $^{13}$CNMR (125 MHz, CDCl$_3$): δ ppm 170.34, 162.03 (d, J=245.5 Hz), 161.99 (d, J=246.8 Hz), 154.93, 154.84, 154.41, 154.22, 133.02, 132.93, 131.26, 130.99, 130.80 (d, J=7.6 Hz), 129.90, 129.78, 128.45, 127.56, 127.35, 114.91 (d, J=20.9 Hz), 114.78 (d, J=21.2 Hz), 113.67, 113.57, 79.46, 79.41, 77.09, 76.20, 51.28, 50.79, 46.55, 44.63, 43.96, 43.59, 31.37, 30.59, 28.31, 22.22, 10.42.

f. Preparation of tert-butyl (S)-3-((4'-fluoro-5-((S)-2-isopropylpiperazine-1-carbonyl)-[1,1'-biphenyl]-2-yl)oxy)pyrrolidine-1-carboxylate (60C)

The synthesis of compound 60c followed the same procedure as for compound 34 to afford an off-white solid (0.0673 g, 97% yield). $^1$HNMR (500 MHz, CDCl$_3$): δ ppm 7.40 (dd, 2H, J=5.5 Hz, J=8.5 Hz), 7.35-7.27 (m, 2H), 7.28 (d, J=7.9 Hz), 7.08-7.04 (m, 2H), 6.92 (d, J=8.4 Hz), 4.88-4.86 (m, 1H), 4.45-4.33 (m, 1H), 3.64-2.66 (m, 10H), 2.44-2.38 (m, 1H), 2.24-2.23 (m, 1H), 2.08-2.01 (m, 2H), 1.44 (s, 4.5H), 1.42 (s, 4.5H), 1.03 (bs, 1H), 0.99-0.95 (m, 3H), 0.84-0.79 (m, 3H). $^{13}$CNMR (125 MHz, CDCl$_3$): δ (ppm 169.92, 162.05 (d, J=162.1 Hz), 154.49, 154.33, 133.37, 133.27, 130.98, 130.92, 130.87, 129.84, 127.64, 127.30, 115.05, 114.90, 114.73, 113.71, 113.68, 79.54, 79.47, 77.20, 76.36, 55.92, 55.82, 55.18, 51.37, 50.94, 46.87, 46.55, 46.39, 44.88, 44.07, 43.71, 31.49, 30.74, 28.42, 25.28, 19.94, 19.01.

g. Preparation of tert-butyl 4-(3-((S)-4-(6-(((S)-1-(tert-butoxycarbonyl)pyrrolidin-3-yl)oxy)-4'-fluoro-[1,1'-biphenyl]-3-carbonyl)-3-methylpiperazine-1-carbonyl)-5-fluorophenyl)piperazine-1-carboxylate (61A)

The synthesis of compound 61a followed the same procedure as for compound 35 to afford a white solid (0.112 g, 80% yield). $^1$HNMR (500 MHz, CDCl$_3$): δ (ppm 7.40-7.36 (m, 2H), 7.33-7.31 (m, 2H), 7.05 (dd, 2H, J=7.8 Hz, J=13.8 Hz), 6.93 (d, 1H, J=8.2 Hz), 6.66 (s, 1H), 6.59 (d, 1H, J=11.8 Hz), 6.51 (d, 1H, J=7.6 Hz), 4.90-4.87 (m, 1H), 4.64-4.49 (m, 1H), 4.13-4.01 (m, 1H), 3.73-2.88 (m, 17H), 2.08-2.02 (m, 2H), 1.46 (s, 9H), 1.43 (s, 4.5H), 1.42 (s, 4.5H), 1.33-1.23 (m, 3H). $^{13}$CNMR (125 MHz, CDCl$_3$): δ (ppm 170.33, 170.08, 163.34 (d, J=246.0 Hz), 162.09 (d, J=246.7 Hz), 162.04 (d, J=247.0 Hz), 155.04, 154.91, 154.45, 154.23, 152.88 (d, J=10.2 Hz), 137.47 (d, J=8.5 Hz), 133.09 (d, J=2.3 Hz), 132.98, 131.25, 131.07, 130.84 (d, J=7.6 Hz), 129.83, 129.73, 128.60, 128.54, 127.42, 114.95 (d, J=21.5 Hz), 114.82 (d, J=21.2 Hz), 113.82, 113.57, 109.67 (d, J=1.6 Hz), 104.37 (d, J=21.2 Hz), 103.81 (d, J=25.1 Hz), 80.04, 79.49, 79.43, 77.15, 76.25, 51.50, 51.34, 50.81, 47.44, 46.24, 44.00, 43.62, 42.19, 34.54, 34.38, 31.45, 31.42, 30.63, 28.36, 28.28, 26.78, 25.15, 22.52, 20.59, 18.65, 15.50, 14.01, 11.32.

h. Preparation of tert-butyl 4-(3-((S)-4-(6-(((S)-1-(tert-butoxycarbonyl)pyrrolidin-3-yl)oxy)-4'-fluoro-[1,1'-biphenyl]-3-carbonyl)-3-ethylpiperazine-1-carbonyl)-5-fluorophenyl)piperazine-1-carboxylate (61B)

The synthesis of compound 61b followed the same procedure as for compound 35 to afford a white solid (0.0828 g, 49% yield). $^1$HNMR (500 MHz, CDCl$_3$): δ (ppm 7.39-7.37 (m, 2H), 7.33-7.29 (m, 2H), 7.08-7.03 (m, 2H), 6.92 (d, 1H, J=8.3 Hz), 6.65 (s, 1H), 6.59 (d, 1H, J=11.7 Hz), 6.50 (d, 1H, J=7.6 Hz), 4.89-4.87 (m, 1H), 4.66-4.60 (m, 1H), 3.67-2.82 (m, 16H), 2.06-2.02 (m, 2H), 1.73 (dt, 1H, J=6.9 Hz, J=13.8 Hz), 1.46 (s, 9H), 1.43 (s, 4.5H), 1.42 (s, 4.5H), 0.93-0.78 (m, 6H). $^{13}$CNMR (125 MHz, CDCl$_3$): δ (ppm 170.35, 163.36 (d, J=246.0 Hz), 162.12 (d, J=246.3 Hz), 162.07 (d, J=247.3 Hz), 155.01, 154.89, 154.48, 154.45, 154.26, 152.91, (d, J=9.5 Hz), 137.52 (d, J=9.1 Hz), 133.11, 133.01, 131.34, 131.09, 130.85 (d, J=7.5 Hz), 129.98, 128.71, 127.63, 127.44, 114.99 (d, J=20.8 Hz), 114.85 (d, J=21.6 Hz), 113.76, 113.63, 109.73 (d, J=1.6 Hz), 104.40 (d, J=22.4 Hz), 103.84 (d, J=25.1 Hz), 80.07, 79.52, 79.46, 77.20, 76.30, 51.35, 50.84, 48.23, 44.03, 43.65, 31.47, 30.67, 28.39, 28.31, 22.13, 10.37.

i. Preparation of tert-butyl 4-(3-((S)-4-(6-(((S)-1-(tert-butoxycarbonyl)pyrrolidin-3-yl)oxy)-4'-fluoro-[1,1'-biphenyl]-3-carbonyl)-3-isopropylpiperazine-1-carbonyl)-5-fluorophenyl)piperazine-1-carboxylate (61C)

The synthesis of compound 61c followed the same procedure as for compound 35 to afford a white solid (0.0467 g, 45% yield). $^1$HNMR (300 MHz, CDCl$_3$): δ (ppm 7.41-7.33 (m, 4H), 7.06 (t, 2H, J=7.9 Hz), 6.93 (d, 1H, J=8.2 Hz), 6.66 (s, 1H), 6.60 (d, 1H, J=11.3 Hz), 6.51 (d, 1H, J=6.7 Hz), 4.90-4.88 (m, 1H), 4.56-4.36 (m, 1H), 3.85-2.80 (m, 18H), 2.08-2.05 (m, 2H), 1.46 (s, 9H), 1.43 (s, 9H), 0.96-0.81 (m, 6H). $^{13}$CNMR (75 MHz, CDCl$_3$): δ (ppm 170.08, 163.36 (d, J=246.2 Hz), 162.15 (d, J=248.1 Hz), 154.97, 154.96, 154.93, 154.90, 154.52, 154.31, 152.93 (d, J=10.2 Hz), 137.48 (d, J=8.9 Hz), 133.11, 133.04, 131.48, 131.44, 131.09, 130.89 (d, J=8.0 Hz), 130.15, 130.00, 128.84, 127.69, 127.38, 115.03 (d, J=21.2 Hz), 114.89 (d, J=21.4 Hz), 113.78, 113.62, 109.83, 104.45 (d, J=22.8 Hz), 103.92 (d, J=24.9 Hz), 80.12, 79.53, 77.15, 76.31, 58.26, 51.35, 50.87, 48.27, 47.82, 44.04, 43.68, 34.58, 31.51, 30.70, 29.62, 28.40, 28.32, 26.83, 25.20, 22.58, 20.63, 18.35, 14.07.

j. Preparation of 4-(3-fluoro-5-((S)-4-(4'-fluoro-6-(((S)-pyrrolidin-1-ium-3-yl)oxy)-[1,1'-biphenyl]-3-carbonyl)-3-methylpiperazine-1-carbonyl)phenyl)piperazin-1-ium Chloride (62)

The synthesis of compound 62 followed the same procedure as for compound 2 to afford a white solid (0.102 g, quantitative yield). $^1$HNMR (500 MHz, D$_2$O): δ ppm 7.41-7.36 (m, 3H), 7.17-7.09 (m, 4H), 6.88-6.89 (m, 2H), 6.57-6.55 (m, 1H), 5.19-5.17 (m, 1H), 4.56-4.16 (m, 2H), 3.89-2.97 (m, 17H), 2.24-2.16 (m, 2H), 1.25-1.09 (m, 3H). $^{13}$CNMR (125 MHz, D$_2$O): δ ppm 171.74, 171.51, 163.37 (d, J=245.2 Hz), 162.12 (d, J=245.8 Hz), 154.58, 136.88, 133.04, 131.37 (d, J=7.7 Hz), 130.65, 128.23, 115.31 (d, J=21.5 Hz), 114.62, 110.47, 105.39, 76.71, 50.53, 45.68, 44.37, 43.04, 30.56. HRMS (ESI) m/z calculated for C$_{33}$H$_{38}$F$_2$N$_5$O$_3^+$ (M+H)$^+$=590.2937, found 590.2959.

k. Preparation of 4-(3-((S)-3-ethyl-4-(4'-fluoro-6-(((S)-pyrrolidin-1-ium-3-yl)oxy)-[1,1'-biphenyl]-3-carbonyl)piperazine-1-carbonyl)-5-fluorophenyl)piperazin-1-ium Chloride (63)

The synthesis of compound 63 followed the same procedure as for compound 2 to afford a white solid (0.0643 g, 94% yield). $^1$HNMR (500 MHz, D$_2$O): δ ppm 7.43-7.37 (m, 3H), 7.21-7.11 (m, 4H), 6.95-6.79 (m, 2H), 6.67-6.57 (m, 1H), 5.21-5.18 (m, 1H), 4.60-4.12 (m, 2H) 3.96-2.91 (m, 17H), 2.23-2.18 (m, 2H), 1.69-1.62 (m, 1.3H), 1.52-1.33 (m, 0.7H), 0.90 (t, 0.75H, J=6.2 Hz), 0.71-0.63 (m, 1.5H), 0.43 (t, 0.75H, J=6.2 Hz). $^{13}$CNMR (125 MHz, D$_2$O): δ ppm 172.45, 172.31, 171.68, 171.44, 171.22, 171.14, 163.17 (d, J=244.7 Hz), 161.98 (d, J=245.2 Hz), 154.41, 151.89 (d, J=9.5 Hz), 136.69 (d, J=8.5 Hz), 132.88, 131.17 (d, J=6.4 Hz), 130.61, 129.38, 128.13, 115.14 (d, J=21.4 Hz), 114.57, 110.26, 105.48 (d, J=25.8 Hz), 105.08 (d, J=21.3 Hz), 76.63, 56.85, 56.77, 51.23, 50.40, 49.76, 49.26, 47.32, 46.93, 45.51, 44.20, 42.87, 42.49, 42.17, 41.65, 30.36, 22.22, 22.00, 21.59, 21.44, 9.73, 9.54. HRMS (ESI) m/z calculated for C$_{34}$H$_{40}$F$_2$N$_5$O$_3^+$ (M+H)$^+$=604.3094, found 604.3104.

l. Preparation of 4-(3-fluoro-5-((S)-4-(4'-fluoro-6-(((S)-pyrrolidin-1-ium-3-yl)oxy)-[1,1'-biphenyl]-3-carbonyl)-3-isopropylpiperazine-1-carbonyl)phenyl)piperazin-1-ium Chloride (64)

The synthesis of compound 64 followed the same procedure as for compound 2 to afford a white solid (0.0382 g, 99% yield). $^1$HNMR (500 MHz, D$_2$O): δ ppm 7.50-7.42 (m, 3H), 7.34-7.29 (m, 1H), 7.23-7.16 (m, 3H), 6.99-6.81 (m, 2H), 6.74-6.63 (m, 1H), 5.26-5.25 (m, 0.5H), 5.23-5.22 (m, 0.5H), 4.42-4.14 (m, 1H), 3.85-2.93 (m, 18H), 2.27-2.24 (m, 2H), 2.08-1.99 (m, 1H), 1.13 (d, 0.75H, J=6.3 Hz), 0.92 (d, 0.75H, J=6.3 Hz), 0.85 (d, 1.5H, J=6.2 Hz) 0.73 (d, 0.6H, J=6.5 Hz) 0.67 (d, 0.6H, J=6.2 Hz) 0.61 (d, 1.2H, J=6.2 Hz) 0.30 (d, 0.6H, J=6.1 Hz). $^{13}$CNMR (125 MHz, D$_2$O): δ ppm 173.27, 173.20, 172.15, 171.76, 171.70, 171.53, 171.30, 163.44 (d, J=245.8 Hz), 163.33 (d, J=244.6 Hz), 162.28 (d, J=245.0 Hz), 154.60, 154.57, 152.04, 136.82, 136.68, 132.99, 131.40 (d, J=7.4 Hz), 131.08, 130.01, 129.94, 129.55, 129.42, 128.45, 128.28, 128.06, 115.41 (d, J=21.5 Hz), 114.76, 110.74, 110.47, 110.43, 106.07 (d, J=24.8 Hz), 105.84 (d, J=23.5 Hz), 105.55 (d, J=24.5 Hz), 105.42 (d, J=25.9 Hz), 90.63, 90.61, 76.86, 71.75, 71.73, 70.90, 70.88, 62.71, 62.67, 62.19, 61.86, 60.48, 60.44, 56.26, 56.03, 50.61, 48.36, 47.95, 47.56, 47.11, 45.85, 45.75, 44.36, 43.76, 43.38, 43.03, 42.43, 41.89, 38.19, 38.18, 37.72, 30.48, 30.42, 30.40, 26.46, 25.93, 25.78, 25.25, 19.59, 19.45, 19.23, 19.20, 19.19, 18.42, 18.23, 18.22, 18.08, 18.07, 17.75. HRMS (ESI) m/z calculated for C$_{35}$H$_{42}$F$_2$N$_5$O$_3^+$ (M+H)$^+$=618.3250, found 618.3262.

14. Preparation of Compound 68

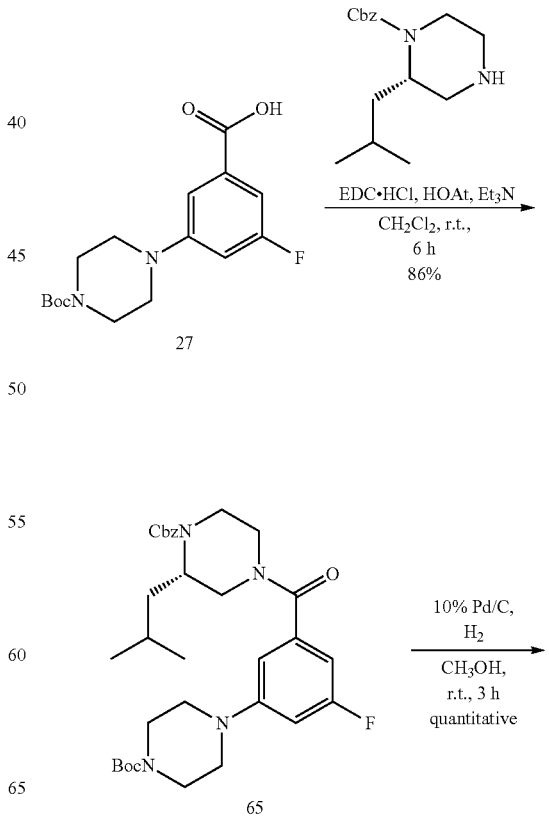

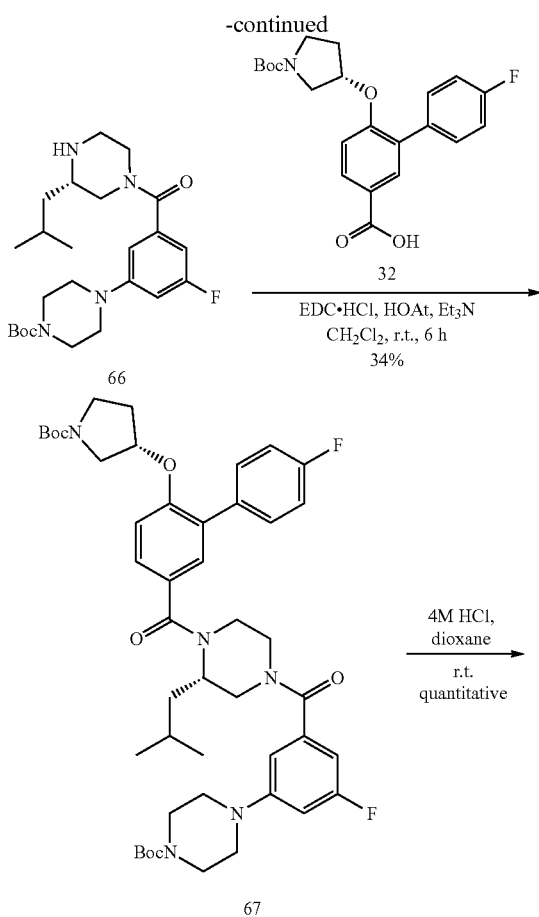

a. Preparation of (S)-4-(3-(4-(tert-butoxycarbonyl)piperazin-1-yl)-5-fluorobenzoyl)-2-isobutylpiperazine-1-carboxylate (65)

The synthesis of compound 65 followed the same procedure as for compound 33 to afford a colorless oil (0.241 g, 86% yield). $^1$HNMR (500 MHz, CDCl$_3$): δ (ppm 7.34-7.29 (m, 5H), 6.64 (s, 1H), 6.59 (d, 1H, J=11.8 Hz), 6.48 (d, 1H, J=7.8 Hz), 5.12 (q, 2H, J=12.3 Hz), 4.56-3.96 (m, 3H), 3.53 (t, 4H, J=4.8 Hz), 3.27-3.23 (m, 0.6H), 3.15-3.16 (m, 4.4H), 3.08-2.81 (m, 2H), 1.48-1.42 (m, 11H), 1.23-1.18 (m, 2H), 0.88-0.81 (m, 6H). $^{13}$CNMR (125 MHz, CDCl$_3$): δ (ppm 163.29 (d, J=245.9 Hz), 154.91, 154.45, 152.78, 137.66 (d, J=8.8 Hz), 136.20, 128.39, 128.06, 127.96, 109.71 (d, J=2.1 Hz), 104.33 (d, J=21.9 Hz), 103.73 (d, J=25.1 Hz), 80.01, 67.37, 60.24, 49.94, 49.56, 49.42, 48.18, 47.19, 44.73, 41.85, 38.99, 38.34, 37.90, 28.27, 24.46, 22.51, 20.92, 20.91, 14.08.

b. Preparation of tert-butyl (S)-4-(3-fluoro-5-(3-isobutylpiperazine-1-carbonyl)phenyl)piperazine-1-carboxylate (66)

The synthesis of compound 66 followed the same procedure as for compound 34 to afford an off-white solid (0.189 g, quantitative yield). $^1$HNMR (500 MHz, CDCl$_3$): δ (ppm 6.60 (s, 1H), 6.55 (d, 1H, J=11.5 Hz), 6.44 (d, 1H, J=5.6 Hz), 4.58-4.48 (m, 1H), 3.74-3.65 (m, 1H), 3.49-3.47 (m, 4H), 3.33 (s, 1H), 3.12-3.09 (m, 5H), 3.02-2.82 (m, 3H), 1.56-1.50 (m, 1H), 1.40 (s, 10H), 1.38-1.32 (m, 1H), 0.87-0.80 (m, 6H). $^{13}$CNMR (125 MHz, CDCl$_3$): δ ppm 169.64 (d, J=2.4 Hz), 163.64 (d, J=246.3 Hz), 154.73, 153.18 (d, J=10.1 Hz), 137.19 (d, J=8.8 Hz), 109.80, 104.35 (d, J=22.5 Hz), 104.19 (d, J=25.2 Hz), 80.33, 53.96, 50.45, 48.35, 28.55, 24.30, 22.96.

c. Preparation of tert-butyl 4-(3-((S)-4-(6-(((S)-1-(tert-butoxycarbonyl)pyrrolidin-3-yl)oxy)-4'-fluoro-[1,1'-biphenyl]-3-carbonyl)-3-isobutylpiperazine-1-carbonyl)-5-fluorophenyl)piperazine-1-carboxylate (67)

The synthesis of compound 67 followed the same procedure as for compound 35 to afford a white solid (0.0576 g, 34% yield). $^1$HNMR (500 MHz, CDCl$_3$): δ (ppm 7.37-7.29 (m, 4H), 7.08-7.03 (m, 2H), 6.93 (d, 1H, J=8.2 Hz), 6.65 (s, 1H), 6.59 (d, 1H, J=11.1 Hz), 6.50 (d, 1H, J=7.0 Hz), 4.89-4.87 (m, 1H), 4.62-4.56 (m, 1H), 3.81-2.79 (m, 18H), 2.05-2.01 (m, 2.5H), 1.91-1.88 (m, 0.5H), 1.46 (s, 4.5H), 1.46 (s, 4.5H), 1.45-1.40 (m, 2H), 1.43 (s, 4.5H), 1.41 (s, 4.5H), 0.91-0.78 (m, 6H). $^{13}$CNMR (125 MHz, CDCl$_3$): δ ppm 170.34, 163.35 (d, J=246.4 Hz), 162.12 (d, J=247.4 Hz), 162.08 (d, J=247.6 Hz), 155.04, 154.98, 154.48, 154.43, 154.27, 152.91, 152.84, 137.50 (d, J=7.8 Hz), 133.12, 133.01, 131.41, 131.17, 130.86, 130.82, 130.07, 128.72, 128.61, 127.71, 127.51, 115.00 (d, J=17.7 Hz), 114.85 (d, J=20.8 Hz), 113.81, 113.67, 109.72, 104.36 (d, J=24.4 Hz), 103.83 (d, J=25.4 Hz), 80.07, 79.51, 79.45, 77.20, 76.36, 51.31, 50.83, 50.17, 48.19, 43.99, 43.64, 38.11, 31.42, 30.82, 30.64, 29.58, 28.37, 28.29, 24.72, 22.59.

d. Preparation of 4-(3-fluoro-5-((S)-4-(4'-fluoro-6-(((S)-pyrrolidin-1-ium-3-yl)oxy)-[1,1'-biphenyl]-3-carbonyl)-3-isobutylpiperazine-1-carbonyl)phenyl)piperazin-1-ium Chloride (68)

The synthesis of compound 68 followed the same procedure as for compound 2 to afford a white solid (0.0353 g, 75% yield). $^1$HNMR (500 MHz, D$_2$O): δ ppm 7.50-7.45 (m, 3H) 7.36-7.27 (m, 1H), 7.23-7.17 (m, 3H) 6.99-6.85 (m, 2H), 6.78-6.67 (m, 1H), 5.26-5.21 (m, 1H), 4.69-4.13 (m, 2H), 3.86-3.40 (m, 14H), 3.23-2.95 (m, 3H), 2.28-2.20 (m, 2H), 1.72-1.25 (m, 3H), 0.98-0.40 (m, 6H). $^{13}$CNMR (125 MHz, D$_2$O): δ ppm 172.23, 171.62, 171.37, 163.24 (d, J=245.2 Hz), 163.16 (d, J=248.2 Hz), 162.06 (d, J=244.8 Hz), 154.47, 151.81 (d, J=9.1 Hz), 136.59 (d, J=9.7 Hz), 132.89, 131.17 (d, J=8.1 Hz), 129.52, 129.46, 129.37, 129.10, 128.13, 115.19 (d, J=21.4 Hz), 114.58, 110.41, 110.31, 105.55 (d, J=21.3 Hz), 105.18 (d, J=20.8 Hz), 90.44, 76.72, 62.52, 60.29, 53.64, 50.59, 50.43, 49.94, 49.48, 48.01, 45.58, 45.09, 44.76, 44.17, 43.24, 42.86, 42.67, 42.35, 41.74, 38.10, 37.74, 37.67, 37.35, 37.24, 37.09, 30.28, 30.24, 24.30, 24.15, 23.94, 23.92, 22.10, 22.02, 21.74, 21.27, 20.73. HRMS (ESI) m/z calculated for C$_{36}$H$_{44}$F$_2$N$_5$O$_3$O$^+$ (M+H)$^+$=632.3407, found 632.3423.

15. Preparation of Compound 71

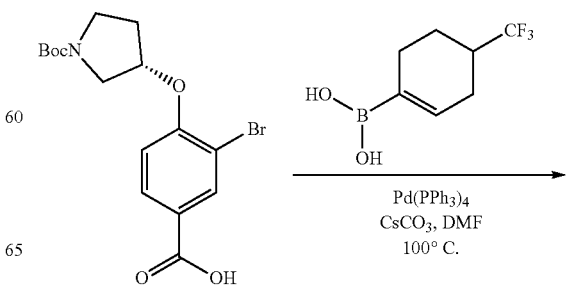

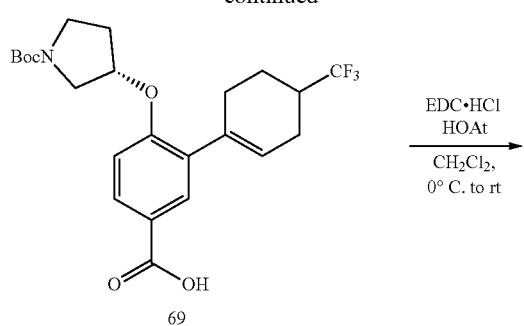
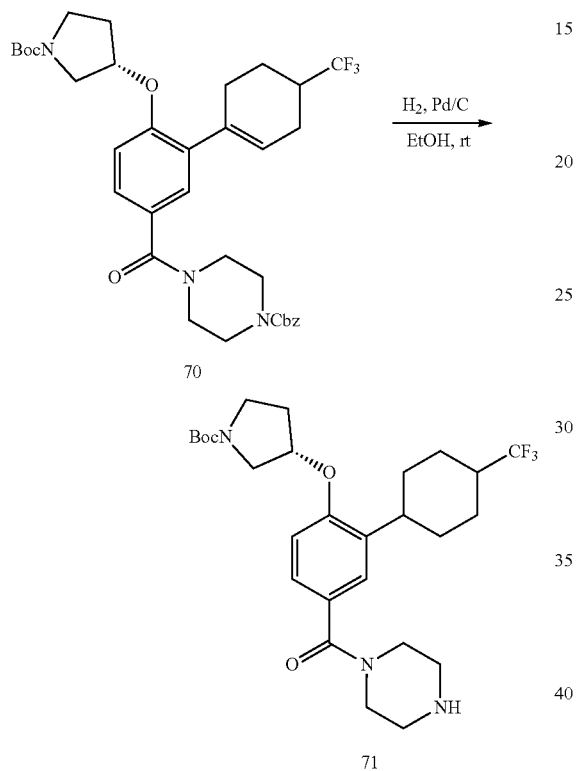
16. Preparation of Compounds 75 and 76
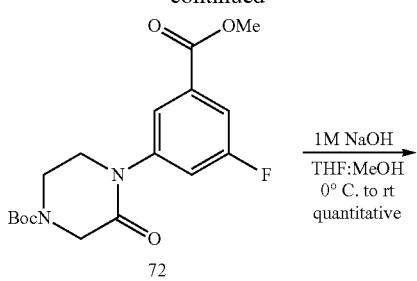
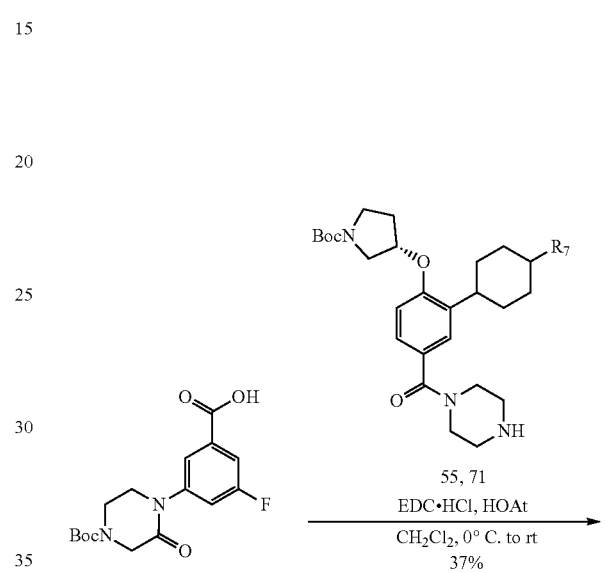
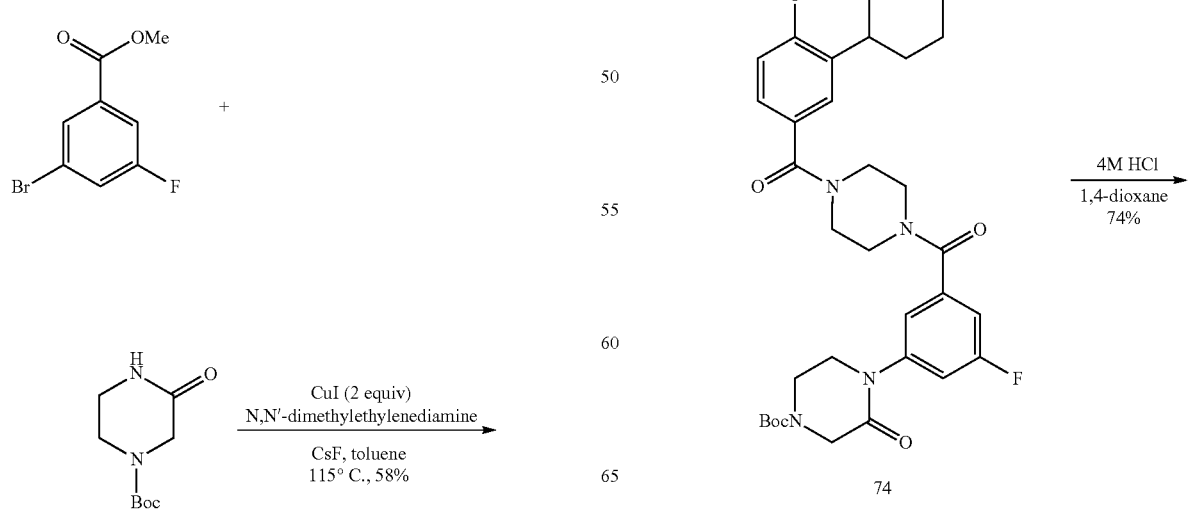

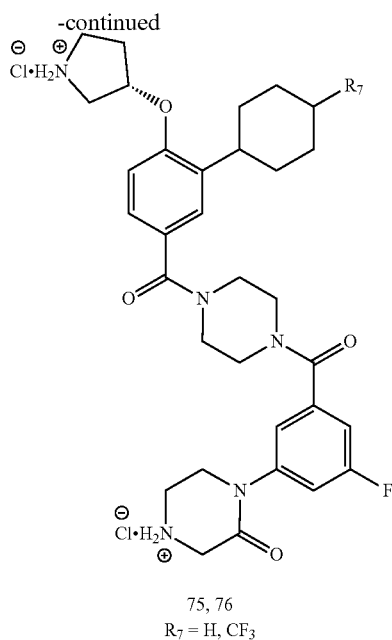

75, 76
R₇ = H, CF₃ a. Preparation of tert-butyl 4-(3-fluoro-5-(methoxy-carbonyl)phenyl)-3-oxopiperazine-1-carboxylate (72)

To a solution of methyl 3-bromo-5-fluorobenzoate (0.050 g, 0.219 mmol) in dry toluene (12 mL) under anhydrous conditions was added 1-boc-3-oxopiperazine (0.047 g, 0.236 mmol), CsF (0.065 g, 0.429 mmol), N,N'-dimethylethylenediamine (0.13 mL, 1.205 mmol), and CuI (0.082 g, 0.429 mmol). The mixture was heated to 115° C. in a pressurized flask and stirred for 24 h under an argon atmosphere. The solvent was then removed under reduced pressure, and the residue was taken into EtOAc (100 mL). The organic solution was washed with water (2×50 mL) and brine (50 mL), dried over Na₂SO₄, solids filtered, and solvent removed under reduced pressure. The residue was purified by column chromatography (silica gel, hexanes:EtOAc=4:1) to yield 72 (0.045 g, 58% yield). ¹H NMR (500 MHz, CDCl₃): δ (ppm 7.74-7.73 (m, 1H), 7.63-7.61 (m, 1H), 7.35-7.32 (m, 1H), 4.25 (s, 2H), 3.90 (s, 3H), 3.78-3.75 (m, 4H), 1.48 (s, 9H); ¹³C NMR (100 MHz, CDCl₃): δ (ppm 165.66, 165.09 (d, J=3.9 Hz), 162.26 (d, J=246.4 Hz), 153.56, 143.11 (d, J=10 Hz), 132.66 (d, J=8.4 Hz), 121.70, 117.66 (d, J=23.7 Hz), 114.83 (d, J=22.9 Hz), 80.97, 52.47, 49.27, 28.24; LRMS-ESI: Exact mass calcd for $C_{17}H_{22}FN_2O_5$ [M+H]⁺=353.15; found: 353.14.

b. Preparation of 3-(4-(tert-butoxycarbonyl)-2-oxopiperazin-1-yl)-5-fluorobenzoic Acid (73)

To a solution of 72 (0.046 g, 0.129 mmol) in THF:MeOH (1:1 v/v, 2 mL) was added 1 M NaOH (1 mL) at 0° C., and the reaction was warmed to room temperature and stirred for 6 h. The THF:MeOH was then removed under reduced pressure. The remaining aqueous solution was acidified with 2 M HCl to pH=4. The product was extracted with CH₂Cl₂ (50 mL) and the organics washed with water, brine, dried over Na₂SO₄, solids filtered, and solvent removed under reduced pressure to yield 73 (0.035 g, 82% yield) as white solid. ¹H NMR (500 MHz, d⁶-DMSO): δ (ppm 12.74 (s, 1H), 7.00 (s, 1H), 6.74 (d, J=8.5 Hz, 1H), 6.57 (t, J=10 Hz, 1H), 3.87 (d, J=9 Hz, 2H), 3.33-3.30 (m, 2H), 3.21-3.17 (m, 2H), 1.31 (s, 9H); ¹³C NMR (100 MHz, d⁶-DMSO): δ (ppm 172.00, 167.23, 155.30, 151.03, 133.44, 110.28, 79.57, 49.53, 46.98, 41.30, 28.27.

c. Preparation of tert-butyl (S)-4-(3-(4-(4-((1-(tert-butoxycarbonyl)pyrrolidin-3-yl)oxy)-3-cyclohexylbenzoyl)piperazine-1-carbonyl)-5-fluorophenyl)-3-oxopiperazine-1-carboxylate (74A)

To a solution of 73 (0.100 g, 0.296 mmol) in anhydrous CH₂Cl₂ (10 mL) was added EDC☐HCl (0.085 g, 0.443 mmol), and HOAt (0.048 g, 0.355 mmol) at 0° C. The solution was stirred for 30 min. Then, 55 (0.137 g, 0.299 mmol), and N,N-diisopropylethylamine (0.15 mL, 0.887 mmol) were added at 0° C. The stirred mixture was allowed to warm to room temperature overnight. The mixture was diluted with CH₂Cl₂ (50 mL), and the organic solution was washed with water, brine, dried over Na₂SO₄, solids filtered, and solvent removed under reduced pressure. The residue was then purified by column chromatography (silica gel, EtOAc:Acetone=10:1) to yield 74a as white solid (0.084 g, 37% yield). ¹H NMR (500 MHz, CDCl₃): δ (ppm 7.22 (s, 1H), 7.19 (s, 2H), 7.12 (d, J=9 Hz, 1H), 7.01 (d, J=7 Hz, 1H), 6.76 (d, J=8.5 Hz, 1H), 4.91 (m, 1H), 4.20 (s, 2H), 3.74-3.41 (m, 17H), 2.83-2.80 (m, 1H), 2.17-2.10 (m, 2H), 1.78-1.69 (m, 5H), 1.46 (s, 9H), 1.42 (s, 9H), 1.39-1.25 (m, 4H); ¹³C NMR (100 MHz, CDCl₃): δ (ppm 170.93, 168.29, 165.74, 162.48 (d, J=248.0 Hz), 155.66, 154.57, 153.58, 143.23 (d, J=10.0 Hz), 137.39, 127.16, 126.56, 126.11, 119.97, 114.04 (d, J=22.9 Hz), 112.67 (d, J=21.4 Hz), 111.89, 81.14, 79.45, 76.51, 75.43, 51.51, 51.09, 49.19, 48.19, 44.20, 43.84, 37.31, 33.05, 32.82, 31.63, 30.95, 28.44, 28.29, 26.91, 26.24. LRMS-ESI: Exact mass calcd for $C_{42}H_{56}ClFN_5O_8$ [M+Cl⁻]⁻=812.38; found: 812.01.

d. Preparation of tert-butyl (S)-4-(3-(4-(4-((1-(tert-butoxycarbonyl)pyrrolidin-3-yl)oxy)-3-(4-(trifluoromethyl)cyclohexyl)benzoyl)piperazine-1-carbonyl)-5-fluorophenyl)-3-oxopiperazine-1-carboxylate (74B)

The synthesis of compound 71 followed the same procedure as for compound 74a. Column chromatography (silica gel, EtOAc:Acetone=10:1) afforded 74b as a white solid (0.0564 g, 42% yield). ¹H NMR (500 MHz, CDCl₃): δ (ppm 7.24-7.20 (m, 3H), 7.14-7.12 (m, 1H), 7.03 (d, J=8 Hz, 1H), 6.79 (d, J=8.5, 1H), 4.93 (brs, 1H), 4.22 (s, 2H), 3.76-3.43 (m, 16H), 2.92-2.90 (m, 1H), 2.37-2.30 (m, 1H). 2.18-2.11 (m, 2H), 2.03-1.99 (m, 3H), 1.92-1.87 (m, 1H), 1.77-1.63 (m, 4H), 1.48 (s, 9H), 1.44 (s, 9H). ¹³C NMR (100 MHz, CDCl₃): δ 8 ppm 170.76, 170.71, 168.29, 165.77, 162.53 (d, J=249.5 Hz), 155.75, 154.51, 153.61, 143.24 (d, J=9.2 Hz), 137.30, 135.65, 130.08, 127.27, 126.91, 126.57, 120.01, 114.12 (d, J=23.7 Hz), 112.74 (d, J=22.1 Hz), 111.94, 81.19, 79.59, 69.46, 53.81, 51.48, 51.02, 49.23, 48.27, 44.11, 36.97, 36.71, 35.69, 31.71, 30.98, 29.25, 28.45, 28.30, 27.62, 27.42, 25.35, 23.95.

e. Preparation of (S)-1-(3-(4-(3-cyclohexyl-4-(pyrrolidin-3-yloxy)benzoyl)piperazine-1-carbonyl)-5-fluorophenyl)piperazin-2-one Hydrochloride (75)

To compound 74a (0.080 g, 0.103 mmol) under anhydrous conditions was added 4 M HCl in dioxane (3 mL), and the mixture was stirred at room temperature for 1 h. The solvent was then removed under reduced pressure. The product was dissolved in DI water (20 mL) and the aqueous layer was washed with ethyl acetate (3×20 mL). The resulting aqueous solution was frozen and lyophilized to yield 75 (0.0493 g, 74% yield) as white solid. $^1$H NMR (500 MHz, d$^6$-DMSO): δ (ppm 9.91 (brs, 2H), 9.45 (brs, 2H), 7.36 (d, J=10 Hz, 1H), 7.28 (s, 1H), 7.25-7.23 (m, 3H), 7.00 (d, J=9 Hz, 1H), 5.17 (brs, 1H), 3.94-3.92 (m, 2H), 3.86 (s, 2H), 3.69-3.63 (m, 2H), 3.55-3.45 (m, 7H), 3.30-3.28 (m, 2H), 3.24-3.17 (m, 1H), 2.90-2.86 (m, 1H), 2.20-2.12 (m, 2H), 1.76-1.70 (m, 5H), 1.40-1.20 (m, 5H).

f. Preparation of (S)-1-(3-fluoro-5-(4-(4-(pyrrolidin-3-yloxy)-3-(4-(trifluoromethyl)cyclohexyl)benzoyl)piperazine-1-carbonyl)phenyl)piperazin-2-one Hydrochloride (76)

The synthesis of compound 76 followed the same procedure as for compound 75. Column chromatography (silica gel, EtOAc:Acetone=10:1) afforded 76 as a white solid (0.0354 g, 79% yield). $^1$H NMR (500 MHz, d$^6$-DMSO): δ (ppm 10.04 (brs, 2H), 9.63 (brs, 2H), 7.36 (d, J=10 Hz, 1H), 7.28-7.21 (m, 4H), 7.02 (d, J=8.5 Hz, 1H), 5.19 (brs, 1H), 3.95-3.92 (m, 2H), 3.85 (s, 2H), 3.76-3.63 (m, 4H), 3.55-3.45 (m, 9H), 3.24-3.18 (m, 2H), 3.06-3.02 (m, 1H), 2.19-2.14 (m, 3H), 1.93-1.81 (m, 4H), 1.68-1.57 (m, 3H), 1.50-1.35 (m, 2H).

17. HPLC Conditions

The purity of final compounds 2-22 was determined by HPLC analysis. The instrument was an Agilent 1260 Infinity Quaternary LC with an Agilent 1260 Infinity ELSD detector. The purity of all tested compounds was ≥90%.

a. Compound 2

Condition A: Elute with 0.10% TFA in water for first 5 minutes, and then change to a 5 minutes' gradient starting with 0.10% TFA in water and ending with 0.10% TFA in water and acetonitrile mixture (water with 0.1% TFA:acetonitrile=1:1), and at last eluent with 0.1% TFA in water and acetonitrile 1:1 mixture for 10 minutes (FIG. 1A).

Figure 1B:
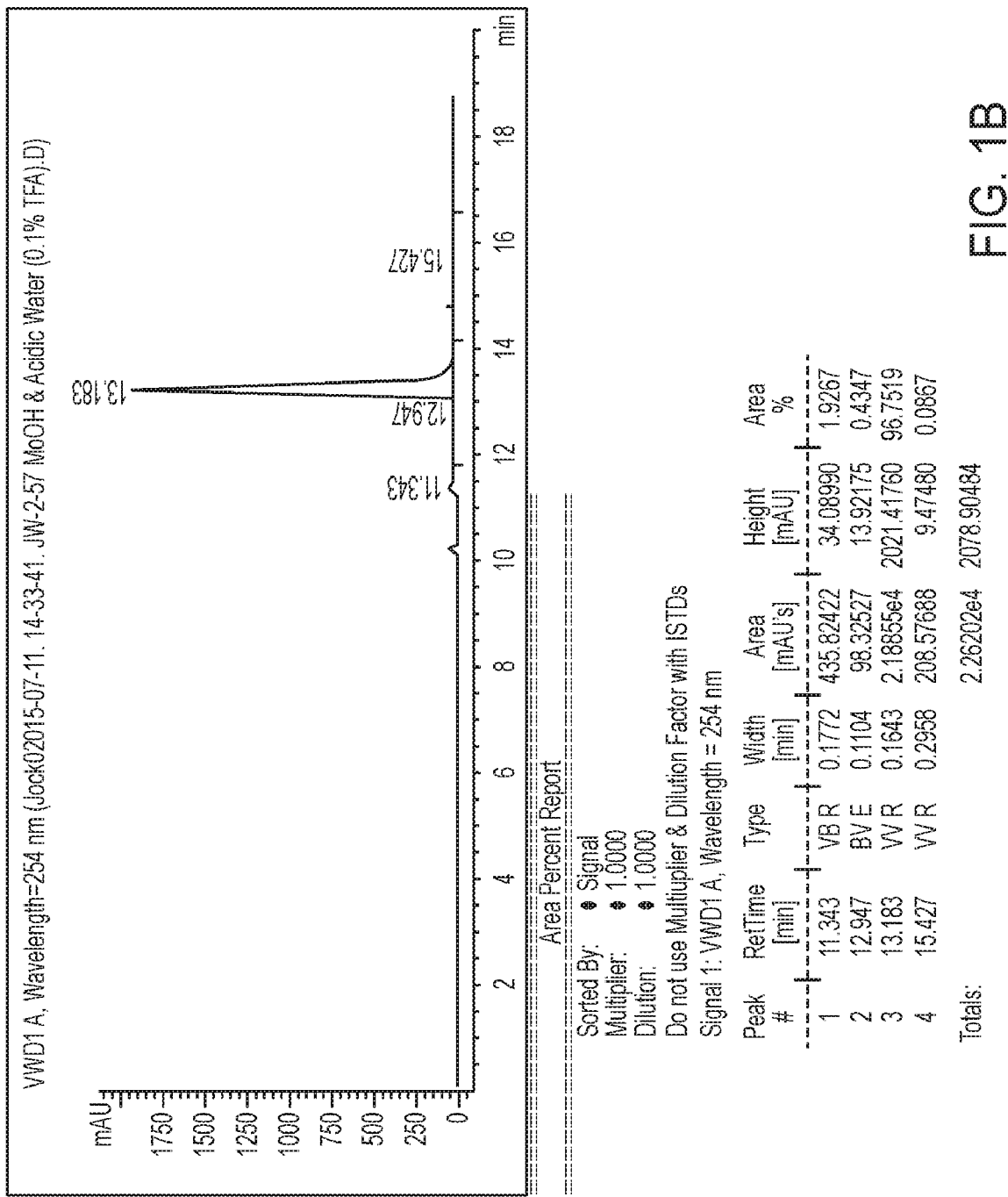

Condition B: Elute with 0.10% TFA in water for first 5 minutes, and then change to a 5 minutes' gradient starting with 0.10% TFA in water and ending with 0.10% TFA in water and methanol mixture (water with 0.1% TFA:methanol=1:1), and at last eluent with 0.1% TFA in water and methanol 1:1 mixture for 10 minutes (FIG. 1B).

b. Compound 10

Figure 2A:
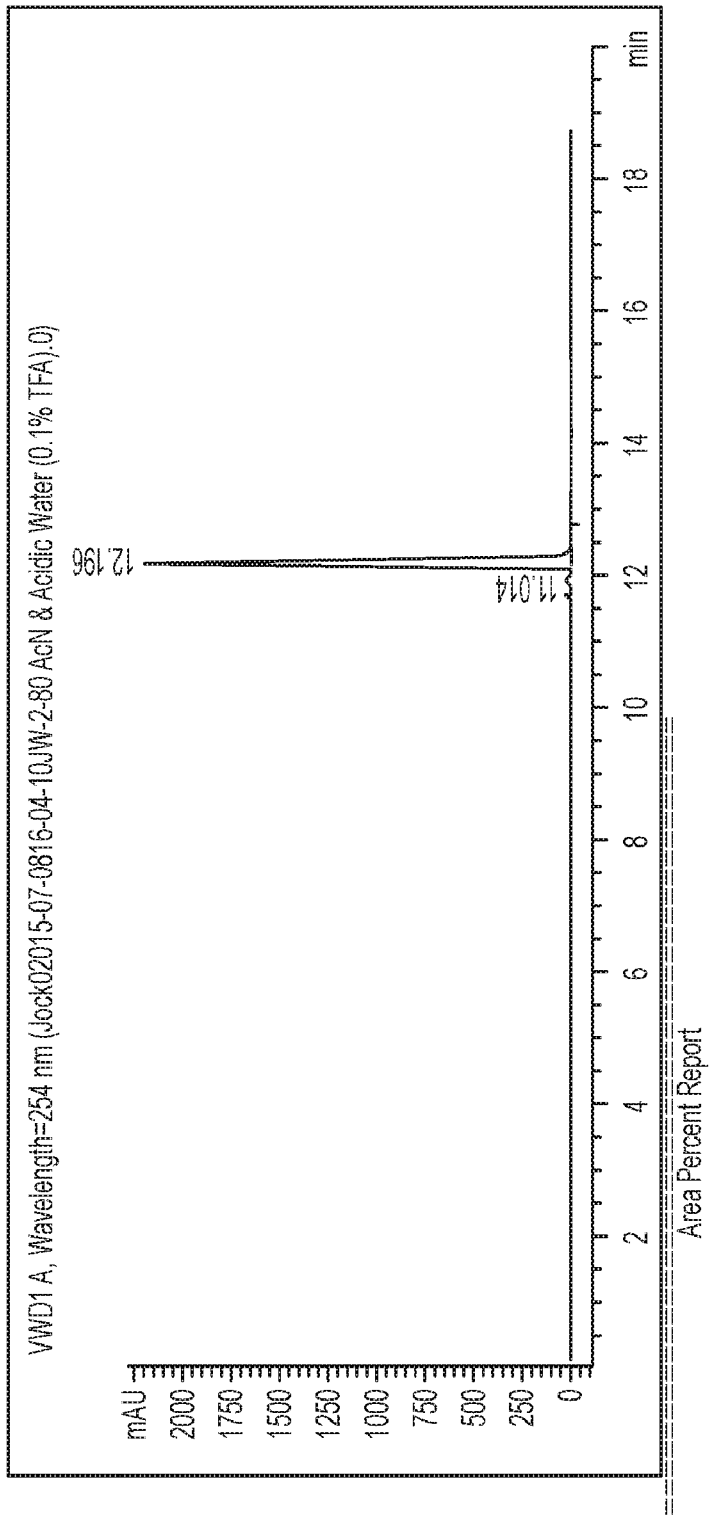
FIG. 2A and FIG. 2B show representative HPLC spectra of compound 10 run over a water/acetonitrile gradient (plus 0.1% TFA) (1A) and over a water/methanol gradient (plus 0.10% TFA (1B).

Condition A: Elute with 0.10% TFA in water for first 8 minutes, and then change to a 2 minutes' gradient starting with 0.1% TFA in water and ending with 0.1% TFA in water and acetonitrile mixture (water with 0.1% TFA:acetonitrile=1:1), and later eluent with 0.1% TFA in water and acetonitrile 1:1 mixture for 5 minutes. Then change mobile phase from the above mixture to 100% acetonitrile in 1 minute, and then keep eluting for 4 minutes (FIG. 2A).

Figure 2B:
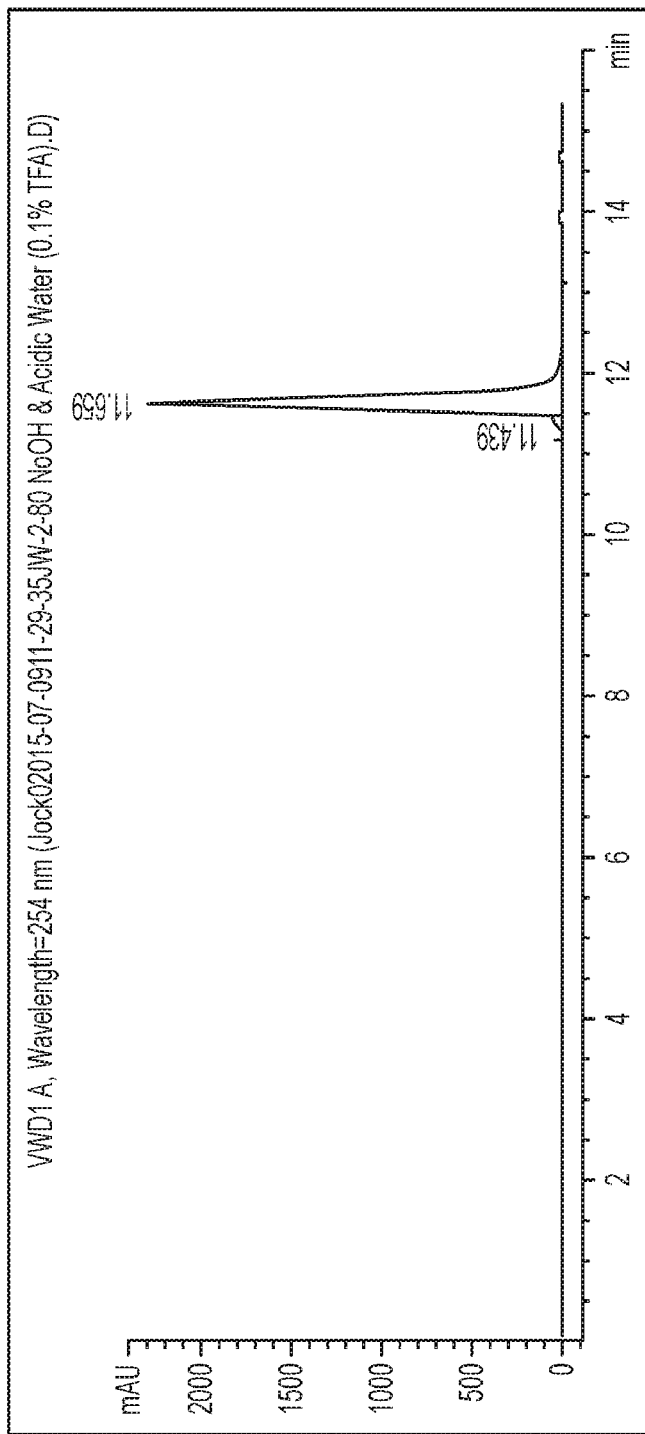

Condition B: Elute with 0.10% TFA in water for first 8 minutes, and then change to a 3 minutes' gradient starting with 0.10% TFA in water and ending with 0.10% TFA in water and methanol mixture (water with 0.1% TFA:methanol=1:1), and later eluent with 0.1% TFA in water and methanol 1:1 mixture for 4 minutes. Then change mobile phase from the above mixture to 100% methanol in 1 minute (FIG. 2B).

18. Protein Structure for Computer Modeling

The crystallographic coordinates for human β-catenin (PDB id, 2GL7[1], 2.60 Å resolution, $R_{cryst}$=0.223) were obtained from the Research Collaboratory for Structural Bioinformatics (RCSB) protein data bank. The preparation of the crystal structure and molecular modeling were achieved with the commercially available Schrodinger (http://www.schrodinger.com/), Accelrys Discovery Studio 3.0 (http://accelrys.com/), and SYBYL X2.0 (http://www.tripos.com/) software packages. The missing side chains of β-catenin were added in SYBYL X2.0. The protonation states of the residues were set to pH 7.0 when adding hydrogen. The AMBER 7 force field 99 and the AMBER FF99 charges within SYBYL X2.0 were used to optimize the orientation of hydrogen atoms and the missing side chains of the protein. After the protein complex was optimized. Chains B (Tcf4), C (BCL9), D (the second monomer of β-catenin), E (the second monomer of Tcf4), F (the second monomer of BCL9), and solvent molecules were removed, leaving only one monomer of β-catenin for further calculation. The residues in the BCL9 L366/I369/L373 binding site of β-catenin include D144-A146, L148, A149, A152, I153, E155-L160, D162-A171, M174, V175, Q177, L178, K180, K181, A183, S184, A187, I188, M194, and I198.

19. Sitemap Calculation

This calculation was performed with SiteMap 2.6 in Schrodinger. The evaluation on a single binding site region was selected, and all residues of the BCL9 L366/I369/L373 binding site were included. At least 15 site points per reported site were required to initiate the SiteMap calculation. The more restrictive definition for hydrophobicity was used. The grid spacing was set to 0.35 Å. The site maps were cropped at 4 Å from nearest site point, and the OPLS-2005 force field was used to map the hydrophobic, H-bond donor and H-bond acceptor regions.

20. Ligand Docking Using Autodock 4.2

The three-dimensional (3D) structures of the ligands were built, and the partial atomic charges were calculated using the Gasteiger-Marsili method. The rotatable bonds in the ligands were defined using AutoTors, which also united the nonpolar hydrogens and partial atomic charges to the bonded carbon atoms. The grid maps were calculated using AutoGrid. The AutoDock area was defined to include all of the residues in the BCL9 L366/1369/L373 binding site, and the grid spacing was set to 0.375 Å. Docking was performed using the Lamarckian genetic algorithm, and the pseudo-Solis and Wets method was applied for the local search. Each docking experiment was performed 100 times, yielding 100 docked conformations. The other settings were the default parameters. All of the ligands followed the same docking protocol. The results of the docking experiments were evaluated by the auxiliary clustering analysis and the visual inspection to match the proposed critical binding elements.

21. Protein Expression and Purification

β-Catenin mutants D145A, E155A, D145A/E155A have been made previously.[5] Wild-type β-catenin and its mutants (residues 138-686) were cloned into a pET-28b vector carrying a C-terminal 6× histidine (Novagen), and transformed into *Escherichia coli* BL21 DE3 (Novagen). Cells were cultured in LB medium with 30 μg/mL kanamycin until the OD$_{600}$ was approximately 0.8, and then protein expression was induced with 400 μM of IPTG at 20° C. overnight. Cells were lysed by sonication. The proteins were purified by Ni-NTA affinity chromatography (30210, Qiagen) and dialyzed against a buffer containing 20 mM of Tris (pH 8.5), 100 mM NaCl, 10% glycerol, and 3 mM DTT. The purity of β-catenin was greater than 95% as determined by SDS-PAGE gel analysis. Native non-denaturing gel electrophoresis was performed to confirm the homogeneity of the purified proteins. Thermal-shift assay was performed on an iCycler iQ Real Time Detection System (Bio-Rad) to monitor protein stability and detect protein aggregation. Protein unfolding was evaluated through measuring the fluorescence changes of fluorescent dye Sypro Orange when interacting with wild-type or mutant β-catenin proteins. A temperature increment of 1°/min was applied. CD spectra were measured on a J-815 spectropolarimeter (Jasco). All spectra were recorded at room temperature, and the baseline control containing all of the substances except protein. Sample were prepared at a concentration around 1-5 μM in a buffer of 10 mM potassium phosphate and 100 mM potassium fluoride at pH 7.0 to ensure that the transmission of light through the sample was not restricted. All proteins were stable and no aggregation was observed under storage or assay conditions. Proteins were aliquoted and stored at −80° C.

22. BCL9 Peptide Synthesis and Purification

Human BCL9 (residues 350-375), N-terminally biotinylated human BCL9 (residues 350-375), N-terminally fluorescein-labeled human BCL9 (residues 350-375), and N-terminally biotinylated human E-cadherin (residues 824-877) were synthesized by InnoPep Inc. (www.innopep.com) and HPLC purified by HPLC with purity >95%. The structures were validated by LC/MS. The sequences of these peptides have been described previously.[6]

23. Alphascreen Assays to Determine the Apparent $K_d$ values for Wild-Type and Mutant β-Catenin/BCL9 Interactions The experimental detail using AlphaScreen to determine the apparent $K_d$ values for β-catenin/BCL9 and β-catenin/E-cadherin PPIs has been described previously (Zhang et al. (2015) *Anal. Biochem.* 469: 43-53). The concentrations of mutant β-catenin proteins used in the assays were the same as that of wild-type β-catenin.

24. Fluorescence Polarization (FP) Assays to Determine the Apparent $K_d$ values for Wild-Type and Mutant β-catenin/BCL9 Interactions The FP experiments were performed in 96-well Microfluor 2 black plates (Waltham, MA), and the sample signals were read by a Synergy 2 plate reader (Biotek, Winooski, VT). The polarization was measured at room temperature with an excitation wavelength at 485 nm and an emission wavelength at 535 nm. All of the FP experiments were performed in an assay buffer of 137 mM NaCl, 2.7 mM KCl, 10 mM $Na_2HPO_4$, 2 mM $KH_2PO_4$, 100 pug/mL of bovine γ-globulin, and 0.010% Triton X-100. The final reaction volume was set to 100 μL. In the FP saturation binding experiments, the concentration of human BCL9 fluorescent tracer was fixed at 5 nM. The concentrations of β-catenin were ranged from 0 to 10 μM in the assay buffer giving a final volume of 100 μL. After the addition, each assay plate was covered black and gently mixed on an orbital shaker for 3 h before the polarization signals were recorded. The data were analyzed by nonlinear least-square analyses using GraphPad Prism 5.0 to derive the apparent $K_d$ value. Each experiment was repeated three times, and the results were expressed as mean±standard deviation.

25. Alphascreen Competitive Inhibition Assays Using Wild-Type and Mutant β-Catenin Proteins The experimental details of the AlphaScreen competitive inhibition assays for the β-catenin/BCL9 and β-catenin/E-cadherin PPIs have been described previously.[5] The concentrations of mutant β-catenin proteins used in the AlphaScreen competitive inhibition assays were the same as that of wild-type β-catenin protein.

26. MTS Cell Viability Assay

Colorectal cancer cell lines, SW480 and HCT116 were seeded in 96-well plates at $4 \times 10^3$ cells/well, maintained overnight at 37° C., and incubated with the tested compounds at various concentrations. Cell viability was monitored after 72 h using a freshly prepared mixture of 1 part phenazine methosulfate (PMS, Sigma) solution (0.92 mg/mL) and 19 parts 3-(4,5-dimethylthiazol-2-yl)-5-(3-carboxymethoxyphenyl)-2-(4-sulfophenyl)-2H-tetrazolium (MTs, Promega) solution (2 mg/mL). Cells were incubated in 10 μL of this solution at 37° C. for 3 h, and $A_{490}$ was measured. The effect of each compound is expressed as the concentration required to reduce $A_{490}$ by 50% ($IC_{50}$) relative to DMSO-treated cells. Experiments were performed in triplicate.

27. Cell Transfection and Luciferase Assay

FuGENE 6 (E2962, Promega) in a 96-well plate format was used for the transfection of HEK293 and SW480 cells according to the manufacturer's instructions. HEK293 cells were co-transfected with 45 ng of the TOPFlash (with three wild-type Tcf binding sites) or FOPFlash (with three mutant Tcf binding sites) reporter gene, 135 ng pcDNA3.1-β-catenin and 20 ng pCMV-RL normalization reporter gene. SW480 cells were co-transfected with 60 ng of the TOPFlash or FOPFlash reporter gene and 40 ng pCMV-RL normalization reporter. Cells were cultured at 37° C. for 24 h, and different concentrations of inhibitors were then added. After 24 h, the luciferase reporter activity was measured using the Dual-Glo system (E2940, Promega). Normalized luciferase activity in response to the treatment with the inhibitors was compared with that obtained from the cells treated with DMSO. Experiments were performed in triplicate.

28. Characterization of Exemplary Compounds

The compounds in Table 1 were synthesized with methods identical or analogous to those described herein. The requisite starting materials were commercially available, described in the literature, or readily synthesized by one skilled in the art of organic synthesis.

TABLE 1

| No. | Structure | Name |
|---|---|---|
| 1 | [Structure image] | 2-((5-carbamoyl-4'-fluoro-[1,1'-biphenyl]-2-yl)oxy)ethan-1-aminium chloride |

TABLE 1-continued

| No. | Structure | Name |
|---|---|---|
| 2 | 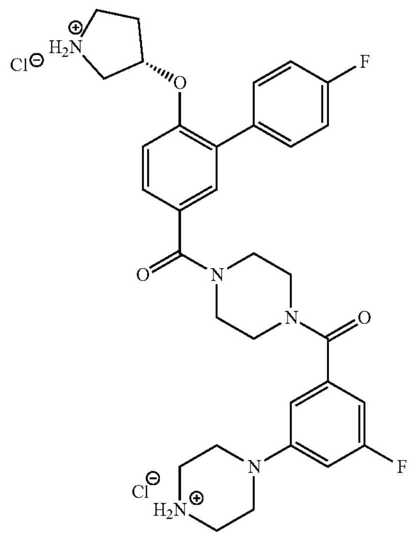 [SMILES: [Cl-] ; O=C(c1cc(F)cc(N2CC[NH2+]CC2)c1)N1CCN(C(=O)c2ccc(O[C@H]3CC[NH2+]C3)c(-c3ccc(F)cc3)c2)CC1 ; [Cl-]] | S)-(4-(3-Fluoro-5-(piperazin-1-yl)benzoyl)piperazin-1-yl)(4'-fluoro-6-(pyrrolidin-3-yloxy)-[1,1'-biphenyl]-3-yl)methanone hydrochloride |
| 3 | 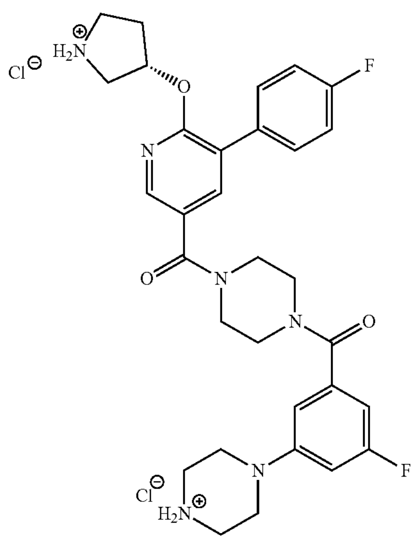 [SMILES: [Cl-] ; O=C(c1cc(F)cc(N2CC[NH2+]CC2)c1)N1CCN(C(=O)c2cnc(O[C@H]3CC[NH2+]C3)c(-c3ccc(F)cc3)c2)CC1 ; [Cl-]] | (S)-(4-(3-Fluoro-5-(piperazin-1-yl)benzoyl)piperazin-1-yl)(5-(4-fluorophenyl)-6-(pyrrolidin-3-yloxy)pyridin-3-yl)methanone hydrochloride |
| 4 | 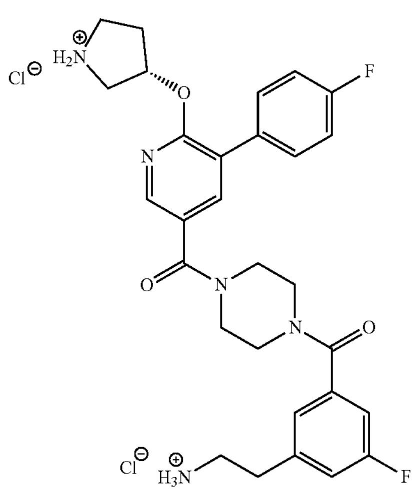 [SMILES: [Cl-] ; [NH3+]CCc1cc(F)cc(C(=O)N2CCN(C(=O)c3cnc(O[C@H]4CC[NH2+]C4)c(-c4ccc(F)cc4)c3)CC2)c1 ; [Cl-]] | (S)-(4-(3-(2-Aminoethyl)-5-fluorobenzoyl)piperazin-1-yl)(5-(4-fluorophenyl)-6-(pyrrolidin-3-yloxy)pyridin-3-yl)methanone hydrochloride |

TABLE 1-continued

| No. | Structure | Name |
|---|---|---|
| 5 | 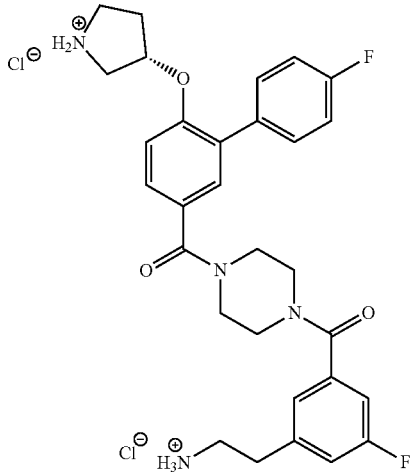 | (S)-(4-(3-(2-Aminoethyl)-5-fluorobenzoyl)piperazin-1-yl)(4'-fluoro-6-(pyrrolidin-3-yloxy)-[1,1'-biphenyl]-3-yl)methanone hydrochloride |
| 6 | 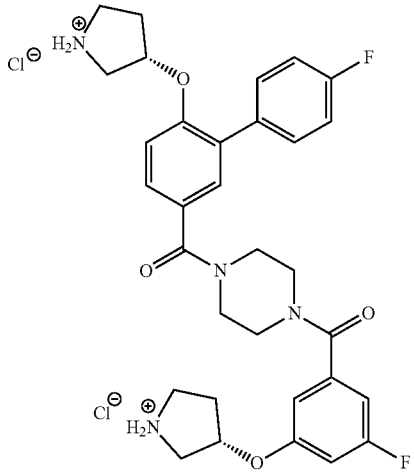 [SMILES: [Cl-] ; O=C(c1cc(F)cc(O[C@H]2CC[NH2+]C2)c1)N1CCN(C(=O)c2ccc(O[C@H]3CC[NH2+]C3)c(-c3ccc(F)cc3)c2)CC1 ; [Cl-]] | (4-(3-Fluoro-5-(((S)-pyrrolidin-3-yl)oxy)benzoyl)piperazin-1-yl)(4'-fluoro-6-(((S)-pyrrolidin-3-yl)oxy)-[1,1'-biphenyl]-3-yl)methanone hydrochloride |
| 7 | 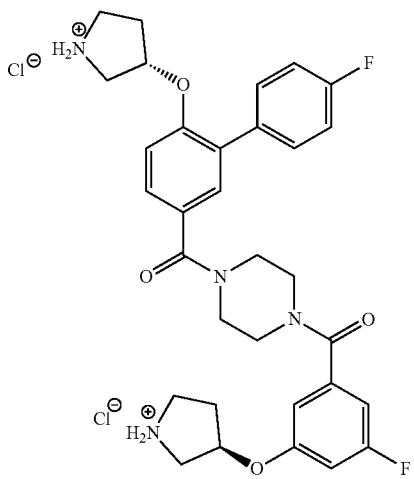 [SMILES: [Cl-] ; O=C(c1cc(F)cc(O[C@@H]2CC[NH2+]C2)c1)N1CCN(C(=O)c2ccc(O[C@H]3CC[NH2+]C3)c(-c3ccc(F)cc3)c2)CC1 ; [Cl-]] | (4-(3-Fluoro-5-(((R)-pyrrolidin-3-yl)oxy)benzoyl)piperazin-1-yl)(4'-fluoro-6-(((S)-pyrrolidin-3-yl)oxy)-[1,1'-biphenyl]-3-yl)methanone hydrochloride |

TABLE 1-continued

| No. | Structure | Name |
|---|---|---|
| 8 | 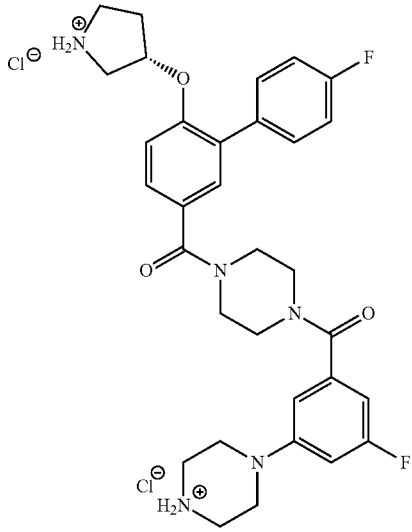 [SMILES: [Cl-] ; O=C(c1cc(F)cc(N2CC[NH2+]CC2)c1)N1CCN(C(=O)c2ccc(O[C@H]3CC[NH2+]C3)c(-c3ccc(F)cc3)c2)CC1 ; [Cl-]] | (S)-(4-(3-Fluoro-5-(piperidin-4-yl)benzoyl)piperazin-1-yl)(4'-fluoro-6-(pyrrolidin-3-yloxy)-[1,1'-biphenyl]-3-yl)methanone hydrochloride |
| 9 | 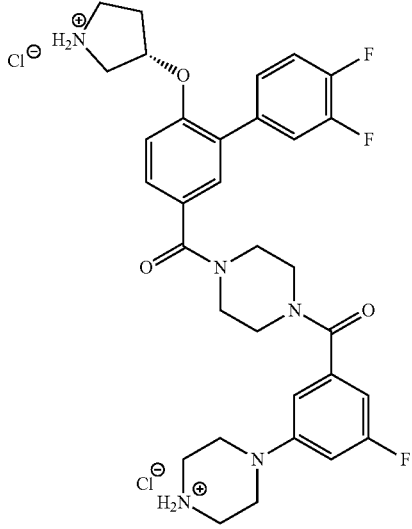 [SMILES: [Cl-] ; O=C(c1cc(F)cc(N2CC[NH2+]CC2)c1)N1CCN(C(=O)c2ccc(O[C@H]3CC[NH2+]C3)c(-c3ccc(F)c(F)c3)c2)CC1 ; [Cl-]] | (S)-(4-(3',4'-Difluoro-6-(pyrrolidin-3-yloxy)-[1,1'-biphenyl]-3-carbonyl)piperazin-1-yl)(3-fluoro-5-(piperazin-1-yl)phenyl)methanone hydrochloride |
| 10 | 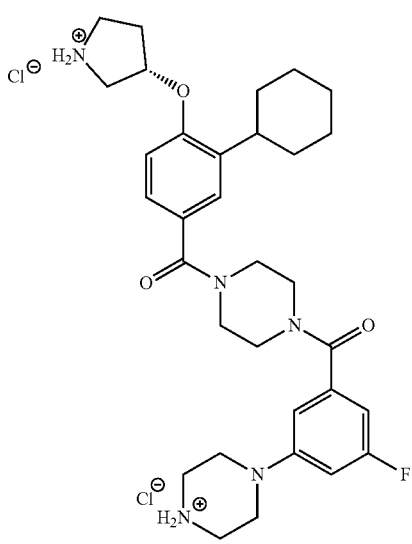 [SMILES: [Cl-] ; O=C(c1cc(F)cc(N2CC[NH2+]CC2)c1)N1CCN(C(=O)c2ccc(O[C@H]3CC[NH2+]C3)c(C3CCCCC3)c2)CC1 ; [Cl-]] | (S)-(4-(3-Cyclohexyl-4-(pyrrolidin-3-yloxy)benzoyl)piperazin-1-yl)(3-fluoro-5-(piperazin-1-yl)phenyl)methanone hydrochloride |

TABLE 1-continued

| No. | Structure | Name |
|---|---|---|
| 11 | 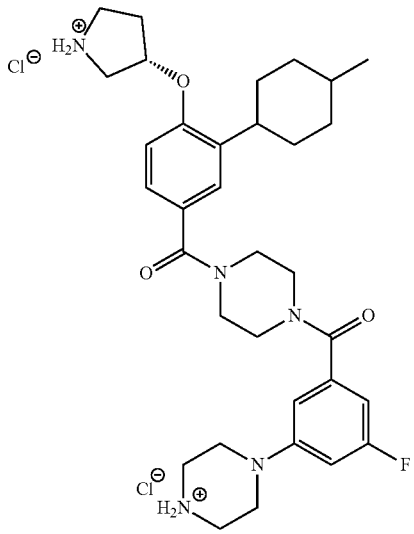 [SMILES: [Cl-] ; CC1CCC(c2cc(C(=O)N3CCN(C(=O)c4cc(F)cc(N5CC[NH2+]CC5)c4)CC3)ccc2O[C@H]2CC[NH2+]C2)CC1 ; [Cl-]] | (S)-(4-(3-Cyclopentyl-4-(pyrrolidin-3-yloxy)benzoyl)piperazin-1-yl)(3-fluoro-5-(piperazin-1-yl)phenyl)methanone hydrochloride |
| 12 | 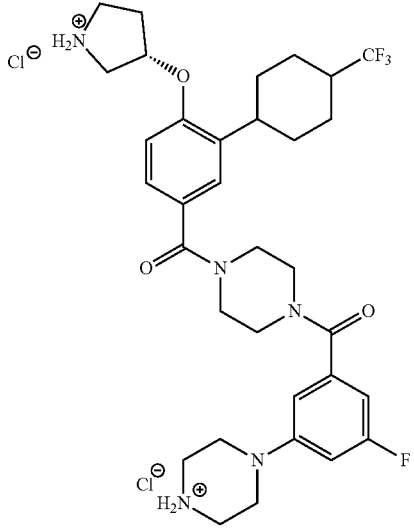 [SMILES: [Cl-] ; O=C(c1cc(F)cc(N2CC[NH2+]CC2)c1)N1CCN(C(=O)c2ccc(O[C@H]3CC[NH2+]C3)c(C3CCC(C(F)(F)F)CC3)c2)CC1 ; [Cl-]] | (S)-(4-(3-Fluoro-5-(piperazin-1-yl)methylcyclohexyl)-4-(pyrrolidin-3-yloxy)phenyl)methanone hydrochloride |
| 13 | 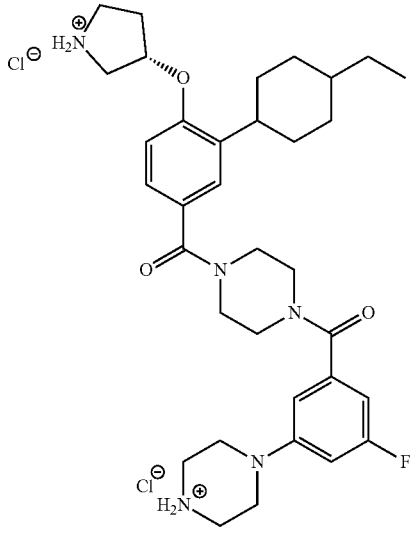 [SMILES: [Cl-] ; CCC1CCC(c2cc(C(=O)N3CCN(C(=O)c4cc(F)cc(N5CC[NH2+]CC5)c4)CC3)ccc2O[C@H]2CC[NH2+]C2)CC1 ; [Cl-]] | (S)-(4-(3-Fluoro-5-(piperazin-1-yl)benzoyl)piperazin-1-yl)(4-(pyrrolidin-3-yloxy)-3-(4-(trifluoromethyl)cyclohexyl)phenyl)methanone hydrochloride |

TABLE 1-continued

| No. | Structure | Name |
|---|---|---|
| 14 | 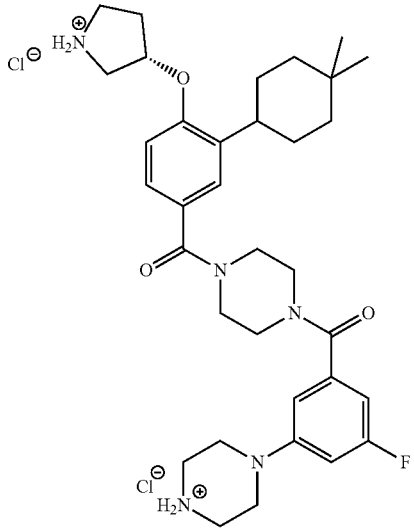 [SMILES: [Cl-] ; CC1(C)CCC(c2cc(C(=O)N3CCN(C(=O)c4cc(F)cc(N5CC[NH2+]CC5)c4)CC3)ccc2O[C@H]2CC[NH2+]C2)CC1 ; [Cl-]] | (S)-(4-(3-(4-Ethylcyclohexyl)-4-(pyrrolidin-3-yloxy)benzoyl)piperazin-1-yl)(3-fluoro-5-(piperazin-1-yl)phenyl)methanone hydrochloride |
| 15 | 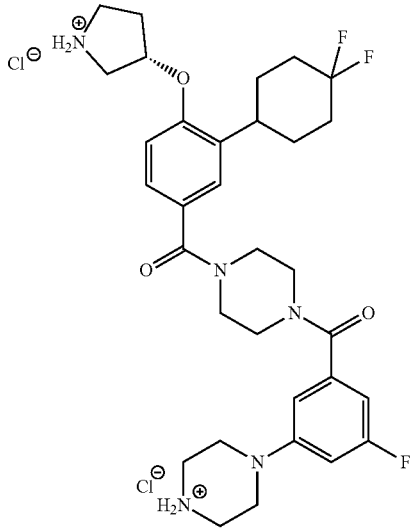 [SMILES: [Cl-] ; O=C(c1cc(F)cc(N2CC[NH2+]CC2)c1)N1CCN(C(=O)c2ccc(O[C@H]3CC[NH2+]C3)c(C3CCC(F)(F)CC3)c2)CC1 ; [Cl-]] | (S)-(4-(3-(4,4-Dimethylcyclohexyl)-4-(pyrrolidin-3-yloxy)benzoyl)piperazin-1-yl)(3-fluoro-5-(piperazin-1-yl)phenyl)methanone hydrochloride |
| 16 | 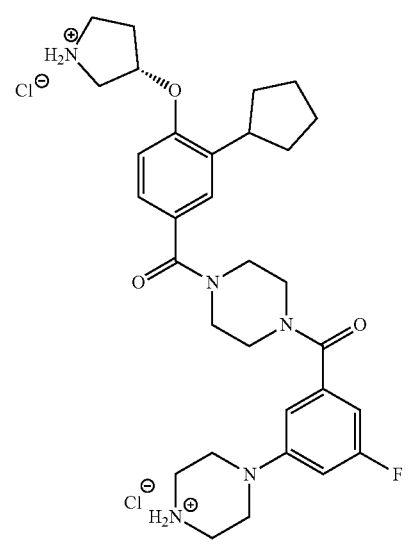 [SMILES: [Cl-] ; O=C(c1cc(F)cc(N2CC[NH2+]CC2)c1)N1CCN(C(=O)c2ccc(O[C@H]3CC[NH2+]C3)c(C3CCCC3)c2)CC1 ; [Cl-]] | (S)-(4-(3-(4,4-Difluorocyclohexyl)-4-(pyrrolidin-3-yloxy)benzoyl)piperazin-1-yl)(3-fluoro-5-(piperazin-1-yl)phenyl)methanone hydrochloride |

TABLE 1-continued
| No. | Structure | Name |
|---|---|---|
| 17 | 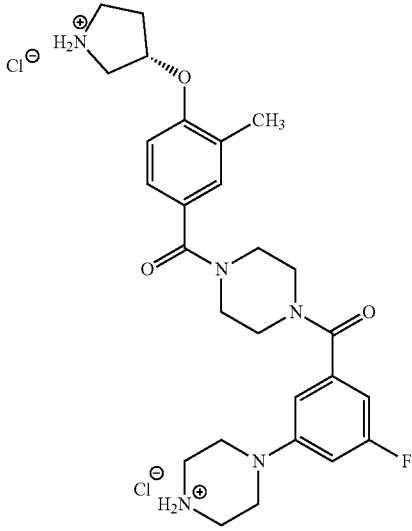 [SMILES: [Cl-] ; Cc1cc(C(=O)N2CCN(C(=O)c3cc(F)cc(N4CC[NH2+]CC4)c3)CC2)ccc1O[C@H]1CC[NH2+]C1 ; [Cl-]] | (S)-(4-(3-Fluoro-5-(piperazin-1-yl)benzoyl)piperazin-1-yl)(3-methyl-4-(pyrrolidin-3-yloxy)phenyl)methanone hydrochloride |
| 18 | 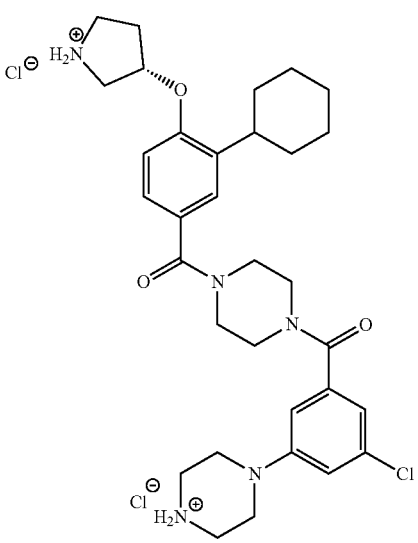 [SMILES: [Cl-] ; O=C(c1cc(Cl)cc(N2CC[NH2+]CC2)c1)N1CCN(C(=O)c2ccc(O[C@H]3CC[NH2+]C3)c(C3CCCCC3)c2)CC1 ; [Cl-]] | (S)-(4-(3-Chloro-5-(piperazin-1-yl)benzoyl)piperazin-1-yl)(3-cyclohexyl-4-(pyrrolidin-3-yloxy)phenyl)methanone hydrochloride |
| 19 | 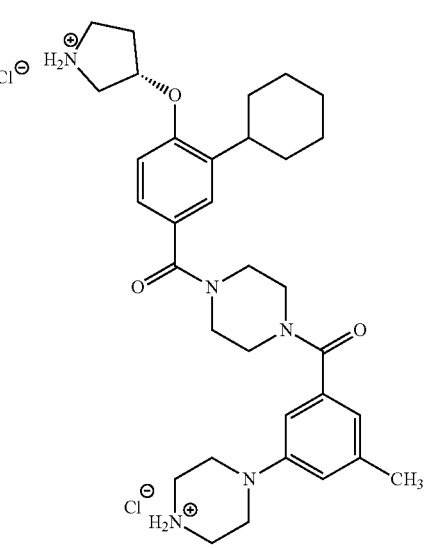 | (S)-(4-(3-Cyclohexyl-4-(pyrrolidin-3-yloxy)benzoyl)piperazin-1-yl)(3-methyl-5-(piperazin-1-yl)phenyl)methanone hydrochloride |

TABLE 1-continued

| No. | Structure | Name |
|---|---|---|
| 20 | 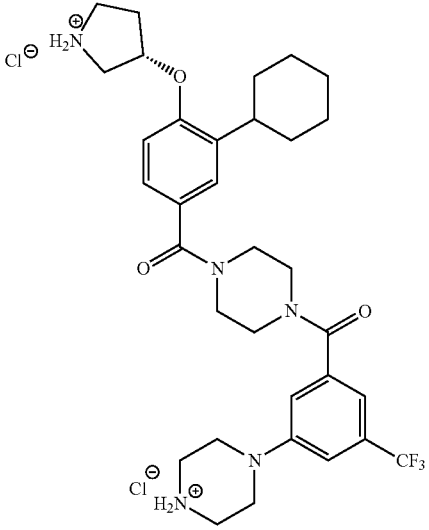 [SMILES: [Cl-] ; O=C(c1cc(N2CC[NH2+]CC2)cc(C(F)(F)F)c1)N1CCN(C(=O)c2ccc(O[C@H]3CC[NH2+]C3)c(C3CCCCC3)c2)CC1 ; [Cl-]] | (S)-(4-(3-Cyclohexyl-4-(pyrrolidin-3-yloxy)benzoyl)piperazin-1-yl)(3-(piperazin-1-yl)-5-(trifluoromethyl)phenyl)methanone hydrochloride |
| 21 | 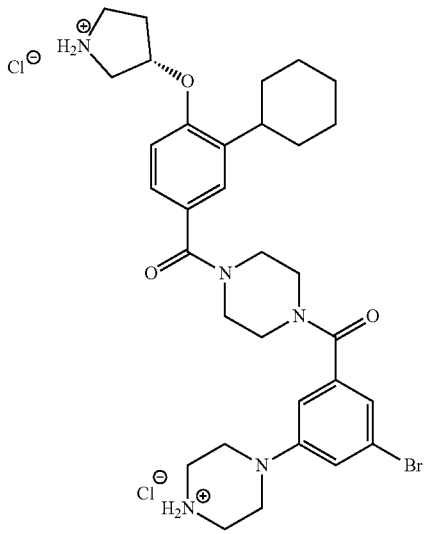 [SMILES: [Cl-] ; O=C(c1cc(Br)cc(N2CC[NH2+]CC2)c1)N1CCN(C(=O)c2ccc(O[C@H]3CC[NH2+]C3)c(C3CCCCC3)c2)CC1 ; [Cl-]] | (S)-(4-(3-Bromo-5-(piperazin-1-yl)benzoyl)piperazin-1-yl)(3-cyclohexyl-4-(pyrrolidin-3-yloxy)phenyl)methanone hydrochloride |
| 62 | 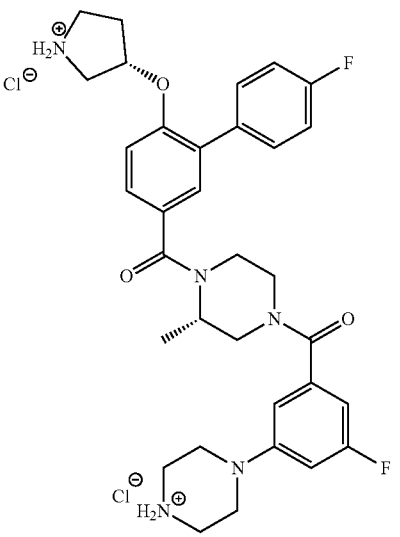 [SMILES: [Cl-] ; C[C@H]1CN(C(=O)c2cc(F)cc(N3CC[NH2+]CC3)c2)CCN1C(=O)c1ccc(O[C@H]2CC[NH2+]C2)c(-c2ccc(F)cc2)c1 ; [Cl-]] | 4-(3-Fluoro-5-((S)-4-(4'-fluoro-6-(((S)-pyrrolidin-1-ium-3-yl)oxy)-[1,1'-biphenyl]-3-carbonyl)-3-methylpiperazine-1-carbonyl)phenyl)piperazin-1-ium chloride |

TABLE 1-continued

| No. | Structure | Name |
|---|---|---|
| 63 | 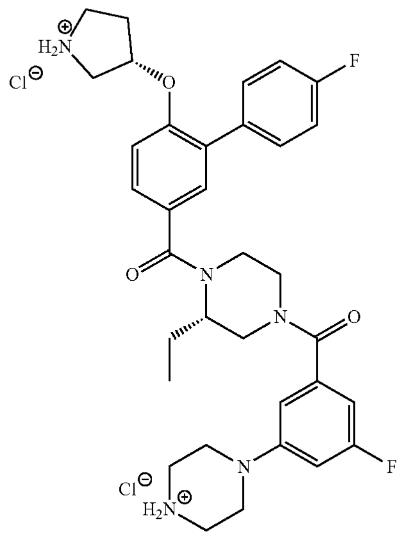 [SMILES: [Cl-] ; CC[C@H]1CN(C(=O)c2cc(F)cc(N3CC[NH2+]CC3)c2)CCN1C(=O)c1ccc(O[C@H]2CC[NH2+]C2)c(-c2ccc(F)cc2)c1 ; [Cl-]] | 4-(3-((S)-3-Ethyl-4-(4'-fluoro-6-(((S)-pyrrolidin-1-ium-3-yl)oxy)-[1,1'-biphenyl]-3-carbonyl)piperazine-1-carbonyl)-5-fluorophenyl)piperazin-1-ium chloride |
| 64 | 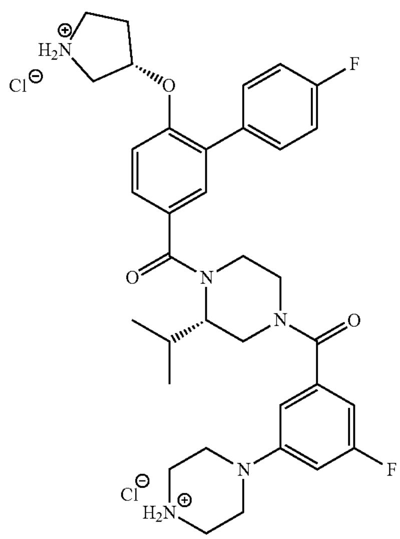 [SMILES: [Cl-] ; CC(C)[C@H]1CN(C(=O)c2cc(F)cc(N3CC[NH2+]CC3)c2)CCN1C(=O)c1ccc(O[C@H]2CC[NH2+]C2)c(-c2ccc(F)cc2)c1 ; [Cl-]] | 4-(3-Fluoro-5-((S)-4-(4'-fluoro-6-(((S)-pyrrolidin-1-ium-3-yl)oxy)-[1,1'-biphenyl]-3-carbonyl)-3-isopropylpiperazine-1-carbonyl)phenyl)piperazin-1-ium chloride |
| 68 | 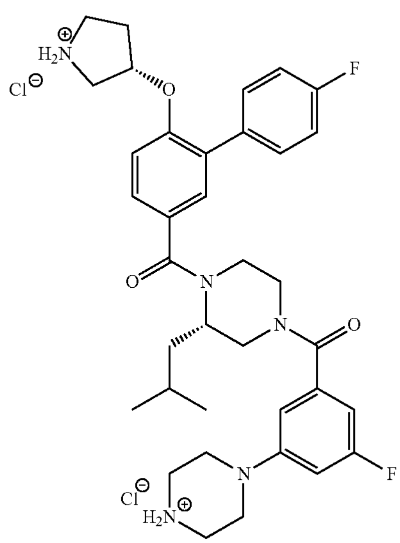 [SMILES: [Cl-] ; CC(C)C[C@H]1CN(C(=O)c2cc(F)cc(N3CC[NH2+]CC3)c2)CCN1C(=O)c1ccc(O[C@H]2CC[NH2+]C2)c(-c2ccc(F)cc2)c1 ; [Cl-]] | 4-(3-Fluoro-5-((S)-4-(4'-fluoro-6-(((S)-pyrrolidin-1-ium-3-yl)oxy)-[1,1'-biphenyl]-3-carbonyl)-3-isobutylpiperazine-1-carbonyl)phenyl)piperazin-1-ium chloride |

TABLE 1-continued

| No. | Structure | Name |
|---|---|---|
| 75 | 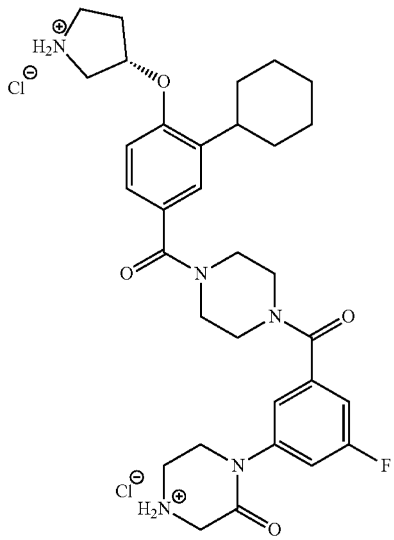 [SMILES: [Cl-] ; O=C(c1cc(F)cc(N2CC[NH2+]CC2=O)c1)N1CCN(C(=O)c2ccc(O[C@H]3CC[NH2+]C3)c(C3CCCCC3)c2)CC1 ; [Cl-]] | (S)-1-(3-(4-(3-Cyclohexyl-4-(pyrrolidin-3-yloxy)benzoyl)piperazine-1-carbonyl)-5-fluorophenyl)piperazin-2-one hydrochloride |
| 76 | 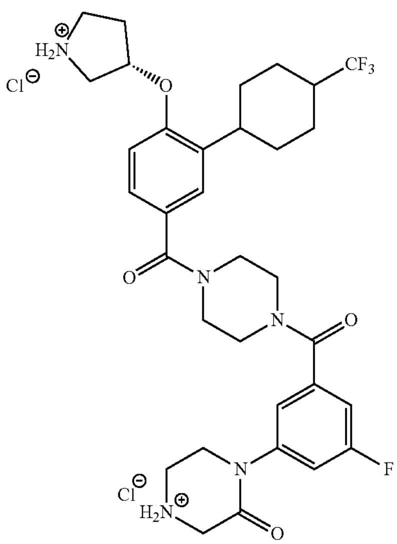 [SMILES: [Cl-] ; O=C(c1cc(F)cc(N2CC[NH2+]CC2=O)c1)N1CCN(C(=O)c2ccc(O[C@H]3CC[NH2+]C3)c(C3CCC(C(F)(F)F)CC3)c2)CC1 ; [Cl-]] | (S)-1-(3-Fluoro-5-(4-(4-(pyrrolidin-3-yloxy)-3-(4-(trifluoromethyl)cyclohexyl)benzoyl)piperazine-1-carbonyl)phenyl)piperazin-2-one hydrochloride |

29. Activity of Substituted N-(3-(pyrimidin-4-yl)phenyl)acrylamide Analogs in an Alphascreen Assay Substituted N-(3-(pyrimidin-4-yl)phenyl)acrylamide analogs were synthesized as described above. Inhibition ($K_i$) was determined in the AlphaScreen assay as described above (see Table 2 and FIG. The compound number in Table 2 corresponds to the compound numbers used in Table 1.

TABLE 2

| No. | $K_i \pm SD$ (μM) |
|---|---|
| 1 | 130 ± 6.9 |
| 2 | 19 ± 6.4 |
| 3 | 82 ± 12 |
| 4 | >500 |
| 5 | 67 ± 13 |
| 6 | 48 ± 11 |
| 7 | 35 ± 9.6 |
| 8 | 20 ± 2.3 |
| 9 | 57 ± 33 |
| 10 | 5.2 ± 0.74 |

TABLE 2-continued

| No. | $K_i \pm SD$ (μM) |
|---|---|
| 11 | 37 ± 8.0 |
| 12 | 16 ± 5.5 |
| 13 | 170 ± 7.5 |
| 14 | 70 ± 5.8 |
| 15 | 45 ± 6.7 |
| 16 | 53 ± 22 |
| 17 | 490 ± 150 |
| 18 | 76 ± 9.9 |
| 19 | 25 ± 1.7 |
| 20 | 69 ± 8.7 |
| 21 | 55 ± 2.7 |
| 62 | 110 ± 50 |
| 63 | 10 ± 10 |
| 64 | 45 |
| 68 | 22 |
| 75 | 39 ± 7.0 |
| 76 | 14 ± 3.6 |
| canosic acid | 5.3 ± 0.80 |

30. Sitemap Results at the β-Catenin/BCL9 PPI Interface

Figure 3B:
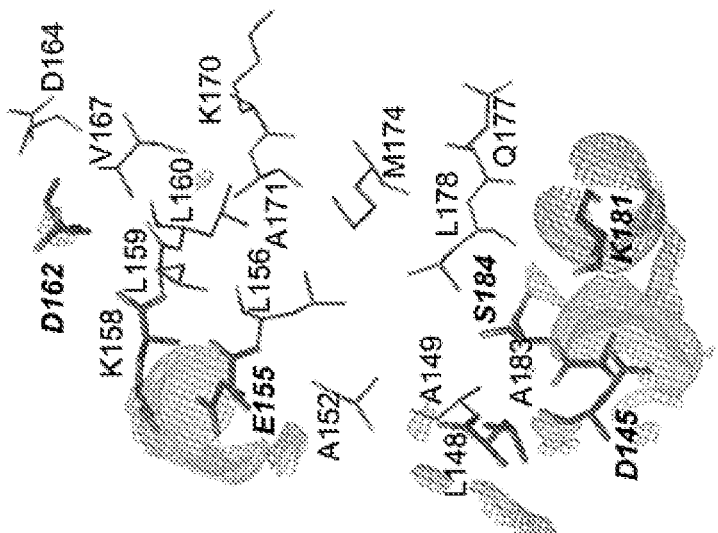
FIG. 3A-C show representative SiteMap results at the β-catenin/BCL9 PPI interface (PDB id, 2GL7; Sampietro et al. (2006) *Mol. Cell* 24: 293-300). Specifically, a surface model (3A), hydrogen bond map (3B), and stick model (3C) are shown.
Figure 3A:
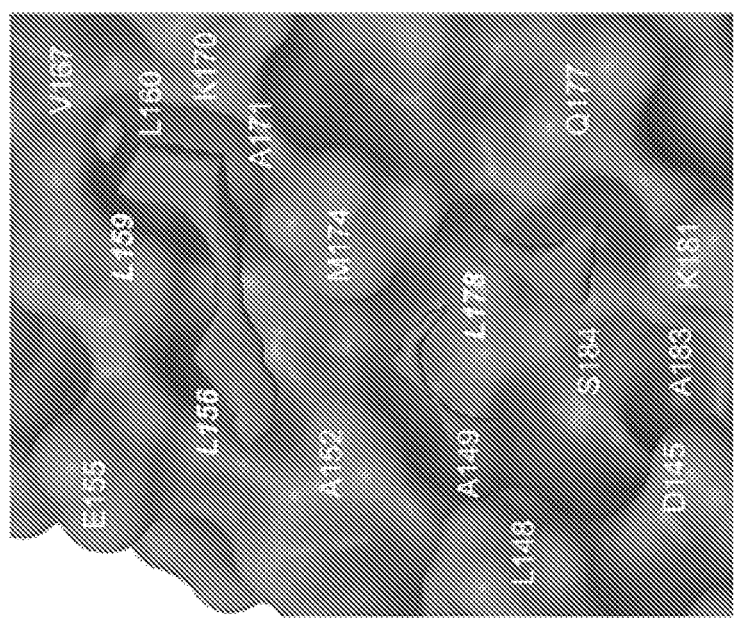
Figure 3C:
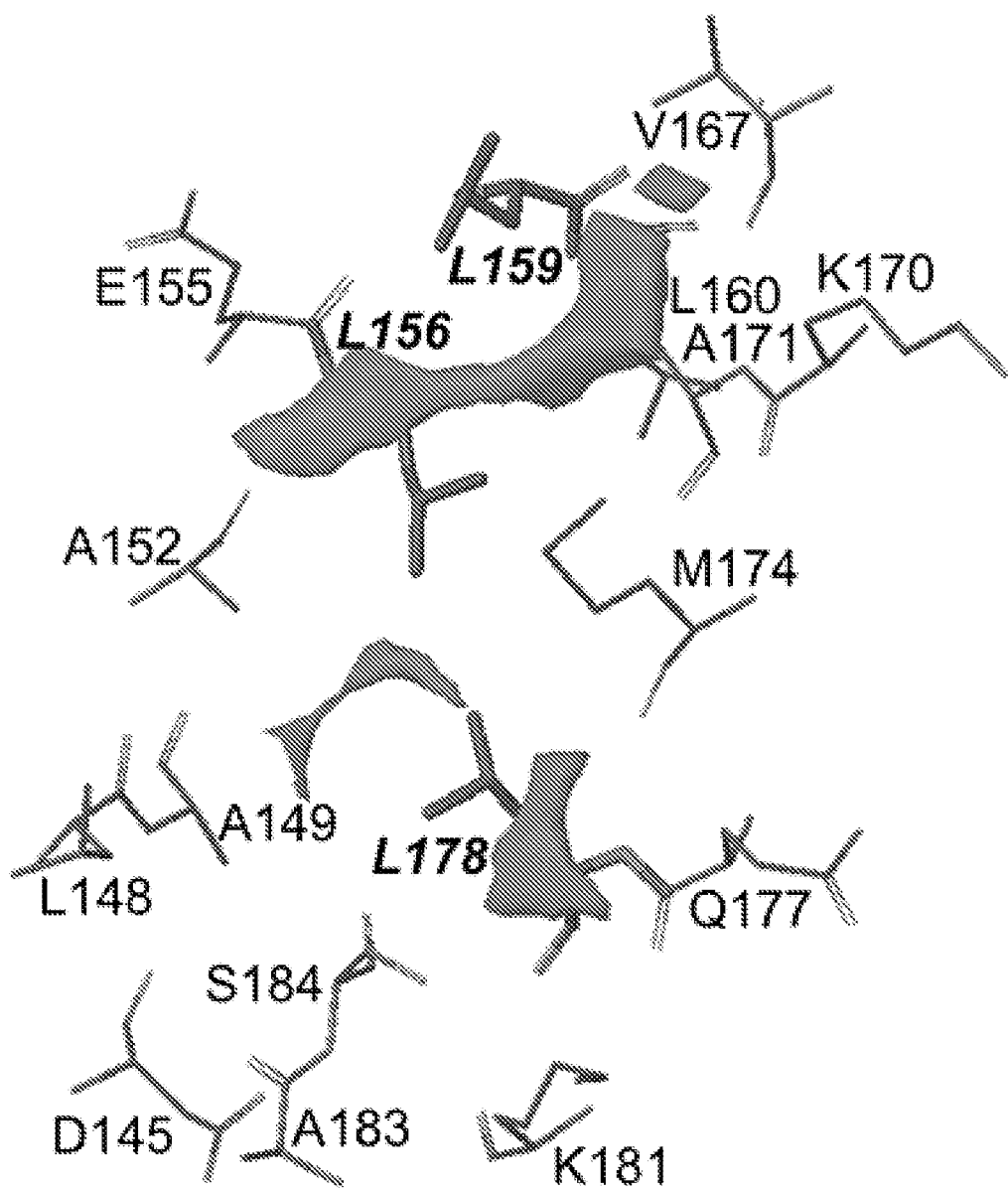

The mutational and crystallographic studies have identified that residues L366, I369, and L373 of BCL9 are the projecting hot spots that form close contact with a hot spot pocket that contains L156, L159, and L178 of β-catenin (Sampietro et al. (2006) *Mol. Cell* 24: 293-300; Hoggard et al. (2015) *J. Am. Chem. Soc.* 137: 12249-12260; de la Roche et al. (2008) *BMC Cancer* 8: 199; Kawamoto et al. (2009) *Biochemistry* 48: 9543-9541). SiteMap (Halgren, T. A. (2009) *J. Chem. Inf. Model.* 49: 377-389) was used to calculate the three-dimensional energy maps around the BCL9 L366/I369/L373 binding site and highlight the favorable sites for a specific functional group. The molecular interaction fields (MIFs) for hydrophobic interactions were mainly from the upper pocket that is lined with the side chains of A152, L156, L159, L160, V167, K170, A171, and M174 of β-catenin, as shown in FIG. 3A. SiteMap also identified additional hydrophobic MIFs generated from the side chains of L148, A149, A152, M174, L178, and K181 in the bottom pocket. The hydrophobic side chains of these residues were extracted as critical binding elements for inhibitor design. The SiteMap MIFs for H-bond acceptors were determined by the side chain carboxylic oxygen atoms of β-catenin D145, E155, D162, and S184 (FIG. 3B and FIG. 3C). The SiteMap MIFs for H-bond donors were from the side chain $NH_3$ off-catenin K181. These functional groups were also extracted as critical binding elements for H-bond and charge-charge interactions.

Referring to FIG. 3A, a hydrophobic map illustrating β-catenin as a surface model is shown. The threshold for the hydrophobic contour was set to −0.5 kcal/mol.

Referring to FIG. 3B, a hydrogen bond (H-bond) map is shown. The threshold for the H-bond donor and acceptor contours was set to −8 kcal/mol.

Referring to FIG. 3C, a stick model for the results of the hydrophobic SiteMap analysis (PDB id, 2GL7; Sampietro et al. (2006) *Mol. Cell* 24: 293-300) is shown. The threshold for the SiteMap contour was set to −0.5 kcal/mol.

31. Design of New β-Catenin/BCL9 Inhibitors

Figure 4C:
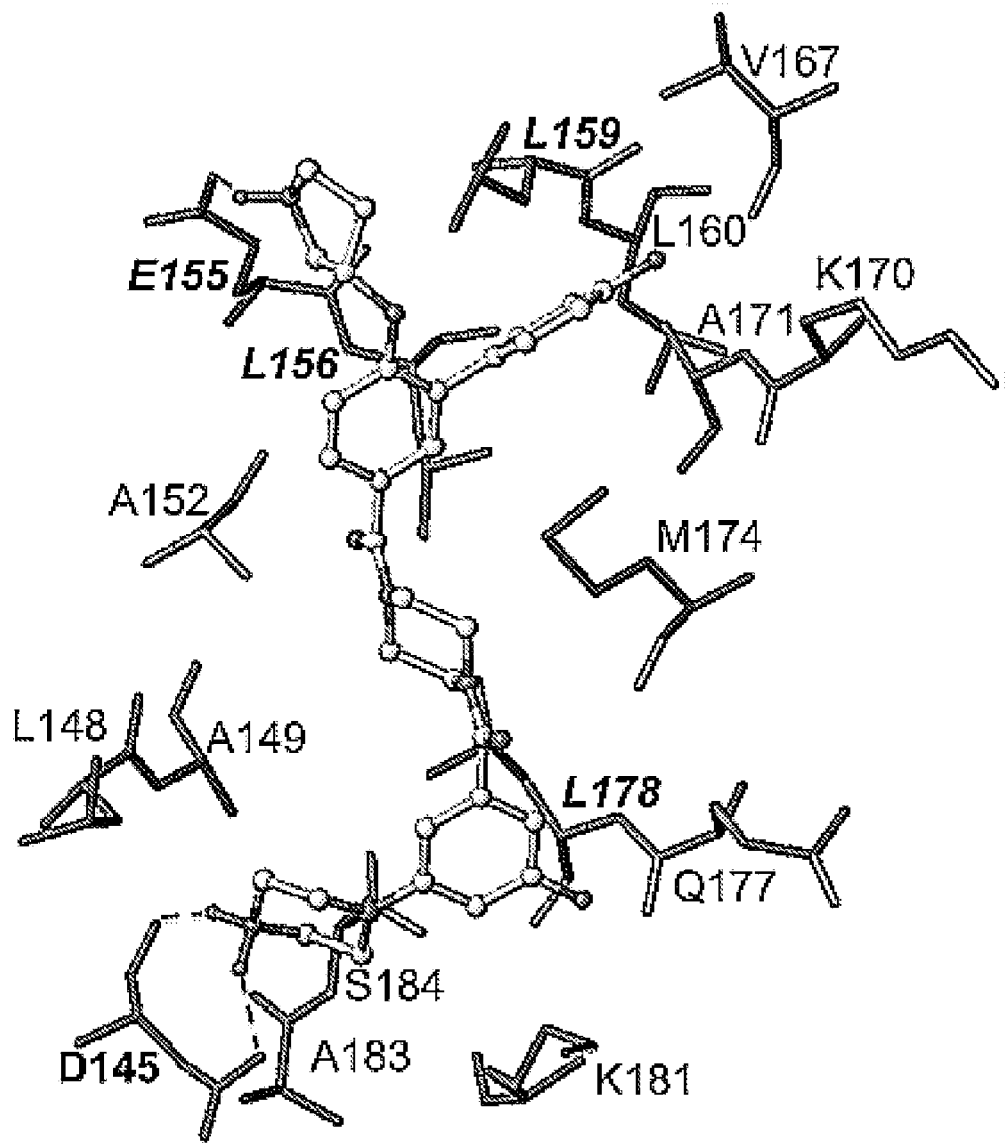

It was previously demonstrated that a small molecule that is capable of binding to the BCL9 L366/I369/L373 binding site can disrupt the β-catenin/BCL9 PPI (Hoggard et al. (2015) *J. Am. Chem. Soc.* 137: 12249-12260). Starting from fragment 1 from a previous study (Hoggard et al. (2015) *J. Am. Chem. Soc.* 137: 12249-12260), compound 2 in FIG. 4A was designed to meet the critical binding elements derived from the SiteMap analysis. The AutoDock model of 2 with β-catenin is shown in FIG. 4B and FIG. 4C. The 4-fluorobiphenyl substructure was designed to match the hydrophobic critical binding elements in the upper pocket. The phenyl group of the 3-fluoro-5-(piperazin-1-yl)benzamide substructure was designed to match the hydrophobic critical binding elements in the lower pocket, as shown in FIG. 3A. The positively charged pyrrolidin-3-yl and piperazin-1-yl groups aimed to form salt bridge interactions with β-catenin E155 and D145, respectively. The AlphaScreen assay showed that 2 can disrupt the β-catenin/BCL9 PPI with a $K_i$ value of 19±6.4 μM. The introduction of a hydrophilic pyridine nitrogen atom to 2 afforded 3, which was designed to evaluate the importance of the hydrophobic interactions in the upper pocket. The AlphaScreen $K_i$ value of 3 is 4-fold higher than 2 (see Table 2 and FIG. 5), indicating the importance of hydrophobicity of this pocket. Compound 4 with a shorter ethylamine side chain exhibited no obvious inhibition at the highest concentration tested (500 μM). Compounds 5-8 were designed to further explore the bottom pocket. A comparison of the $K_i$ values of 2 and 5-7 indicated that the piperazine substructure worked best for this series of inhibitors. The piperazine nitrogen atom attaching to the phenyl ring does not provide additional contribution to the inhibitory potency, as the $K_i$ value of 8 is similar to that of 2. The different $K_i$ values between 4 and 5 again suggested the importance of hydrophobic interactions in the upper pocket for inhibitor binding.

Figure 5:
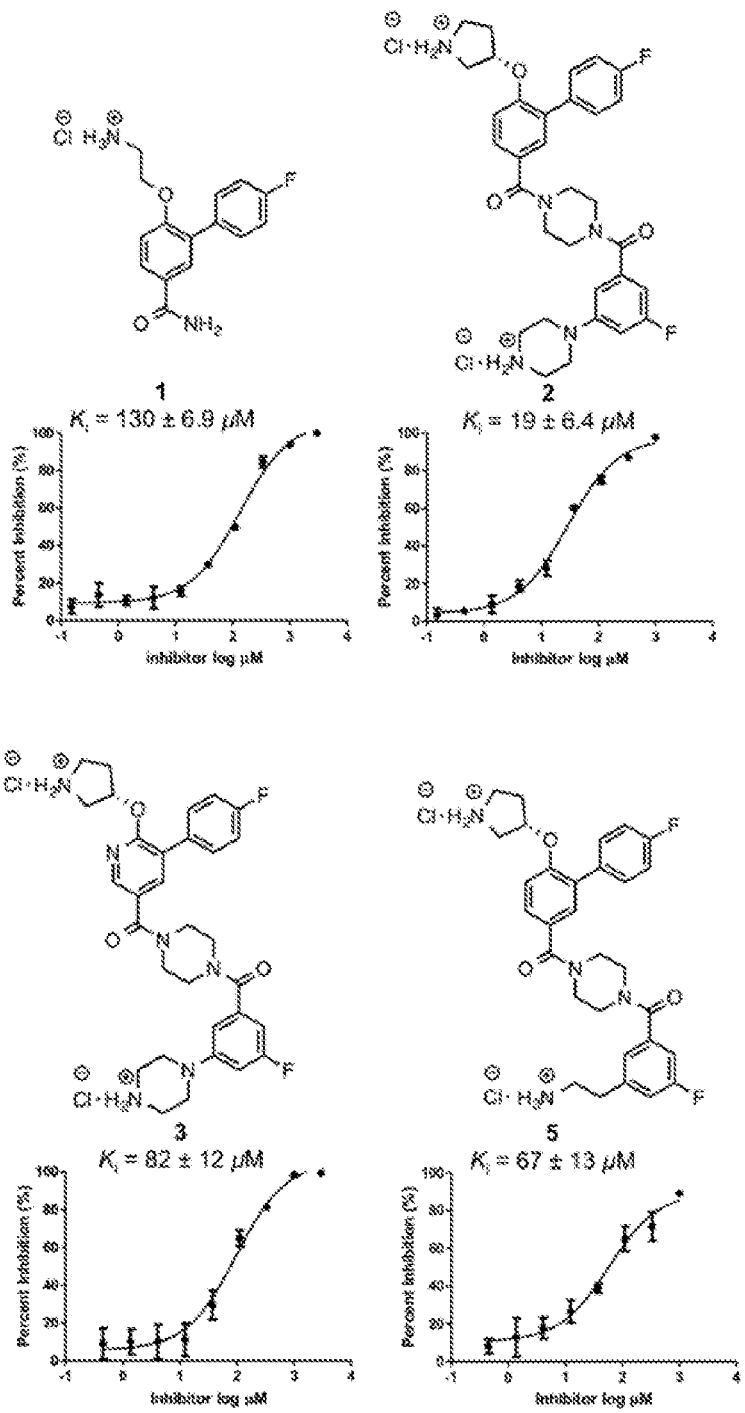
FIG. 5 shows representative data illustrating the AlphaScreen competitive inhibition assay results of compound 1, 2, 4-8, and carnosic acid for the inhibition of the β-catenin/BCL9 PPI.
Figure 5:
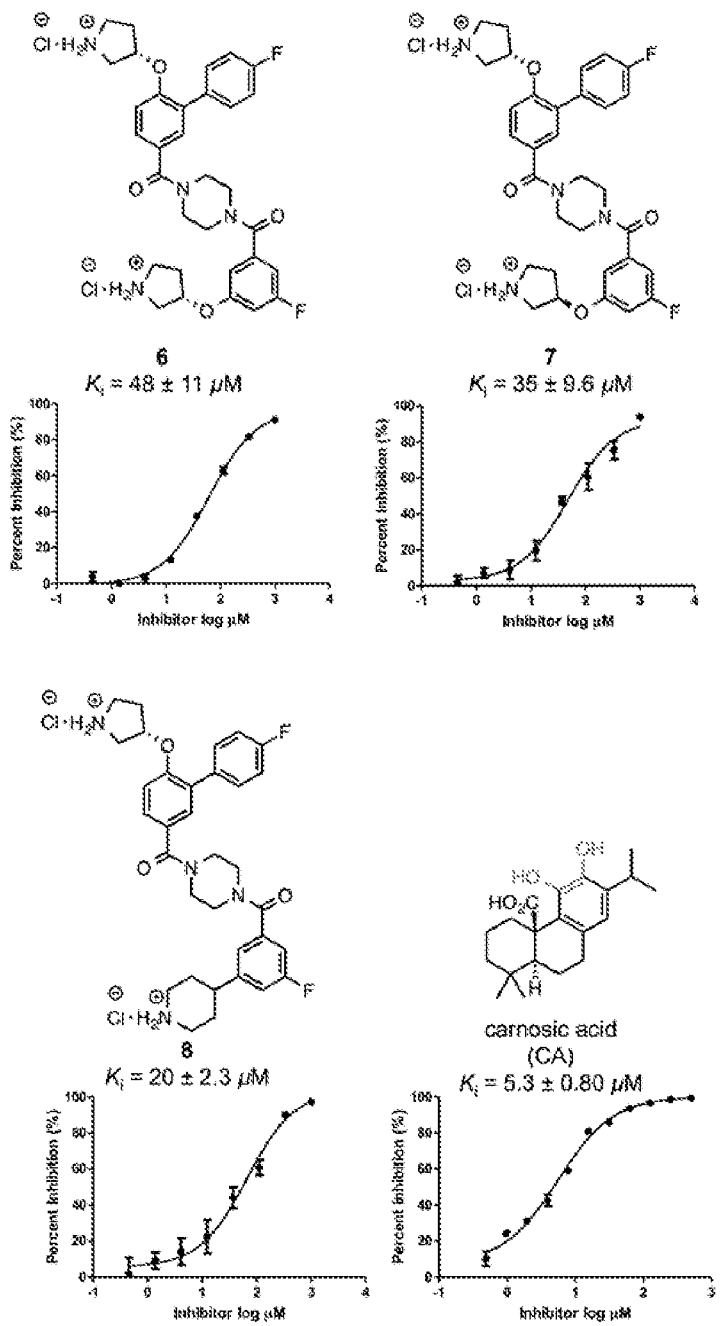

Referring to FIG. 5, the AlphaScreen competitive inhibition assay results of compounds 1, 2, 4-8, and carnosic acid for the inhibition of the β-catenin/BCL9 PPI are shown. Each set of data is expressed as mean±standard deviation (n=3).

32. Optimization of β-Catenin/BCL9 Inhibitors

Figure 7:
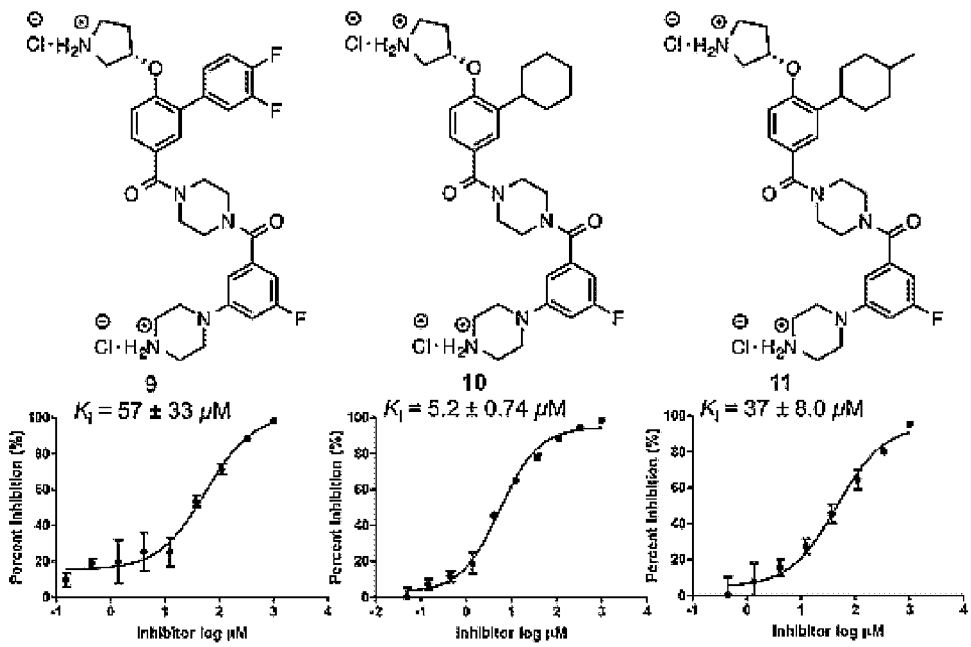
FIG. 7 shows representative data illustrating the AlphaScreen competitive inhibition assay results of compounds 9-21 for the inhibition of the β-catenin/BCL9 PPI.
Figure 7:
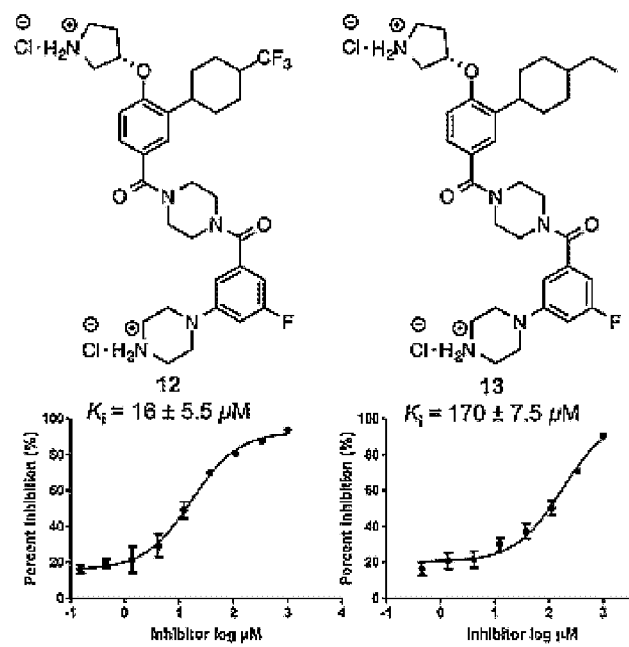
Figure 7:
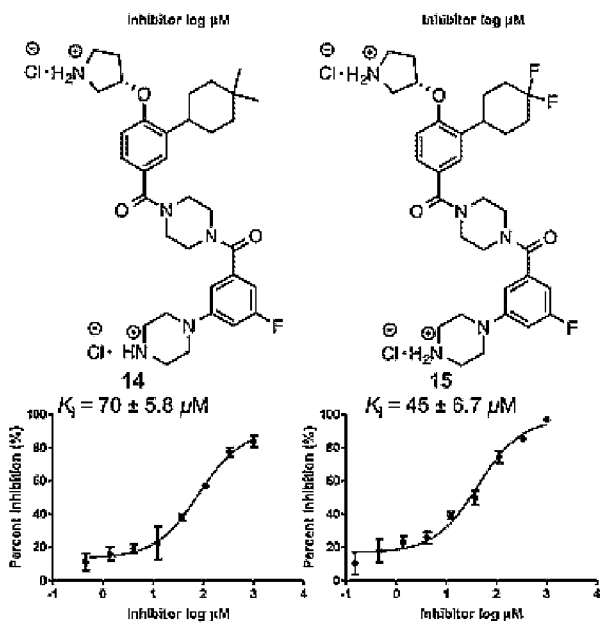
Figure 7:
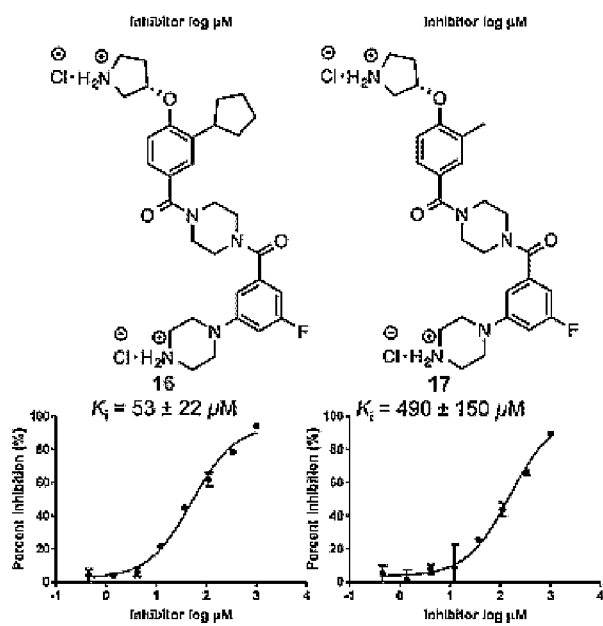
Figure 7:
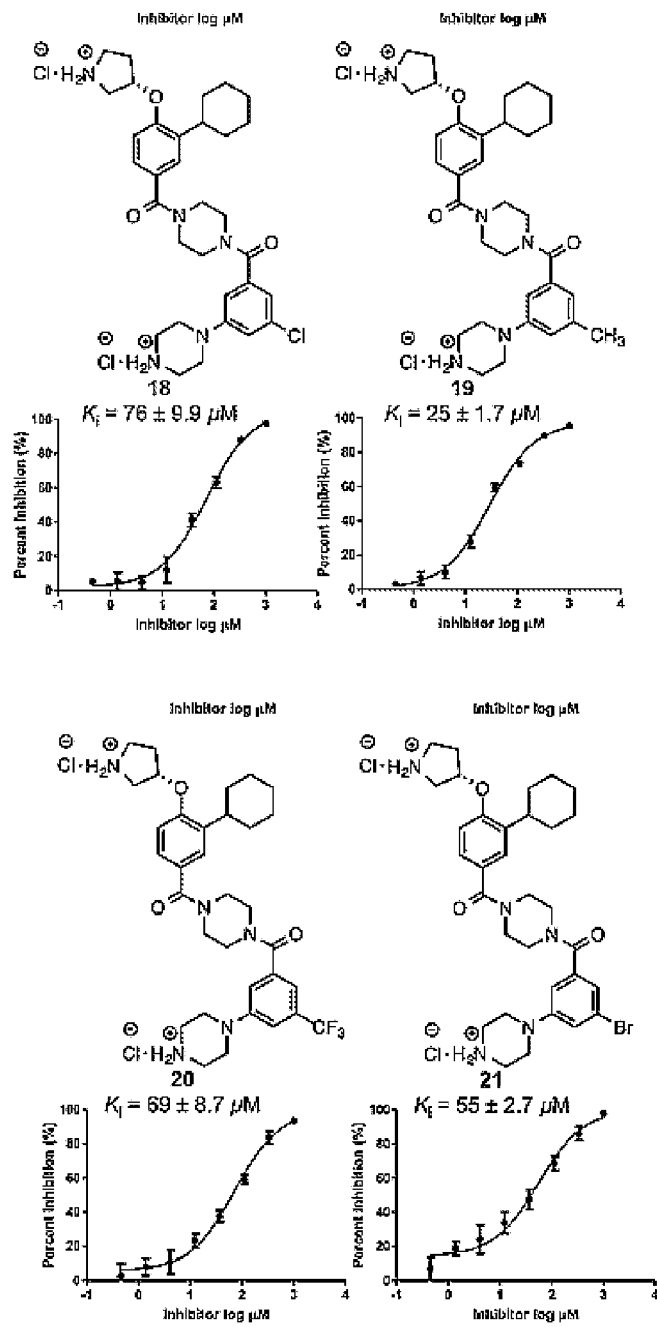

In lieu of the SAR of 1-8 and the proposed binding mode of 2 with β-catenin in FIG. 2B, a second series of potential inhibitors was designed to explore the BCL9 L366 binding pocket (compounds 9-13, see Table 1, FIG. 6A, and FIG. 6B). Compound 9 was a fairly conservative alteration from 2. One reason to synthesize this compound was because the 3,4-difluoro substituted derivative exhibited the best activity for the previous scaffold (Hoggard et al. (2015) *J. Am. Chem. Soc.* 137: 12249-12260). Unfortunately, the AlphaScreen assay showed the activity of 9 was approximately 3-fold worse than 2. Since the upper hydrophobic pocket was evolved to accept aliphatic L366, the modification of aromatic to aliphatic ring was envisioned. The choice to use a ring over a chain (to more directly mimic leucine) was made in an effort to keep the number of rotatable bonds and the entropic penalty of binding low. Compound 10 with an unsubstituted cyclohexyl ring was designed and synthesized. The $K_i$ value of this compound is 5.2±0.74 μM and comparable with that of carnosic acid (FIG. 7). The introduction of a methyl group to the cyclohexyl group decreased the activity. The replacement of the methyl group with a trifluoromethyl group afforded 12 with gained inhibitory potency. The bulkier 4-ethyl, 4-dimethyl, and 4-difluoro derivatives all were worse than 10 (see Table 2). Compound 16 with a cyclopentyl substitution and 17 with a methyl group exhibited lower activities than 10, suggesting the importance of van der Waals contact in the BCL9 L366 binding pocket.

Referring to FIG. 7, the AlphaScreen competitive inhibition assay results of compounds 9-21 for the inhibition of the β-catenin/BCL9 PPI are shown. Each set of data is expressed as mean±standard deviation (n=3).

a. Site-Directed Mutagenesis

Figure 8:
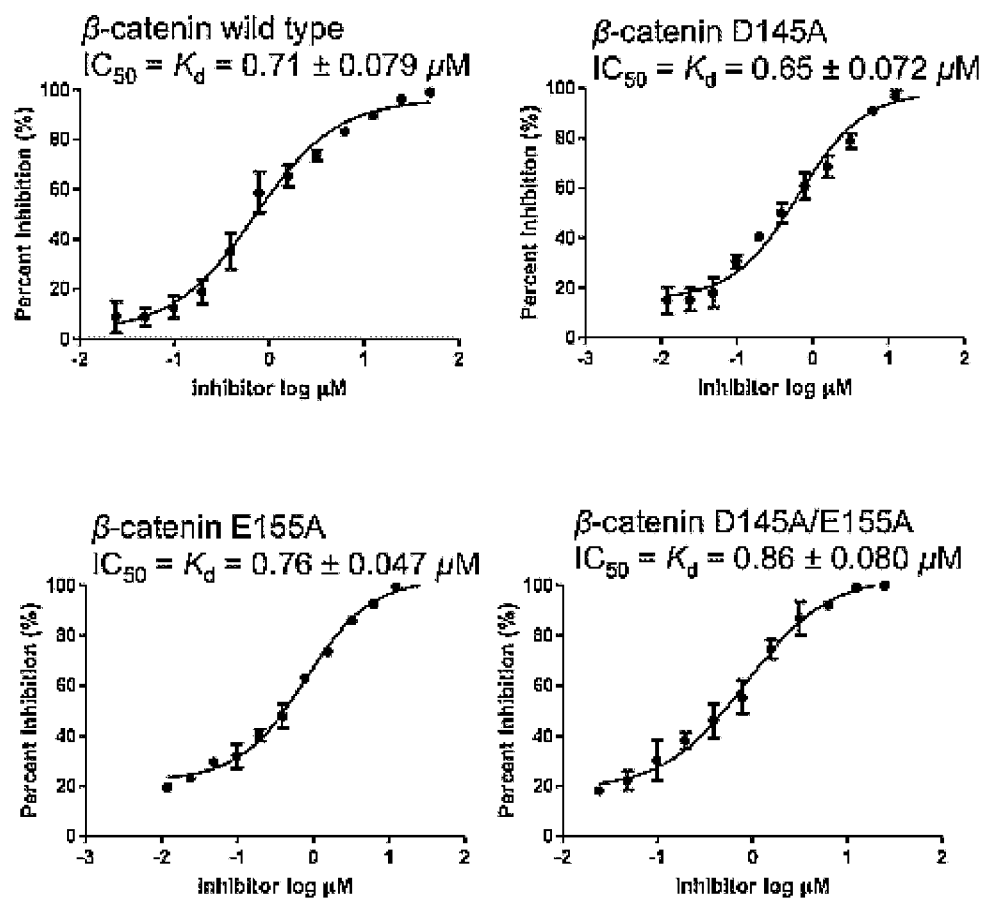
FIG. 8 shows representative data from an AlphaScreen competitive binding assay to determine the apparent $K_d$ values for the wild-type β-catenin/wild-type BCL9 PPI and the mutant β-catenin/wild-type BCL9 PPIs.
Figure 9:
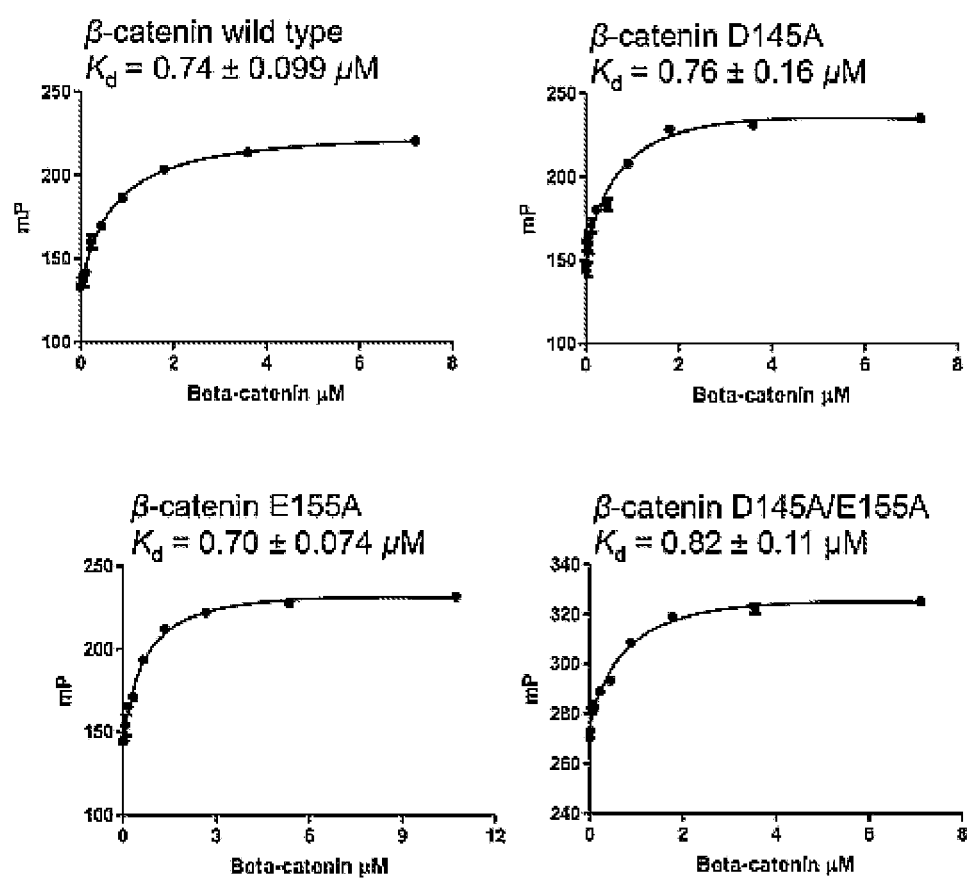
FIG. 9 shows representative data from fluorescence polarization saturation binding experiments to determine the $K_d$ values for the wild-type β-catenin/wild-type BCL9 PPI and the mutant β-catenin/wild-type BCL9 PPIs.
Figure 10:
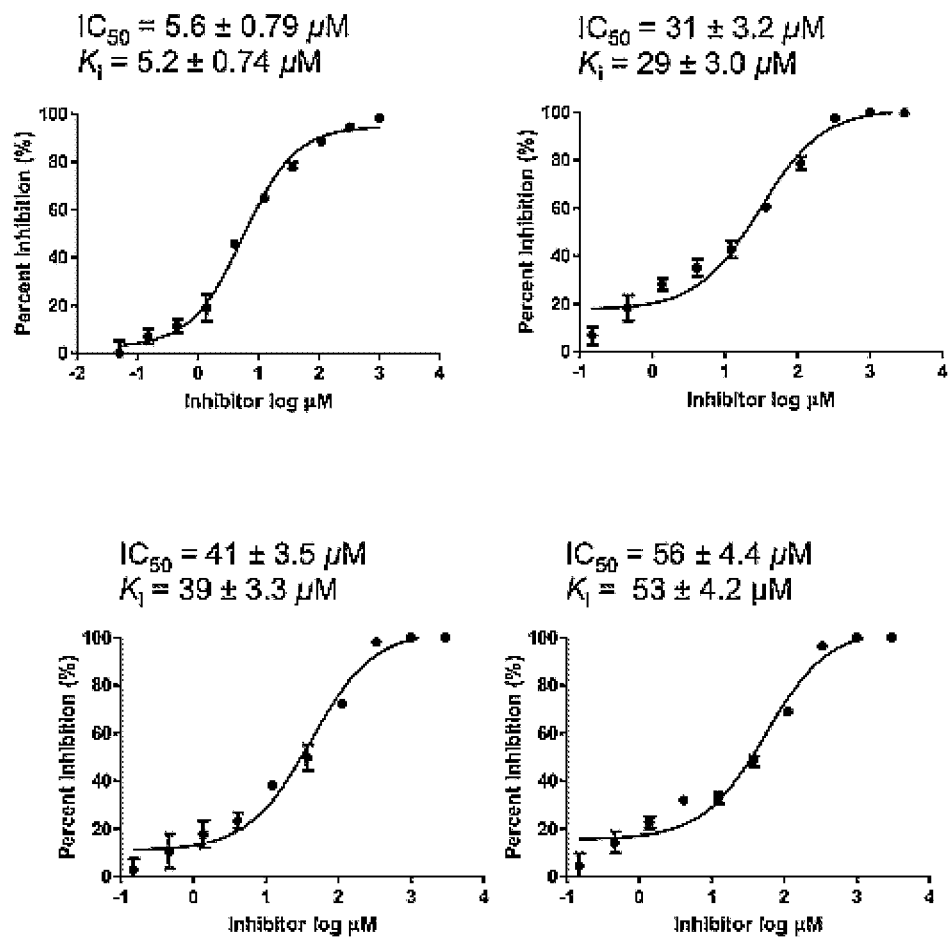
FIG. 10 shows representative AlphaScreen competitive inhibition assay results of compound 10 with wild-type and mutant β-catenin proteins.

Site-directed mutagenesis studies were performed to evaluate the binding mode of new β-catenin/BCL9 inhibitors. Previous crystallographic analysis indicated that D145 and E155 of β-catenin did not interfere with the β-catenin/BCL9 PPI (Hoggard et al. (2015) *J. Am. Chem. Soc.* 137: 12249-12260). Three β-catenin mutants, D145A, E155A, and D145A/E155A, were made. Native gel electrophoresis, thermal shift, and CD experiments confirmed the homogeneity, the thermal stability, and the secondary structure integrity of the purified proteins. The AlphaScreen competitive binding assays and the fluorescence polarization binding assays demonstrated that D145A, E155A, and D145A/E155A of β-catenin had the same $K_d$ values as wild-type β-catenin when binding with wild-type BCL9, as shown in FIG. 8 and FIG. 9. The AlphaScreen competitive inhibition assay was performed to evaluate the roles of D145 and E155 in inhibitor binding. As shown in Table 3, the $K_i$ values of 10 for β-catenin D145A/BCL9 and β-catenin E155A/BCL9 PPIs were 6-8 fold higher than that for the wild-type β-catenin/BCL9 PPI (FIG. 10). Further, the $K_i$ value of 10 for the β-catenin D145A/E155A double mutant/BCL9 interaction was 53±4.2 µM and higher than that for the β-catenin D145A/BCL9 or β-catenin E155A/BCL9 PPI, indicating that the carboxylate side chains of D145 and E155 of β-catenin were important for the inhibitory potency of 10. A further optimization was centered on the evaluation of the $R_2$ group (compounds 18-21, see Tables 1 and 2). The results of the AlphaScreen competitive inhibition assay indicated that the fluorine atom was the best substituent for this position.

TABLE 3

| β-catenin | $K_i$ ± SD (µM) |
|---|---|
| wild type | 5.2 ± 0.74 |
| D145A | 29 ± 3.0 |
| E155A | 39 ± 3.3 |
| D145A/E155A | 53 ± 4.2 |

Referring to FIG. 8, the AlphaScreen competitive binding assay results to determine the apparent $K_d$ values for the wild-type β-catenin/wild-type BCL9 PPI and the mutant β-catenin/wild-type BCL9 PPIs are shown. Each set of data is expressed as mean standard deviation (n=3). The concentrations of mutant β-catenin proteins used in the assays were the same as that of wild-type β-catenin protein.

Referring to FIG. 9, the fluorescence polarization saturation binding experiment results to determine the $K_d$ values for the wild-type β-catenin/wild-type BCL9 PPI and the mutant β-catenin/wild-type BCL9 PPIs. Each set of data is expressed as mean±standard deviation (n=3). The concentrations of mutant β-catenin proteins used in the assays were the same as that of wild-type β-catenin protein.

Referring to FIG. 10, the AlphaScreen competitive inhibition assay results of compound 10 with wild-type and mutant β-catenin proteins are shown. Each set of data is expressed as mean±standard deviation (n=3).

Figure 11A:
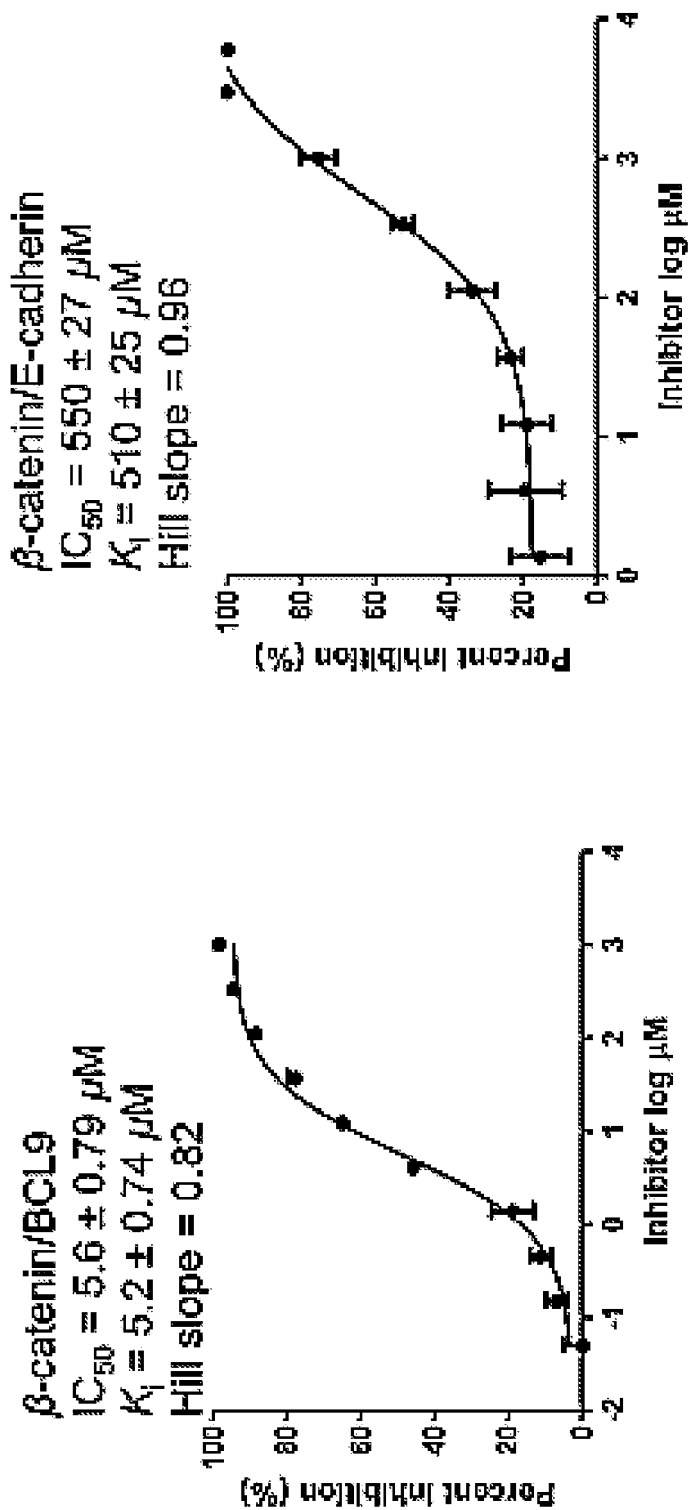
FIG. 11A-C shows representative data illustrating the inhibitor selectivity of compound 10 for β-catenin/BCL9 PPIs and cell-based characterization of compound 10 as a new β-catenin/BCL9 inhibitor. Specifically, in-parallel Alpha Screen selectivity assay results (11A) and TOPFlash (11B) and FOPFlash (11C) luciferase reporter assay results are shown.

33. Inhibitor Selectivity of Compound 10 for β-Catenin/BCL9 Over β-Catenin/Cadherin PPIS The AlphaScreen selectivity assay was used to quantify inhibitor selectivity. As shown in FIG. 11A, compound 10 exhibited 98-fold selectivity for β-catenin/BCL9 over β-catenin/cadherin PPIs.

Referring to FIG. 11A, in-parallel Alpha Screen selectivity assay results for compound 10 are shown. Each set of data is expressed as mean±standard deviation (n=3).

34. Cell-Based Characterization of Compound 10

The Wnt-responsive luciferase reporter assays were performed with pcDNA3.1-β-catenin transfected HEK293 cells for 10, 12, and carnosic acid. As shown in FIG. 11B, FIG. 11C, and FIG. 12A-C, compounds 10 and 12 suppressed the TOPFlash (with wild-type Tcf binding sites) luciferase activity in a dose-dependent manner. This compound did not affect the FOPFlash (with mutant Tcf binding sites) luciferase activity even at 100 µM. The MTs cell viability assay was performed to assess the inhibitory effects of 2, 10, and 12 on growth of colorectal cancer cell lines SW480 and HCT116. Compound 10 inhibited the growth of Wnt-activated cancer cells with the $IC_{50}$ values of 22±4.0 µM and 26±6.6 µM for SW480 and HCT116 cells, respectively (Table 4).

TABLE 4

| | $IC_{50}$ ± SD (µM) | |
|---|---|---|
| No. | SW480 | HCT116 |
| 2 | 86 ± 8.8 | 120 ± 16 |
| 10 | 22 ± 4.0 | 26 ± 6.6 |
| 12 | 44 ± 6.5 | 39 ± 5.4 |

Figure 11C:
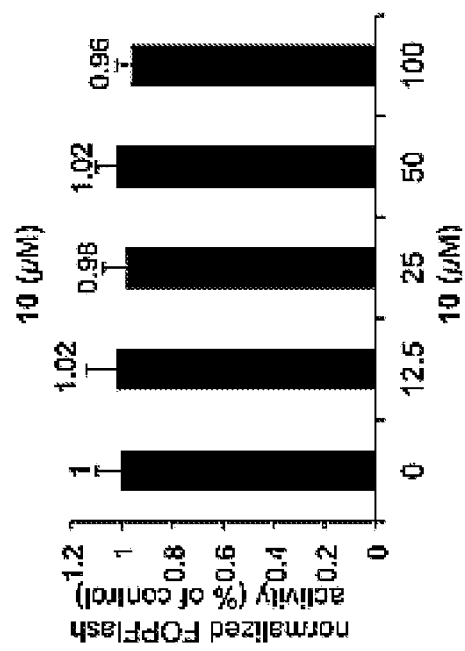
Figure 11B:
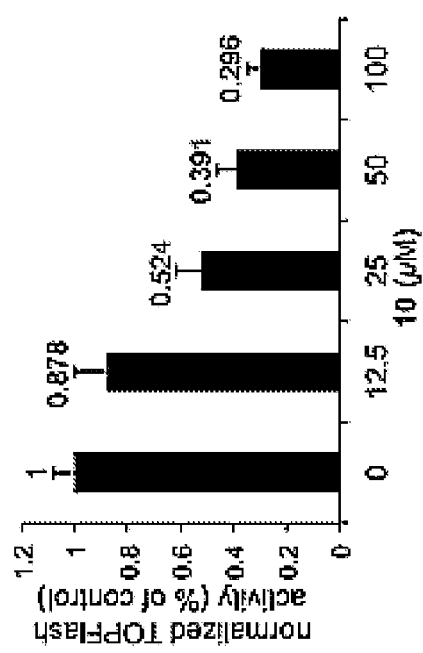

Referring to FIG. 11B and FIG. 11C, TOPFlash (11B) and FOPFlash (11C) luciferase reporter assay results of compound 10 using pcDNA3.1-β-catenin transfected HEK293 cells are shown. The data are expressed as mean±standard deviation (n=2).

Figure 12C:
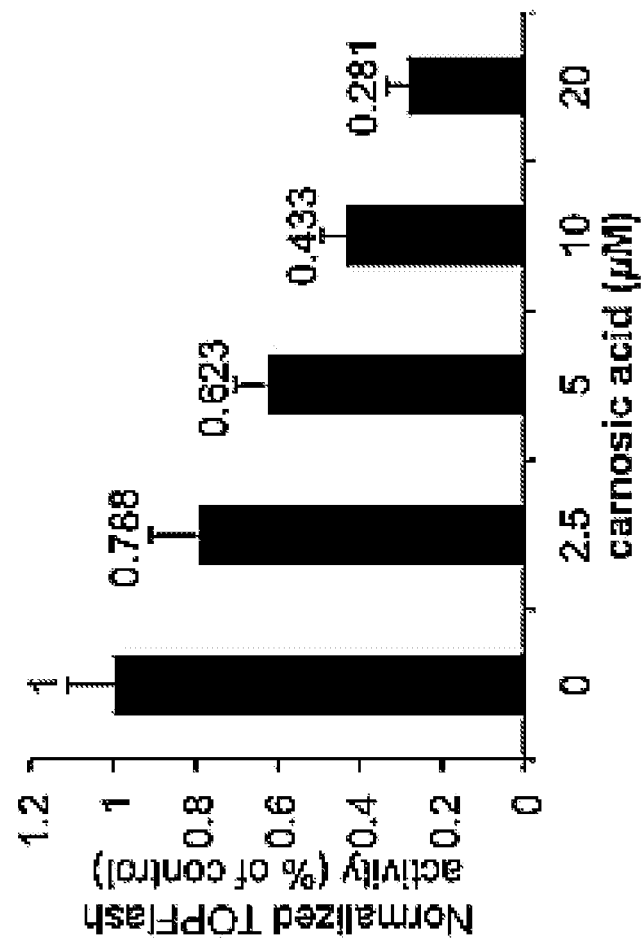
Figure 12C:
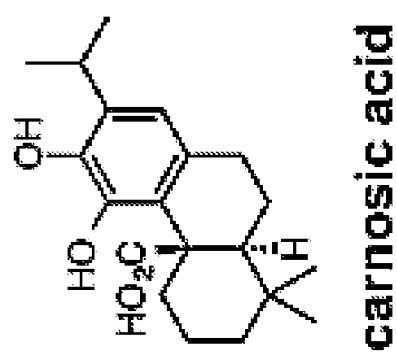

Referring to FIG. 12A-C, TOPFlash (12A) and FOPFlash (12B) luciferase reporter assay results of compound 12 and TOPFlash luciferase assay results of carnosic acid (12C) are shown. Each set of data is expressed as mean±standard deviation (n=3).

The β-catenin/BCL9 PPI, a key downstream effector of canonical Wnt signaling, represents an appealing therapeutic target for the treatment of cancer and fibrosis and the eradication of cancer stem cells. In this study, the critical binding elements at the BCL9 binding site for hydrophobic, H-bond, and charge-charge interactions were extracted from the crystal structure of the β-catenin/BCL9 PPI (PDB ids, 2GL7 (Sampietro et al. (2006) *Mol. Cell* 24: 293-300) and 3SL9 (de la Roche et al. (2012) *Nature Commun.* 3: 680)). A small-molecule inhibitor with a novel scaffold was designed to match the proposed critical binding elements. A further structural optimization resulted in 10 and 12. Compound 10 exhibited a $K_i$ value of 5.2±0.74 µM for the inhibition of the β-catenin/BCL9 PPI and 98-fold selectivity for β-catenin/BCL9 over β-catenin/cadherin PPIs. The structure-activity relationship and site-directed mutagenesis results are in agreement with the proposed binding mode of this series of inhibitors. The cell-based studies demonstrated that 10 and 12 can suppress the transactivation of canonical Wnt signaling and inhibit the growth of cancer cells with hyperactivated Wnt signaling.

G. REFERENCES

Clevers, H.; Loh, K. M.; Nusse, R. Stem cell signaling. An integral program for tissue renewal and regeneration: Wnt signaling and stem cell control. *Science* 2014, 346, 1248012.

Zeng, X.; Huang, H.; Tamai, K.; Zhang, X.; Harada, Y.; Yokota, C.; Almeida, K.; Wang, J.; Doble, B.; Woodgett, J.; Wynshaw-Boris, A.; Hsieh, J. C.; He, X. Initiation of Wnt signaling: control of Wnt coreceptor Lrp6 phosphorylation/activation via frizzled, disheveled and axin functions. *Development* 2008, 135, 367-375.

Mosimann, C.; Hausmann, G.; Basler, K. β-Catenin hits chromatin: regulation of Wnt target gene activation. *Nature Rev. Mol. Cell Biol.* 2009, 10, 276-286.

Clevers, H.; Nusse, R. Wnt/β-catenin signaling and disease. *Cell* 2012, 149, 1192-1205.

Anastas, J. N.; Moon, R. T. WNT signalling pathways as therapeutic targets in cancer. *Nature Rev. Cancer* 2013, 13, 11-26.

Singh, S. K.; Hawkins, C.; Clarke, I. D.; Squire, J. A.; Bayani, J.; Hide, T.; Henkelman, R. M.; Cusimano, M. D.; Dirks, P. B. Identification of human brain tumour initiating cells. *Nature* 2004, 432, 396-401.

O'Brien, C. A.; Pollett, A.; Gallinger, S.; Dick, J. E. A human colon cancer cell capable of initiating tumour growth in immunodeficient mice. *Nature* 2007, 445, 106-110.

Ricci-Vitiani, L.; Lombardi, D. G.; Pilozzi, E.; Biffoni, M.; Todaro, M.; Peschle, C.; De Maria, R. Identification and expansion of human colon-cancer-initiating cells. *Nature* 2007, 445, 111-115.

Malanchi, I.; Peinado, H.; Kassen, D.; Hussenet, T.; Metzger, D.; Chambon, P.; Huber, M.; Hohl, D.; Cano, A.; Birchmeier, W.; Huelsken, J. Cutaneous cancer stem cell maintenance is dependent on β-catenin signalling. *Nature* 2008, 452, 650-653.

Yeung, J.; Esposito, M. T.; Gandillet, A.; Zeisig, B. B.; Griessinger, E.; Bonnet, D.; So, C. W. E. β-Catenin mediates the establishment and drug resistance of MLL leukemic stem cells. *Cancer Cell* 2010, 18, 606-618.

Hahne, G.; Grossmann, T. N. Direct targeting of β-catenin: Inhibition of protein-protein interactions for the inactivation of Wnt signaling. *Bioorg. Med. Chem.* 2013, 21, 4020-4026.

Brembeck, F. H.; Wiese, M.; Zatula, N.; Grigoryan, T.; Dai, Y.; Fritzmann, J.; Birchmeier, W. BCL9-2 promotes early stages of intestinal tumor progression. *Gastroenterology* 2011, 141, 1359-1370.

Deka, J.; Wiedemann, N.; Anderle, P.; Murphy-Seiler, F.; Bultinck, J.; Eyckerman, S.; Stehle, J. C.; André, S.; Vilain, N.; Zilian, O.; Robine, S.; Delorenzi, M.; Basler, K.; Aguet, M. Bcl9/Bcl91 are critical for Wnt-mediated regulation of stem cell traits in colon epithelium and adenocarcinomas. *Cancer Res.* 2010, 70, 6619-6628.

Adachi, S.; Jigami, T.; Yasui, T.; Nakano, T.; Ohwada, S.; Omori, Y.; Sugano, S.; Ohkawara, B.; Shibuya, H.; Nakamura, T.; Akiyama, T. Role of a BCL9-related β-catenin-binding protein, B9L, in tumorigenesis induced by aberrant activation of Wnt signaling. *Cancer Res.* 2004, 64, 8496-8501.

de la Roche, M.; Worm, J.; Bienz, M. The function of BCL9 in Wnt/β-catenin signaling and colorectal cancer cells. *BMC Cancer* 2008, 8, 199.

Mani, M.; Carrasco, D. E.; Zhang, Y.; Takada, K.; Gatt, M. E.; Dutta-Simmons, J.; Ikeda, H.; Diaz-Griffero, F.; Pena-Cruz, V.; Bertagnolli, M.; Myeroff, L. L.; Markowitz, S. D.; Anderson, K. C.; Carrasco, D. R. BCL9 promotes tumor progression by conferring enhanced proliferative, metastatic, and angiogenic properties to cancer cells. *Cancer Res.* 2009, 69, 7577-7586.

Brembeck, F. H.; Schwarz-Romond, T.; Bakkers, J.; Wilhelm, S.; Hammerschmidt, M.; Birchmeier, W. Essential role of BCL9-2 in the switch between β-catenin's adhesive and transcriptional functions. *Genes Dev.* 2004, 18, 2225-2230.

Zhao, J. J.; Lin, J.; Zhu, D.; Wang, X.; Brooks, D.; Chen, M.; Chu, Z. B.; Takada, K.; Ciccarelli, B.; Admin, S.; Tao, J.; Tai, Y. T.; Treon, S.; Pinkus, G.; Kuo, W. P.; Hideshima, T.; Bouxsein, M.; Munshi, N.; Anderson, K.; Carrasco, R. miR-30-5p functions as a tumor suppressor and novel therapeutic tool by targeting the oncogenic Wnt/β-catenin/BCL9 pathway. *Cancer Res.* 2014, 74, 1801-1813.

Moor, A. E.; Anderle, P.; Cantu, C.; Rodriguez, P.; Wiedemann, N.; Baruthio, F.; Deka, J.; André, S.; Valenta, T.; Moor, M. B.; Györffy, B.; Barras, D.; Delorenzi, M.; Basler, K.; Aguet, M. BCL9/9L-β-catenin signaling is associated with poor outcome in colorectal cancer. *EBioMedicine* 2015, 2, 1932-1943.

Sampietro, J.; Dahlberg, C. L.; Cho, U. S.; Hinds, T. R.; Kimelman, D.; Xu, W. Crystal structure of a β-catenin/BCL9/Tcf4 complex. *Mol. Cell* 2006, 24, 293-300.

Kawamoto, S. A.; Thompson, A. D.; Coleska, A.; Nikolovska-Coleska, Z.; Yi, H.; Wang, S. Analysis of the interaction of BCL9 with beta-catenin and development of fluorescence polarization and surface plasmon resonance binding assays for this interaction. *Biochemistry* 2009, 48, 9534-9541.

Zhang, M.; Wisniewski, J. A.; Ji, H. AlphaScreen selectivity assay for β-catenin/B-cell lymphoma 9 inhibitors. *Anal. Biochem.* 2015, 469, 43-53.

de la Roche, M.; Rutherford, T. J.; Gupta, D.; Veprintsev, D. B.; Saxty, B.; Freund, S. M.; Bienz, M. An intrinsically labile α-helix abutting the BCL9-binding site of β-catenin is required for its inhibition by carnosic acid. *Nature Commun.* 2012, 3, 680.

Kawamoto, S. A.; Coleska, A.; Ran, X.; Yi, H.; Yang, C. Y.; Wang, S. Design of triazole-stapled BCL9 α-helical peptides to target the β-catenin/B-cell CLL/lymphoma 9 (BCL9) protein-protein interaction. *J. Med. Chem.* 2012, 55, 1137-1146.

Takada, K.; Zhu, D.; Bird, G. H.; Sukhdeo, K.; Zhao, J. J.; Mani, M.; Lemieux, M.; Carrasco, D. E.; Ryan, J.; Horst, D.; Fulciniti, M.; Munshi, N. C.; Xu, W.; Kung, A. L.; Shivdasani, R. A.; Walensky, L. D.; Carrasco, D. R. Targeted disruption of the BCL9/β-catenin complex inhibits oncogenic Wnt signaling. *Sci. Transl. Med.* 2012, 4, 148ra117.

Zhao, J. J.; Lin, J.; Zhu, D.; Wang, X.; Brooks, D.; Chen, M.; Chu, Z. B.; Takada, K.; Ciccarelli, B.; Admin, S.; Tao, J.; Tai, Y. T.; Treon, S.; Pinkus, G.; Kuo, W. P.; Hideshima, T.; Bouxsein, M.; Munshi, N.; Anderson, K.; Carrasco, R. miR-30-5p functions as a tumor suppressor and novel therapeutic tool by targeting the oncogenic Wnt/β-catenin/BCL9 pathway. *Cancer Res.* 2014, 74, 1801-1813.

Hoggard, L. R.; Zhang, Y.; Zhang, M.; Panic, V.; Wisniewski, J. A.; Ji, H. Rational design of selective small-molecule inhibitors for catenin/B-cell lymphoma 9 protein-protein interactions. *J Am. Chem. Soc.* 2015, 137, 12249-12260.

de la Roche, M.; Worm, J.; Bienz, M. The function of BCL9 in Wnt/β-catenin signaling and colorectal cancer cells. *BMC Cancer* 2008, 8, 199.

Kawamoto, S. A.; Thompson, A. D.; Coleska, A.; Nikolovska-Coleska, Z.; Yi, H.; Wang, S. Analysis of the interaction of BCL9 with β-catenin and development of fluorescence polarization and surface plasmon resonance binding assays for this interaction. *Biochemistry* 2009, 48, 9534-9541.

Halgren, T. A. Identifying and characterizing binding sites and assessing druggability. *J Chem. Inf Model.* 2009, 49, 377-389.

Sampietro, J.; Dahlberg, C. L.; Cho, U. S.; Hinds, T. R.; Kimelman, D.; Xu, W. Crystal structure of a β-catenin/BCL9/Tcf4 complex. *Mol. Cell* 2006, 24 (2), 293-300.

Baell, J. B.; Holloway, G. A. New substructure filters for removal of pan assay interference compounds (PAINS) from screening libraries and for their exclusion in bioassays. *J. Med. Chem.* 2010, 53, 2719-2740.

Baell, J.; Walters, M. A. Chemistry: Chemical con artists foil drug discovery. *Nature* 2014, 513, 481-483.

Everson, D. A.; Jones, B. A.; Weix, D. J. Replacing conventional carbon nucleophiles with electrophiles: nickel-catalyzed reductive alkylation of aryl bromides and chlorides. *J Am. Chem. Soc.* 2012, 134, 6146-6159.

Hoggard, L. R.; Zhang, Y.; Zhang, M.; Panic, V.; Wisniewski, J. A.; Ji, H. Rational design of selective small-molecule inhibitors for catenin/B-cell lymphoma 9 protein-protein interactions. *J. Am. Chem. Soc.* 2015, 137, 12249-12260.

Zhang, M.; Wisniewski, J. A.; Ji, H. AlphaScreen selectivity assay for β-catenin/B-cell lymphoma 9 inhibitors. *Anal. Biochem.* 2015, 469, 43-53.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the treatment of a disorder of uncontrolled cellular proliferation associated with a β-catenin/BCL9 dysfunction in a mammal comprising the step of administering to the mammal an effective amount of at least one compound having a structure represented by a formula:

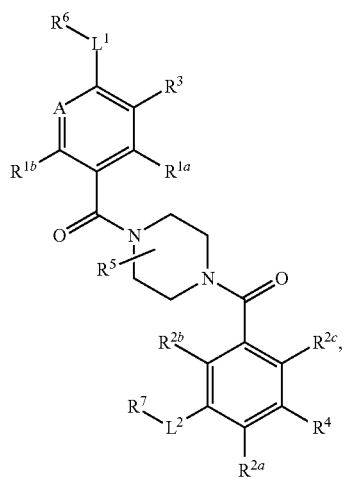

wherein A is —N— or —$CR^8$—;
  wherein $R^8$ is hydrogen, halogen, unsubstituted C1-C3 alkyl, C1-C3 monohaloalkyl, or C1-C3 polyhaloalkyl;
wherein $L^1$ is optionally present, and when present, is O, S, or NH;
wherein $L^2$ is optionally present, and when present, is O, S, $NR^9$, or —$(CR^{10a}R^{10b})_n$—;
  wherein n is an integer having the value of 1, 2, or 3;
  wherein $R^9$ is hydrogen, unsubstituted C1-C3 alkyl, C1-C3 monohaloalkyl, or C1-C3 polyhaloalkyl;
  wherein each occurrence of $R^{10a}$ and $R^{10b}$ is independently hydrogen, unsubstituted C1-C3 alkyl, C1-C3 monohaloalkyl, or C1-C3 polyhaloalkyl;
wherein each of $R^{1a}$ and $R^{1b}$ is independently hydrogen, halogen, unsubstituted C1-C3 alkyl, C1-C3 monohaloalkyl, or C1-C3 polyhaloalkyl;
wherein each of $R^{2a}$, $R^{2b}$, and $R^{2c}$ is independently hydrogen, halogen, unsubstituted C1-C3 alkyl, C1-C3 haloalkyl, or C1-C3 polyhaloalkyl;
wherein $R^3$ is $Cy^3$ or $Ar^1$;
  wherein $Cy^3$ is a C3-C8 cycloalkyl or a C2-C7 heterocycloalkyl; and wherein $Cy^3$ is substituted with 0, 1, 2, or 3 groups independently selected from halogen, —CN, unsubstituted C1-C3 alkyl, C1-C3 monohaloalkyl, C1-C3 polyhaloalkyl, cyclopropyl, and —$CO_2H$;
  wherein $Ar^1$ is selected from aryl and heteroaryl, and wherein $Ar^1$ is substituted with 0, 1, 2, or 3 groups independently selected from halogen, —CN, unsubstituted C1-C3 alkyl, C1-C3 monohaloalkyl, C1-C3 polyhaloalkyl, unsubstituted cyclopropyl, and —$CO_2H$;
wherein $R^4$ is hydrogen, halogen, unsubstituted C1-C3 alkyl, C1-C3 haloalkyl, or C1-C3 polyhaloalkyl;
wherein each occurrence of $R^5$ is independently selected from hydrogen, unsubstituted C1-C8 alkyl, C1-C8 monohaloalkyl, or C1-C8 polyhaloalkyl;
wherein $R^6$ is C1-C6 aminoalkyl, C1-C6 hydroxyalkyl, or $Cy^1$; and wherein $Cy^1$ is an amino C3-C8 cycloalkyl, or a C2-C7 heterocycloalkyl comprising at least one oxygen or nitrogen atom; and wherein $Cy^1$ is substituted 0, 1, 2, or 3 groups independently selected from halogen, unsubstituted C1-C4 alkyl, C1-C4 monohaloalkyl, and C1-C4 polyhaloalkyl;
wherein $R^7$ is $H_2N$—(C1-C6 alkyl)-(C=O)—; HO—(C1-C6 alkyl)-(C=O)—; C1-C6 aminoalkyl, C1-C6 hydroxyalkyl, or $Cy^2$; and wherein $Cy^2$ is a C2-C7 heterocycloalkyl comprising at least one oxygen or nitrogen atom; and wherein $Cy^2$ is substituted 0, 1, 2, or 3 groups independently selected from halogen, unsubstituted C1-C4 alkyl, C1-C4 monohaloalkyl, and C1-C4 polyhaloalkyl;
or a pharmaceutically acceptable salt thereof,
wherein the disorder is cancer.

2. The method of claim 1, wherein the mammal is human; and wherein the human has been identified to have a 1q21 chromosomal abnormality.

3. The method of claim 1, further comprising the step of identifying a human in need of treatment of the disorder; and wherein the step of identifying the human in need of treatment of the disorder comprises the steps of:
  (a) obtaining a sample from the human, wherein the sample comprises cells suspected of being associated with the disorder of uncontrolled cellular proliferaton; and
  (b) determining if the sample comprises cells with a 1q21 chromosomal abnormality.

4. The method of claim 1, wherein the cancer is selected from breast cancer and colorectal cancer.

5. The method of claim 1, wherein the cancer is colorectal cancer.

* * * * *